(12) United States Patent
Green et al.

(10) Patent No.: US 8,497,275 B2
(45) Date of Patent: Jul. 30, 2013

(54) HCV PROTEASE INHIBITORS AND USES THEREOF

(75) Inventors: Brian E. Green, Wonder Lake, IL (US); David D. Anderson, Groton, CT (US); Todd D. Bosse, Chicago, IL (US); Curt S. Cooper, Vernon Hills, IL (US); Larry L. Klein, Lake Forest, IL (US); Allan C. Krueger, Gurnee, IL (US); Daniel P. Larson, Oak Creek, WI (US); Dachun Liu, Waukegan, IL (US); Keith F. McDaniel, Wauconda, IL (US); Christopher E. Motter, Oak Creek, WI (US); John K. Pratt, Kenosha, WI (US); Todd W. Rockway, Grayslake, IL (US); Teresa A. Rosenberg, Gurnee, IL (US); Ming C. Yeung, Grayslake, IL (US); Hui-Ju Chen, Grayslake, IL (US); Jason P. Shanley, Chicago, IL (US)

(73) Assignee: AbbVie Inc., North Chicago, IL (US)

( * ) Notice: Subject to any disclaimer, the term of this patent is extended or adjusted under 35 U.S.C. 154(b) by 958 days.

(21) Appl. No.: 12/492,518

(22) Filed: Jun. 26, 2009

(65) Prior Publication Data
US 2010/0029686 A1 Feb. 4, 2010

Related U.S. Application Data

(63) Continuation of application No. PCT/US2007/088936, filed on Dec. 27, 2007.

(60) Provisional application No. 60/877,254, filed on Dec. 27, 2006.

(51) Int. Cl.
A61K 31/4965 (2006.01)
A61K 31/40 (2006.01)
A61K 38/00 (2006.01)
A61K 38/05 (2006.01)

(52) U.S. Cl.
USPC ....... 514/255.05; 514/423; 514/4.3; 514/21.9

(58) Field of Classification Search
USPC .............................. 514/255.05, 423, 4.3, 21.9
See application file for complete search history.

(56) References Cited

U.S. PATENT DOCUMENTS

| | | | | |
|---|---|---|---|---|
| 5,541,206 | A | 7/1996 | Kempf et al. | 514/365 |
| 6,534,523 | B1 | 3/2003 | Bailey et al. | 514/312 |
| 6,667,299 | B1 | 12/2003 | Ahlem et al. | 514/178 |
| 6,803,374 | B2 | 10/2004 | Priestley et al. | 514/303 |
| 6,872,805 | B2 | 3/2005 | Campbell et al. | 530/331 |
| 2005/0024702 | A1 | 2/2005 | Takeuchi et al. | 359/205 |

FOREIGN PATENT DOCUMENTS

| | | |
|---|---|---|
| WO | WO9414436 A1 | 7/1994 |
| WO | WO0218369 A2 | 3/2002 |
| WO | WO0218369 A3 | 3/2002 |
| WO | WO03006490 A1 | 1/2003 |
| WO | WO03062264 A2 | 7/2003 |
| WO | WO03062264 A3 | 7/2003 |
| WO | WO03062265 A2 | 7/2003 |
| WO | WO03062265 A3 | 7/2003 |
| WO | WO2005051410 A1 | 6/2005 |
| WO | WO2005107745 A1 | 11/2005 |
| WO | WO2005123076 A2 | 12/2005 |
| WO | WO2005123076 A3 | 12/2005 |
| WO | WO2008074035 A1 | 6/2008 |

OTHER PUBLICATIONS

Arasappan et al. "Hepatitis C virus NS3-4A serine protease inhibitors: SAR of P'2 moiety with improved potency," Bioorganic & Medicinal Chemistry Letters, 2005, vol. 15, pp. 4180-4184.*
M.E. Bunnage et al., *Asymmetric Synthesis of the Cis- and Trans-Stereoisomers of 4-Aminopyrrolidine-3-carboxylic Acid and 4-Aminotetrahydrofuran-3-carboxylic Acid*, Org. Biomol. Chem. 2:2763-76 (2004).
T. Chou et al., *Quantitative Analysis of Dose-Effect Relationships: The Combined Effects of Multiple Drugs or Enzyme Inhibitors*, Adv. Enz. Regul. 22:27-55 (1984).
B.E. Green et al., *Novel P2β-Amino Amino Acid Containing Inhibitors of HCV Protease*, 31st National Medicinal Chemistry Symposium, Medi#221, Pittsburgh, PA (Jun. 15-19, 2008).
G.T. Wang et al., *Design, Synthesis, and Structural Analysis of Influenza Neuraminidase Inhibitors Containing Pyrrolidine Cores*, J. Med. Chem. 44:1192-1201 (2001).

* cited by examiner

*Primary Examiner* — Shengjun Wang
(74) *Attorney, Agent, or Firm* — Bradley E. Davis

(57) ABSTRACT

This invention relates to: (a) compounds of formula I and salts thereof that, inter alia, are useful as hepatitis C virus (HCV) inhibitors; (b) intermediates useful for the preparation of such compounds and salts; (c) pharmaceutical compositions comprising such compounds and salts; and (d) methods of use of such compounds, salts, and compositions.

14 Claims, No Drawings

HCV PROTEASE INHIBITORS AND USES THEREOF

CROSS-REFERENCE TO RELATED PATENT APPLICATIONS

This patent application is a continuation of International Patent Application No. PCT/US2007/088936 (filed Dec. 27, 2007), which, in turn, claims priority to U.S. Provisional Patent Application No. 60/877,254 (filed Dec. 27, 2006). The entire text of these patent applications is incorporated by reference into this patent application.

FIELD OF THE INVENTION

This invention is directed to: (a) compounds and salts thereof that, inter alia, are useful as hepatitis C virus (HCV) inhibitors; (b) intermediates useful for the preparation of such compounds and salts; (c) pharmaceutical compositions comprising such compounds and salts; and (d) methods of use of such compounds, salts, and compositions.

BACKGROUND OF THE INVENTION

Hepatitis C is a blood-borne, infectious, viral disease that is caused by a hepatotropic virus called HCV. At least six different HCV genotypes (with several subtypes within each genotype) are known to date. In North America, HCV genotype 1a predominates, followed by HCV genotypes 1b, 2a, 2b, and 3a. In the United States, HCV genotypes 1, 2, and 3 are the most common, with about 80% of the hepatitis C patients having HCV genotype 1. In Europe, HCV genotype 1b is predominant, followed by HCV genotypes 2a, 2b, 2c, and 3a. HCV genotypes 4 and 5 are found almost exclusively in Africa. As discussed below, the patient's HCV genotype is clinically important in determining the patient's potential response to therapy and the required duration of such therapy.

An HCV infection can cause liver inflammation (hepatitis) that is often asymptomatic, but ensuing chronic hepatitis can result in cirrhosis of the liver (fibrotic scarring of the liver), liver cancer, and/or liver failure. The World Health Organization estimates that about 170 million persons worldwide are chronically infected with HCV, and from about three to about four million persons are newly infected globally each year. According to the Centers for Disease Control and Prevention, about four million people in the United States are infected with HCV. Co-infection with the human immunodeficiency virus (HIV) is common, and rates of HCV infection among HIV positive populations are higher.

There is a small chance of clearing the virus spontaneously, but the majority of patients with chronic hepatitis C will not clear it without treatment. Indications for treatment typically include proven HCV infection and persistent abnormal liver function tests. There are two treatment regimens that are primarily used to treat hepatitis C: monotherapy (using an interferon agent—either a "conventional" or longer-acting pegylated interferon) and combination therapy (using an interferon agent and ribavirin). Interferon, which is injected into the bloodstream, works by bolstering the immune response to HCV; and ribavirin, which is taken orally, is believed to work by preventing HCV replication. Taken alone, ribavirin does not effectively suppress HCV levels, but an interferon/ribavirin combination is more effective than interferon alone. Typically, hepatitis C is treated with a combination of pegylated interferon alpha and ribavirin for a period of 24 or 48 weeks, depending on the HCV genotype.

The goal of treatment is sustained viral response—meaning that HCV is not measurable in the blood after therapy is completed. Following treatment with a combination of pegylated interferon alpha and ribavirin, sustained cure rates (sustained viral response) of about 75% or better occur in people with HCV genotypes 2 and 3 in 24 weeks of treatment, about 50% in those with HCV genotype 1 with 48 weeks of treatment, and about 65% in those with HCV genotype 4 in 48 weeks of treatment.

Treatment may be physically demanding, particularly for those with prior history of drug or alcohol abuse, because both interferon and ribavirin have numerous side effects. Common interferon-associated side effects include flu-like symptoms, extreme fatigue, nausea, loss of appetite, thyroid problems, high blood sugar, hair loss, and skin reactions at the injection site. Possible serious interferon-associated side effects include psychoses (e.g., suicidal behavior), heart problems (e.g., heart attack, low blood pressure), other internal organ damage, blood problems (e.g., blood counts falling dangerously low), and new or worsening autoimmune disease (e.g., rheumatoid arthritis). Ribavirin-associated side effects include anemia, fatigue, irritability, skin rash, nasal stuffiness, sinusitis, and cough. Ribavirin can also cause birth defects, so pregnancy in female patients and female partners of male patients must be avoided during treatment and for six months afterward.

Some patients do not complete treatment because of the serious side effects discussed above; other patients (non-responders) continue to have measurable HCV levels despite treatment; and yet other patients (relapsers) "clear" the virus during therapy, but the virus returns sometime after completion of the treatment regimen. Thus, there continues to be a need for alternative compounds, compositions, and methods of treatment (used either in combination with or in lieu of an interferon agent and/or ribavirin) to alleviate the symptoms of hepatitis C, thereby providing partial or complete relief. This invention provides compounds (including salts thereof), compositions, and methods of treatment that generally address such a need.

SUMMARY OF THE INVENTION

This invention is directed to compounds that correspond in structure to formula I:

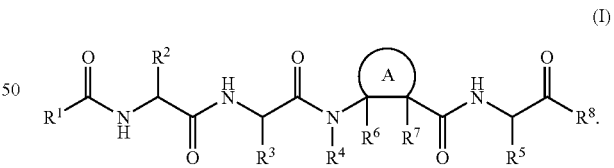

(I)

In formula I:

A is selected from the group consisting of carbocyclyl and heterocyclyl, wherein:
  the carbocyclyl and heterocyclyl optionally are substituted with one or more independently selected $R^A$ substituents;
each $R^A$ is independently selected from the group consisting of alkyl, alkenyl, alkynyl, carbocyclyl, heterocyclyl, alkylcarbonyl, alkenylcarbonyl, alkynylcarbonyl, alkyloxycarbonyl, alkenyloxycarbonyl, alkynyloxycarbonyl, alkyloxy, alkenyloxy, alkynyloxy, carbocyclyloxy, heterocyclyloxy, aminocarbonyl, carbocyclylcarbonyl, heterocyclylcarbonyl, carbocyclyloxycarbonyl, heterocyclyloxycarbonyl, aminoalkylcarbonyl, carbocyclylaminocarbonyl, heterocyclylaminocarbonyl, carbocyclylalkylcarbonyl, heterocyclylalkylcarbonyl, carbocyclylalkyloxycarbonyl, heterocyclylalkyoxycarbonyl, alkylsulfonyl, alkenylsulfonyl, alkynylsulfonyl, carbocyclylsulfonyl, heterocyclylsulfonyl, alkylcarbocyclylsulfonyl, alkenylcarbocyclylsulfonyl, alkynylcarbonylsulfonyl, alkylheterocyclylsulfonyl, alkenylheterocyclylsulfonyl, alkynylheterocyclysulfonyl, amino, alkylamino, carbocyclylamino, heterocyclylamino, alkylcarbocyclylamino, and alkylheterocyclylamino, wherein:

the amino portion of the aminoalkylcarbonyl optionally is substituted with one or two substituents independently selected from the group consisting of alkyloxycarbonyl, carbocyclylalkyloxycarbonyl, and heterocyclylalkyloxycarbonyl;

$R^1$ is selected from the group consisting of optionally substituted carbocyclyl and optionally substituted heterocyclyl;

$R^2$ is selected from the group consisting of optionally substituted carbocyclyl and optionally substituted heterocyclyl;

$R^3$ is selected from the group consisting of hydrogen, alkyl, alkenyl, alkynyl, carbocyclylalkyl, carbocyclylalkenyl, carbocyclylalkynyl, heterocyclylalkyl, heterocyclylalkenyl, heterocyclylalkynyl, aminocarbonylalkyl, aminocarbonylalkenyl, aminocarbonylalkynyl, carbocyclyl, and heterocyclyl;

$R^4$ is selected from the group consisting hydrogen, alkyl, alkenyl, and alkynyl;

$R^5$ is selected from the group consisting of hydrogen, alkyl, alkenyl, alkynyl, carbocyclylalkyl, carbocyclylalkenyl, carbocyclylalkynyl, heterocyclylalkyl, heterocyclylalkenyl, heterocyclylalkynyl, aminocarbonylalkyl, aminocarbonylalkenyl, aminocarbonylalkynyl, carbocyclyl, and heterocyclyl;

$R^6$ is selected from the group consisting of hydrogen, alkyl, alkenyl, alkynyl, alkylcarbonyl, alkenylcarbonyl, alkynylcarbonyl, carbocyclyl, heterocyclyl, amino, carbocyclylalkyl, and heterocyclylalkyl;

$R^7$ is selected from the group consisting of hydrogen, alkyl, alkenyl, alkynyl, alkylcarbonyl, alkenylcarbonyl, alkynylcarbonyl, carbocyclyl, heterocyclyl, amino, carbocyclylalkyl, and heterocyclylalkyl;

$R^8$ is aminocarbonyl optionally is substituted with one or two substituents independently selected from the group consisting of $R^B$ and $R^C$;

each $R^B$ is independently selected from the group consisting of aminocarbonylalkyl, alkyloxy, alkenyloxy, alkynyloxy, carbocyclyloxy, heterocyclyloxy, alkylcarbonyl, alkenylcarbonyl, alkynylcarbonyl, carbocyclyl, and heterocyclyl, wherein:

the amino portion of the aminocarbonylalkyl optionally is substituted with one or two substituents independently selected from the group consisting of alkyl, alkenyl, and alkynyl, wherein:

the alkyl, alkenyl, and alkynyl optionally are substituted one or more substituents independently selected from the group consisting of hydroxy, alkyloxy, carbocycyloxy, heterocyclyloxy, carbocyclyl, heterocyclyl, and aminocarbonyl, wherein:

the carbocyclyl and heterocyclyl optionally are substituted with one or more substituents independently selected from the group consisting of halo, alkyl, alkenyl, alkenyl, alkynyl, hydroxy, alkyloxy, alkenyloxy, and alkynyloxy, and the aminocarbonyl optionally is substituted with one or two independently selected alkyl; and each $R^C$ is independently selected from the group consisting of alkyl, alkenyl, and alkynyl.

This invention is also directed to the salts (including pharmaceutically acceptable salts) of the compounds of the invention.

This invention is also directed to pharmaceutical compositions that comprise one or more compounds and/or salts of the invention, and, optionally, one or more additional therapeutic agents.

This invention is also directed to methods of use of the compounds, salts, and/or compositions of the invention to, for example, treat hepatitis C in a mammal in need of such treatment.

This invention is also directed to a use of one or more compounds and/or salts of the invention to prepare a medicament. This medicament optionally can comprise one or more additional therapeutic agents. In some embodiments, the medicament is useful for treating hepatitis C in a mammal in need of such treatment.

Further benefits of Applicants' invention will be apparent to one skilled in the art from reading this patent application.

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

A. Definitions

The term "alkyl" (alone or in combination with another term(s)) means a straight-or branched-chain saturated hydrocarbyl substituent typically containing from 1 to about 20 carbon atoms, more typically from 1 to about 8 carbon atoms, and even more typically from 1 to about 6 carbon atoms. Examples of such substituents include methyl, ethyl, n-propyl, isopropyl, n-butyl, isobutyl, sec-butyl, tert-butyl, pentyl, iso-amyl, and hexyl. As in this definition, throughout this detailed description Applicants have provided illustrative examples. The provision of such illustrative examples should not be interpreted as if the provided illustrative examples are the only options available to one skilled in the art.

The term "alkenyl" (alone or in combination with another term(s)) means a straight- or branched-chain hydrocarbyl substituent containing one or more double bonds and typically from 2 to about 20 carbon atoms, more typically from about 2 to about 8 carbon atoms, and even more typically from about 2 to about 6 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl.

The term "alkynyl" (alone or in combination with another term(s)) means a straight- or branched-chain hydrocarbyl substituent containing one or more triple bonds and typically from 2 to about 20 carbon atoms, more typically from about 2 to about 8 carbon atoms, and even more typically from about 2 to about 6 carbon atoms. Examples of such substituents include ethynyl, 2-propynyl, 3-propynyl, 2-butynyl, and 3-butynyl.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 7 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 7 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl" (alone or in combination with another term(s)) means an aromatic carbocyclyl containing from 6 to 14 carbon ring atoms. Examples of aryls include phenyl, naphthalenyl, and indenyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

A substituent is "substitutable" if it comprises at least one carbon or nitrogen atom that is bonded to one or more hydrogen atoms. Thus, for example, hydrogen, halogen, and cyano do not fall within this definition. In addition, a sulfur atom in a heterocyclyl containing such atom is substitutable with one or two oxo substituents.

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxy" (alone or in combination with another term(s)) means an ether substituent, and may be depicted as —O—.

The term "alkyloxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused ring heterocyclyls containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

If substituents are described as being "independently selected" from a group, each substituent is selected independent of the other. Each substituent therefore may be identical to or different from the other substituent(s).

When words are used to describe a substituent, the rightmost-described component of the substituent is the component that has the free valence.

When a chemical formula is used to describe a substituent, the dash on the left side of the formula indicates the portion of the substituent that has the free valence.

When a chemical formula is used to describe a linking element between two other elements of a depicted chemical structure, the leftmost dash of the substituent indicates the portion of the substituent that is bound to the left element in the depicted structure. The rightmost dash, on the other hand, indicates the portion of the substituent that is bound to the right element in the depicted structure. To illustrate, if the depicted chemical structure is X-L-Y and L is described as —C(O)—N(H)—, then the chemical would be X—C(O)—N(H)—Y.

With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below.

B. Compounds

This invention is directed, in part, to compounds that correspond in structure to formula 1:

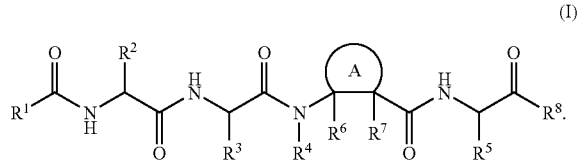

(I)

In the compounds of formula I:

A is selected from the group consisting of carbocyclyl and heterocyclyl, wherein:
the carbocyclyl and heterocyclyl optionally are substituted with one or more independently selected $R^A$ substituents;
each $R^A$ is independently selected from the group consisting of alkyl, alkenyl, alkynyl, carbocyclyl, heterocyclyl, alkylcarbonyl, alkenylcarbonyl, alkynylcarbonyl, alkyloxycarbonyl, alkenyloxycarbonyl, alkynyloxycarbonyl, alkyloxy, alkenyloxy, alkynyloxy, carbocyclyloxy, heterocyclyloxy, aminocarbonyl, carbocyclylcarbonyl, heterocyclylcarbonyl, carbocyclyloxycarbonyl, heterocyclyloxycarbonyl, aminoalkylcarbonyl, carbocyclylaminocarbonyl, heterocyclylaminocarbonyl, carbocyclylalkylcarbonyl, heterocyclylalkylcarbonyl, carbocyclylalkyloxycarbonyl, heterocyclylalkyoxycarbonyl, alkylsulfonyl, alkenylsulfonyl, alkynylsulfonyl, carbocyclylsulfonyl, heterocyclylsulfonyl, alkylcarbocyclylsulfonyl, alkenylcarbocyclylsulfonyl, alkynylcarbonylsulfonyl, alkylheterocyclylsulfonyl, alkenylheterocyclylsulfonyl, alkynylheterocyclysulfonyl, amino, alkylamino, carbocyclylamino, heterocyclylamino, alkylcarbocyclylamino, and alkylheterocyclylamino, wherein:
the amino portion of the aminoalkylcarbonyl optionally is substituted with one or two substituents independently selected from the group consisting of alkyloxycarbonyl, carbocyclylalkyloxycarbonyl, and heterocyclylalkyloxycarbonyl;

$R^1$ is selected from the group consisting of optionally substituted carbocyclyl and optionally substituted heterocyclyl;
$R^2$ is selected from the group consisting of optionally substituted carbocyclyl and optionally substituted heterocyclyl;
as to $R^3$, $R^4$, and $R^5$:
$R^3$ and $R^5$ are independently selected from the group consisting of hydrogen, alkyl, alkenyl, alkynyl, carbocyclylalkyl, carbocyclylalkenyl, carbocyclyalkynyl, heterocyclylalkyl, heterocyclylalkenyl, heterocyclylalkynyl, aminocarbonylalkyl, aminocarbonylalkenyl, aminocarbonylalkynyl, carbocyclyl, and heterocyclyl, and $R^4$ is selected from the group consisting hydrogen, alkyl, alkenyl, and alkynyl, or
one of $R^3$ and $R^4$, together with $R^5$, forms an optionally substituted heterocyclyl, and the other one of $R^3$ and $R^4$ is as defined above;
$R^6$ is selected from the group consisting of hydrogen, alkyl, alkenyl, alkynyl, alkylcarbonyl, alkenylcarbonyl, alkynylcarbonyl, carbocyclyl, heterocyclyl, amino, carbocyclylalkyl, and heterocyclylalkyl;
$R^7$ is selected from the group consisting of hydrogen, alkyl, alkenyl, alkynyl, alkylcarbonyl, alkenylcarbonyl, alkynylcarbonyl, carbocyclyl, heterocyclyl, amino, carbocyclylalkyl, and heterocyclylalkyl;
$R^8$ is selected from the group consisting of aminocarbonyl, hydroxy, alkoxy, and alkylsulfonylamino, wherein:
the aminocarbonyl optionally is substituted with one or two substituents independently selected from the group consisting of $R^B$ and $R^C$;
each $R^B$ is independently selected from the group consisting of aminocarbonylalkyl, alkyloxy, alkenyloxy, alkynyloxy, carbocyclyloxy, heterocyclyloxy, alkylcarbonyl, alkenylcarbonyl, alkynylcarbonyl, carbocyclyl, and heterocyclyl, wherein:
the amino portion of the aminocarbonylalkyl optionally is substituted with one or two substituents independently selected from the group consisting of alkyl, alkenyl, and alkynyl, wherein:
the alkyl, alkenyl, and alkynyl optionally are substituted one or more substituents independently selected from the group consisting of hydroxy, alkyloxy, carbocyclyloxy, heterocyclyloxy, carbocyclyl, heterocyclyl, and aminocarbonyl, wherein:
the carbocyclyl and heterocyclyl optionally are substituted with one or more substituents independently selected from the group consisting of halo, alkyl, alkenyl, alkynyl, hydroxy, alkoxy, alkenyloxy, and alkynyloxy, and
the aminocarbonyl optionally is substituted with one or two independently selected alkyl; and
each $R^C$ is independently selected from the group consisting of alkyl, alkenyl, and alkynyl.

The compounds of formula I are peptidomimetic ketoamide compounds that differ from peptidomimetic ketoamide compounds known to Applicants (e.g., US 2005/0249702 A1, U.S. Pat. No. 6,534,523) by having a beta-amino acid residue rather than an alpha-amino acid residue as the P2 residue. Applicants have discovered that such compounds (and their salts) tend to inhibit HCV NS3 protease.

In some embodiments of the compounds of formula I:
$R^3$ is selected from the group consisting of hydrogen, alkyl, alkenyl, alkynyl, carbocyclylalkyl, carbocyclylalkenyl, carbocyclyalkynyl, heterocyclylalkyl, heterocyclylalkenyl, heterocyclylalkynyl, aminocarbonylalkyl, aminocarbonylalkenyl, aminocarbonylalkynyl, carbocyclyl, and heterocyclyl;
$R^4$ is selected from the group consisting hydrogen, alkyl, alkenyl, and alkynyl;

R[5] is selected from the group consisting of hydrogen, alkyl, alkenyl, alkynyl, carbocyclylalkyl, carbocyclylalkenyl, carbocyclyalkynyl, heterocyclylalkyl, heterocyclylalkenyl, heterocyclylalkynyl, aminocarbonylalkyl, aminocarbonylalkenyl, aminocarbonylalkynyl, carbocyclyl, and heterocyclyl;

R[8] is aminocarbonyl optionally is substituted with one or two substituents independently selected from the group consisting of R[B] and R[C];

each R[B] is independently selected from the group consisting of aminocarbonylalkyl, alkyloxy, alkenyloxy, alkynyloxy, carbocyclyloxy, heterocyclyloxy, alkylcarbonyl, alkenylcarbonyl, alkynylcarbonyl, carbocyclyl, and heterocyclyl, wherein:

the amino portion of the aminocarbonylalkyl optionally is substituted with one or two substituents independently selected from the group consisting of alkyl, alkenyl, and alkynyl, wherein:

the alkyl, alkenyl, and alkynyl optionally are substituted one or more substituents independently selected from the group consisting of hydroxy, alkyloxy, carbocyclyloxy, heterocyclyloxy, carbocyclyl, heterocyclyl, and aminocarbonyl, wherein:

the carbocyclyl and heterocyclyl optionally are substituted with one or more substituents independently selected from the group consisting of halo, alkyl, alkenyl, alkenyl, alkynyl, hydroxy, alkyloxy, alkenyloxy, and alkynyloxy, and the aminocarbonyl optionally is substituted with one or two independently selected alkyl; and each R[C] is independently selected from the group consisting of alkyl, alkenyl, and alkynyl.

The compounds of formula I are discussed in more detail below.

B1. Ring/Ring Structure A

As discussed above, A is selected from the group consisting of carbocyclyl and heterocyclyl, wherein the carbocyclyl and heterocyclyl optionally are substituted with one or more independently selected R[A] substituents. In some embodiments, the carbocyclyl and heterocyclyl are substituted with one, two, or three independently selected R[A] substituents. In some such embodiments, the carbocyclyl and heterocyclyl are substituted with three independently selected R[A] substituents. In other such embodiments, the carbocyclyl and heterocyclyl are substituted with two independently selected R[A] substituents. In yet other such embodiments, the carbocyclyl and heterocyclyl are substituted with one R[A] substituent. In other embodiments, the carbocyclyl and heterocyclyl are not substituted.

In some embodiments, A is selected from the group consisting of $C_5$-$C_7$-carbocyclyl and 5-6-membered heterocyclyl, wherein the $C_5$-$C_7$-carbocyclyl and 5-6-membered heterocyclyl optionally are substituted with one, two, or three independently selected R[A] substituents. In some such embodiments, the $C_5$-$C_7$-carbocyclyl and 5-6-membered heterocyclyl are substituted with three independently selected R[A] substituents. In other such embodiments, the $C_5$-$C_7$-carbocyclyl and 5-6-membered heterocyclyl are substituted with two independently selected R[A] substituents. In yet other such embodiments, the $C_5$-$C_7$-carbocyclyl and 5-6-membered heterocyclyl are substituted with one R[A] substituent. In further such embodiments, the $C_5$-$C_7$-carbocyclyl and 5-6-membered heterocyclyl are not substituted.

In some embodiments, A is selected from the group consisting of $C_5$-$C_6$-carbocyclyl, $C_7$-bridged carbocyclyl, and 5-membered nitrogen-containing heterocyclyl, wherein each substituent optionally is substituted with one, two, or three independently selected R[A] substituents. In some such embodiments, the $C_5$-$C_6$-carbocyclyl, $C_7$-bridged carbocyclyl, and 5-membered nitrogen-containing heterocyclyl are substituted with three independently selected R[A] substituents. In other such embodiments, the $C_5$-$C_6$-carbocyclyl, $C_7$-bridged carbocyclyl, and 5-membered nitrogen-containing heterocyclyl are substituted with two independently selected R[A] substituents. In yet other such embodiments, the $C_5$-$C_6$-carbocyclyl, $C_7$-bridged carbocyclyl, and 5-membered nitrogen-containing heterocyclyl are substituted with one R[A] substituent. In further such embodiments, the $C_5$-$C_6$-carbocyclyl, $C_7$-bridged carbocyclyl, and 5-membered nitrogen-containing heterocyclyl are not substituted.

In some embodiments, A is carbocyclyl optionally substituted with one or more independently selected R[A] substituents. In some such embodiments, the carbocyclyl is substituted with three independently selected R[A] substituents. In other such embodiments, the carbocyclyl is substituted with two independently selected R[A] substituents. In yet other such embodiments, the carbocyclyl is substituted with one R[A] substituent. In further such embodiments, the carbocyclyl is not substituted.

In some embodiments, A is $C_5$-$C_7$-carbocyclyl optionally substituted with one or more independently selected R[A] substituents. In some such embodiments, the $C_5$-$C_7$-carbocyclyl is substituted with three independently selected R[A] substituents. In other such embodiments, the $C_5$-$C_7$-carbocyclyl is substituted with two independently selected R[A] substituents. In yet other such embodiments, the $C_5$-$C_7$-carbocyclyl is substituted with one R[A] substituent. In further such embodiments, the $C_5$-$C_7$-carbocyclyl is not substituted. In some of latter embodiments, the compounds of formula I are selected from the group consisting of:

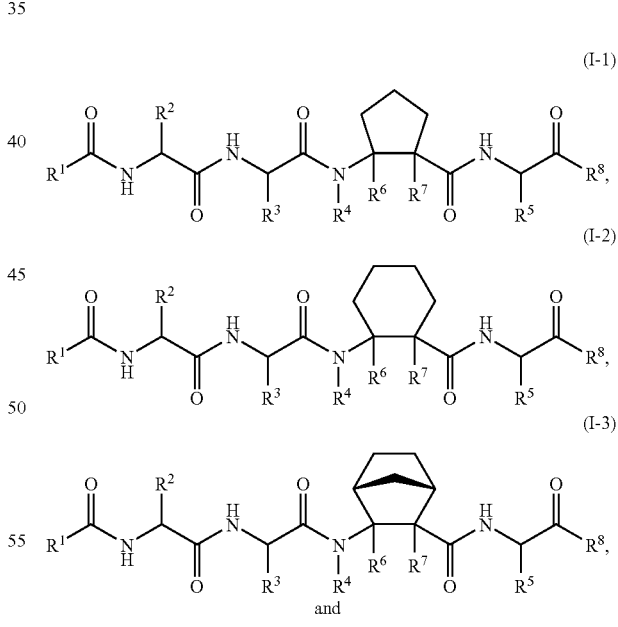

In some embodiments, A is single-ring carbocyclyl optionally substituted with one or more independently selected $R^A$ substituents. In some such embodiments, the single-ring carbocyclyl is substituted with three independently selected $R^A$ substituents. In other such embodiments, the single-ring carbocyclyl is substituted with two independently selected $R^A$ substituents. In yet other such embodiments, the single-ring carbocyclyl is substituted with one $R^A$ substituent. In further such embodiments, the single-ring carbocyclyl is not substituted.

In some embodiments, A is $C_5$-$C_6$-cycloalkyl optionally substituted with one or more independently selected $R^A$ substituents. In some such embodiments, the $C_5$-$C_6$-cycloalkyl is substituted with three independently selected $R^A$ substituents. In other such embodiments, the $C_5$-$C_6$-cycloalkyl is substituted with two independently selected $R^A$ substituents. In yet other such embodiments, the $C_5$-$C_6$-cycloalkyl is substituted with one $R^A$ substituent. In further such embodiments, the $C_5$-$C_6$-cycloalkyl is not substituted.

In some embodiments, A is single-ring $C_5$-$C_6$-carbocyclyl optionally substituted with one or more $R^A$ substituents. In some such embodiments, the single-ring $C_5$-$C_6$-carbocyclyl is substituted with three independently selected $R^A$ substituents. In other such embodiments, the single-ring $C_5$-$C_6$-carbocyclyl is substituted with two independently selected $R^A$ substituents. In yet other such embodiments, the single-ring $C_5$-$C_6$-carbocyclyl is substituted with one $R^A$ substituent. In further such embodiments, the single-ring $C_5$-$C_6$-carbocyclyl is not substituted.

In some embodiments, A is $C_5$-carbocyclyl optionally substituted with one or more $R^A$ substituents. In some such embodiments, the $C_5$-carbocyclyl is substituted with three independently selected $R^A$ substituents. In other such embodiments, the $C_5$-carbocyclyl is substituted with two independently selected $R^A$ substituents. In yet other such embodiments, the $C_5$-carbocyclyl is substituted with one $R^A$ substituent. In further such embodiments, the $C_5$-carbocyclyl is not substituted.

In some embodiments, A is cyclopentyl optionally substituted with one or more independently selected $R^A$ substituents. In some such embodiments, the cyclopentyl is substituted with three independently selected $R^A$ substituents. In other such embodiments, the cyclopentyl is substituted with two independently selected $R^A$ substituents. In yet other such embodiments, the cyclopentyl is substituted with one $R^A$ substituent. In further such embodiments, the cyclopentyl is not substituted. In these embodiments, the compounds of formula I correspond in structure to formula I-1:

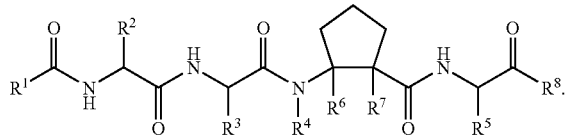

(I-1)

In some embodiments, A is $C_6$-carbocyclyl optionally substituted with one or more independently selected $R^A$ substituents. In some such embodiments, the $C_6$-carbocyclyl is substituted with three independently selected $R^A$ substituents. In other such embodiments, the $C_6$-carbocyclyl is substituted with two independently selected $R^A$ substituents. In yet other such embodiments, the $C_6$-carbocyclyl is substituted with one $R^A$ substituent. In further such embodiments, the $C_6$-carbocyclyl is not substituted.

In some embodiments, A is cyclohexyl optionally substituted with one or more independently selected $R^A$ substituents. In some such embodiments, the cyclohexyl is substituted with three independently selected $R^A$ substituents. In other such embodiments, the cyclohexyl is substituted with two independently selected $R^A$ substituents. In yet other such embodiments, the cyclohexyl is substituted with one $R^A$ substituent. In further such embodiments, the cyclohexyl is not substituted. In these embodiments, the compounds of formula I correspond in structure to formula I-2:

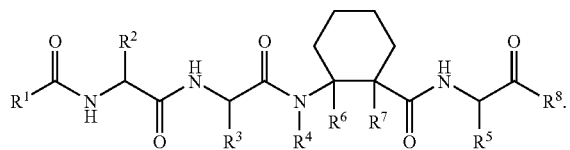

(I-2)

In some embodiments, A is polycyclic carbocyclyl optionally substituted with one or more independently selected $R^A$ substituents. In some such embodiments, the polycyclic carbocyclyl is substituted with three independently selected $R^A$ substituents. In other such embodiments, the polycyclic carbocyclyl is substituted with two independently selected $R^A$ substituents. In yet other such embodiments, the polycyclic carbocyclyl is substituted with one $R^A$ substituent. In further such embodiments, the polycyclic carbocyclyl is not substituted.

In some embodiments, A is bridged carbocyclyl optionally substituted with one or more independently selected $R^A$ substituents. In some such embodiments, the bridged carbocyclyl is substituted with three independently selected $R^A$ substituents. In other such embodiments, the bridged carbocyclyl is substituted with two independently selected $R^A$ substituents. In yet other such embodiments, the bridged carbocyclyl is substituted with one $R^A$ substituent. In further such embodiments, the bridged carbocyclyl is not substituted.

In some embodiments, A is bicyclo[2.2.1]heptanyl optionally substituted with one or more independently selected $R^A$ substituents. In some such embodiments, the bicyclo[2.2.1]heptanyl is substituted with three independently selected $R^A$ substituents. In other such embodiments, the bicyclo[2.2.1]heptanyl is substituted with two independently selected $R^A$ substituents. In yet other such embodiments, the bicyclo[2.2.1]heptanyl is substituted with one $R^A$ substituent. In further such embodiments, the bicyclo[2.2.1]heptanyl in not substituted. In the latter embodiments, the compounds of formula I correspond in structure to formula I-3.

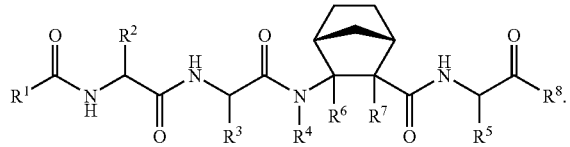

(I-3)

In some embodiments, A is bicyclo[2.2.1]hept-2-enyl optionally substituted with one or more independently selected $R^A$ substituents. In some such embodiments, the bicyclo[2.2.1]hept-2-enyl is substituted with three independently selected $R^A$ substituents. In other such embodiments, the bicyclo[2.2.1]hept-2-enyl is substituted with two independently selected $R^4$ substituents. In yet other such embodiments, the bicyclo[2.2.1]hept-2-enyl is substituted with one $R^4$ substituent. In some such embodiments, the bicyclo[2.2.1]hept-2-enyl in not substituted. In the latter embodiments, the compounds of formula I correspond in structure to formula I-4:

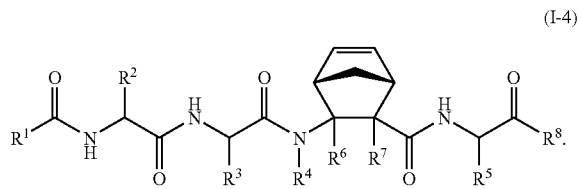

(I-4)

In some embodiments, A is heterocyclyl optionally substituted with one or more independently selected $R^4$ substituents. In some such embodiments, the heterocyclyl is substituted with three independently selected $R^4$ substituents. In other such embodiments, the heterocyclyl is substituted with two independently selected $R^4$ substituents. In yet other such embodiments, the heterocyclyl is substituted with one $R^4$ substituent. In further embodiments, the heterocyclyl is not substituted.

In some embodiments, A is single-ring heterocyclyl optionally substituted with one or more independently selected $R^4$ substituents. In some such embodiments, the single-ring heterocyclyl is substituted with three independently selected $R^4$ substituents. In other such embodiments, the single-ring heterocyclyl is substituted with two independently selected $R^4$ substituents. In yet other such embodiments, the single-ring heterocyclyl is substituted with one $R^4$ substituent. In further such embodiments, the single-ring heterocyclyl is not substituted.

In some embodiments, A is 5-6-membered heterocyclyl optionally substituted with one or more independently selected $R^4$ substituents. In some such embodiments, the 5-6-membered heterocyclyl is substituted with three independently selected $R^4$ substituents. In other such embodiments, the 5-6-membered heterocyclyl is substituted with two independently selected $R^4$ substituents. In yet other such embodiments, the 5-6-membered heterocyclyl is substituted with one $R^4$ substituent. In further such embodiments, the 5-6-membered heterocyclyl is not substituted.

In some embodiments, A is 5-membered heterocyclyl optionally substituted with one or more independently selected $R^4$ substituents. In some such embodiments, the 5-membered heterocyclyl is substituted with three independently selected $R^4$ substituents. In other such embodiments, the 5-membered heterocyclyl is substituted with two independently selected $R^4$ substituents. In yet other such embodiments, the 5-membered heterocyclyl is substituted with an $R^4$ substituent. In further such embodiments, the 5-membered heterocyclyl is not substituted.

In some embodiments, A is 5-membered nitrogen-containing heterocyclyl optionally substituted with one or more independently selected $R^4$ substituents. In some such embodiments, the 5-membered nitrogen-containing heterocyclyl is substituted with three independently selected $R^4$ substituents. In other such embodiments, the 5-membered nitrogen-containing heterocyclyl is substituted with two independently selected $R^4$ substituents. In yet other such embodiments, the 5-membered nitrogen-containing heterocyclyl is substituted with one $R^4$ substituent. In further such embodiments, the 5-membered nitrogen-containing heterocyclyl is not substituted.

In some embodiments, A is pyrrolidinyl optionally substituted with one or more independently selected $R^4$ substituents. In some such embodiments, A is pyrrolidinyl optionally substituted with three independently selected $R^4$ substituents. In other such embodiments, A is pyrrolidinyl optionally substituted with two independently selected $R^4$ substituents. In yet other such embodiments, A is pyrrolidinyl optionally substituted with one $R^4$ substituent. In these embodiments, the compounds of formula I correspond in structure to formula I-5:

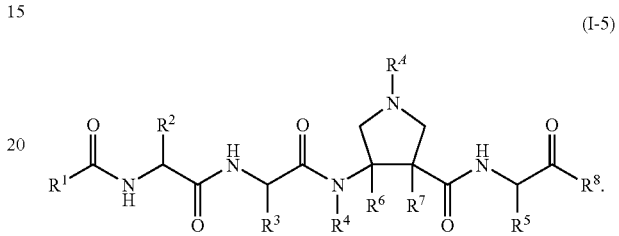

(I-5)

In further such embodiments, A is pyrrolidinyl, wherein the pyrrolidinyl is not substituted. In these embodiments, the compounds of formula I correspond in structure to formula I-6:

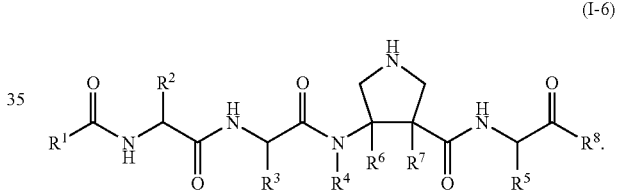

(I-6)

In some embodiments, A is 6-membered heterocyclyl optionally substituted with one or more independently selected $R^4$ substituents. In some such embodiments, the 6-membered heterocyclyl is substituted with three independently selected $R^4$ substituents. In other such embodiments, the 6-membered heterocyclyl is substituted with two independently selected $R^4$ substituents. In yet other such embodiments, the 6-membered heterocyclyl is substituted with an $R^4$ substituent. In further such embodiments, the 6-membered heterocyclyl is not substituted.

Suitable $C_5$-$C_7$-carbocyclyls for the embodiments discussed above include cyclopentyl, cyclopentenyl, cyclopentadienyl, cyclohexyl, cyclohexenyl, cyclohexadienyl, phenyl, cycloheptyl, cycloheptenyl, cyclcoheptadienyl, bicyclo[2.2.1]hept-2-eny, and bicyclo[2.2.1]heptanyl.

Suitable single-ring carbocyclyls for the embodiments discussed above include cyclopropyl, cyclobutyl, cyclopentyl, cyclopentenyl, cyclohexyl, cyclohexenyl, cyclohexadienyl, and phenyl.

Suitable $C_5$-$C_6$-carbocyclyls for the embodiments discussed above include cyclopentyl, cyclopentenyl, cyclopentadienyl, cyclohexyl, cyclohexenyl, cyclohexadienyl, and phenyl.

Suitable $C_5$-carbocyclyls for the embodiments discussed above include cyclopentyl, cyclopentenyl, and cyclopentadienyl.

Suitable $C_6$-carbocyclyls for the embodiments discussed above include cyclohexyl, cyclohexenyl, cyclohexadienyl, and phenyl.

Suitable polycyclic carbocyclyls for the embodiments discussed above include spiropentanyl, bicyclo[2.2.1]heptanyl, bicycle[2.2.1]hept-2-enyl, adamantanyl, naphthalenyl, tetrahydronaphthalenyl, indenyl, indanyl, anthracenyl, phenanthrenyl, and decalinyl.

Suitable bridged carbocyclyls for the embodiments discussed above include bicyclo[2.2.1]heptanyl and bicyclo[2.2.1]hept-2-enyl.

Suitable 5-6-membered heterocyclyls for the embodiments discussed above furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, oxazolyl, dihydrooxazolyl, isoxazolyl, dihydroisoxazolyl, oxazolidinyl, isoxazolidinyl, thiazolyl, isothiazolyl, thiazolinyl, isothiazolinyl, thiazolidinyl, isothiazolidinyl, imidazolyl, imidazolidinyl, pyrazolyl, pyrazolinyl, pyrazolidinyl, oxathiolyl, oxathiolanyl, triazolyl, oxadiazolyl, furazanyl, tetrazolyl, oxatriazolyl, dioxazolyl, oxathiazolyl, oxathiazolidinyl, dihydrooxadiazolyl, dioxazolidinyl, pyranyl, dihydropyranyl, tetrahydropyranyl, pyridinyl, dihydropyridinyl, tetrahydropyridinyl, piperidinyl, diazinyl, pyrazinyl, pyridazinyl, pyrimidinyl, dihydropyrazinyl, tetrahydropyrazinyl, piperazinyl, triazinyl, dihydrotriazinyl, tetrahydrotriazinyl, triazinanyl, oxazinyl, dihydrooxazinyl, morpholinyl, oxathiazinyl, dihydrooxathiazinyl, oxathiazinanyl, oxadiazinyl, dihydrooxadiazinyl, oxadiazinanyl, thiopyranyl, dihydrothiopyranyl, and tetrahydrothiopyranyl.

Suitable 6-membered heterocyclyls for the embodiments discussed above include pyranyl, dihydropyranyl, tetrahydropyranyl, pyridinyl, dihydropyridinyl, tetrahydropyridinyl, piperidinyl, diazinyl, pyrazinyl, pyridazinyl, pyrimidinyl, dihydropyrazinyl, tetrahydropyrazinyl, piperazinyl, triazinyl, dihydrotriazinyl, tetrahydrotriazinyl, triazinanyl, oxazinyl, dihydrooxazinyl, morpholinyl, oxathiazinyl, dihydrooxathiazinyl, oxathiazinanyl, oxadiazinyl, dihydrooxadiazinyl, oxadiazinanyl, thiopyranyl, dihydrothiopyranyl, and tetrahydrothiopyranyl.

Suitable 5-membered heterocyclyls for the embodiments discussed above include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, oxazolyl, dihydrooxazolyl, isoxazolyl, dihydroisoxazolyl, oxazolidinyl, isoxazolidinyl, thiazolyl, isothiazolyl, thiazolinyl, isothiazolinyl, thiazolidinyl, isothiazolidinyl, imidazolyl, imidazolidinyl, pyrazolyl, pyrazolinyl, pyrazolidinyl, oxathiolyl, oxathiolanyl, triazolyl, oxadiazolyl, furazanyl, tetrazolyl, oxatriazolyl, dioxazolyl, oxathiazolyl, oxathiazolidinyl, dihydrooxadiazolyl, and dioxazolidinyl.

Suitable 5-membered nitrogen-containing heterocyclyls for the embodiments discussed above include pyrrolyl, pyrrolinyl, pyrrolidinyl, oxazolyl, dihydrooxazolyl, isoxazolyl, dihydroisoxazolyl, oxazolidinyl, isoxazolidinyl, thiazolyl, isothiazolyl, thiazolinyl, isothiazolinyl, thiazolidinyl, isothiazolidinyl, imidazolyl, imidazolidinyl, pyrazolyl, pyrazolinyl, pyrazolidinyl, triazolyl, oxadiazolyl, furazanyl, tetrazolyl, oxatriazolyl, dioxazolyl, oxathiazolyl, oxathiazolidinyl, dihydrooxadiazolyl, and dioxazolidinyl.

B2. Substituent $R^A$

As discussed above, A is selected from the group consisting of carbocyclyl and heterocyclyl, wherein the carbocyclyl and heterocyclyl optionally are substituted with one or more independently selected $R^A$ substituents. Each of these $R^A$ substituents is independently selected as discussed below.

As discussed above, $R^A$ is selected from the group consisting of alkyl, alkenyl, alkynyl, carbocyclyl, heterocyclyl, alkylcarbonyl, alkenylcarbonyl, alkynylcarbonyl, alkyloxycarbonyl, alkenyloxycarbonyl, alkynyloxycarbonyl, alkyloxy, alkenyloxy, alkynyloxy, carbocyclyloxy, heterocyclyloxy, aminocarbonyl, carbocyclylcarbonyl, heterocyclylcarbonyl, carbocyclyloxycarbonyl, heterocyclyloxycarbonyl, aminoalkylcarbonyl, carbocyclylaminocarbonyl, heterocyclylaminocarbonyl, carbocyclylalkylcarbonyl, heterocyclylalkylcarbonyl, carbocyclylalkyloxycarbonyl, heterocyclylalkyoxycarbonyl, alkylsulfonyl, alkenylsulfonyl, alkynylsulfonyl, carbocyclylsulfonyl, heterocyclylsulfonyl, alkylcarbocyclylsulfonyl, alkenylcarbocyclylsulfonyl, alkynylcarbonylsulfonyl, alkylheterocyclylsulfonyl, alkenylheterocyclylsulfonyl, alkynylheterocyclysulfonyl, amino, alkylamino, carbocyclylamino, heterocyclylamino, alkylcarbocyclylamino, and alkylheterocyclylamino, wherein:
  the amino portion of the aminoalkylcarbonyl optionally is substituted with one or two substituents independently selected from the group consisting of alkyloxycarbonyl, carbocyclylalkyloxycarbonyl, and heterocyclylalkyloxycarbonyl.

In some embodiments, $R^A$ is selected from the group consisting of alkyl, alkenyl, alkynyl, carbocyclyl, heterocyclyl, alkylcarbonyl, alkenylcarbonyl, alkynylcarbonyl, alkyloxycarbonyl, alkenyloxycarbonyl, alkynyloxycarbonyl, alkyloxy, alkenyloxy, alkynyloxy, carbocyclyloxy, heterocyclyloxy, aminocarbonyl, carbocyclylcarbonyl, heterocyclylcarbonyl, carbocyclyloxycarbonyl, heterocyclyloxycarbonyl, aminoalkylcarbonyl, carbocyclylaminocarbonyl, heterocyclylaminocarbonyl, carbocyclylalkylcarbonyl, heterocyclylalkylcarbonyl, carbocyclylalkyloxycarbonyl, heterocyclylalkyoxycarbonyl, alkylsulfonyl, alkenylsulfonyl, alkynylsulfonyl, carbocyclylsulfonyl, heterocyclylsulfonyl, alkylcarbocyclylsulfonyl, alkenylcarbocyclylsulfonyl, alkynylcarbonylsulfonyl, alkylheterocyclylsulfonyl, alkenylheterocyclylsulfonyl, alkynylheterocyclysulfonyl, amino, alkylamino, carbocyclylamino, heterocyclylamino, alkylcarbocyclylamino, and alkylheterocyclylamino, wherein:
  the amino portion of the aminoalkylcarbonyl optionally is substituted with a substituent selected from the group consisting of alkyloxycarbonyl, carbocyclylalkyloxycarbonyl, and heterocyclylalkyloxycarbonyl.

In some embodiments, $R^A$ is selected from the group consisting of carbocyclyl, heterocyclyl, alkylcarbonyl, alkenylcarbonyl, alkynylcarbonyl, alkyloxycarbonyl, alkenyloxycarbonyl, alkynyloxycarbonyl, carbocyclylcarbonyl, heterocyclylcarbonyl, carbocyclyloxycarbonyl, heterocyclyloxycarbonyl, aminoalkylcarbonyl, carbocyclylaminocarbonyl, heterocyclylaminocarbonyl, carbocyclylalkyloxycarbonyl, heterocyclylalkyoxycarbonyl, alkylcarbocyclylsulfonyl, and alkylheterocyclylsulfonyl, wherein:
  the amino portion of the aminoalkylcarbonyl optionally is substituted with one or two substituents independently selected from the group consisting of alkyloxycarbonyl, carbocyclylalkyloxycarbonyl, and heterocyclylalkyloxycarbonyl.

In some embodiments, $R^A$ is selected from the group consisting of carbocyclyl, heterocyclyl, alkylcarbonyl, alkyloxycarbonyl, carbocyclylcarbonyl, carbocyclyloxycarbonyl, aminoalkylcarbonyl, heterocyclylaminocarbonyl, carbocyclylalkyloxycarbonyl, and alkylcarbocyclylsulfonyl, wherein:
  the amino portion of the aminoalkylcarbonyl optionally is substituted with one or two independently selected carbocyclylalkyloxycarbonyl.

In some embodiments, each $R^A$ is independently selected from the group consisting of carbocyclyl, heterocyclyl, alkylcarbonyl, alkyloxycarbonyl, carbocyclylcarbonyl, carbocyclyloxycarbonyl, aminoalkylcarbonyl, heterocyclylaminocarbonyl, carbocyclylalkyloxycarbonyl, and alkylcarbocyclylsulfonyl, wherein:

the amino portion of the aminoalkylcarbonyl optionally is substituted with carbocyclylalkyloxycarbonyl.

In some embodiments, $R^A$ is alkylcarbonyl. In some such embodiments, $R^A$ is $C_1$-$C_6$-alkyl-carbonyl. In some such embodiments, $R^A$ is methylcarbonyl.

In some embodiments, $R^A$ is carbocyclylcarbonyl. In some such embodiments, $R^A$ is aryl-carbonyl. In some such embodiments, $R^A$ is phenylcarbonyl.

In some embodiments, $R^A$ is alkyloxycarbonyl. In some such embodiments, $R^A$ is $C_1$-$C_6$-alkyloxycarbonyl.

In some embodiments, $R^A$ is carbocyclylalkyloxycarbonyl. In some such embodiments, $R^A$ is phenylalkyloxycarbonyl. In other such embodiments, $R^A$ is naphthalenylalkyloxycarbonyl. In further such embodiments, $R^A$ is fluorenylalkyloxycarbonyl.

In some embodiments, $R^A$ is carbocycloxycarbonyl. In some such embodiments, $R^A$ is aryloxycarbonyl. In some such embodiments, $R^A$ is phenoxycarbonyl. In other such embodiments, $R^A$ is naphthalenoxycarbonyl.

In some embodiments, $R^A$ is carbocyclylaminocarbonyl. In some such embodiments, $R^A$ is arylaminocarbonyl. In some such embodiments, $R^A$ is phenylaminocarbonyl. In other such embodiments, $R^A$ is naphthalenylaminocarbonyl.

In some embodiments, $R^A$ is aminoalkylcarbonyl, wherein the amino portion of the aminoalkylcarbonyl is substituted with carbocyclylalkyloxycarbonyl. In some such embodiments, $R^A$ is aminoalkylcarbonyl, wherein the amino portion of the aminoalkylcarbonyl is substituted with arylalkyloxycarbonyl. In some such embodiments, $R^A$ is aminoalkylcarbonyl, wherein the amino portion of the aminoalkylcarbonyl is substituted with phenylalkyloxycarbonyl.

In some embodiments, $R^A$ is alkylcarbocyclylsulfonyl. In some such embodiments, $R^A$ is alkylphenylsulfonyl.

B3. Substituent $R^8$

As discussed above, $R^8$ is selected from the group consisting of aminocarbonyl, hydroxy, alkyloxy, and alkylsulfonylamino, wherein the aminocarbonyl optionally is substituted with one or two substituents independently selected from the group consisting of $R^B$ and $R^C$.

In some embodiments, $R^8$ is aminocarbonyl optionally substituted with one or two substituents independently selected from the group consisting of $R^B$ and $R^C$.

In some such embodiments, $R^8$ is aminocarbonyl optionally substituted with one or two independently selected $R^B$ substituents. In some such embodiments, the aminocarbonyl is substituted with two independently selected $R^B$ substituents. In other such embodiments, the aminocarbonyl is substituted with $R^B$. In these embodiments, the compounds of formula I correspond in structure to formula IA:

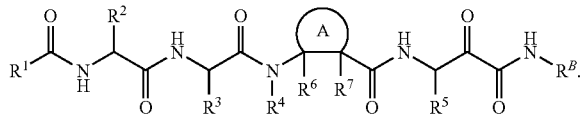

(IA)

In other such embodiments, $R^8$ is aminocarbonyl optionally substituted with one or two independently selected $R^C$ substituents. In some such embodiments, the aminocarbonyl is substituted with two independently selected $R^C$ substituents. In other such embodiments, the aminocarbonyl is substituted with $R^C$. In these embodiments, the compounds of formula I correspond in structure to formula IB:

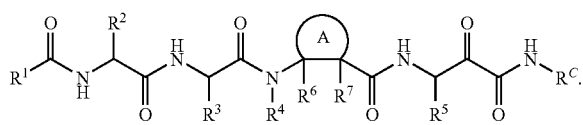

(IB)

In further such embodiments, $R^8$ is aminocarbonyl, wherein the aminocarbonyl is not substituted.

B4. Substituent $R^B$

As discussed above, $R^8$ is selected from the group consisting of aminocarbonyl, hydroxy, alkyloxy, and alkylsulfonylamino, wherein the aminocarbonyl optionally is substituted with one or two substituents independently selected from the group consisting of $R^B$ and $R^C$. Each of these $R^B$ substituents is independently selected as discussed below.

As discussed above, $R^B$ is selected from the group consisting of aminocarbonylalkyl, alkyloxy, alkenyloxy, alkynyloxy, carbocyclyloxy, heterocyclyloxy, alkylcarbonyl, alkenylcarbonyl, alkynylcarbonyl, carbocyclyl, and heterocyclyl, wherein:

the amino portion of the aminocarbonylalkyl optionally is substituted with one or two substituents independently selected from the group consisting of alkyl, alkenyl, and alkynyl, wherein:

the alkyl, alkenyl, and alkynyl optionally are substituted one or more substituents independently selected from the group consisting of hydroxy, alkyloxy, carbocyclyloxy, heterocyclyloxy, carbocyclyl, heterocyclyl, and aminocarbonyl, wherein:

the carbocyclyl and heterocyclyl optionally are substituted with one or more substituents independently selected from the group consisting of halo, alkyl, alkenyl, alkenyl, alkynyl, hydroxy, alkyloxy, alkenyloxy, and alkynyloxy, and the aminocarbonyl optionally is substituted with one or two independently selected alkyl.

In some embodiments, $R^B$ is selected from the group consisting of aminocarbonylalkyl, carbocyclyl, and heterocyclyl, wherein:

the amino portion of the aminocarbonylalkyl optionally is substituted with a substituent selected from the group consisting of alkyl, alkenyl, and alkynyl, wherein:

the alkyl, alkenyl, and alkynyl optionally are substituted one or two substituents independently selected from the group consisting of hydroxy, alkyloxy, carbocyclyl, heterocyclyl, and aminocarbonyl, wherein:

the carbocyclyl and heterocyclyl optionally are substituted with one or more substituents independently selected from the group consisting of halo, hydroxy, and alkyloxy, and the aminocarbonyl optionally is substituted with one or two independently selected alkyl.

In some embodiments, $R^B$ is selected from the group consisting of aminocarbonylalkyl, carbocyclyl, and heterocyclyl, wherein:
the amino portion of the aminocarbonylalkyl optionally is substituted with alkyl, wherein:
the alkyl optionally is substituted two substituents independently selected from the group consisting of alkyloxy, carbocyclyl, heterocyclyl, and aminocarbonyl, wherein:
the carbocyclyl and heterocyclyl optionally are substituted with one or more substituents independently selected from the group consisting of halo, hydroxy, and alkyloxy, and
the aminocarbonyl optionally is substituted with two independently selected alkyl.

In some embodiments, $R^B$ is selected from the group consisting of aminocarbonylalkyl and carbocyclyl, wherein:
the amino portion of the aminocarbonylalkyl is substituted with alkyl, wherein:
the alkyl optionally is substituted with one or more substituents independently selected from the group consisting of carbocyclyl and aminocarbonyl, wherein:
the carbocyclyl optionally is substituted with one or more substituents independently selected from the group consisting of halo and alkyloxy, and
the aminocarbonyl optionally is substituted with one or two independently selected alkyl.

In some embodiments, $R^B$ is selected from the group consisting of aminocarbonylalkyl and cycloalkyl, wherein:
the amino portion of the aminocarbonylalkyl optionally is substituted with alkyl, wherein:
the alkyl optionally is substituted with aminocarbonyl, wherein:
the aminocarbonyl optionally is substituted with one or two independently selected alkyl.

In some embodiments, $R^B$ is carbocyclyl. In some such embodiments, $R^B$ is $C_3$-$C_6$-carbocyclyl.

In some embodiments, $R^B$ is cycloalkyl. In some such embodiments, $R^B$ is $C_3$-$C_6$-cycloalkyl. In some such embodiments, $R^B$ is cyclopropyl.

In some embodiments, $R^B$ is aminocarbonylalkyl, wherein the amino portion of the aminocarbonylalkyl is substituted with alkyl, alkenyl, and alkynyl, wherein:
the alkyl, alkenyl, and alkynyl optionally are substituted one or two substituents independently selected from the group consisting of hydroxy, alkyloxy, carbocyclyl, heterocyclyl, and aminocarbonyl, wherein:
the carbocyclyl and heterocyclyl optionally are substituted with one or more substituents independently selected from the group consisting of halo, hydroxy, and alkyloxy, and
the aminocarbonyl optionally is substituted with one or two independently selected alkyl.

In some embodiments, $R^B$ is aminocarbonylalkyl, wherein the amino portion of the aminocarbonylalkyl is substituted with alkyl, alkenyl, and alkynyl, wherein:
the alkyl, alkenyl, and alkynyl are substituted with aminocarbonyl, wherein:
the aminocarbonyl optionally is substituted with one or two independently selected alkyl.

In some embodiments, $R^B$ is aminocarbonylalkyl, wherein the amino portion of the aminocarbonylalkyl is substituted with alkyl, alkenyl, and alkynyl, wherein:
the alkyl, alkenyl, and alkynyl are substituted with aminocarbonyl, wherein:
the aminocarbonyl optionally is substituted with two $C_1$-$C_3$-alkyl substituents.

In some embodiments, $R^B$ is aminocarbonylalkyl, wherein the amino portion of the aminocarbonylalkyl is substituted with alkyl, alkenyl, and alkynyl, wherein:
the alkyl, alkenyl, and alkynyl optionally are substituted one or two substituents independently selected from the group consisting of alkyloxy and carbocyclyl, wherein:
the carbocyclyl optionally is substituted with a substituent selected from the group consisting of alkyloxy and halo.

In some embodiments, $R^B$ is aminocarbonylalkyl, wherein the amino portion of the aminocarbonylalkyl is substituted with alkyl, alkenyl, and alkynyl, wherein:
the alkyl, alkenyl, and alkynyl optionally are substituted with alkyloxy.

In some embodiments, $R^B$ is aminocarbonylalkyl, wherein the amino portion of the aminocarbonylalkyl is substituted with alkyl, alkenyl, and alkynyl, wherein:
the alkyl, alkenyl, and alkynyl optionally are substituted with cycloalkyl.

In some embodiments, $R^B$ is aminocarbonylalkyl, wherein the amino portion of the aminocarbonylalkyl is substituted with alkyl, alkenyl, and alkynyl, wherein:
the alkyl, alkenyl, and alkynyl optionally are substituted with phenyl, wherein:
the phenyl optionally is substituted with a substituent selected from the group consisting of alkyloxy and halo.

B5. Substituent $R^C$

As discussed above, $R^8$ is selected from the group consisting of aminocarbonyl, hydroxy, alkyloxy, and alkylsulfonylamino, wherein the aminocarbonyl optionally is substituted with one or two substituents independently selected from the group consisting of $R^B$ and $R^C$. Each of these $R^C$ substituents is independently selected as discussed below.

$R^C$ is selected from the group consisting of alkyl, alkenyl, and alkynyl.

In some embodiments, $R^C$ is alkyl. In some such embodiments, $R^C$ is $C_1$-$C_6$-alkyl.

B6. Substituent $R^1$

As discussed above, $R^1$ is selected from the group consisting of optionally substituted carbocyclyl and optionally substituted heterocyclyl. In some such embodiments, the carbocyclyl and heterocyclyl are not substituted.

In some embodiments, $R^1$ is selected from the group consisting of $C_5$-$C_6$-carbocyclyl and 5-6-membered heterocyclyl.

In some embodiments, $R^1$ is carbocyclyl. In some such embodiments, $R^1$ is $C_5$-$C_6$-carbocyclyl.

In some embodiments, $R^1$ is heterocyclyl. In some such embodiments, $R^1$ is 5-6-membered heterocyclyl.

In some embodiments, $R^1$ is 6-membered heterocyclyl. In some such embodiments, $R^1$ is 6-membered nitrogen-containing heterocyclyl.

In some embodiments, $R^1$ is heteroaryl. In some such embodiments, $R^1$ is 6-membered heteroaryl.

In some embodiments, $R^1$ is 6-membered nitrogen-containing heteroaryl. In some such embodiments, $R^1$ is pyrazinyl.

Suitable $C_5$-$C_6$-carbocyclyls for the embodiments discussed above include cyclopentyl, cyclopentenyl, cyclopentadienyl, cyclohexyl, cyclohexenyl, cyclohexadienyl, and phenyl.

Suitable 5-6-membered-heterocyclyls for the above embodiments include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, oxazolyl, dihydrooxazolyl, isoxazolyl, dihydroisoxazolyl, oxazolidinyl, isoxazolidinyl, thiazolyl, isothiazolyl, thiazolinyl, isothiazolinyl, thiazolidinyl, isothiazolidinyl, imidazolyl, imidazolidinyl, pyrazolyl, pyrazolinyl, pyrazolidinyl, oxathiolyl, oxathiolanyl, triazolyl, oxadiazolyl, furazanyl, tetrazolyl, oxatriazolyl, dioxazolyl, oxathiazolyl, oxathiazolidinyl, dihydrooxadiazolyl, dioxazolidinyl, pyranyl, dihydropyranyl, tetrahydropyranyl, pyridinyl, dihydropyridinyl, tetrahydropyridinyl, piperidinyl, diazinyl, pyrazinyl, pyridazinyl, pyrimidinyl, dihydropyrazinyl, tetrahydropyrazinyl, piperazinyl, triazinyl, dihydrotriazinyl, tetrahydrotriazinyl, triazinanyl, oxazinyl, dihydrooxazinyl, morpholinyl, oxathiazinyl, dihydrooxathiazinyl, oxathiazinanyl, oxadiazinyl, dihydrooxadiazinyl, oxadiazinanyl, thiopyranyl, dihydrothiopyranyl, and tetrahydrothiopyranyl.

Suitable 6-membered heterocyclyls for the embodiments discussed above include pyranyl, dihydropyranyl, tetrahydropyranyl, pyridinyl, dihydropyridinyl, tetrahydropyridinyl, piperidinyl, diazinyl, pyrazinyl, pyridazinyl, pyrimidinyl, dihydropyrazinyl, tetrahydropyrazinyl, piperazinyl, triazinyl, dihydrotriazinyl, tetrahydrotriazinyl, triazinanyl, oxazinyl, dihydrooxazinyl, morpholinyl, oxathiazinyl, dihydrooxathiazinyl, oxathiazinanyl, oxadiazinyl, dihydrooxadiazinyl, oxadiazinanyl, thiopyranyl, dihydrothiopyranyl, and tetrahydrothiopyranyl.

Suitable 6-membered nitrogen-containing heterocyclyls for the embodiments discussed above include pyridinyl, dihydropyridinyl, tetrahydropyridinyl, piperidinyl, diazinyl, pyrazinyl, pyridazinyl, pyrimidinyl, dihydropyrazinyl, tetrahydropyrazinyl, piperazinyl, triazinyl, dihydrotriazinyl, tetrahydrotriazinyl, triazinanyl, oxazinyl, dihydrooxazinyl, morpholinyl, oxathiazinyl, dihydrooxathiazinyl, oxathiazinanyl, oxadiazinyl, dihydrooxadiazinyl, and oxadiazinanyl.

Suitable 6-membered heteroaryls for the embodiments discussed above include pyridyl, pyrazyl, pyrimidinyl, pyridazinyl, and 1,3,5-, 1,2,4- or 1,2,3-triazinyl.

Suitable 6-membered nitrogen-containing heteroaryls for the embodiments discussed above include pyridyl, pyrazyl, pyrimidinyl, pyridazinyl, and 1,3,5-, 1,2,4- or 1,2,3-triazinyl.

B7. Substituent $R^2$

As discussed above, $R^2$ is selected from the group consisting of optionally substituted carbocyclyl and optionally substituted heterocyclyl. In some such embodiments, the carbocyclyl and heterocyclyl are not substituted.

In some embodiments, $R^2$ is selected from the group consisting of $C_5$-$C_6$-carbocyclyl and 5-6-membered heterocyclyl.

In some embodiments, $R^2$ is carbocyclyl. In some such embodiments, $R^2$ is $C_5$-$C_6$-carbocyclyl.

In some embodiments, $R^2$ is cycloalkyl. In some such embodiments, $R^2$ is $C_5$-$C_6$-cycloalkyl.

In some such embodiments, $R^2$ is $C_5$-carbocyclyl. In some such embodiments, $R^2$ is cyclopentyl.

In other such embodiments, $R^2$ is $C_6$-carbocyclyl. In some such embodiments, $R^2$ is cyclohexyl.

In some embodiments, $R^2$ is heterocyclyl. In some such embodiments, $R^2$ is 5-6-membered heterocyclyl.

Suitable $C_5$-$C_6$-carbocyclyls for the embodiments discussed above include cyclopentyl, cyclopentenyl, cyclopentadienyl, cyclohexyl, cyclohexenyl, cyclohexadienyl, and phenyl.

Suitable $C_5$-carbocyclyls for the embodiments discussed above include cyclopentyl, cyclopentenyl, and cyclopentadienyl.

Suitable $C_6$-carbocyclyls for the embodiments discussed above include cyclohexyl, cyclohexenyl, cyclohexadienyl, and phenyl.

Suitable 5-6-membered-heterocyclyls for the embodiments discussed above include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, oxazolyl, dihydrooxazolyl, isoxazolyl, dihydroisoxazolyl, oxazolidinyl, isoxazolidinyl, thiazolyl, isothiazolyl, thiazolinyl, isothiazolinyl, thiazolidinyl, isothiazolidinyl, imidazolyl, imidazolidinyl, pyrazolyl, pyrazolinyl, pyrazolidinyl, oxathiolyl, oxathiolanyl, triazolyl, oxadiazolyl, furazanyl, tetrazolyl, oxatriazolyl, dioxazolyl, oxathiazolyl, oxathiazolidinyl, dihydrooxadiazolyl, dioxazolidinyl, pyranyl, dihydropyranyl, tetrahydropyranyl, pyridinyl, dihydropyridinyl, tetrahydropyridinyl, piperidinyl, diazinyl, pyrazinyl, pyridazinyl, pyrimidinyl, dihydropyrazinyl, tetrahydropyrazinyl, piperazinyl, triazinyl, dihydrotriazinyl, tetrahydrotriazinyl, triazinanyl, oxazinyl, dihydrooxazinyl, morpholinyl, oxathiazinyl, dihydrooxathiazinyl, oxathiazinanyl, oxadiazinyl, dihydrooxadiazinyl, oxadiazinanyl, thiopyranyl, dihydrothiopyranyl, and tetrahydrothiopyranyl.

B8. Substituent $R^3$

As discussed above, in some embodiments, $R^3$ is selected from the group consisting of hydrogen, alkyl, alkenyl, alkynyl, carbocyclylalkyl, carbocyclylalkenyl, carbocyclyalkynyl, heterocyclylalkyl, heterocyclylalkenyl, heterocyclylalkynyl, aminocarbonylalkyl, aminocarbonylalkenyl, aminocarbonylalkynyl, carbocyclyl, and heterocyclyl.

In some embodiments, $R^3$ is selected from the group consisting of hydrogen, alkyl, carbocyclylalkyl, heterocyclylalkyl, aminocarbonylalkyl, aminocarbonylalkenyl, aminocarbonylalkynyl, carbocyclyl, and heterocyclyl.

In some embodiments, $R^3$ is selected from the group consisting of hydrogen, alkyl, carbocyclylalkyl, aminocarbonylalkyl, and carbocyclyl.

In some embodiments, $R^3$ is alkyl. In some such embodiments, $R^3$ is $C_1$-$C_6$-alkyl. In some such embodiments, $R^3$ is selected from the group consisting of ethyl, propyl, isopropyl, isobutyl, and tert-butyl.

In some embodiments, $R^3$ is carbocyclylalkyl. In some such embodiments, $R^3$ is $C_5$-$C_6$-carbocyclylalkyl. In other such embodiments, $R^3$ is carbocyclyl-$C_1$-$C_6$-alkyl. In yet other such embodiments, $R^3$ is $C_5$-$C_6$-carbocyclyl-$C_1$-$C_6$-alkyl.

In some embodiments, $R^3$ is aminocarbonylalkyl. In some such embodiments, $R^3$ is aminocarbonyl-$C_1$-$C_6$-alkyl.

In some embodiments, $R^3$ is carbocyclyl. In some such embodiments, $R^3$ is $C_5$-$C_6$-carbocyclyl.

In some embodiments, $R^3$ is cycloalkyl. In some such embodiments, $R^3$ is $C_5$-$C_6$-cycloalkyl.

B9. Substituent $R^4$

As described above, in some embodiments, $R^4$ is selected from the group consisting hydrogen, alkyl, alkenyl, and alkynyl.

In some embodiments, $R^4$ is selected from the group consisting of hydrogen and alkyl. In some such embodiments, $R^4$ is selected from the group consisting of hydrogen and $C_1$-$C_6$-alkyl. In some such embodiments, $R^4$ is selected from the group consisting of hydrogen and $C_1$-$C_3$-alkyl. In some such embodiments, $R^4$ is selected from the group consisting of hydrogen and methyl.

In some embodiments, $R^4$ is hydrogen.

In some embodiments, $R^4$ is alkyl. In some such embodiments, $R^4$ is $C_1$-$C_6$-alkyl. In some such embodiments, $R^4$ is methyl.

B10. Substituent $R^5$

As described above, in some embodiments, $R^5$ is selected from the group consisting of hydrogen, alkyl, alkenyl, alkynyl, carbocyclylalkyl, carbocyclylalkenyl, carbocyclyalkynyl, heterocyclylalkyl, heterocyclylalkenyl, heterocyclylalkynyl, aminocarbonylalkyl, aminocarbonylalkenyl, aminocarbonylalkynyl, carbocyclyl, and heterocyclyl.

In some embodiments, $R^5$ is selected from the group consisting of hydrogen, alkyl, carbocyclylalkyl, heterocyclylalkyl, aminocarbonylalkyl, aminocarbonylalkenyl, aminocarbonylalkynyl, carbocyclyl, and heterocyclyl.

In some embodiments, $R^5$ is selected from the group consisting of hydrogen, alkyl, and carbocyclylalkyl.

In some embodiments, $R^5$ is selected from the group consisting of alkyl and carbocyclylalkyl.

In some such embodiments, $R^5$ is selected from the group consisting of $C_1$-$C_6$-alkyl and $C_5$-$C_6$-carbocyclylalkyl. In other such embodiments, $R^5$ is selected from the group consisting of $C_1$-$C_6$-alkyl and carbocyclyl-$C_1$-$C_6$-alkyl. In other such embodiments, $R^5$ is selected from the group consisting of $C_1$-$C_6$-alkyl and $C_5$-$C_6$-carbocyclyl-$C_1$-$C_6$-alkyl.

In some embodiments, $R^5$ is alkyl. In some such embodiments, $R^5$ is $C_1$-$C_6$-alkyl.

In some embodiments, $R^5$ is carbocyclylalkyl. In some such embodiments, $R^5$ is $C_5$-$C_6$-carbocyclylalkyl. In other such embodiments, $R^5$ is carbocyclyl-$C_1$-$C_6$-alkyl. In further such embodiments, $R^5$ is $C_5$-$C_6$-carbocyclyl-$C_1$-$C_6$-alkyl.

In some embodiments, $R^5$ is cycloalkylalkyl. In some such embodiments, $R^5$ is $C_3$-$C_6$-cycloalkylalkyl. In some such embodiments, $R^5$ is $C_3$-$C_6$-cycloalkyl-$C_1$-$C_6$—alkyl.

B11. Substituent $R^6$

As discussed above, $R^6$ is selected from the group consisting of hydrogen, alkyl, alkenyl, alkynyl, alkylcarbonyl, alkenylcarbonyl, alkynylcarbonyl, carbocyclyl, heterocyclyl, amino, carbocyclylalkyl, and heterocyclylalkyl.

In some embodiments, $R^6$ is selected from the group consisting of hydrogen, alkyl, alkenyl, and alkynyl.

In some embodiments, $R^6$ is selected from the group consisting of hydrogen and alkyl. In some such embodiments, $R^6$ is selected from the group consisting of hydrogen and $C_1$-$C_6$-alkyl.

In some embodiments, $R^6$ is hydrogen.

In some embodiments, $R^6$ is alkyl. In some such embodiments, $R^6$ is $C_1$-$C_6$-alkyl.

B12. Substituent $R^7$ $R^7$ is selected from the group consisting of hydrogen, alkyl, alkenyl, alkynyl, alkylcarbonyl, alkenylcarbonyl, alkynylcarbonyl, carbocyclyl, heterocyclyl, amino, carbocyclylalkyl, and heterocyclylalkyl.

In some embodiments, $R^7$ is selected from the group consisting of hydrogen, alkyl, alkenyl, and alkynyl.

In some embodiments, $R^7$ is selected from the group consisting of hydrogen and alkyl. In some such embodiments, $R^7$ is selected from the group consisting of hydrogen and $C_1$-$C_6$-alkyl.

In some embodiments, $R^7$ is hydrogen.

In some embodiments, $R^7$ is alkyl. In some such embodiments, $R^7$ is $C_1$-$C_6$-alkyl.

C. Embodiments of Compounds of Formula I

Various embodiments of substituents $R^1$, $R^2$, $R^3$, $R^4$, $R^5$, $R^6$, $R^7$, $R^8$, $R^A$, $R^B$, and $R^C$ have been discussed above. These substituent embodiments can be combined to form various embodiments of compounds of formula I. All embodiments of compounds of formula I formed by combining the substituent embodiments discussed above are within the scope of Applicants' invention. Illustrative examples are provided below.

In some embodiments, A is cyclopentyl, and $R^8$ is aminocarbonyl substituted with $R^B$. In these embodiments, the compounds correspond in structure to the following formula IA-1:

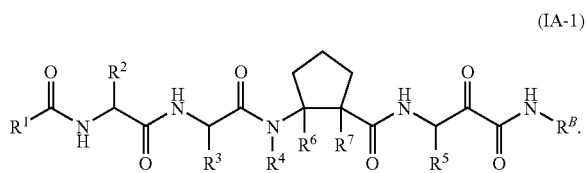

(IA-1)

In some embodiments, A is cyclohexyl, and $R^8$ is aminocarbonyl substituted with $R^B$. In these embodiments, the compounds correspond in structure to the following formula IA-2:

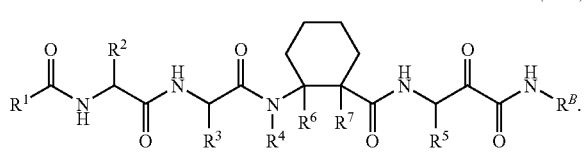

(IA-2)

In some embodiments, A is bicyclo[2.2.1]heptanyl, and $R^8$ is aminocarbonyl substituted with $R^B$. In these embodiments, the compounds correspond in structure to the following formula IA-3:

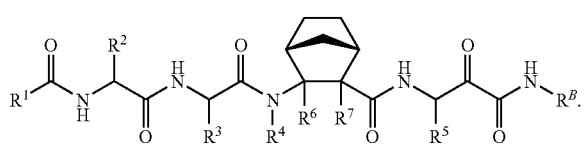

(IA-3)

In some embodiments, A is bicyclo[2.2.1]heptenyl, and $R^8$ is aminocarbonyl substituted with $R^B$. In these embodiments, the compounds correspond in structure to the following formula IA-4:

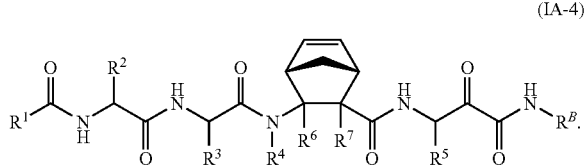

(IA-4)

In some embodiments, A is pyrrolidinyl substituted with $R^A$, and $R^8$ is aminocarbonyl substituted with $R^B$. In these embodiments, the compounds correspond in structure to the following formula IA-5:

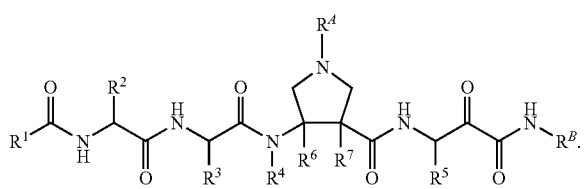

(IA-5)

In some embodiments, A is pyrrolidinyl, and $R^8$ is aminocarbonyl substituted with $R^B$. In these embodiments, the compounds correspond in structure to the following formula IA-6:

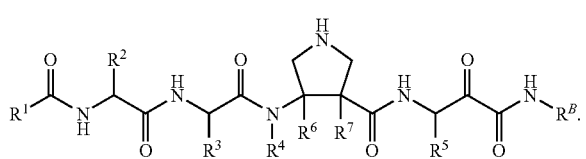

(IA-6)

In some embodiments:

A is selected from the group consisting of $C_5$-$C_7$-carbocyclyl and 5-6-membered heterocyclyl, wherein:
the carbocyclyl and heterocyclyl are optionally substituted with one, two, or three independently selected $R^A$ substituents;
each $R^A$ is independently selected from the group consisting of carbocyclyl, heterocyclyl, alkylcarbonyl, alkyloxycarbonyl, carbocyclylcarbonyl, carbocyclyloxycarbonyl, aminoalkylcarbonyl, heterocyclylaminocarbonyl, carbocyclylalkyloxycarbonyl, and alkylcarbocyclylsulfonyl, wherein:
the amino portion of the aminoalkylcarbonyl optionally is substituted with carbocyclylalkyloxycarbonyl;
$R^1$ is 5-6-membered heterocyclyl;
$R^2$ is $C_5$-$C_6$-carbocyclyl;
$R^3$ is selected from the group consisting of hydrogen, alkyl, carbocyclylalkyl, carbocyclyl, and aminocarbonylalkyl;
$R^4$ is selected from the group consisting of hydrogen and alkyl;
$R^5$ is selected from the group consisting of alkyl and carbocyclylalkyl;
$R^6$ is selected from the group consisting of hydrogen and alkyl;
$R^7$ is selected from the group consisting of hydrogen and alkyl;
$R^8$ is aminocarbonyl optionally substituted with $R^B$; and
$R^B$ is independently selected from the group consisting of aminocarbonylalkyl and carbocyclyl, wherein:
the amino portion of the aminocarbonylalkyl is substituted with alkyl, wherein:
the alkyl optionally is substituted with one or more substituents independently selected from the group consisting of carbocyclyl and aminocarbonyl, wherein:
the carbocyclyl optionally is substituted with one or more substituents selected from the group consisting of halo and alkyloxy, and
the aminocarbonyl optionally is substituted with one or two independently selected alkyl.

In some embodiments:

A is selected from the group consisting of $C_5$-$C_6$-single-ring carbocyclyl, $C_7$-bridged carbocyclyl, and 5-membered nitrogen-containing heterocyclyl, wherein:
each such substituent optionally is substituted with $R^A$;
$R^A$ is selected from the group consisting of carbocyclyl, heterocyclyl, alkylcarbonyl, alkyloxycarbonyl, carbocyclylcarbonyl, carbocyclyloxycarbonyl, aminoalkylcarbonyl, heterocyclylaminocarbonyl, carbocyclylalkyloxycarbonyl, and alkylcarbocyclylsulfonyl, wherein:
the amino portion of the aminoalkylcarbonyl optionally is substituted with carbocyclylalkyloxycarbonyl;
$R^1$ is 5-6-membered nitrogen-containing heterocyclyl;
$R^2$ is $C_5$-$C_6$-cycloalkyl;
$R^3$ is selected from the group consisting of hydrogen, alkyl, aminocarbonylalkyl, cycloalkyl, arylalkyl, and cycloalkylalkyl.
$R^4$ is hydrogen;
$R^5$ is selected from the group consisting of alkyl and cycloalkylalkyl;
$R^6$ is hydrogen;
$R^7$ is hydrogen;
$R^8$ is aminocarbonyl substituted with $R^B$; and
$R^B$ is independently selected from the group consisting of aminocarbonylalkyl and cycloalkyl, wherein:
the amino portion of the aminocarbonylalkyl optionally is substituted with alkyl, wherein:
the alkyl optionally is substituted with aminocarbonyl, wherein:
the aminocarbonyl optionally is substituted with one or two independently selected alkyl.

D. Isomers

This invention also is directed, in part, to all isomers of the compounds of formula I (and their salts) (i.e., structural and stereoisomers). Structural isomers include chain and position isomers. Stereoisomers include E/Z isomers (i.e., isomers with regard to one or more double bonds), enantiomers (i.e., stereo-isomers that have opposite configurations at all stereogenic centers), and diastereoisomers (i.e., stereo-isomers that have the same configuration at one or more stereogenic centers, but differ at other stereogenic centers).

E. Salts

This invention also is directed, in part, to all salts of the compounds of formula I. A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula I can be prepared from an inorganic or organic acid. Examples of often-suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula I include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

F. Purity

Compounds of formula I (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

G. Methods for Preparation of the Compounds and Salts

The compounds of formula I (and their salts) can be prepared as described in the general discussion and/or specific synthesis examples below. In the discussion below, $R^1$, $R^2$, $R^3$, $R^4$, $R^5$, $R^6$, $R^7$, $R^8$, $R^A$, $R^B$, and $R^C$ have the meaning discussed above unless otherwise stated.

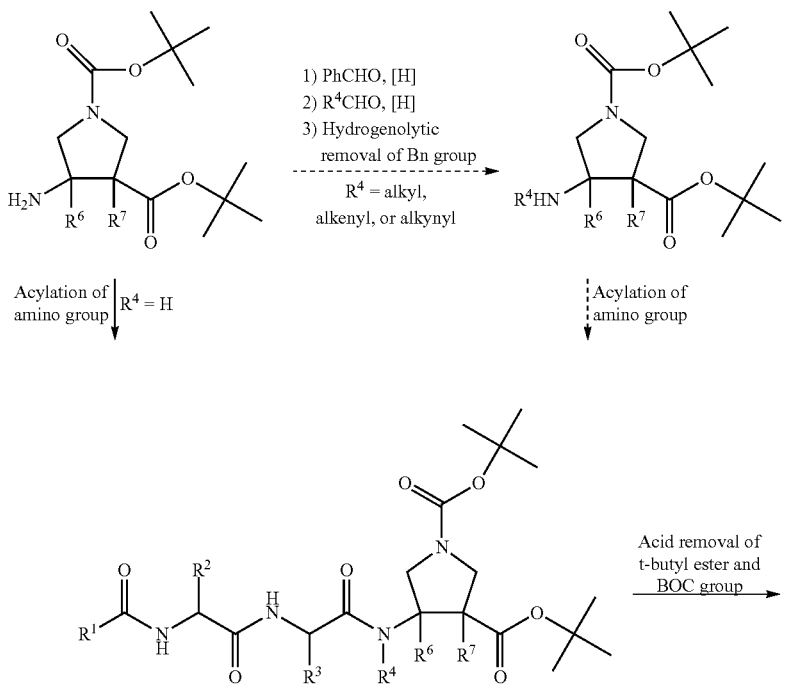

SCHEME 1

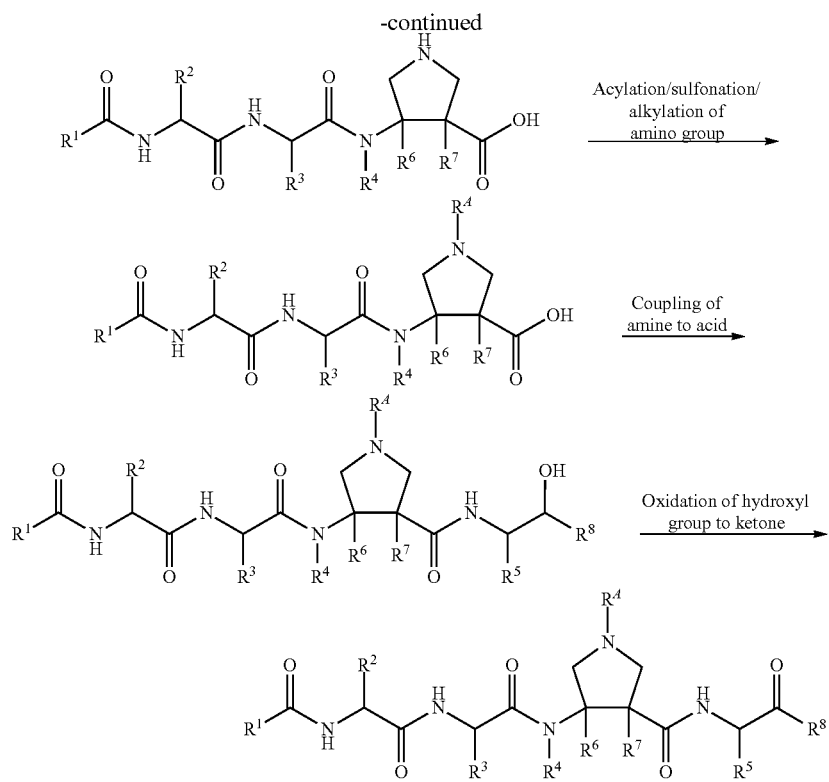
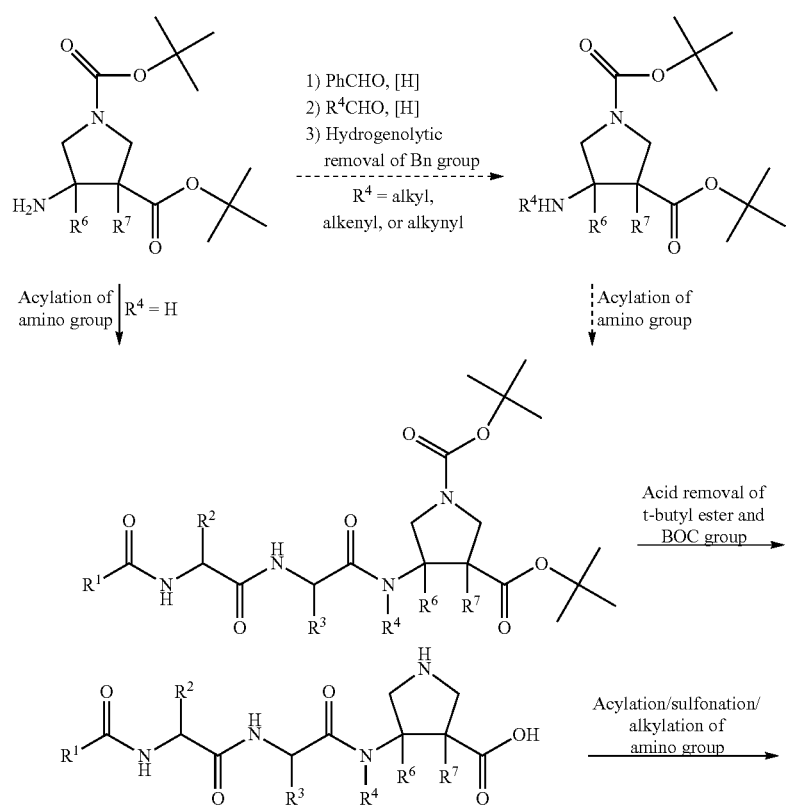
SCHEME 2

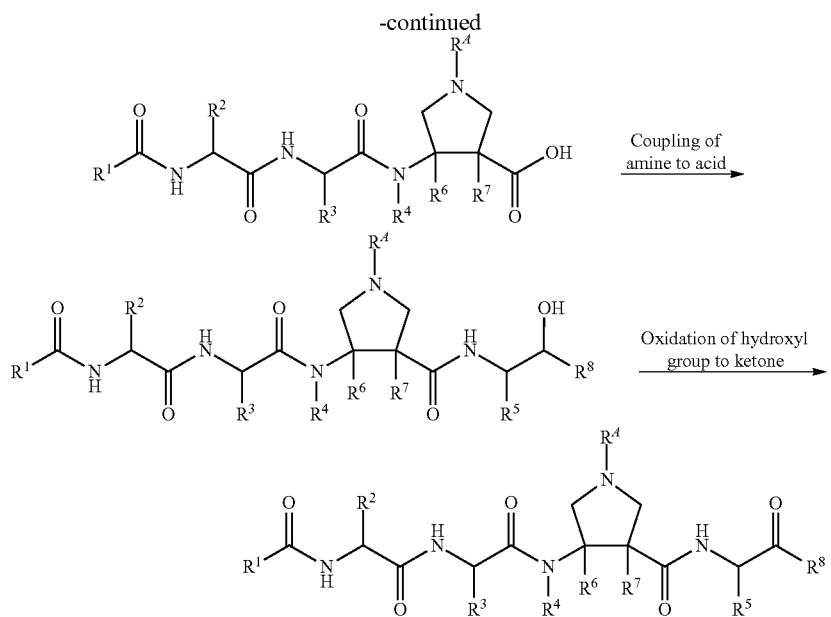

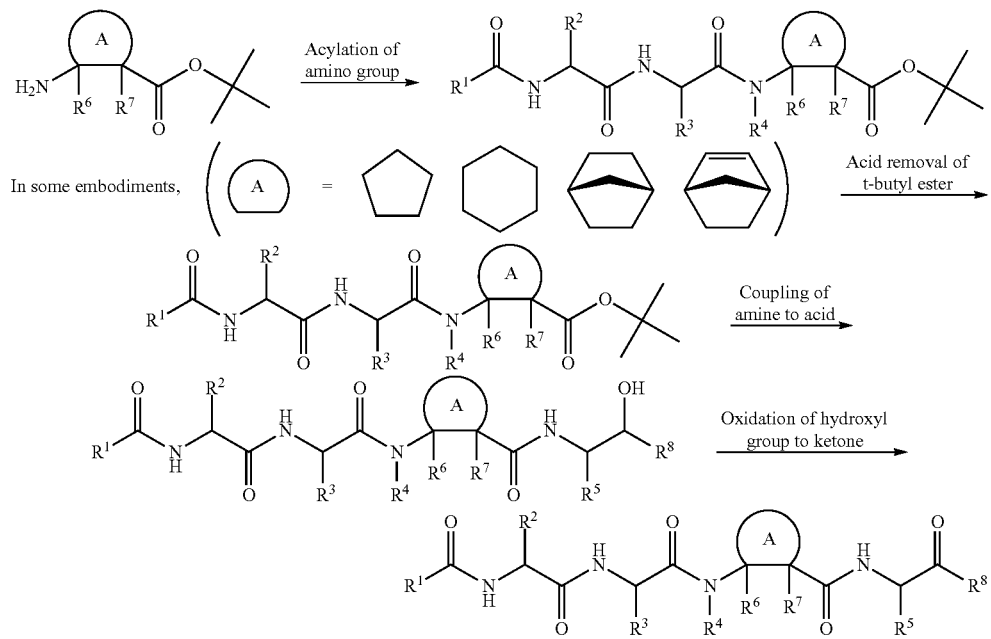

H. Compositions

This invention also is directed, in part, to compositions comprising one or more compounds and/or salts of the in invention. The compositions can be pharmaceutical compositions.

In some embodiments, the compositions further comprise one or more additional therapeutic agents. Such therapeutic agents can be, but need not be, additional HCV inhibitors.

The preferred composition depends on the method of administration, and typically comprises one or more conventional pharmaceutically acceptable carriers, adjuvants, and/or vehicles (together referred to as "excipients"). Formulation of drugs is generally discussed in, for example, Hoover, J., Remington's Pharmaceutical Sciences (Mack Publishing Co., 1975) and Ansel's Pharmaceutical Dosage Forms and Drug Delivery Systems (Lippincott Williams & Wilkins, 2005).

Solid dosage forms for oral administration include, for example, capsules, tablets, pills, powders, and granules. In such solid dosage forms, the compounds or salts are ordinarily combined with one or more excipients. If administered per os, the compounds or salts can be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in, for example, a dispersion of the compound or salt in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

Liquid dosage forms for oral administration include, for example, pharmaceutically acceptable emulsions (including both oil-in-water and water-in-oil emulsions), solutions (including both aqueous and non-aqueous solutions), suspensions (including both aqueous and non-aqueous suspensions), syrups, and elixirs containing inert diluents commonly used in the art (e.g., water). Such compositions also can comprise, for example, wetting, emulsifying, suspending, flavoring (e.g., sweetening), and/or perfuming agents.

Parenteral administration includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

Formulations for parenteral administration may, for example, be prepared from sterile powders or granules having one or more of the excipients mentioned for use in the formulations for oral administration. A compound or salt of the invention can be dissolved in water, polyethylene glycol, propylene glycol, ethanol, corn oil, cottonseed oil, peanut oil, sesame oil, benzyl alcohol, sodium chloride, and/or various buffers. The pH may be adjusted, if necessary, with a suitable acid, base, or buffer.

Suppositories for rectal administration can be prepared by, for example, mixing a compound or salt of the invention with a suitable nonirritating excipient that is solid at ordinary temperatures, but liquid at the rectal temperature, and will therefore melt in the rectum to release the drug. Suitable excipients include, for example, cocoa butter; synthetic mono-, di-, or triglycerides, fatty acids, and/or polyethylene glycols.

Topical administration includes the use of transdermal administration, such as transdermal patches or iontophoresis devices.

Other excipients and modes of administration known in the pharmaceutical art also may be used.

The preferred total daily dose of the compound or salt (administered in single or divided doses) is typically from about 0.001 to about 100 mg/kg, more preferably from about 0.001 to about 30 mg/kg, and even more preferably from about 0.01 to about 10 mg/kg (i.e., mg of the compound or salt per kg body weight). Dosage unit compositions can contain such amounts or submultiples thereof to make up the daily dose. In many instances, the administration of the compound or salt will be repeated a plurality of times. Multiple doses per day typically may be used to increase the total daily dose, if desired.

Factors affecting the preferred dosage regimen include the type, age, weight, sex, diet, and condition of the patient; the severity of the pathological condition; the severity of the pathological condition; the route of administration; pharmacological considerations, such as the activity, efficacy, pharmacokinetic, and toxicology profiles of the particular compound or salt used; whether a drug delivery system is utilized; and whether the compound or salt is administered as part of a drug combination. Thus, the dosage regimen actually employed can vary widely, and therefore, can derive from the preferred dosage regimen set forth above.

I. Kits

This invention also is directed, in part, to a kit comprising one or more compounds and/or salts of the in invention. The kit can optionally contain one or more additional therapeutic agents and/or instructions for, for example, using the kit.

J. Methods of Use

This invention also is directed, in part, to a method for inhibiting HCV serine protease. The method comprises exposing the protease to one or more compounds and/or salts of this invention. In some embodiments, the HCV serine protease is inhibited in vitro. In other embodiments, the HCV serine protease is inhibited in vivo.

The term "inhibiting" means reducing the level of HCV serine protease activity either in vitro or in vivo. If a compound/salt of the invention reduces the protease activity compared to the level of protease activity before the virus was exposed to the compound/salt, then the compound/salt inhibits protease activity. In some embodiments, the compound/salt can inhibit protease activity by at least about 10%, at least about 20%, at least about 30%, at least about 40%, at least about 50%, at least about 60%, at least about 70%, at least about 80%, at least about 90%, or at least about 95%.

This invention also is directed, in part, to a method for treating a disease that can be treated by inhibiting HCV serine protease. Thus, this invention also is directed, in part, to a method for treating hepatitis C in an animal in need of such treatment. These methods comprise administering to the animal one or more compounds and/or salts of the invention, and, optionally, one or more additional therapeutic agents. In some embodiments, a therapeutically effective amount of the compound(s) and/or salt(s) is administered to the animal. "Treating" means ameliorating, suppressing, eradicating, preventing, reducing the risk of, and/or delaying the onset of the disease being treated. The methods of treatment are particularly suitable for use with humans, but may be used with other animals, particularly mammals. A "therapeutically-effective amount" or "effective amount" is an amount that will achieve the goal of treating the targeted condition.

In some embodiments, the methods comprise combination therapy, wherein the compound(s) and/or salt(s) of the invention is/are co-administered with a second (or even a third, fourth, etc.) compound, such as, for example, another therapeutic agent used to treat hepatitis C (e.g., interferon or interferon/ribavirin combination). In these embodiments, the compound(s) and/or salt(s) of the invention and the second therapeutic agent may be administered in a substantially simultaneous manner (e.g., within about 5 minutes of each other), in a sequential manner, or both. It is contemplated that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient.

This invention also is directed, in part, to a use of one or more compounds and/or salts of the invention, and, optionally one or more additional therapeutic agents to prepare a medicament. In some embodiments, the medicament is for co-administration with one or more additional therapeutic agents.

In some embodiments, the medicament is for inhibiting the HCV serine protease enzyme.

In some embodiments, the medicament is for treating hepatitis C.

EXAMPLES

The following examples are merely illustrative, and not limiting to this disclosure in any way.

Example 1

Preparation of

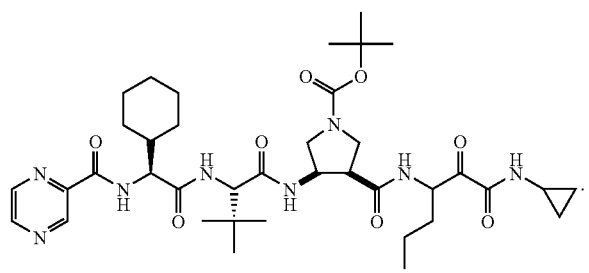

Part A. Preparation of
4-oxo-pyrrolidine-1,3-dicarboxylic acid 1-tert-butyl ester 3-ethyl ester To a solution of BOC glycine methyl ester (*J. Med. Chem.* 2001, 44, 8, 1192-1201) (19.2 g, 101.5 mmol) in THF at 0° C. was added dropwise ethyl acrylate (11 mL, 101.5 mmol) over 10 minutes. The solution was stirred for 20 minutes, then KO$^t$Bu (111.65 mL, 111.65 mmol) was added over 45 minutes. The solution was allowed to warm to 25° C. overnight. The resulting solution concentrated in vacuo and portioned between ethyl acetate and water containing 5 mL of acetic acid. The ethyl acetate layer was removed and aqueous layer extracted with 2×200 mL of ethyl acetate. The combined ethyl acetate layers were washed with brine, dried over MgSO$_4$, filtered and concentrated in vacuo to afford an oil. MS (DCI/NH$_4$) m/z=258 (M+H)+, 275 (M+NH$_4$)+.

Part B. Preparation of 4-(1-phenyl-ethylamino)-2,5-dihydro-pyrrole-1,3-dicarboxylic acid 1-tert-butyl ester 3-ethyl ester To a solution of the product from Part A (21 g, 81.6 mmol) in ethanol (257) containing acetic acid (9.29 mL, 163.2 mmol) was added d,l-alpha-methylbenzyl amine (20.77 mL, 163.20 mmol) in one portion and the reaction mixture was stirred for 3 hours at room temperature. The reaction mixture was poured over water and extracted with ethyl acetate (3×300 mL), the combined organic layers were dried over MgSO$_4$, filtered and concentrated in vacuo to afford an oil that was purified by flash chromatography on SiO$_2$ using ethyl acetate in hexanes as the mobile phase.

Part C. Preparation of 4-(1-phenyl-ethylamino)-pyrrolidine-1,3-dicarboxylic acid 1-tert-butyl ester 3-ethyl ester A solution of Na(OAc)$_3$BH was prepared in acetic acid. This solution was cooled in an ice bath and the imine product from Part B (81.6 mmol) in 20 mL of acetic acid added in one portion. The solution was warmed to 25° C. and stirred for several hours then quenched by pouring the solution over ice, diluting with water and adjust the pH to 8 with NaOH followed by extracting the product into diethyl ether (3×100 mL). The combined organic layers were washed with brine and dried over MgSO$_4$, filtered and concentrated in vacuo to afford an oil that was purified by flash chromatography on SiO$_2$ using ethyl acetate in hexanes as the mobile phase. MS (DCI/NH$_4$) m/z=363 (M+H)+.

Part D. Preparation of 4-amino-pyrrolidine-1,3-dicarboxylic acid 1-tert-butyl ester 3-ethyl ester A solution of the product from Part C (9.7 g, 26.8 mmol), Pd(OH)$_2$/carbon (200 mg) in ethanol (200 mL) was treated with H$_2$ at 60 psi and room temperature. The solution was filtered through celite and concentrated to a foam. MS (DCI/NH$_4$) m/z=259 (M+H)+.

Part E. Preparation of cyclohexyl-[(pyrazine-2-carbonyl)-amino]-acetic acid

To a solution containing 2-pyrazine carboxylic acid (10 g, 80.5 mmol) in dichloromethane (150 mL) was added 1-(3-dimethylaminopropyl)-3-ethylcarbodiimide hydrochloride EDC (18.5 g, 96.6 mmol) and 1-hydroxybenzotriazole HOBT (13.05 g, 96.6 mmol) and the resulting solution stirred at 25° C. for 30 minutes. Then 1-cyclohexylglycine methyl ester (16.7 g, 80.5 mmol) and Hunig's base (31.24 g, 241 mmol) was added and the reaction mixture stirred for 2 hours. The reaction mixture was partitioned between water and dichloromethane. The organic layer was removed and dried over MgSO$_4$, filtered and concentrated in vacuo and purified via flash chromatography using ethyl acetate/hexane (20/80 to 30/70) to give a foam (13.3 g, 60%).

The product of the previous reaction (6.54 g, 24 mmol) was dissolved in ethanol and treated with 1N sodium hydroxide (35.4 mL, 35.3 mmol) at 25° C. for 4 hours. The mixture was neutralized with 10% HCl to pH 4 and extracted with dichloromethane. The organic layer was removed and dried over MgSO$_4$, filtered and concentrated in vacuo to afford a foam (5 g, 81%).

Part F. Preparation of 2-{2-cyclohexyl-2-[(pyrazine-2-carbonyl)-amino]-acetylamino}-3,3-dimethyl-butyric acid tert-butyl ester To a solution of the product from Part E (4.49 g, 17.1 mmol) in methylene chloride (25 mL) was added EDC (3.93 g, 20.5 mmol) and HOBT (2.76 g, 20.5 mmol). The resulting solution was stirred at 25° C. for 20 minutes followed by the addition of Hunig's base (6.55 mL, 37.6 mmol) and tert-leucine tert-butyl ester hydrochloride (3.82 g, 17.1 mmol). After stirring for 2 hours, the reaction mixture was partitioned between water and dichloromethane. The organic layer was removed and dried over MgSO$_4$, filtered and concentrated in vacuo to afford a foam (7.24 g, 98% yield). MS (DCI/NH$_4$) m/z=433 (M+H)+.

Part G. Preparation of 2-{2-cyclohexyl-2-[(pyrazine-2-carbonyl)-amino]-acetylamino}-3,3-dimethyl-butyric acid The product from Part F (1.43 g, 3.3 mmol) was taken up in methylene chloride (5 mL) and treated with TFA (5 mL) at 25° C. for 2 hours. The reaction mixture was concentrated in vacuo and partitioned between water and methylene chloride. The organic layer was removed and dried over MgSO$_4$, filtered and concentrated in vacuo to afford a foam (1.1 g, 88% yield). MS (ESI+) m/z=377 (M+H)+, 399 (M+Na)+; MS (ESI−) m/z=375 (M−H)−.

Part H. Preparation of 4-(2-{2-cyclohexyl-2-[(pyrazine-2-carbonyl)-amino]-acetylamino}-3,3-dimethyl-butyrylamino)-pyrrolidine-1,3-dicarboxylic acid 1-tert-butyl ester 3-ethyl ester To a solution of the product from Part G (0.300 g, 0.694 mmol) in methylene chloride (10 mL) was added EDC (0.159 g, 0.832 mmol) and HOBT (0.112 g, 0.832 mmol) and the resulting solution stirred at 25° C. for 20 minutes. Then, Hunig's base (0.289 mL, 1.665 mmol) and 4-Amino-pyrrolidine-1,3-dicarboxylic acid 1-tert-butyl ester 3-ethyl ester (0.179 g, 0.694 mmol) was added and the reaction continued for 18 hours at room temperature. The reaction mixture was partitioned between water and dichloromethane. The organic layer was removed and dried over MgSO$_4$, filtered and concentrated in vacuo to afford a foam (0.305 g, 71% yield). Separation of diasteomers was accomplished with a Waters delta prep C$_{18}$ column with a water and acetonitrile gradient.

Part I. Preparation of 4-(2-{2-cyclohexyl-2-[(pyrazine-2-carbonyl)-amino]-acetylamino}-3,3-dimethyl-butyrylamino)-pyrrolidine-1,3-dicarboxylic acid 1-tert-butyl ester To a solution of the product from Part H (0.150 g, 0.243 mmol) in ethanol (2 mL) was added 1 N NaOH (0.486 mL, 0.486 mmol) for 4 hours. The solution was diluted with water and the pH adjusted with 1N HCl. The product was extracted into methylene chloride (3×30 mL), dried over MgSO$_4$, filtered and concentrated in vacuo to afford a foam (0.75 g, 52% yield). MS (DCI/NH$_4$) m/z=589 (M+H)+, 606 (M+NH$_4$)+.

Part J. Preparation of

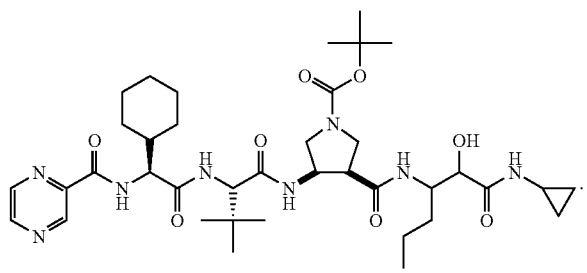

To a solution of the product from Part I (75 mg, 0.127 mmol) in 2 mL of dichloromethane was added EDC (29.3 mg, 0.153 mmol) and HOBT (20.7 mg, 0.153 mmol). The resulting solution was stirred at 25° C. for 20 minutes followed by the addition of Hunig's base (50 uL, 0.280 mmol) and 3-amino-N-cyclopropyl-2-hydroxyhexanamide (as can be found in WO2002018369-A2; Example 119, cpd xiii') (23.4 mg, 0.127 mmol) and the reaction continued for 2 hours at room temperature. The reaction mixture was partitioned between water and dichloromethane. The organic layer was removed and dried over MgSO$_4$, filtered and concentrated in vacuo to afford a foam (0.856 g, 89% yield). MS (DCI/NH$_4$) m/z=757 (M+H)$^+$, 744 (M+NH$_4$)+.

Part K. Preparation of title product

To a solution of the product from Part J (40 mg, 0.053 mmol) in dichloromethane (2 mL) was added Dess-Martin periodine (34 mg, 0.079 mmol) at 25° C. and the reaction mixture stirred for 1 hour. The reaction was quenched with Na$_2$S$_2$O$_3$ (sat. aqueous) and the product was extracted into methylene chloride (3×30 mL), dried over MgSO$_4$, filtered and concentrated in vacuo to afford a foam (0.75 g, 52% yield) that was purified by prep TLC SiO$_2$, (1.0 mm×20 mm×20 mm) using methanol in dichloromethane as the mobile phase. The title product was isolated as a white solid (30.9 mg, 78% yield). MS (ESI+) m/z=755 (M+H)+; MS (ESI−) m/z=753 (M−H)−

Example 2

Preparation of

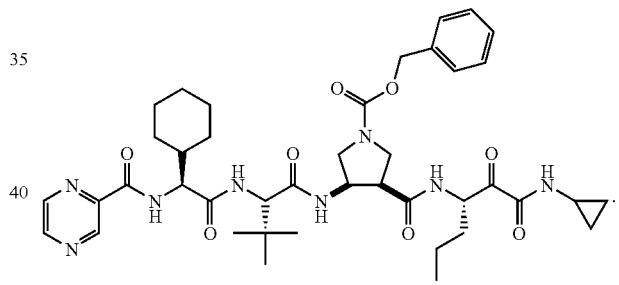

Part A. Preparation of

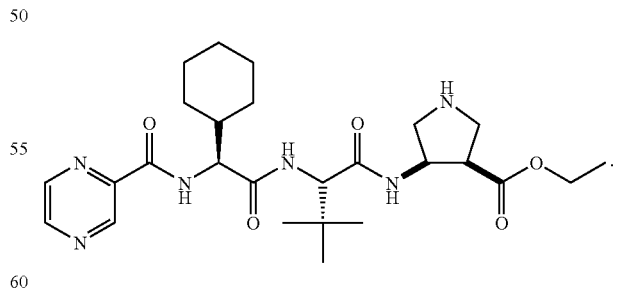

To a solution of the product from Example 1, Part H (100 mg, 0.162 mmol) in 2 mL of dichloromethane was added 2 mL of TFA. The reaction mixture was stirred for 45 minutes and then concentrated in vacuo to afford a solid that was placed on high vacuum overnight. MS (ESI+) m/z=517 (M+H)+; MS (ESI−) m/z=515 (M−H).

Part B. Preparation of

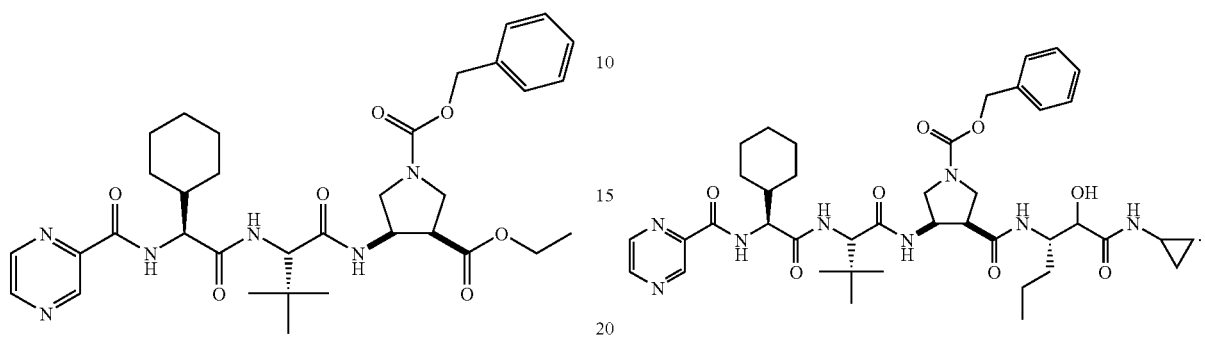

To a solution of the product of Part A (132.6 mg, 0.257 mmol) in 2 mL of dichoromethane was added Hunig's base (0.89 mL, 0.513 mmol) and CBZ-NOS (70.4 mg, 0.282 mmol). The reaction was stirred at 25° C. for 40 minutes. Poured the reaction mixture over 0.5N HCl and extracted with dichloromethane (3×30 mL) The organic layer was removed and dried over $MgSO_4$, filtered and concentrated in vacuo to afford a foam that was purified by reverse phase HPLC chromatography on $C_{18}$ column using water/acetonitrile as the mobile phase to yield pure diastereomers of the above compound. MS (ESI+) m/z=651 (M+H)+; MS (ESI−) m/z=649 (M−H)−.

Part C. Preparation of

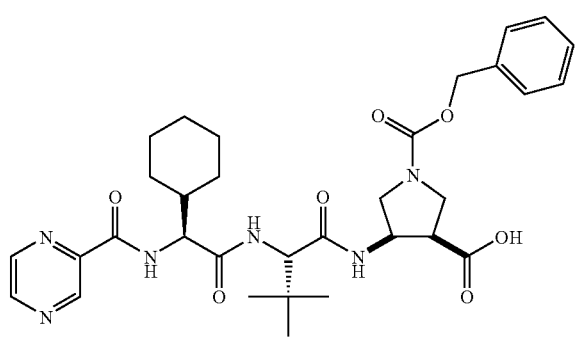

The product from Part B (27 mg, 0.042 mmol) was taken up in 2 mL of ethanol containing 1N NaOH (0.46 mmol) and the resulting solution stirred for 1 hour. The reaction mixture was poured over 0.5 N HCl and extracted with dichloromethane (3×30 mL). The combined organic layers were dried over $MgSO_4$, filtered and concentrated in vacuo to afford a white foam (26 mg, 100% yield). MS ($DCI/NH_4$) m/z=623 (M+H)+, 640 ($M+NH_4$)+.

Part D. Preparation of

To a solution of the product from Part C (27 mg, 0.043 mmol) in 1 mL of dichloromethane was added EDC (10 mg, 0.052 mmol) and HOBT (7.0 mg, 0.052 mmol) and the resulting solution stirred at 25° C. for 20 minutes. Then, Hunig's base (16 uL, 0.096 mmol) and 3-amino-N-cyclopropyl-2-hydroxyhexanamide (WO2002018369-A2; Example 119, cpd xiii') (8.0 mg, 0.052 mmol) was added and the reaction continued for 1 hour at room temperature. The reaction mixture was partitioned between water and dichloromethane. The organic layer was removed and dried over $MgSO_4$, filtered and concentrated in vacuo to afford a foam (14 mg, 41% yield). MS (ESI+) m/z=791 (M+H)+; MS (ESI−) m/z=789 (M−H)−.

Part E. Preparation of Title Product

To a solution of the product from Part D (14 mg, 0.018 mmol) in 1 mL of dichloromethane was added Dess-Martin periodinane (11.3 mg, 0.027 mmol) for 1 hour. The reaction was quenched with Na2S2O3 (sat. aqueous) and the product was extracted into methylene chloride (3×30 mL), dried over $MgSO_4$, filtered and concentrated in vacuo to afford a foam (0.75 g, 52% yield) that was purified by prep TLC $SiO_2$, (1.0 mm×20 mm×20 mm) using methanol in dichloromethane as the mobile phase. The title product was isolated as a white solid (6.8 mg, 49% yield). MS (ESI+) m/z=789 (M+H)+; MS (ESI−) m/z=787 (M−H)−.

Example 3

Preparation of

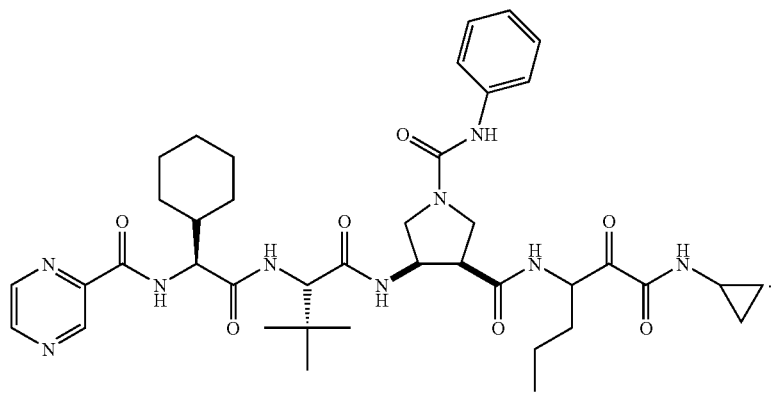

Part A. Preparation of

To a solution of the Example 1G (358.9 mg, 0.953 mmol) in methylene chloride (5 mL) was added EDC (219 mg, 1.144 mmol) and HOBT (155 mg, 1.144 mmol) and the resulting solution stirred at 25° C. for 20 minutes. Then, Hunig's base (0.36 mL, 2.097 mmol) and (3R,4R)-di-tert-butyl 4-aminopyrrolidine-1,3-dicarboxylate (*Org. Biomol Chem.* 2004, 2, 2763-2776) (273 mg, 0.953 mmol) was added and the reaction continued for 18 hours at room temperature. The reaction mixture was partitioned between water and dichloromethane. The organic layer was removed and dried over MgSO$_4$, filtered and concentrated in vacuo to afford a foam that was purified by flash chromatography on SiO$_2$ using methanol in dichloromethane as the mobile phase. The title compound was isolated as a white foam (542 mg, 88% yield). MS (ESI+) m/z=645 (M+H)+; MS (ESI−) m/z=643 (M−H)−

Part B. Preparation of

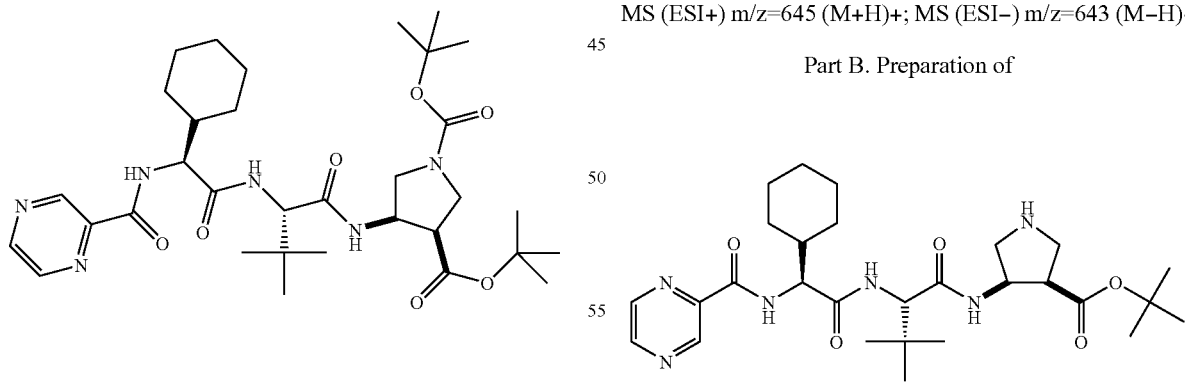

To a solution of the product from Part A (591 mg, 0.917 mmol) in ethyl acetate (4 mL) was added 4N HCl in dioxane (0.8 mL, 3.2 mmol) and the reaction mixture stirred for 5 hours at room temperature. The resulting precipitate was filtered through a paper disk, washed with ethyl acetate, and dried in vacuo yielding 281 mg of the title compound as a crystalline white solid, 56% yield. MS (ESI+) m/z=545 (M+H)+; MS (ESI−) m/z=543 (M−H)−.

Part C. Preparation of

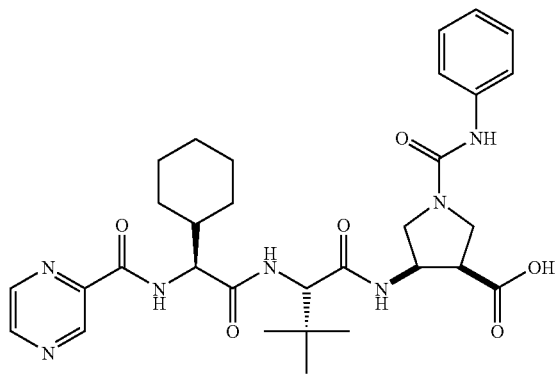

To a solution of the amine product from Part B (84.0 mg, 0.155 mmol), Hunig's base (81 uL, 0.465 mmol) and 4 mL of dichloromethane was added phenyl isocyanate (42 uL, 0.233 mmol) and the reaction mixture stirred for 18 hours. The reaction mixture was poured over 1N HCl and extracted with dichloromethane (3×30 mL). The combined organic layers were dried over MgSO$_4$, filtered and concentrated in vacuo to afford a foam.

The above compound was treated with 2 mL of dichloromethane and 2 mL of TFA for 45 minutes. The solution was concentrated in vacuo to afford an oil that was placed on high vacuum overnight. MS (ESI+) m/z=608 (M+H)+; MS (ESI−) m/z=606 (M−H)−.

Part D. Preparation of

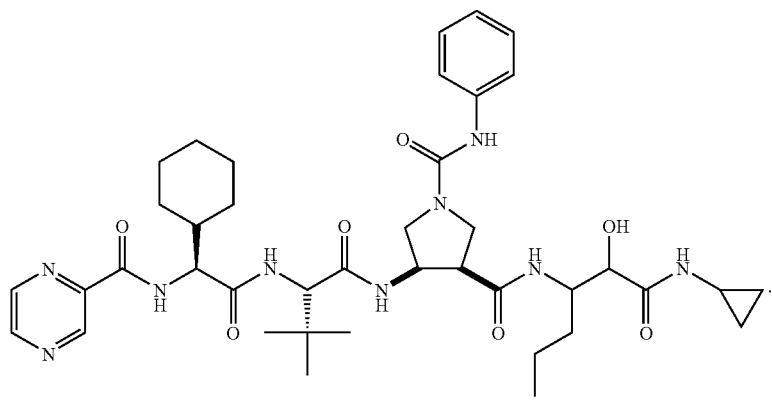

The product of Part C (0.155 mmol) was taken up in 4 mL of dichloromethane and treated with EDC (45 mg, 0.233 mmol) and HOBT (34 mg, 0.233 mmol) for 20 minutes followed by the addition of Hunig's base (60 uL, 0.341 mmol) and 3-amino-N-cyclopropyl-2-hydroxyhexanamide (WO2002018369-A2; Example 119, cpd xiii') (28.0 mg, 0.155 mmol). The reaction continued for 18 hours at room temperature. The reaction mixture was partitioned between water and dichloromethane. The organic layer was removed and dried over MgSO$_4$, filtered and concentrated in vacuo to afford a foam that was purified by flash chromatography on SiO$_2$ using methanol in dichloromethane as the mobile phase to afford the title compound as a white solid. 23 mg, 20% yield.

Part E. Preparation of Title Product

To a solution of the product from Part D (23 mg, 0.030 mmol) in 1 mL of dichloromethane was added Dess-Martin periodinane (19 mg, 0.045 mmol) for 1 hour. The reaction was quenched with Na$_2$S$_2$O$_3$ (sat. aqueous) and the product was extracted into methylene chloride (3×30 mL), dried over MgSO$_4$, filtered and concentrated in vacuo to afford a white solid that was purified by prep TLC SiO$_2$, (1.0 mm×20 mm×20 mm) using methanol in dichloromethane as the mobile phase. The title product was isolated as a white solid (17 mg, 74% yield). MS (ESI+) m/z=774 (M+H)+; MS (ESI−) m/z=772 (M−H)−.

Example 4

Preparation of

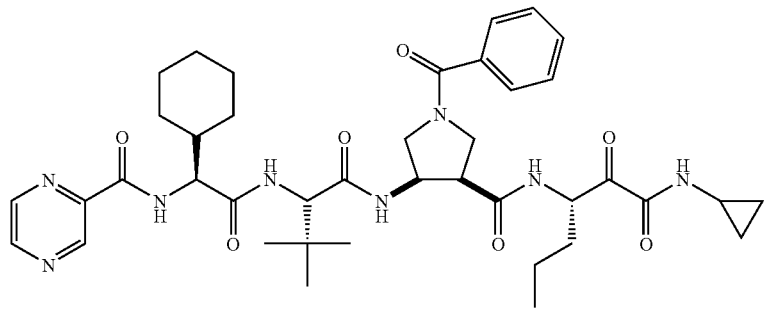

Part A. Preparation of

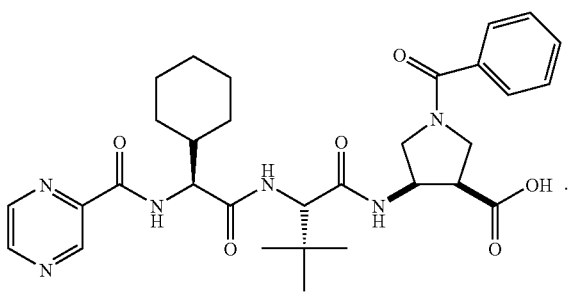

To a solution of the product from Example 3, Part B (136 mg, 0.278 mmol) in 3 mL of dichloromethane and 3 mL of 1N NaOH was added benzoyl chloride (38 uL, 0.334 mmol) for 2 hours. The reaction mixture was poured water and extracted with diethyl ether, then the pH of the aqueous layer was adjusted to pH-2 with 1N HCl and extract with ethyl acetate (3×30 mL). The combined organic layers were dried over MgSO$_4$, filtered and concentrated in vacuo to afford a foam. MS (ESI+) m/z=593 (M+H)+; MS (ESI-) m/z=591 (M-H)-.

Part B. Preparation of

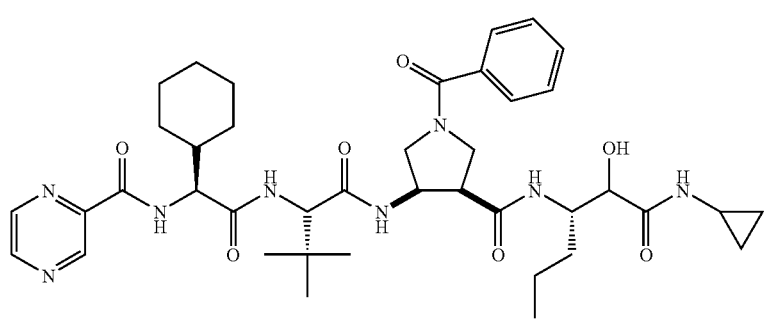

To a solution of the product from Part A (89 mg, 0.152 mmol) in 2 mL of dichloromethane was added EDC (43 mg, 0.225 mmol) and HOBT (30.0 mg, 0.225 mmol) and the resulting solution stirred at 25° C. for 20 minutes. Then, Hunig's base (86 uL, 0.495 mmol) and 3-amino-N-cyclopropyl-2-hydroxyhexanamide (WO2002018369-A2; Example 119, cpd xiii') (42 mg, 0.225 mmol) was added and the reaction continued for 2 hours at room temperature. The reaction mixture was partitioned between water and dichloromethane. The organic layer was removed and dried over MgSO$_4$, filtered and concentrated in vacuo to afford a foam that was purified by flash chromatography on SiO$_2$ using methanol in dichloromethane as the mobile phase to afford the title compound as a white solid (44 mg, 38% yield) MS (ESI+) m/z=761 (M+H)+; MS (ESI-) m/z=759 (M-H)-.

Part C. Preparation of Title Product

To a solution of the product from Part B (44 mg, 0.058 mmol) in 5 mL of dichloromethane was added Dess-Martin periodinane (37 mg, 0.087 mmol) for 1 hour. The reaction was quenched with Na$_2$S$_2$O$_3$ (sat. aqueous) and the product was extracted into methylene chloride (3×30 mL), dried over MgSO$_4$, filtered and concentrated in vacuo to afford a white solid that was purified by prep TLC SiO$_2$, (1.0 mm×20 mm×20 mm) using methanol in dichloromethane as the mobile phase. The title product was isolated as a white solid (24 mg, 55% yield). MS (ESI+) m/z=759 (M+H)+; MS (ESI-) m/z=757 (M-H)-.

Example 5

Preparation of

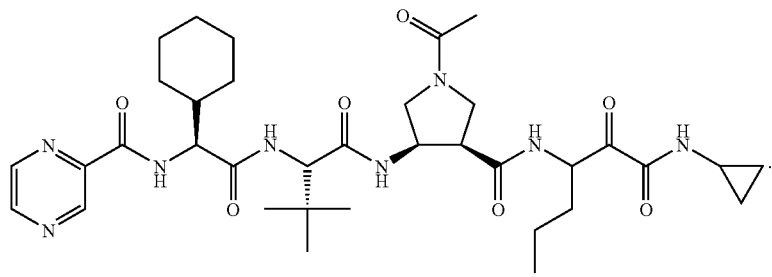

Part A. Preparation of

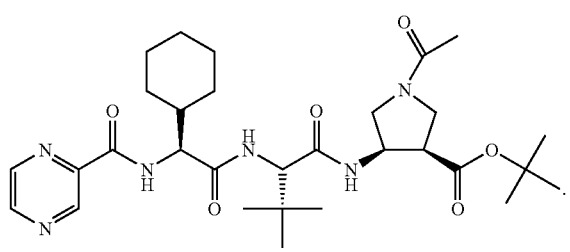

To a solution of the product from Example 3, Part B (140 mg, 0.257 mmol) in 4 mL of pyridine was added acetic anhydride (25 uL, 0.257 mmol) and the reaction continued at 25° C. for 4 hours. The reaction mixture was partitioned between water and ethyl acetate. The organic layer was removed and washed sequentially with bicarbonate, brine, dried over MgSO$_4$, filtered and concentrated in vacuo to afford the title compound as a white solid (91 mg, 61% yield). MS (ESI+) m/z=587 (M+H)+; MS (ESI−) m/z=585 (M−H)−.

Part B. Preparation of

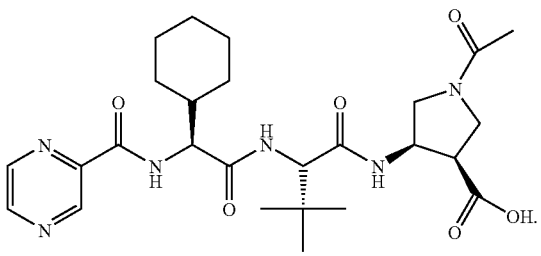

To a solution of the product from Part A (90 mg, 0.153 mmol) in 4 mL of dichloromethane was added 2 mL of TFA. The reaction mixture was stirred for 45 minutes and then concentrated in vacuo to afford a solid that was placed on high vacuum overnight. MS (ESI+) m/z=531 (M+H)+; MS (ESI−) m/z=529 (M−H)−.

Part C. Preparation of

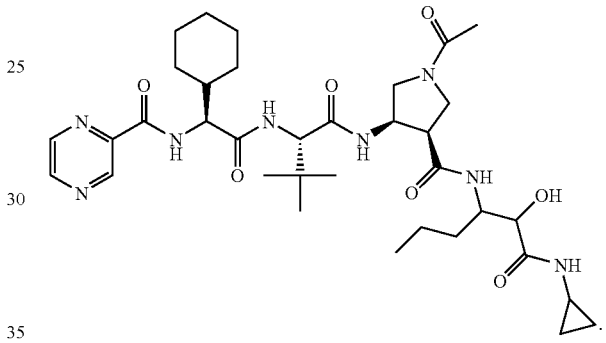

To a solution of the product from Part B (74 mg, 0.140 mmol) in 2 mL of dichloromethane was added EDC (40 mg, 0.209 mmol) and HOBT (28 mg, 0.209 mmol) and the resulting solution stirred at 25° C. for 20 minutes. Then, Hunig's base (73 uL, 0.419 mmol) and 3-amino-N-cyclopropyl-2-hydroxyhexanamide (WO2002018369-A2; Example 119, cpd xiii') (29 mg, 0.153 mmol) was added and the reaction continued for 2 hours at room temperature. The reaction mixture was partitioned between water and dichloromethane. The organic layer was removed and dried over MgSO$_4$, filtered and concentrated in vacuo to afford a foam that was purified by flash chromatography on SiO$_2$ using methanol in dichloromethane as the mobile phase to afford the title compound as a white solid (30 mg, 31% yield). MS (ESI+) m/z=761 (M+H)+; MS (ESI−) m/z=759 (M−H)−.

Part D. Preparation of Title Product

To a solution of the product from Part C (30 mg, 0.043 mmol) in 4 mL of dichloromethane was added Dess-Martin periodinane (27 mg, 0.064 mmol) for 1 hour. The reaction was quenched with Na$_2$S$_2$O$_3$ (sat. aqueous) and the product was extracted into methylene chloride (3×30 mL), dried over MgSO$_4$, filtered and concentrated in vacuo to afford a white solid that was purified by prep TLC SiO$_2$, 1.0 mm×20 mm×20 mm using methanol in dichloromethane as the mobile phase. The title product was isolated as a white solid (17 mg, 56% yield). MS (ESI+) m/z=697 (M+H)+; MS (ESI−) m/z=695 (M−H)−.

Example 6

Preparation of

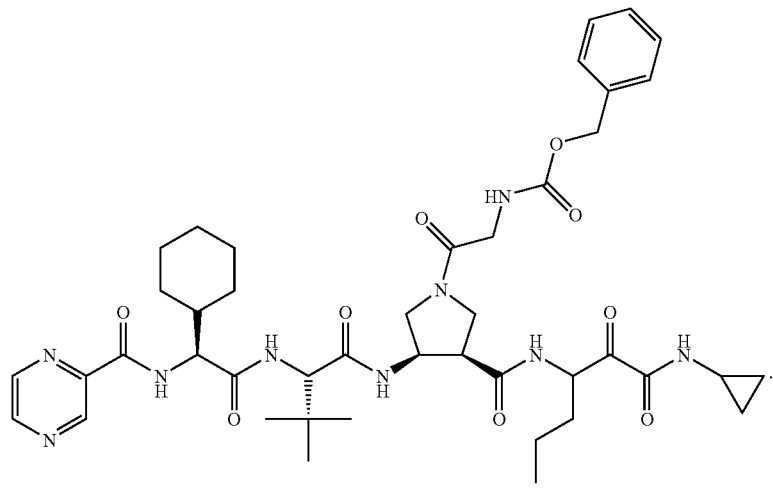

Part A. Preparation of

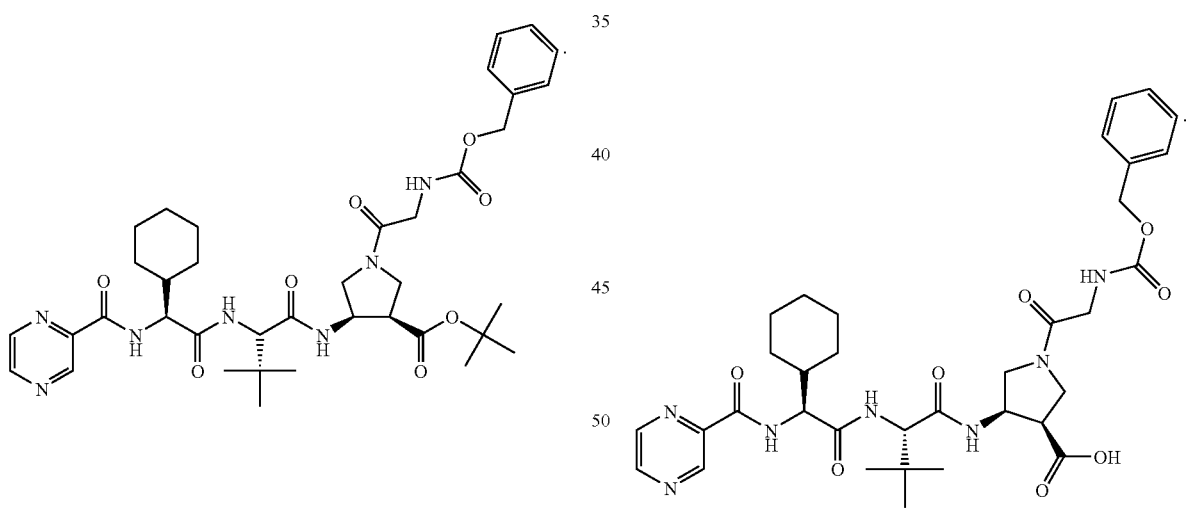

Part B. Preparation of

To a solution of the product from Example 3, Part B (140 mg, 0.257 mmol) in 5 mL of dichloromethane was added EDC (74 mg, 0.386 mmol) and HOBT (52 mg, 0.386 mmol) and the resulting solution stirred at 25° C. for 20 minutes. Then, Hunig's base (134 uL, 0.771 mmol) and CBZ-Gly-OH (65 mg, 0.2084 mmol) was added and the reaction continued for 2 hours at room temperature. The reaction mixture was partitioned between water and dichloromethane. The organic layer was removed and dried over MgSO₄, filtered and concentrated in vacuo to afford a foam that was purified by flash chromatography on SiO₂ using methanol in dichloromethane as the mobile phase to afford the title compound as a white solid (65 mg, 34% yield). MS (ESI+) m/z=736 (M+H)+; MS (ESI−) m/z=734 (M−H)−.

To a solution of the product from Part A (53 mg, 0.072 mmol) in 4 mL of dichloromethane was added 2 mL of TFA. The reaction mixture was stirred for 45 minutes and then concentrated in vacuo to afford a solid that was placed on high vacuum overnight. MS (ESI+) m/z=680 (M+H)+; MS (ESI−) m/z=678 (M−H)−.

Part C. Preparation of

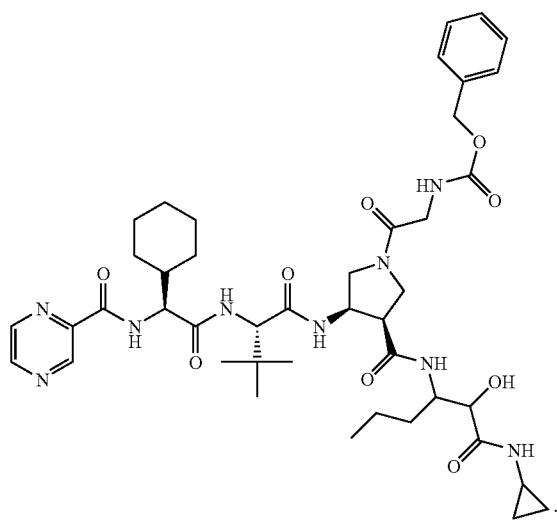 [SMILES: CCCC(NC(=O)[C@@H]1CN(C(=O)CNC(=O)OCc2ccccc2)C[C@@H]1NC(=O)[C@@H](NC(=O)[C@@H](NC(=O)c1cnccn1)C1CCCCC1)C(C)(C)C)C(O)C(=O)NC1CC1]

To a solution of the product from Part B (60 mg, 0.088 mmol) in 5 mL of dichloromethane was added EDC (25 mg, 0.133 mmol) and HOBT (18 mg, 0.133 mmol) and the resulting solution stirred at 25° C. for 20 minutes. Then, Hunig's base (46 uL, 0.265 mmol) and 3-amino-N-cyclopropyl-2-hydroxyhexanamide (WO2002018369-A2; Example 119, cpd xiii') (20 mg, 0.106 mmol) was added and the reaction continued for 2 hours at room temperature. The reaction mixture was partitioned between water and dichloromethane. The organic layer was removed and dried over MgSO$_4$, filtered and concentrated in vacuo to afford a foam that was purified by flash chromatography on SiO$_2$ using methanol in dichloromethane as the mobile phase to afford the title compound as a white solid (47 mg, 63% yield). MS (ESI+) m/z=680 (M+H)+; MS (ESI−) m/z=678 (M−H)−.

Part D. Preparation of Title Product

To a solution of the product from Part C (45 mg, 0.053 mmol) in 4 mL of dichloromethane was added Dess-Martin periodinane (34 mg, 0.079 mmol) for 1 hour. The reaction was quenched with Na$_2$S$_2$O$_3$ (sat. aqueous) and the product was extracted into methylene chloride (3×30 mL), dried over MgSO$_4$, filtered and concentrated in vacuo to afford a white solid that was purified by prep TLC SiO$_2$, 1.0 mm×20 mm×20 mm using methanol in dichloromethane as the mobile phase. The title product was isolated as a white solid (21 mg, 47% yield). MS (ESI+) m/z=846 (M+H)+; MS (ESI−) m/z=844 (M−H)−.

Example 7

Preparation of

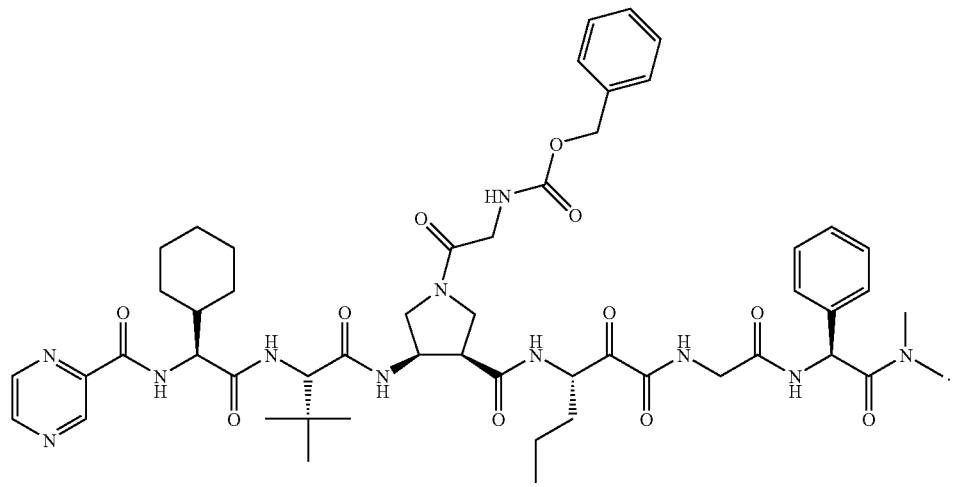

Part A. Preparation of

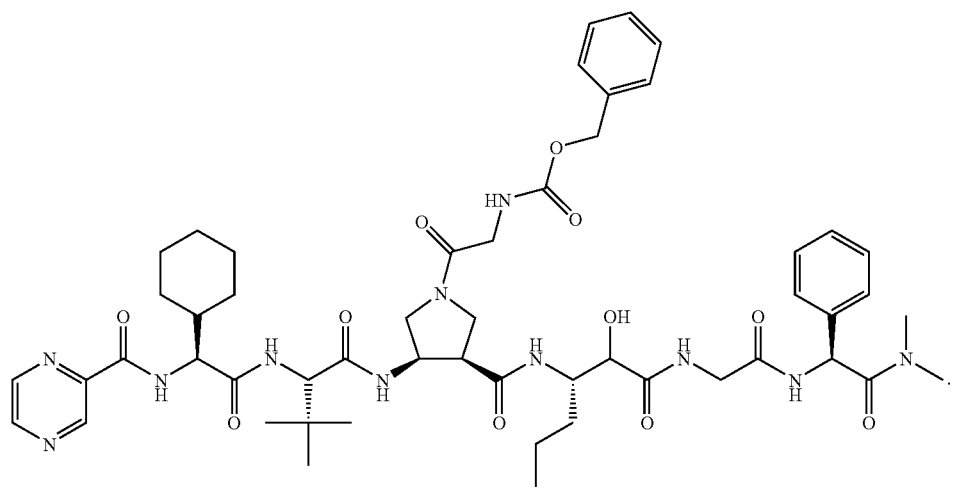

To a solution of the product from Example 6, Part B (60 mg, 0.088 mmol) in 5 mL of dichloromethane was added EDC (25 mg, 0.133 mmol) and HOBT (18 mg, 0.133 mmol) and the resulting solution stirred at 25° C. for 20 minutes. Then, Hunig's base (46 uL, 0.265 mmol) and hydroxyamide (WO2003062265-A2; Example 6, cpd 2.3) (42 mg, 0.106 mmol) was added and the reaction continued for 2 hours at room temperature. The reaction mixture was partitioned between water and dichloromethane. The organic layer was removed and dried over MgSO$_4$, filtered and concentrated in vacuo to afford a foam that was purified by flash chromatography on SiO$_2$ using methanol in dichloromethane as the mobile phase to afford the title compound as a white solid (49 mg, 54% yield). MS (ESI+) m/z=1026 (M+H)+; MS (ESI−) m/z=1024 (M−H)−.

Part B. Preparation of Title Product

To a solution of the product from Part A (30 mg, 0.029 mmol) in 2 mL of dichloromethane was added Dess-Martin periodinane (19 mg, 0.044 mmol) for 1 hour. The reaction was quenched with Na$_2$S$_2$O$_3$ (sat. aqueous) and the product was extracted into methylene chloride (3×30 mL), dried over MgSO$_4$, filtered and concentrated in vacuo to afford a white solid that was purified by prep TLC SiO$_2$, (1.0 mm×20 mm×20 mm) using methanol in dichloromethane as the mobile phase. The title product was isolated as a white solid (25 mg, 83% yield). MS (ESI+) m/z=1024 (M+H)+; MS (ESI−) m/z=1022 (M−H)−.

Example 8

Preparation of

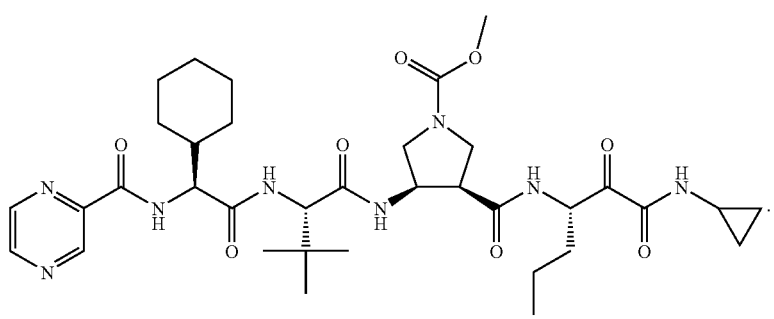 [SMILES: CCC[C@H](NC(=O)[C@@H]1CN(C(=O)OC)C[C@@H]1NC(=O)[C@@H](NC(=O)[C@@H](NC(=O)c1cnccn1)C1CCCCC1)C(C)(C)C)C(=O)C(=O)NC1CC1]

Part A. Preparation of

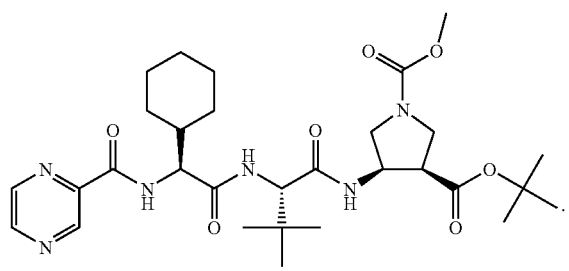 [SMILES: COC(=O)N1C[C@H](NC(=O)[C@@H](NC(=O)[C@@H](NC(=O)c2cnccn2)C2CCCCC2)C(C)(C)C)[C@H](C(=O)OC(C)(C)C)C1]

To a solution of the product from Example 3, Part B (86 mg, 0.158 mmol) in 5 mL of dichloromethane was added Hunig's base (82 uL, 0.474 mmol) and methyl chloroformate (18 uL, 0.237 mmol). The reaction was stirred at 25° C. for 2 hours. The reaction mixture was partitioned between water and dichloromethane. The organic layer was removed and dried over MgSO$_4$, filtered, and concentrated in vacuo to afford a white solid (76 mg, 80% yield). MS (ESI+) m/z=603 (M+H)+; MS (ESI−) m/z=601 (M−H)−.

Part B. Preparation of

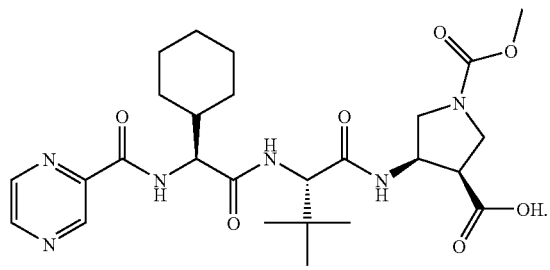 [SMILES: COC(=O)N1C[C@H](NC(=O)[C@@H](NC(=O)[C@@H](NC(=O)c2cnccn2)C2CCCCC2)C(C)(C)C)[C@H](C(=O)O)C1]

To a solution of the product from Part A (73 mg, 0.126 mmol) in 4 mL of dichloromethane was added 4 mL of TFA. The reaction mixture was stirred for 2 hours and then concentrated in vacuo to afford a solid that was placed on high vacuum overnight. The reaction mixture was partitioned between water and dichloromethane. The organic layer was removed and dried over MgSO$_4$, filtered and concentrated in vacuo to afford a white solid. MS (ESI+) m/z=547 (M+H)+; MS (ESI−) m/z=545 (M−H)−.

Part C. Preparation of

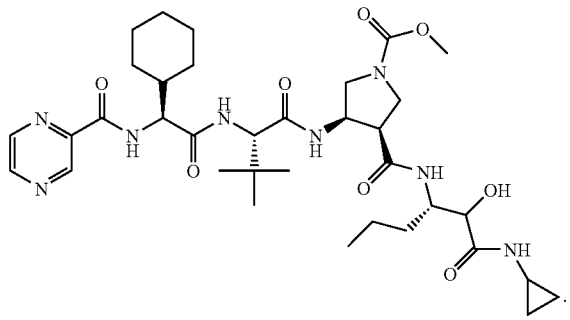 [SMILES: CCC[C@H](NC(=O)[C@@H]1CN(C(=O)OC)C[C@@H]1NC(=O)[C@@H](NC(=O)[C@@H](NC(=O)c1cnccn1)C1CCCCC1)C(C)(C)C)C(O)C(=O)NC1CC1]

To a solution of the product from Part B (40 mg, 0.073 mmol) in 5 mL of dichloromethane was added EDC (21 mg, 0.10 mmol) and HOBT (16 mg, 0.110 mmol) and the resulting solution stirred at 25° C. for 20 minutes. Then, Hunig's base (38 uL, 0.220 mmol) and 3-amino-N-cyclopropyl-2-hydroxyhexanamide (WO2002018369-A2; Example 119, cpd xiii') (16 mg, 0.088 mmol) was added and the reaction continued for 2 hours at room temperature. The reaction mixture was partitioned between water and dichloromethane. The organic layer was removed and dried over MgSO$_4$, filtered and concentrated in vacuo to afford a foam that was purified by flash chromatography on SiO$_2$ using methanol in dichloromethane as the mobile phase to afford the title compound as a white solid (28 mg, 55% yield). MS (ESI+) m/z=715 (M+H)+; MS (ESI−) m/z=713 (M−H)−.

Part D. Preparation of Title Product

To a solution of the product from Part C (52 mg, 0.073 mmol) in 5 mL of dichloromethane was added Dess-Martin periodinane (46 mg, 0.1098 mmol) for 1 hour. The reaction was quenched with Na$_2$S$_2$O$_3$ (sat. aqueous) and the product was extracted into methylene chloride (3×30 mL), dried over MgSO$_4$, filtered and concentrated in vacuo to afford a white solid that was purified by prep TLC SiO$_2$, (1.0 mm×20 mm×20 mm) using methanol in dichloromethane as the mobile phase. The title product was isolated as white solid (15 mg, 28% yield). MS (ESI+) m/z=713 (M+H)+; MS (ESI−) m/z=711 (M−H)−.

Example 9

Preparation of

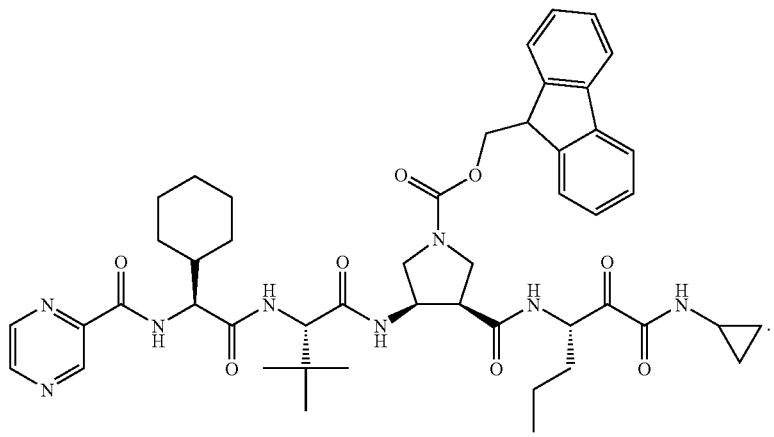 [SMILES: CCC[C@H](NC(=O)[C@@H]1CN(C(=O)OCC2c3ccccc3-c3ccccc32)C[C@@H]1NC(=O)[C@@H](NC(=O)[C@@H](NC(=O)c1cnccn1)C1CCCCC1)C(C)(C)C)C(=O)C(=O)NC1CC1]

Part A. Preparation of

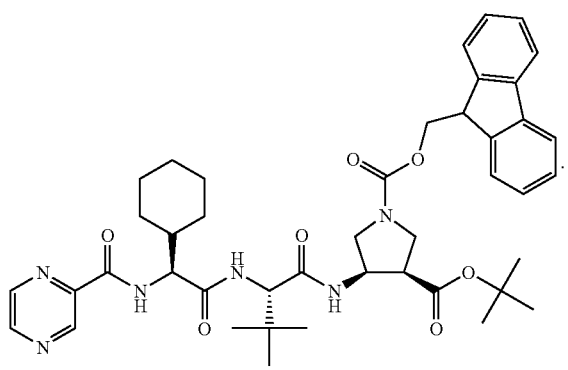 [SMILES: CC(C)(C)OC(=O)[C@@H]1CN(C(=O)OCC2c3ccccc3-c3ccccc32)C[C@@H]1NC(=O)[C@@H](NC(=O)[C@@H](NC(=O)c1cnccn1)C1CCCCC1)C(C)(C)C]

To a solution of the product from Example 3, Part B (50 mg, 0.092 mmol) in 4 mL of dichloromethane was added Hunig's base (48 uL, 0.274 mmol) and FMOC chloroformate (36 mg, 0.138 mmol). The reaction was stirred at 25° C. for 2 hours. The reaction mixture was partitioned between water and dichloromethane. The organic layer was removed and dried over $MgSO_4$, filtered, and concentrated in vacuo to afford a white solid (61 mg, 87% yield). MS (ESI+) m/z=767 (M+H)+

Part B. Preparation of

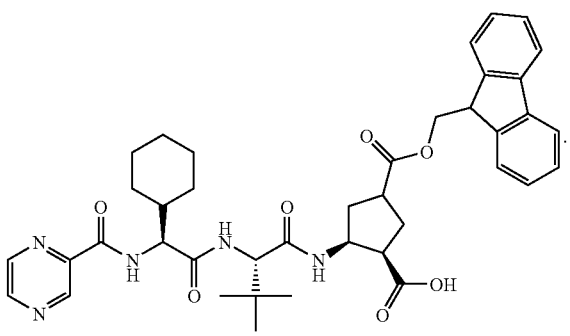 [SMILES: CC(C)(C)[C@H](NC(=O)[C@@H](NC(=O)c1cnccn1)C1CCCCC1)C(=O)N[C@H]1CC(C(=O)OCC2c3ccccc3-c3ccccc32)C[C@H]1C(=O)O]

To a solution of the product from Part A (60 mg, 0.078 mmol) in 5 mL of dichloromethane was added 5 mL of TFA. The reaction mixture was stirred for 2 hours and then concentrated in vacuo to afford a solid that was placed on high vacuum overnight. The reaction mixture was partitioned between water and dichloromethane. The organic layer was removed and dried over $MgSO_4$, filtered and concentrated in vacuo to afford a white solid (43 mg, 77% yield). MS (ESI+) m/z=711 (M+H)+.

Part C. Preparation of

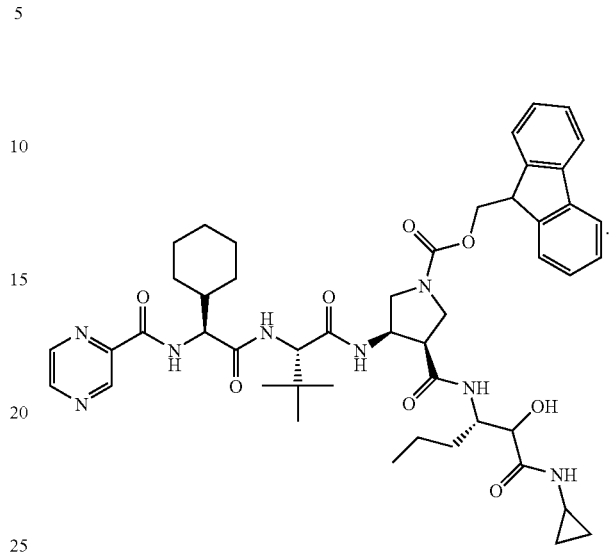

To a solution of the product Part B (39 mg, 0.054 mmol) in 5 mL of dichloromethane was added EDC (16 mg, 0.081 mmol) and HOBT (11 mg, 0.081 mmol) and the resulting solution stirred at 25° C. for 20 minutes. Then, Hunig's base (85 uL, 0.488 mmol) and 3-amino-N-cyclopropyl-2-hydroxyhexanamide (WO2002018369-A2; Example 119, cpd xiii') (12 mg, 0.065 mmol) was added and the reaction continued for 2 hours at room temperature. The reaction mixture was partitioned between water and dichloromethane. The organic layer was removed and dried over $MgSO_4$, filtered and concentrated in vacuo to afford a foam that was purified by flash chromatography on $SiO_2$ using methanol in dichloromethane as the mobile phase to afford the title compound as a white solid (17 mg, 36% yield). MS (ESI+) m/z=880 (M+H)+.

Part D. Preparation of Title Product

To a solution of the product from Part C (15 mg, 0.017 mmol) in 2 mL of dichloromethane was added Dess-Martin periodinane (11 mg, 0.026 mmol) for 1 hour. The reaction was quenched with $Na_2S_2O_3$ (sat. aqueous) and the product was extracted into methylene chloride (3×30 mL), dried over $MgSO_4$, filtered and concentrated in vacuo to afford a white solid that was purified by prep TLC $SiO_2$, (1.0 mm×20 mm×20 mm) using methanol in dichloromethane as the mobile phase. The title product was isolated as white solid (15 mg, 93% yield). MS (ESI+) m/z=877 (M+H)+; MS (ESI−) m/z=875 (M−H)−.

Example 10

Preparation of

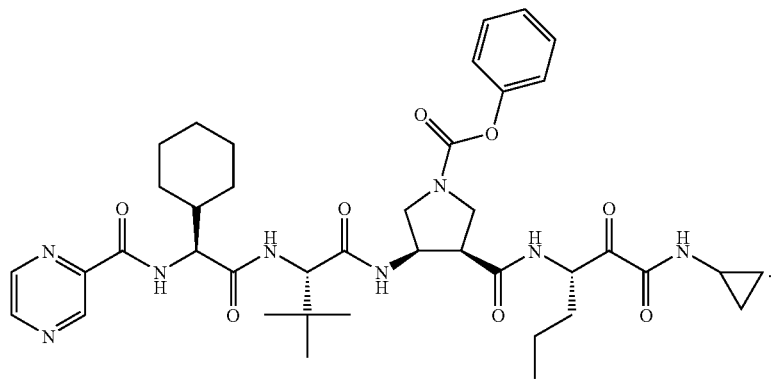 [SMILES: CCC[C@H](NC(=O)[C@@H]1CN(C(=O)Oc2ccccc2)C[C@@H]1NC(=O)[C@@H](NC(=O)[C@@H](NC(=O)c1cnccn1)C1CCCCC1)C(C)(C)C)C(=O)C(=O)NC1CC1]

Part A. Preparation of

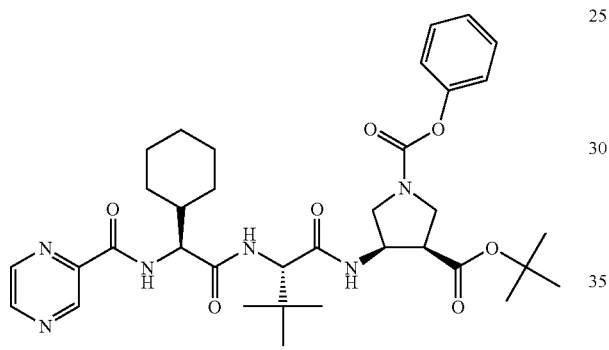

To a solution of the product from Example 3, Part B (50 mg, 0.086 mmol) in 5 mL of dichloromethane was added Hunig's base (45 uL, 0.258 mmol) and phenyl chloroformate (16 uL, 0.129 mmol). The reaction was stirred at 25° C. for 2 hours. The reaction mixture was partitioned between water and dichloromethane. The organic layer was removed and dried over $MgSO_4$, filtered, and concentrated in vacuo to afford white solid. MS (ESI+) m/z=665 (M+H)+; MS (ESI-) m/z=663 (M-H)-.

Part B. Preparation of

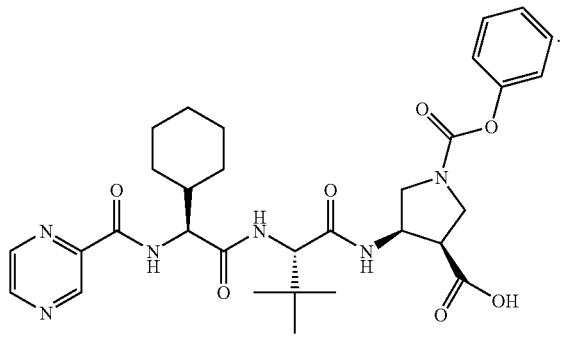 [SMILES: CC(C)(C)[C@H](NC(=O)[C@@H](NC(=O)c1cnccn1)C1CCCCC1)C(=O)N[C@H]1CN(C(=O)Oc2ccccc2)C[C@H]1C(=O)O]

The product from Part A was taken up in 5 mL of dichloromethane and 5 mL of TFA added. The reaction mixture was stirred for 2 hours and then concentrated in vacuo to afford a solid that was placed on high vacuum overnight. The reaction mixture was partitioned between water and dichloromethane. The organic layer was removed and dried over $MgSO_4$, filtered and concentrated in vacuo to afford a white solid. MS (ESI+) m/z=608 (M+H)+; MS (ESI-) m/z=607 (M-H)-.

Part C. Preparation of

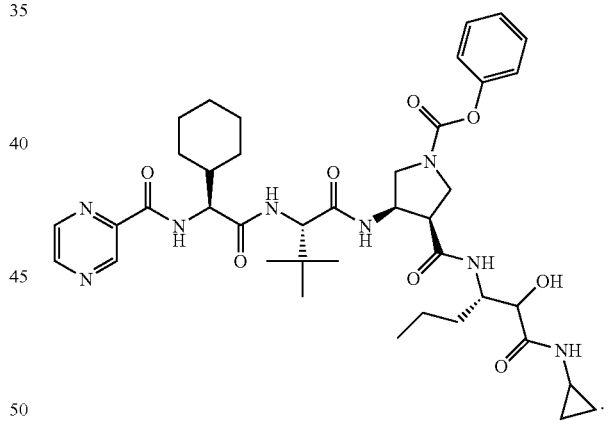

To a solution of the product from Part B (0.086 mmol) in 5 mL of dichloromethane was added EDC (21 mg, 0110 mmol) and HOBT (15 mg, 0.110 mmol) and the resulting solution stirred at 25° C. for 20 minutes. Then, Hunig's base (40 uL, 0.229 mmol) and 3-amino-N-cyclopropyl-2-hydroxyhexan amide (WO2002018369-A2; Example 119, cpd xiii') (18 mg, 0.097 mmol) was added and the reaction continued for 2 hours at room temperature. The reaction mixture was partitioned between water and dichloromethane. The organic layer was removed and dried over $MgSO_4$, filtered and concentrated in vacuo to afford a foam that was purified by flash chromatography on $SiO_2$ using methanol in dichloro methane as the mobile phase to afford the title compound as a white solid (25 mg, 37% yield). MS (ESI+) m/z=777 (M+H)+; MS (ESI-) m/z=775 (M-H)-.

Part D. Preparation of Title Product

To a solution of the product from Part C (18 mg, 0.023 mmol) in 2 mL of dichloromethane was added Dess-Martin periodinane (15 mg, 0.036 mmol) for 1 hour. The reaction was quenched with $Na_2S_2O_3$ (sat. aqueous) and the product was extracted into methylene chloride (3×30 mL), dried over $MgSO_4$, filtered and concentrated in vacuo to afford a white solid that was purified by prep TLC $SiO_2$, (1.0 mm×20 mm×20 mm) using methanol in dichloromethane as the mobile phase. The title product was isolated as a white solid (14 mg, 78% yield). MS (ESI+) m/z=775 (M+H)+; MS (ESI−) m/z=773 (M−H)−.

Example 11

Preparation of

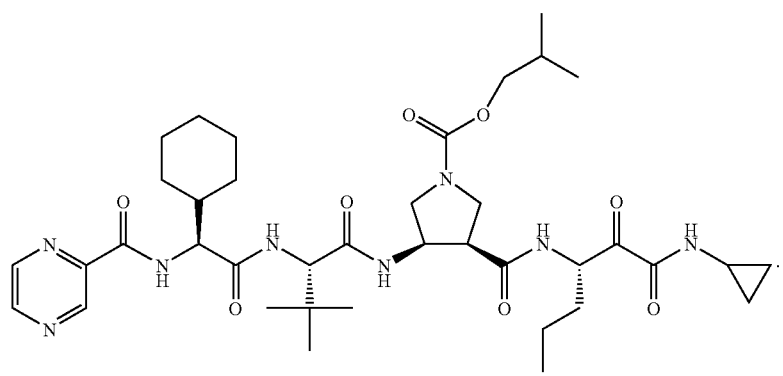 [SMILES: CCC[C@H](NC(=O)[C@@H]1CN(C(=O)OCC(C)C)C[C@@H]1NC(=O)[C@@H](NC(=O)[C@@H](NC(=O)c1cnccn1)C1CCCCC1)C(C)(C)C)C(=O)C(=O)NC1CC1]

Part A. Preparation of

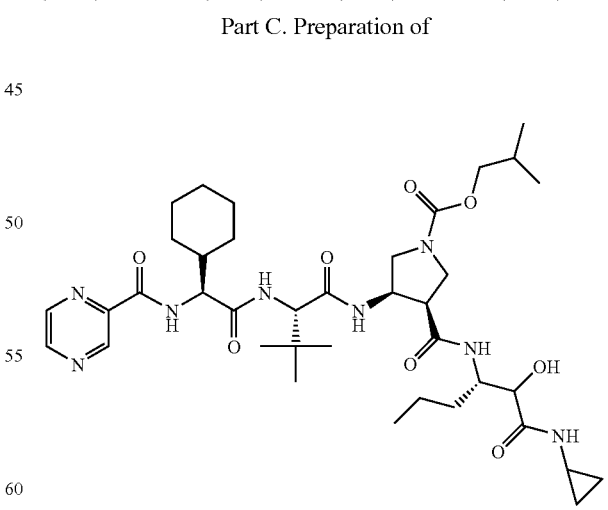

To a solution of the product from Example 3, Part B (50 mg, 0.086 mmol) in 5 mL of dichloromethane was added Hunig's base (45 uL, 0.258 mmol) and isobutyl chloroformate (17 uL, 0.129 mmol). The reaction was stirred at 25° C. for 2 hours. The reaction mixture was partitioned between water and dichloromethane. The organic layer was removed and dried over $MgSO_4$, filtered, and concentrated in vacuo to afford white solid. MS (ESI+) m/z=645 (M+H)+; MS (ESI−) m/z=643 (M−H)−.

Part B. Preparation of

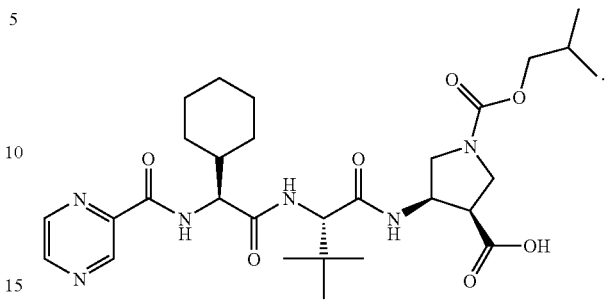

The product from Part A was taken up in 5 mL of dichloromethane and 5 mL of TFA added. The reaction mixture was stirred for 2 hours and then concentrated in vacuo to afford a solid that was placed on high vacuum overnight. The reaction mixture was partitioned between water and dichloromethane. The organic layer was removed and dried over $MgSO_4$, filtered and concentrated in vacuo to afford a white solid. MS (ESI+) m/z=589 (M+H)+; MS (ESI−) m/z=587 (M−H)−.

Part C. Preparation of

To a solution of the product from Part B (0.086 mmol) in 5 mL of dichloromethane was added EDC (21 mg, 0110 mmol) and HOBT (15 mg, 0.110 mmol) and the resulting solution stirred at 25° C. for 20 minutes. Then, Hunig's base (40 uL, 0.229 mmol) and 3-amino-N-cyclopropyl-2-hydroxyhexanamide (WO2002018369-A2; Example 119, cpd xiii') (18 mg, 0.097 mmol) was added and the reaction continued for 2 hours at room temperature. The reaction mixture was partitioned between water and dichloromethane. The organic layer was removed and dried over $MgSO_4$, filtered and concentrated in vacuo to afford a foam that was purified by flash chromatography on $SiO_2$ using methanol in dichloromethane as the mobile phase to afford the title compound as a white solid (39 mg, 61% yield). MS (ESI+) m/z=757 (M+H)+; MS (ESI−) m/z=755 (M−H)−.

Part D. Preparation of Title Product

To a solution of the product of Part C (17 mg, 0.023 mmol) in 2 mL of dichloromethane was added Dess-Martin periodinane (15 mg, 0.036 mmol) for 1 hour. The reaction was quenched with $Na_2S_2O_3$ (sat. aqueous) and the product was extracted into methylene chloride (3×30 mL), dried over $MgSO_4$, filtered and concentrated in vacuo to afford a white solid that was purified by prep TLC $SiO_2$, 1.0 mm×20 mm×20 mm using methanol in dichloromethane as the mobile phase. The title product was isolated as a white solid (15 mg, 86% yield). MS (ESI+) m/z=755 (M+H)+; MS (ESI−) m/z=753 (M−H)−.

Example 12

Preparation of

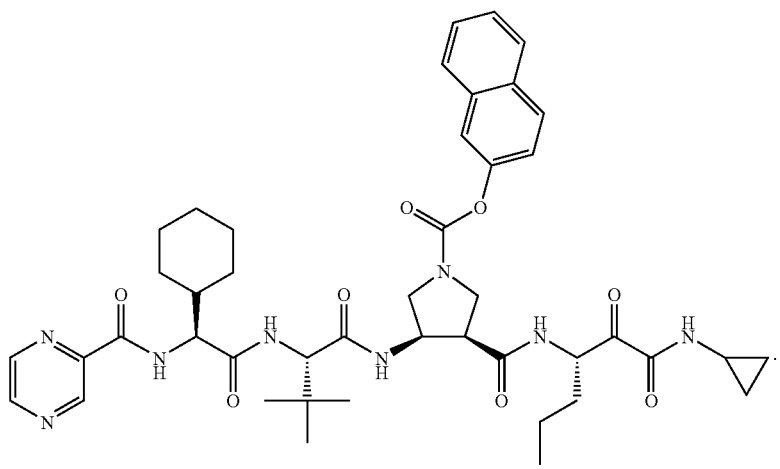 [SMILES: CCC[C@H](NC(=O)[C@@H]1CN(C(=O)Oc2ccc3ccccc3c2)C[C@@H]1NC(=O)[C@@H](NC(=O)[C@@H](NC(=O)c1cnccn1)C1CCCCC1)C(C)(C)C)C(=O)C(=O)NC1CC1]

Part A. Preparation of

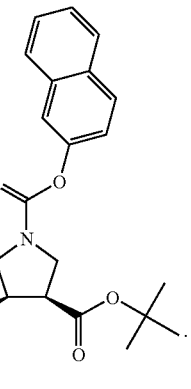

To a solution of the product from Example 3, Part B (50 mg, 0.086 mmol) in 5 mL of dichloromethane was added Hunig's base (45 uL, 0.258 mmol) and 2-naphthyl chloroformate (26 mg, 0.129 mmol). The reaction was stirred at 25° C. for 2 hours. The reaction mixture was partitioned between water and dichloromethane. The organic layer was removed and dried over $MgSO_4$, filtered, and concentrated in vacuo to afford white solid. MS (ESI+) m/z=715 (M+H)+; MS (ESI−) m/z=713 (M−H)−.

Part B. Preparation of

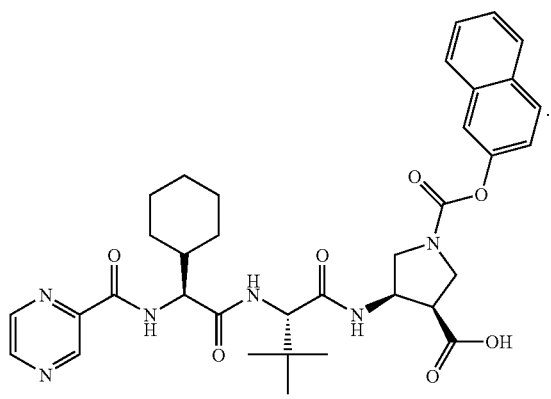 [SMILES: CC(C)(C)[C@H](NC(=O)[C@@H](NC(=O)c1cnccn1)C1CCCCC1)C(=O)N[C@H]1CN(C(=O)Oc2ccc3ccccc3c2)C[C@H]1C(=O)O]

The product from Part A was taken up in 5 mL of dichloromethane and 5 mL of TFA added. The reaction mixture was stirred for 2 hours and then concentrated in vacuo to afford a solid that was placed on high vacuum overnight. The reaction mixture was partitioned between water and dichloromethane. The organic layer was removed and dried over MgSO₄, filtered and concentrated in vacuo to afford a white solid. MS (ESI+) m/z=659 (M+H)+; MS (ESI−) m/z=657 (M−H)−.

Part C. Preparation of

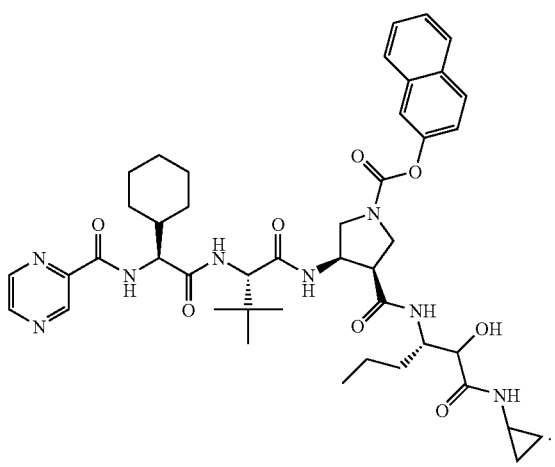 [SMILES: CCC[C@H](NC(=O)[C@@H]1CN(C(=O)Oc2ccc3ccccc3c2)C[C@@H]1NC(=O)[C@@H](NC(=O)[C@@H](NC(=O)c1cnccn1)C1CCCCC1)C(C)(C)C)C(O)C(=O)NC1CC1]

To a solution of the product from Part B (0.086 mmol) in 5 mL of dichloromethane was added EDC (21 mg, 0110 mmol) and HOBT (15 mg, 0.110 mmol) and the resulting solution stirred at 25° C. for 20 minutes. Then, Hunig's base (40 uL, 0.229 mmol) and 3-amino-N-cyclopropyl-2-hydroxyhexanamide (WO2002018369-A2; Example 119, cpd xiii') (18 mg, 0.097 mmol) was added and the reaction continued for 2 hours at room temperature. The reaction mixture was partitioned between water and dichloromethane. The organic layer was removed and dried over MgSO₄, filtered and concentrated in vacuo to afford a foam that was purified by flash chromatography on SiO₂ using methanol in dichloromethane as the mobile phase to afford the title compound as a white solid (18 mg, 25% yield). MS (ESI+) m/z=827 (M+H)+; MS (ESI−) m/z=825 (M−H)−.

Part D. Preparation of Title Product

To a solution of the product from Part C (19 mg, 0.023 mmol) in 2 mL of dichloromethane was added Dess-Martin periodinane (15 mg, 0.036 mmol) for 1 hour. The reaction was quenched with Na₂S₂O₃ (sat. aqueous) and the product was extracted into methylene chloride (3×30 mL), dried over MgSO₄, filtered and concentrated in vacuo to afford a white solid that was purified by prep TLC SiO₂, (1.0 mm×20 mm×20 mm using methanol in dichloromethane as the mobile phase. The title product was isolated as white solid (12 mg, 65% yield). MS (ESI+) m/z=825 (M+H)+; MS (ESI−) m/z=823 (M−H)−.

Example 13

Preparation of

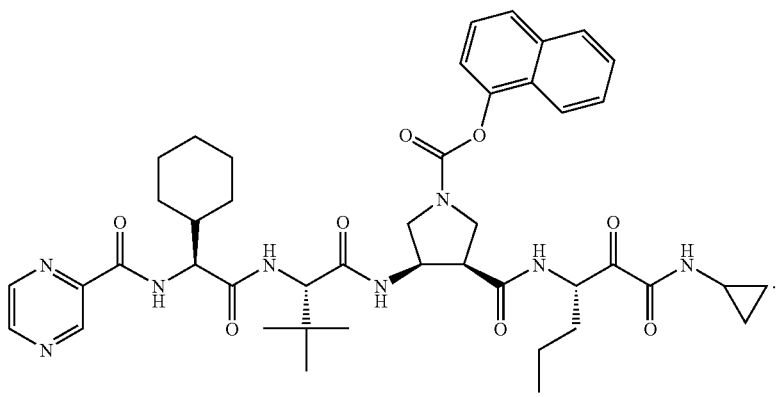 [SMILES: CCC[C@H](NC(=O)[C@@H]1CN(C(=O)Oc2cccc3ccccc23)C[C@@H]1NC(=O)[C@@H](NC(=O)[C@@H](NC(=O)c1cnccn1)C1CCCCC1)C(C)(C)C)C(=O)C(=O)NC1CC1]

Part A. Preparation of

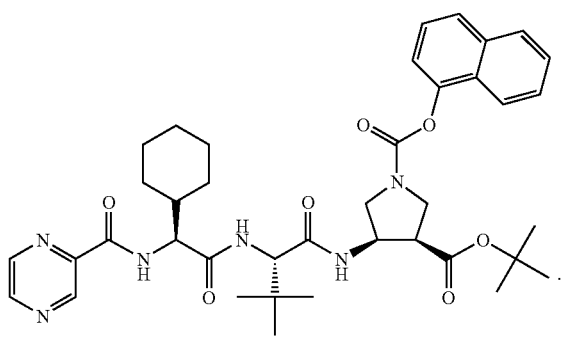 [SMILES: CC(C)(C)OC(=O)[C@@H]1CN(C(=O)Oc2cccc3ccccc23)C[C@@H]1NC(=O)[C@@H](NC(=O)[C@@H](NC(=O)c1cnccn1)C1CCCCC1)C(C)(C)C]

To a solution of the product from Example 3, Part B (50 mg, 0.086 mmol) in 5 mL of dichloromethane was added Hunig's base (45 uL, 0.258 mmol) and 1-naphthyl chloroformate (21 uL, 0.129 mmol). The reaction was stirred at 25° C. for 2 hours. The reaction mixture was partitioned between water and dichloromethane. The organic layer was removed and dried over MgSO$_4$, filtered, and concentrated in vacuo to afford white solid. MS (ESI+) m/z=715 (M+H)+; MS (ESI−) m/z=713 (M−H)−.

Part B. Preparation of

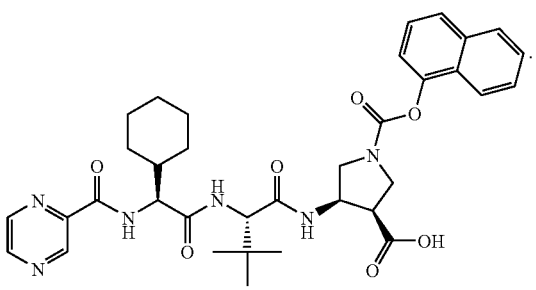

The product from Part A was taken up in 5 mL of dichloromethane and 5 mL of TFA added. The reaction mixture was stirred for 2 hours and then concentrated in vacuo to afford a solid that was placed on high vacuum overnight. The reaction mixture was partitioned between water and dichloromethane. The organic layer was removed and dried over MgSO$_4$, filtered and concentrated in vacuo to afford white solid (43 mg, 77% yield) MS (ESI+) m/z=659 (M+H)+; MS (ESI−) m/z=657 (M−H)−

Part C. Preparation of

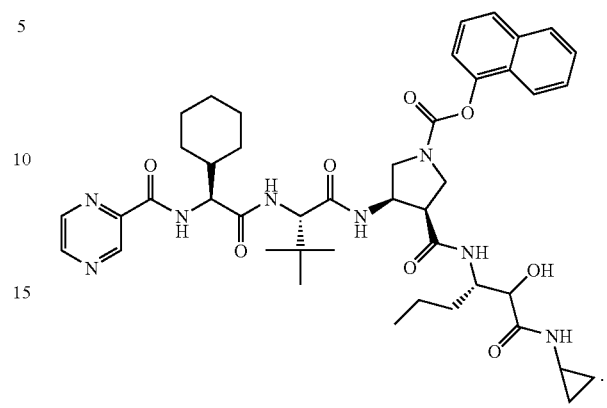

To a solution of the product from Part B (0.086 mmol) in 5 mL of dichloromethane was added EDC (21 mg, 0110 mmol) and HOBT (15 mg, 0.110 mmol) and the resulting solution stirred at 25° C. for 20 minutes. Then, Hunig's base (40 uL, 0.229 mmol) and 3-amino-N-cyclopropyl-2-hydroxyhexanamide (WO2002018369-A2; Example 119, cpd xiii') (18 mg, 0.097 mmol) was added and the reaction continued for 2 hours at room temperature. The reaction mixture was partitioned between water and dichloromethane. The organic layer was removed and dried over MgSO$_4$, filtered and concentrated in vacuo to afford a foam that was purified by flash chromatography on SiO$_2$ using methanol in dichloromethane as the mobile phase to afford the title compound as a white solid (39 mg, 55% yield). MS (ESI+) m/z=827 (M+H)+; MS (ESI−) m/z=825 (M−H)−.

Part D. Preparation of Title Product

To a solution of the product from Part C (19 mg, 0.023 mmol) in 2 mL of dichloromethane was added Dess-Martin periodinane (15 mg, 0.036 mmol) for 1 hour. The reaction was quenched with Na$_2$S$_2$O$_3$ (sat. aqueous) and the product was extracted into methylene chloride (3×30 mL), dried over MgSO$_4$, filtered and concentrated in vacuo to afford a white solid that was purified by prep TLC SiO$_2$, (1.0 mm×20 mm×20 mm) using methanol in dichloromethane as the mobile phase. The title product was isolated as white solid (14 mg, 75% yield). MS (ESI+) m/z=825 (M+H)+; MS (ESI−) m/z=823 (M−H)−.

Example 14

Preparation of

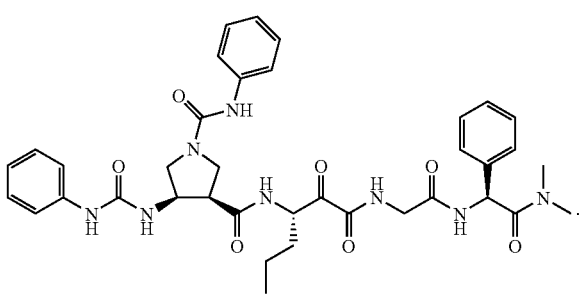 [SMILES: CCC[C@H](NC(=O)[C@@H]1CN(C(=O)Nc2ccccc2)C[C@@H]1NC(=O)Nc1ccccc1)C(=O)C(=O)NCC(=O)N[C@H](C(=O)N(C)C)c1ccccc1]

Part A. Preparation of

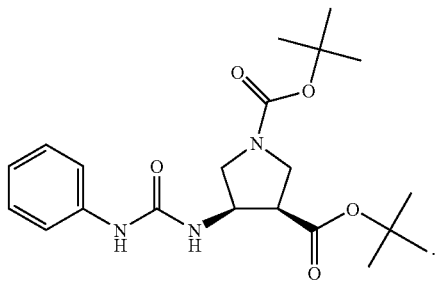 [SMILES: CC(C)(C)OC(=O)[C@@H]1CN(C(=O)OC(C)(C)C)C[C@@H]1NC(=O)Nc1ccccc1]

To a solution of the (3R,4R)-di-tert-butyl 4-aminopyrrolidine-1,3-dicarboxylate (*Org. Biomol. Chem.* 2004, 2, 2763-2776) (200 mg, 0.698 mmol) in 5 mL of dichloromethane was added phenyl isocyanate (75 uL, 0.698 mmol) and the reaction mixture was stirred for 18 hours. The reaction mixture was partitioned between water and dichloromethane. The organic layer was removed and dried over MgSO$_4$, filtered and concentrated in vacuo to afford a white solid. MS (ESI+) m/z=406 (M+H)+; MS (ESI−) m/z=404 (M−H)−.

Part B. Preparation of

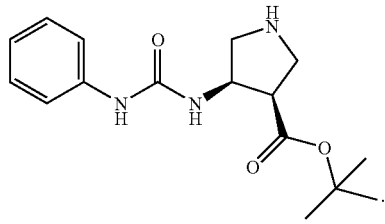 [SMILES: CC(C)(C)OC(=O)[C@@H]1CNC[C@@H]1NC(=O)Nc1ccccc1]

To a solution of the product from Part A (220 mg, 0.543 mmol) in 10 mL of ethyl acetate was added 4N HCl (1.36 mL, 5.42 mmol) and the reaction mixture was stirred for 18 hours. Then the solution was concentrated in vacuo and triturated with dichloromethane and hexanes resulting in off white solid. MS (ESI+) m/z=306 (M+H)+.

Part C. Preparation of

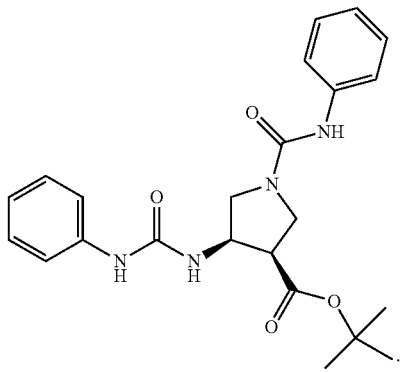 [SMILES: CC(C)(C)OC(=O)[C@@H]1CN(C(=O)Nc2ccccc2)C[C@@H]1NC(=O)Nc1ccccc1]

To a solution of the amine product from Part B (92 mg, 0.301 mmol), Hunig's base (157 uL, 0.904 mmol) and 4 mL of dichloromethane was added phenyl isocyanate (32 uL, 0.301 mmol) and the reaction mixture stirred for 18 hours. The reaction mixture was poured over water and extracted with dichloromethane (3×30 mL). The combined organic layers were dried over MgSO$_4$, filtered and concentrated in vacuo to afford a foam that was purified by flash chromatography on SiO$_2$ using methanol in dichloromethane as the mobile phase. The title compound was isolated as a white solid (65 mg, 51% yield). MS (ESI+) m/z=425 (M+H)+; MS (ESI−) m/z=423 (M−H)−.

Part D. Preparation of

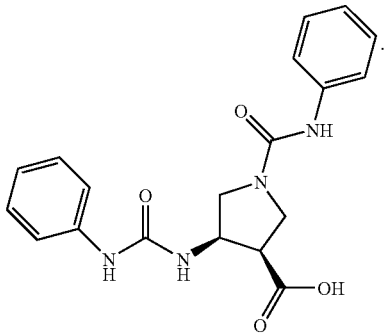 [SMILES: O=C(Nc1ccccc1)N[C@H]1CN(C(=O)Nc2ccccc2)C[C@H]1C(=O)O]

The product from Part C (47 mg, 0.111 mmol) was taken up in 4 mL of dichloromethane and 4 mL of TFA added. The reaction mixture was stirred for 2 hours and then concentrated in vacuo to afford a solid that was placed on high vacuum overnight. The reaction mixture was partitioned between water and dichloromethane. The organic layer was removed and dried over MgSO$_4$, filtered and concentrated in vacuo to afford a white solid (36 mg, 88% yield). MS (ESI+) m/z=368 (M+H)+.

Part E. Preparation of

To a solution of the product from Part D (41 mg, 0.111 mmol) in 5 mL of dichloromethane was added EDC (32 mg, 0.166 mmol) and HOBT (22 mg, 0.166 mmol) and the resulting solution stirred at 25° C. for 20 minutes. Then, Hunig's base (58 uL, 0.332 mmol) and hydroxyamide (WO2003062265-A2; Example 6, cpd 2.3) (53 mg, 0.133 mmol) was added and the reaction continued for 2 hours at room temperature. The reaction mixture was partitioned between water and dichloromethane. The organic layer was removed and dried over MgSO$_4$, filtered and concentrated in vacuo to afford a foam that was purified by flash chromatography on SiO$_2$ using methanol in dichloromethane as the mobile phase to afford the title compound as a white solid (43 mg, 54% yield). MS (ESI+) m/z=715 (M+H)+; MS (ESI−) m/z=713 (M−H)−.

Part F. Preparation of Title Product

To a solution of the product from Part E (40 mg, 0.056 mmol) in 4 mL of dichloromethane was added Dess-Martin periodinane (36 mg, 0.084 mmol) for 1 hour. The reaction was quenched with Na$_2$S$_2$O$_3$ (sat. aqueous) and the product was extracted into methylene chloride (3×30 mL), dried over MgSO$_4$, filtered and concentrated in vacuo to afford a white solid that was purified by prep TLC SiO$_2$, (1.0 mm×20 mm×20 mm) using methanol in dichloromethane as the mobile phase. The title product was isolated as white solid (16 mg, 40% yield). MS (ESI+) m/z=713 (M+H)+; MS (ESI−) m/z=711 (M−H)−.

Example 15

Preparation of

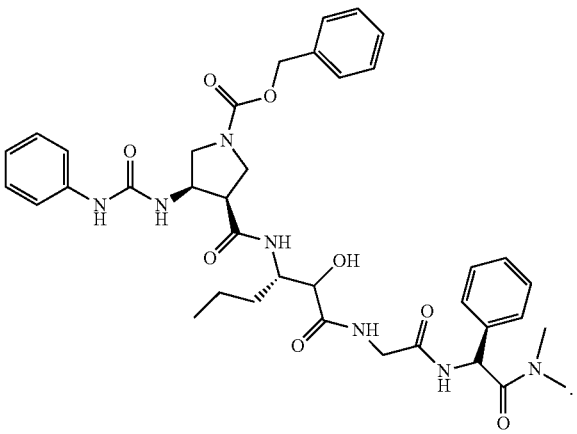

Part A. Preparation of

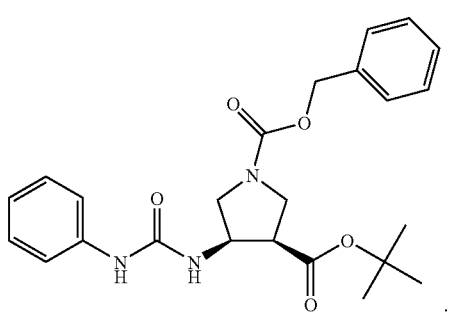 [SMILES: CC(C)(C)OC(=O)[C@@H]1CN(C(=O)OCc2ccccc2)C[C@@H]1NC(=O)Nc1ccccc1]

The product from Example 14, Part B (92 mg, 0.301 mmol) was taken up in 5 mL of dichloromethane and treated with Hunig's base (157 uL, 0.904 mmol) followed by the addition of CBZ-NOS (75 mg, 0.301 mmol) and the reaction mixture stirred for 18 hours. The reaction mixture was partitioned between water and dichloromethane. The organic layer was removed and dried over MgSO$_4$, filtered and concentrated in vacuo to afford a white solid (55 mg, 41% yield). MS (ESI+) m/z=440 (M+H)+; MS (ESI−) m/z=438 (M−H)−.

Part B. Preparation of

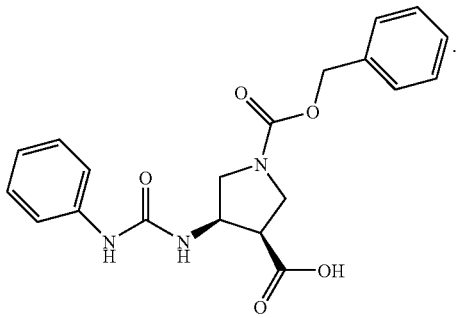 [SMILES: O=C(Nc1ccccc1)N[C@H]1CN(C(=O)OCc2ccccc2)C[C@H]1C(=O)O]

The product from Part A (50 mg, 0.114 mmol) was taken up in 2 mL of dichloromethane and 2 mL of TFA added. The reaction mixture was stirred for 2 hours and then concentrated in vacuo to afford a solid that was placed on high vacuum overnight. The reaction mixture was partitioned between water and dichloromethane. The organic layer was removed and dried over MgSO$_4$, filtered and concentrated in vacuo to afford white solid (38 mg, 88% yield). MS (ESI+) m/z=384 (M+H)+; MS (ESI−) m/z=382 (M−H)−

Part C. Preparation of:

To a solution of the product from Part B (43 mg, 0.114 mmol) in 4 mL of dichloromethane was added EDC (33 mg, 0.17 mmol) and HOBT (23 mg, 0.171 mmol) and the resulting solution stirred at 25° C. for 20 minutes. Then, Hunig's base (60 uL, 0.341 mmol) and hydroxyamide (WO2003062265-A2; Example 6, cpd 2.3) (55 mg, 0.137 mmol) was added and the reaction continued for 2 hours at room temperature. The reaction mixture was partitioned between water and dichloromethane. The organic layer was removed and dried over MgSO$_4$, filtered and concentrated in vacuo to afford a foam that was purified by flash chromatography on SiO$_2$ using methanol in dichloromethane as the mobile phase to afford the title compound as a white solid (70 mg, 85% yield). MS (ESI+) m/z=715 (M+H)+; MS (ESI−) m/z=713 (M−H)−.

Part D. Preparation of Title Product

To a solution of the product from Part C (20 mg, 0.027 mmol) in 4 mL of dichloromethane was added Dess-Martin periodinane (17 mg, 0.041 mmol) for 1 hour. The reaction was quenched with Na₂S₂O₃ (sat. aqueous) and the product was extracted into methylene chloride (3×30 mL), dried over MgSO₄, filtered and concentrated in vacuo to afford a white solid that was purified by prep TLC SiO₂, (1.0 mm×20 mm×20 mm) using methanol in dichloromethane as the mobile phase. The title product was isolated as a white solid (16 mg, 80% yield). MS (ESI+) m/z=728 (M+H)+; MS (ESI−) m/z=726 (M−H)−

Example 16

Preparation of N—((S)-1-cyclohexyl-2-((S)-1-((1S,2R)-2-((S)-1-(cyclopropyl amino)-1,2-dioxohexan-3-ylcarbamoyl)cyclopentylamino)-3,3-dimethyl-1-oxobutan-2-ylamino)-2-oxo ethyl)pyrazine-2-carboxamide

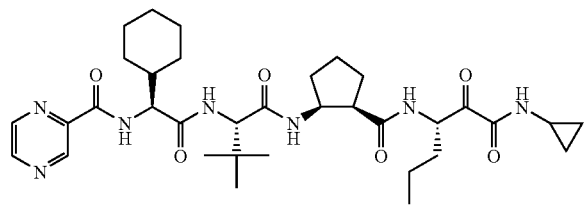 [SMILES: CCC[C@H](NC(=O)[C@@H]1CCC[C@@H]1NC(=O)[C@@H](NC(=O)[C@@H](NC(=O)c1cnccn1)C1CCCCC1)C(C)(C)C)C(=O)C(=O)NC1CC1]

Part A. Preparation of (1R,2S)-methyl 2-aminocyclopentanecarboxylate

To a solution of (1R,2S)-2-aminocyclopentanecarboxylic acid (0.15 g, 0.9 mmol) in methanol (5 mL) was added 4N HCl in dioxane (1 mL) and the reaction mixture was stirred at reflux overnight. The reaction mixture was concentrated in vacuo to afford an oil which was used directly for the next step.

Part B. Preparation of (1R,2S)-methyl 2-((S)-2-((S)-2-cyclohexyl-2-(pyrazine-2-carboxamido)acetamido)-3,3-dimethylbutanamido)cyclopentanecarboxylate To a solution of the product from Example 1, Part G (0.148 g, 0.394 mmol) in methylene chloride (5 mL) was added EDC (0.091 g, 0.474 mmol) and HOBT (0.064 g, 0.474 mmol) and the resulting solution stirred at 25° C. for 20 minutes. Then, Hunig's base (0.151 mL, 0.87 mmol) and (1R, 2S)-methyl 2-aminocyclopentanecarboxylate (0.071 g, 0.395 mmol) was added and the reaction continued for 18 hours at room temperature. The reaction mixture was partitioned between water and dichloromethane. The organic layer was removed and dried over MgSO₄, filtered and concentrated in vacuo to afford a foam that was purified by flash chromatography on SiO₂ using 0-5% methanol in dichloromethane as the mobile phase to afford the title compound as a white solid (104 mg, 52% yield). MS (ESI+) m/z=502 (M+H)+.

Part C. Preparation of (1R,2S)-2-((S)-2-((S)-2-cyclohexyl-2-(pyrazine-2-carboxamido) acetamido)-3,3-dimethylbutanamido)cyclopentanecarboxylic acid A solution of the product from Part B (0.104 g, 0.207 mmol) in ethanol (10 mL) was treated with sodium hydroxide (1N, 2 mL) for 2 h room temperature. The solution was neutralized with 1N HCl and extracted with dichloromethane (3×30 mL), dried over MgSO₄, filtered and concentrated in vacuo to afford a white solid (77 mg, 76%) which was used directly for the next step. MS (DCI/NH₄) m/z=488 (M+H)+; MS (DCI/NH₄) m/z=505 (M+NH4)+.

Part D. Preparation of N-((1S)-1-cyclohexyl-2-((2S)-1-((1S,2R)-2-(1-(cyclopropylamino)-2-hydroxy-1-oxohexan-3-ylcarbamoyl)cyclopentylamino)-3,3-dimethyl-1-oxobutan-2-ylamino)-2-oxoethyl) pyrazine-2-carboxamide To a solution containing the product from Part C (0.077 g, 0.158 mmol) in dichloromethane (5 mL) was added 1-(3-dimethylaminopropyl)-3-ethylcarbodiimide hydrochloride EDC (0.036 g, 0.189 mmol) and 1-hydroxybenzotriazole HOBT (25.6 mg, 0.189 mmol) and the resulting solution stirred at 25° C. for 30 minutes. Then 3-amino-N-cyclopropyl-2-hydroxyhexanamide (WO2002018369-A2; Example 119, cpd xiii') (29 mg, 0.158 mmol) and Hunig's base (0.06 mL, 0.347 mmol) was added and the reaction mixture stirred for 3 hours. The reaction mixture was partitioned between 1N HCl and dichloromethane. The organic layer was removed and dried over MgSO₄, filtered and concentrated in vacuo to afford a foam (97 mg, 93%). MS (ESI+) m/z=656 (M+H)+; MS (ESI−) m/z=654 (M−H)−.

Part E. Preparation of Title Product

To a solution of the product from Part D (68 mg, 0.104 mmol) in 5 mL of dichloromethane was added Dess-Martin periodinane (65 mg, 0.156 mmol) for 1 hour. The reaction was quenched with Na₂S₂O₃ (sat. aqueous) and the product was extracted into methylene chloride (3×30 mL), dried over MgSO₄, filtered and concentrated in vacuo to afford a white solid that was purified by prep TLC SiO₂, (1.0 mm×20 mm×20 mm) using methanol in dichloromethane as the mobile phase. The title product was isolated as a white solid (44 mg, 65% yield). MS (ESI+) m/z=654 (M+H)+; MS (ESI−) m/z=652 (M−H)−

Example 17

Preparation of N-((1S)-1-cyclohexyl-2-((2S)-1-((1S,2R)-2-(1-(cyclopropyl amino)-1,2-dioxohexan-3-ylcarbamoyl)cyclopentylamino)-3,3-dimethyl-1-oxobutan-2-ylamino)-2-oxoethyl)pyrazine-2-carboxamide mixture stirred for 1 hour. The reaction was quenched with $Na_2S_2O_3$ (sat. aqueous) and the product was extracted into methylene chloride (3×30 mL), dried over $MgSO_4$, filtered and concentrated in vacuo to afford a foam that was purified by prep TLC $SiO_2$, (1.0 mm×20 mm×20 mm) using methanol in dichloromethane as the mobile phase. The title product was isolated as a white solid (mg, % yield). MS (ESI+) m/z=(M+H)+; MS (ESI−) m/z=(M−H)−.

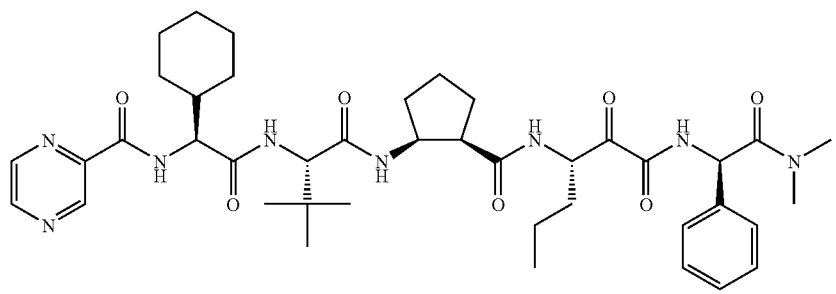 [SMILES: CCC[C@H](NC(=O)[C@@H]1CCC[C@@H]1NC(=O)[C@@H](NC(=O)[C@@H](NC(=O)c1cnccn1)C1CCCCC1)C(C)(C)C)C(=O)C(=O)N[C@@H](C(=O)N(C)C)c1ccccc1]

Part A. Preparation of

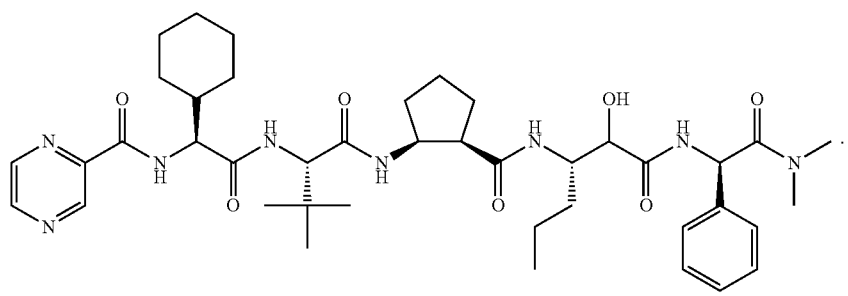 [SMILES: CCC[C@H](NC(=O)[C@@H]1CCC[C@@H]1NC(=O)[C@@H](NC(=O)[C@@H](NC(=O)c1cnccn1)C1CCCCC1)C(C)(C)C)C(O)C(=O)N[C@@H](C(=O)N(C)C)c1ccccc1]

To a solution of the product from Example 16, Part C (43 mg, 0.087 mmol) in 5 mL of dichloromethane was added EDC (25 mg, 0.087 mmol) and HOBT (18 mg, 0.13 mmol) and the resulting solution stirred at 25° C. for 20 minutes. Then, Hunig's base (45 uL, 0.261 mmol) and hydroxyamide (WO2003062265-A2; Example 6, cpd 2.3) (35 mg, 0.087 mmol) was added and the reaction continued for 2 hours at room temperature. The reaction mixture was partitioned between water and dichloromethane. The organic layer was removed and dried over $MgSO_4$, filtered and concentrated in vacuo to afford a foam that was purified by flash chromatography on $SiO_2$ using methanol in dichloromethane as the mobile phase to afford the title compound as a white solid (40 mg, 55% yield). MS (ESI+) m/z=(M+H)+; MS (ESI−) m/z=(M−H)−.

Part B. Preparation of Title Product

To a solution of the product from Part A (30 mg, 0.036 mmol) in dichloromethane (mL) was added Dess-Martin periodine (23 mg, 0.054 mmol) at 25° C. and the reaction

Example 18

Preparation of N-((1S)-1-cyclohexyl-2-((2S)-1-((1S,2R)-2-(1-(cyclopropyl amino)-1,2-dioxohexan-3-ylcarbamoyl)cyclohexylamino)-3,3-dimethyl-1-oxobutan-2-ylamino)-2-oxoethyl)pyrazine-2-carboxamide

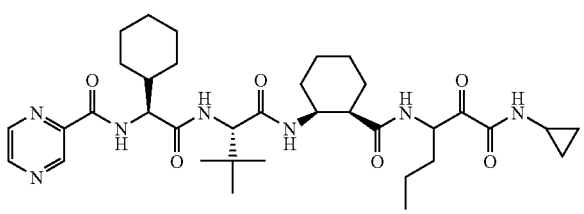 [SMILES: CCCC(NC(=O)[C@@H]1CCCC[C@@H]1NC(=O)[C@@H](NC(=O)[C@@H](NC(=O)c1cnccn1)C1CCCCC1)C(C)(C)C)C(=O)C(=O)NC1CC1]

Part A. Preparation of (1R,2S)-methyl 2-aminocyclohexanecarboxylate

To a solution of (1R,2S)-2-aminocyclohexanecarboxylic acid (0.13 g, 0.91 mmol) in methanol (5 mL) was added 4N HCl in dioxane (1 mL) and the reaction mixture was stirred at reflux overnight. The reaction mixture was concentrated in vacuo to afford an oil which was used directly for the next step.

Part B. Preparation of (1R,2S)-methyl 2-((S)-2-((S)-2-cyclohexyl-2-(pyrazine-2-carboxamido)acetamido)-3,3-dimethylbutanamido)cyclohexanecarboxylate To a solution of the product from Example 1, Part G (0.342 g, 0.9 mmol) in methylene chloride (10 mL) was added EDC (0.21 g, 1.09 mmol) and HOBT (0.147 g, 1.09 mmol) and the resulting solution stirred at 25° C. for 20 minutes. Then, Hunig's base (0.347 mL, 1.99 mmol) and –154 (crude from above) was added and the reaction continued for 18 hours at room temperature. The reaction mixture was partitioned between water and dichloromethane. The organic layer was removed and dried over MgSO$_4$, filtered and concentrated in vacuo to afford a foam that was purified by flash chromatography on SiO$_2$ using 0-5% methanol in dichloromethane as the mobile phase to afford the title compound as a white solid (327 mg, 70% yield). MS (ESI+) m/z=516 (M+H)+.

Part C. Preparation of (1R,2S)-2-((S)-2-((S)-2-cyclohexyl-2-(pyrazine-2-carboxamido) acetamido)-3,3-dimethylbutanamido)cyclohexanecarboxylic acid A solution of the product from Part B (0.156 g, 0.302 mmol) in ethanol (10 mL) was treated with sodium hydroxide (1N, 1 mL) for 2 h room temperature. The solution was neutralized with 1N HCl and extracted with dichloromethane (3×30 mL), dried over MgSO$_4$, filtered and concentrated in vacuo to afford a white solid (144 mg, 95%) which was used directly for the next step. MS (ESI+) m/z=502 (M+H)+.

Part D. Preparation of N-((1S)-1-cyclohexyl-2-((2S)-1-((1S,2R)-2-(1-(cyclopropylamino)-2-hydroxy-1-oxohexan-3-ylcarbamoyl)cyclohexylamino)-3,3-dimethyl-1-oxobutan-2-ylamino)-2-oxoethyl)pyrazine-2-carboxamide To a solution containing the product from Part C (0.02 g, 0.04 mmol) in dichloromethane (2 mL) was added 1-(3-dimethylaminopropyl)-3-ethylcarbodiimide hydrochloride EDC (0.0 09 g, 0.048 mmol) and 1-hydroxybenzotriazole HOBT (6.5 mg, 0.048 mmol) and the resulting solution stirred at 25° C. for 30 minutes. Then 3-amino-N-cyclopropyl-2-hydroxy-hexanamide (WO2002018369-A2; Example 119, cpd xiii') (7.4 mg, 0.04 mmol) and Hunig's base (0.015 mL, 0.088 mmol) was added and the reaction mixture stirred for 1 hours. The reaction mixture was partitioned between 1N HCl and dichloromethane. The organic layer was removed and dried over MgSO$_4$, filtered and concentrated in vacuo to afford a foam (97 mg, 93%) that was purified by preparative thin-layer chromatography (1.0 mm×20×20 mm, SiO2) using 5% methanol in dichloromethane to give a solid (13.6 mg, 51%). MS (ESI+) m/z=670 (M+H)+; MS (ESI–) m/z=668 (M–H)–.

Part E. Preparation of Title Product

To a solution of the product from Part D (13 mg, 0.019 mmol) in dichloromethane (2 mL) was added Dess-Martin periodine (12.6 mg, 0.03 mmol) at 25° C. and the reaction mixture stirred for 1 hour. The reaction was quenched with Na$_2$S$_2$O$_3$ (sat. aqueous) and the product was extracted into methylene chloride (3×30 mL), dried over MgSO$_4$, filtered and concentrated in vacuo to afford a foam (g, % yield) that was purified by preparative thin-layer chromatography (11.0 mm×20 mm×20 mm, SiO$_2$) using 5% methanol in dichloromethane. The title product was isolated as a white solid (10 mg, 77% yield). MS (ESI+) m/z=668 (M+H)+; MS (ESI–) m/z=666 (M–H)–.

Example 19

Preparation of N—((S)-1-cyclohexyl-2-((S)-1-((1S,2R)-2-((S)-1-(2-((S)-2-(dimethylamino)-2-oxo-1-phenylethylamino)-2-oxoethylamino)-1,2-dioxohexan-3-ylcarbamoyl)cyclohexylamino)-3,3-dimethyl-1-oxobutan-2-ylamino)-2-oxoethyl) pyrazine-2-carboxamide

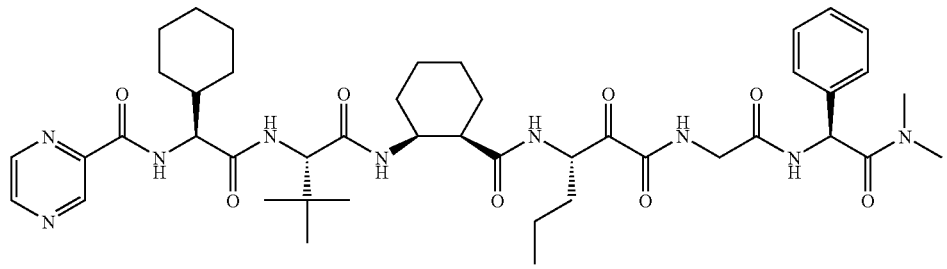 [SMILES: CCC[C@H](NC(=O)[C@@H]1CCCC[C@@H]1NC(=O)[C@@H](NC(=O)[C@@H](NC(=O)c1cnccn1)C1CCCCC1)C(C)(C)C)C(=O)C(=O)NCC(=O)N[C@H](C(=O)N(C)C)c1ccccc1]

Part A. Preparation of N-((1S)-1-cyclohexyl-2-((2S)-1-((1S,2R)-2-((3S)-1-(2-((S)-2-(dimethylamino)-2-oxo-1-phenylethylamino)-2-oxoethylamino)-2-hydroxy-1-oxohexan-3-ylcarbamoyl) cyclohexylamino)-3,3-dimethyl-1-oxobutan-2-ylamino)-2-oxoethyl)pyrazine-2-carboxamide To a solution of the product from Example 18, Part C (115 mg, 0.23 mmol) in 4 mL of dichloromethane was added EDC (66 mg, 0.344 mmol) and HOBT (46 mg, 0.344 mmol) and the resulting solution stirred at 25° C. for 20 minutes. Then, Hunig's base (120 uL, 0.688 mmol) and hydroxyamide (WO2003062265-A2; Example 6, cpd 2.3) (110 mg, 0.275 mmol) was added and the reaction continued for 2 hours at room temperature. The reaction mixture was partitioned between water and dichloromethane. The organic layer was removed and dried over MgSO$_4$, filtered and concentrated in vacuo to afford a foam that was purified by flash chromatography on SiO₂ using 0-10% methanol in dichloromethane as the mobile phase to afford the title compound as a white solid (74.7 mg, 38% yield) MS (ESI+) m/z=848 (M+H)+; MS (ESI−) m/z=846 (M−H)−.

Part B. Preparation of Title Product

To a solution of the product from Part A (74 mg, 0.087 mmol) in dichloromethane (5 mL) was added Dess-Martin periodine (55.5 mg, 0.13 mmol) at 25° C. and the reaction mixture stirred for 1 hour. The reaction was quenched with Na₂S₂O₃ (sat. aqueous) and the product was extracted into methylene chloride (3×30 mL), dried over MgSO₄, filtered and concentrated in vacuo to afford a foam (82 mg) that was purified by preparative thin-layer chromatography (1.0 mm×20 mm×20 mm, SiO₂) using 6% methanol in dichloromethane. The title product was isolated as a white solid (49 mg, 66% yield). MS (ESI+) m/z=846 (M+H)+; MS (ESI−) m/z=844 (M−H)−.

Example 20

Preparation of (3R,4R)-4-((S)-2-((S)-2-cyclohexyl-2-(pyrazine-2-carboxamido) acetamido)-3,3-dimethylbutanamido)-N3-((S)-1-(2-((S)-2-(dimethylamino)-2-oxo-1-phenylethylamino)-2-oxoethylamino)-1,2-dioxohexan-3-yl)-N1-phenylpyrrolidine-1,3-dicarboxamide added phenyl isocyanate (55 mg, 0.45 mmol) at 25° C. After 30 minutes the mixture was quenched with excess HCl (1N) and extracted (3×25 mL) with ethyl acetate. The organic layers were combined, dried over sodium sulfate, and the solvents were evaporated. The crude residue was purified via flash chromatography using 10% methanol in dichloromethane to give a white solid (0.118 g, 62% for two steps). MS (DCI/NH₄) m/z=608 (M+H)+.

Part C. Preparation of (3R,4R)-4-((S)-2-((S)-2-cyclohexyl-2-(pyrazine-2-carboxamido) acetamido)-3,3-dimethylbutanamido)-N3-((3S)-1-(2-((S)-2-(dimethylamino)-2-oxo-1-phenylethylamino)-2-oxoethylamino)-2-hydroxy-1-oxohexan-3-yl)-N1-phenylpyrrolidine-1,3-dicarboxamide To a solution of the product from Part B (59 mg, 0.097 mmol) in 4 mL of dimethylformamide was added EDC (28 mg, 0.146 mmol) and HOBT (20 mg, 0.146 mmol) and the resulting solution stirred for 10 minutes. Hunig's base (69 uL, 0.388 mmol) and hydroxyamide (WO2003062265-A2; Example 6, cpd 2.3) (39 mg, 0.097 mmol) was added and the reaction was stirred for 2 hours at 25° C. The reaction mixture was concentrated, and partitioned between 5% citric acid and dichloromethane. The

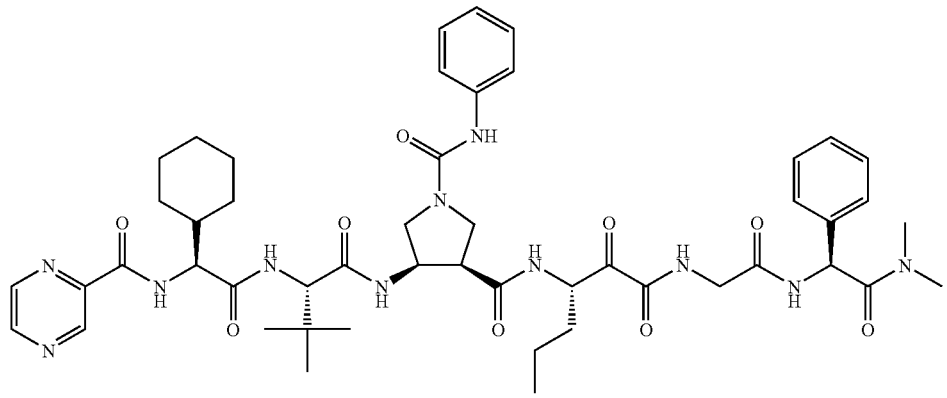 [SMILES: CCC[C@H](NC(=O)[C@@H]1CN(C(=O)Nc2ccccc2)C[C@@H]1NC(=O)[C@@H](NC(=O)[C@@H](NC(=O)c1cnccn1)C1CCCCC1)C(C)(C)C)C(=O)C(=O)NCC(=O)N[C@H](C(=O)N(C)C)c1ccccc1]

Part A. Preparation of (3R,4R)-4-((S)-2-((S)-2-cyclohexyl-2-(pyrazine-2-carboxamido) acetamido)-3,3-dimethylbutanamido)pyrrolidine-3-carboxylic acid A solution of the product from Example 3, Part A (0.2 g, 0.3 mmol) in dichloromethane (1 mL) was treated with trifluoroacetic acid (4 mL) at 25° C. for 2 h. The solvents were evaporated and the residue was twice azeotroped with toluene. The crude material was used directly for the next step.

Part B. Preparation of (3R,4R)-4-((S)-2-((S)-2-cyclohexyl-2-(pyrazine-2-carboxamido) acetamido)-3,3-dimethylbutanamido)-1-(phenylcarbamoyl)pyrrolidine-3-carboxylic acid To a suspension of the product from Part A and Hunig's base (0.16 mL, 0.12 mmol) in dichloromethane (5 mL) was organic layer was removed and dried over sodium sulfate and concentrated in vacuo. to afford a foam (74.7 mg, 38% yield). MS (DCI/NH₄) m/z=954 (M+H)+.

Part D. Preparation of Title Product

To a solution of the product from Part C (33 mg, 0.035 mmol) in dichloromethane (3 mL) was added Dess-Martin periodine (23 mg, 0.052 mmol) at 25° C. and the reaction mixture stirred for 2 hour. The reaction was quenched with 10% Na₂S₂O₃ and the product was extracted into methylene chloride (3×10 mL), dried over sodium sulfate and concentrated in vacuo. to afford a foam that was purified by flash chromatography using 5% methanol in dichloromethane. The title product was isolated as a white solid (25 mg, 76% yield).

Example 21

Preparation of pyrazine-2-carboxylic acid (cyclohexyl-{1-[3-[1-(1-cyclopropyl aminooxalyl-butylcarbamoyl)-bicyclo[2.2.1]hept-2-ylcarbamoyl]-2,2-dimethyl-propylcarbamoyl}-methyl)-amide

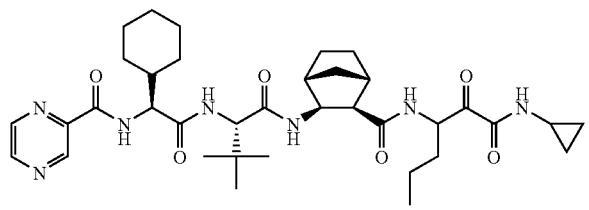 [SMILES: CCCC(NC(=O)[C@@H]1[C@H]2CC[C@H](C2)[C@@H]1NC(=O)[C@@H](NC(=O)[C@@H](NC(=O)c1cnccn1)C1CCCCC1)C(C)(C)C)C(=O)C(=O)NC1CC1]

Part A. Preparation of 3-exo-amino-bicyclo[2.2.1]heptane-2-exo-carboxylic acid methyl ester To 3-exo-amino-bicyclo[2.2.1]heptane-2-exo-carboxylic acid (243.7 mg, 1.57 mmol) in methanol (15 ml) was added 4N HCl in dioxane (1 mL). The solution was refluxed overnight then cooled and concentrated in vacuo and the resulting clear oil dissolved in minimal DCM. Ether and hexane were added and the product crystallized. The crystals were collected and dried to give white crystals (304 mg, 94% yield). MS (APCI) m/z 170 [M+H]+.

Part B. Preparation of 3-(2-{2-cyclohexyl-2-[(pyrazine-2-carbonyl)-amino]-acetylamino}-3,3-dimethyl-butyrylamino)-bicyclo[2.2.1]heptane-2-carboxylic acid methyl ester.

To a solution of the product from Example 1, Part G (150 mg, 0.4 mmol) in DCM (4 ml) was added HOBT (64.6 mg, 0.48 mmol) followed by EDAC (91.7 mg, 0.48 mmol). The mixture was stirred for 30 min then the ester product from Part A (122.9 mg, 0.60 mmol) added followed by TEA (117 ul, 0.84 mmol). The mixture was stirred overnight, the milky suspension diluted with DCM and the resulting organic suspension washed with water, 1N HCl and brine. The organic layer was dried and concentrated in vacuo to give a pale yellow solid (207.1 mg, 98% yield). MS (APCI) m/z 528 [M+H]+.

Part C. Preparation of 1S,2R,3S,4R)-3-((S)-2-((S)-2-cyclohexyl-2-(pyrazine-2-carboxamido)acetamido)-3,3-dimethylbutanamido)bicyclo[2.2.1]heptane-2-carboxylic acid.

To a solution of the peptide product from Part B (207 mg, 0.39 mmol) in methanol was added 1N NaOH (4 eq, 1.56 mmol, 1.56 mL). The mixture was stirred over a weekend. The methanol was removed in vacuo and the aqueous solution acidified with 1N HCl then extracted with ethyl acetate. The organic layer was washed with brine, dried and concentrated in vacuo to give a white solid (185 mg, 92% yield) as a mixture of diastereomers. The isomers were separable by RP-HPLC (0.1% TFA in water/CH3CN gradient) giving 74.9 mg of the more polar isomer. MS (APCI) m/z 514 [M+H]+.

Part D. Preparation of pyrazine-2-carboxylic acid [cyclohexyl-(1-{3-[1-(cyclopropyl carbamoyl-hydroxy-methyl)-butylcarbamoyl]-bicyclo[2.2.1]hept-2-ylcarbamoyl}-2,2-dimethylpropyl carbamoyl)-methyl]-amide To a solution of the product from Part C (74.9 mg, 0.15 mmol) and TEA (61 ul, 0.44 mmol) in DCM (1.5 ml) was added HOBT (23.6 mg, 0.18 mmol) followed by EDAC (33.5 mg, 0.18 mmol). The mixture was stirred for 30 min then 3-amino-N-cyclopropyl-2-hydroxyhexanamide (WO2002018369-A2; Example 119, cpd xiii') (51 mg, 0.29 mmol) added as a solid. The mixture was stirred overnight then loaded on to a 10 g silica plug with DCM. The plug was eluted with 2-5% methanol in dichloromethane. Fractions were combined to give the desired product as a mixture of diastereomers (23.7 mg, 24% yield). MS (APCI) m/z 682 [M+H]+.

Part E. Preparation of Title Product

To a solution of the product from Part D (23.7 mg, 0.03 mmol) in DCM (0.99 ml) was added Dess-Martin reagent (22.1 mg, 0.05 mmol) and the mixture stirred overnight. The cloudy suspension was quenched with 10% aqueous $Na_2S_2O_3$ and stirred for 30 min. The now clear layers were separated and the organic layer dried and concentrated in vacuo to give the crude diketoamide. The crude material was loaded onto silica with DCM then the column eluted with hexane, 1:1 hexane/ethyl acetate, 1:2 hexane/ethyl acetate then ethyl acetate. Fractions were combined and concentrated to give the ketoamide (17.4 mg, 73.6% yield). MS (ESI) m/z 702 [M+Na]+, m/z 680 [M+H]+, m/z 678 [M−H]−.

Example 22

Preparation of Pyrazine-2-carboxylic acid (cyclohexyl-{1-[3-(1-cyclopropyl aminooxalyl-butylcarbamoyl)-bicyclo[2.2.1]hept-5-en-2-ylcarbamoyl]-2,2-dimethyl-propylcarbamoyl}-methyl)-amide

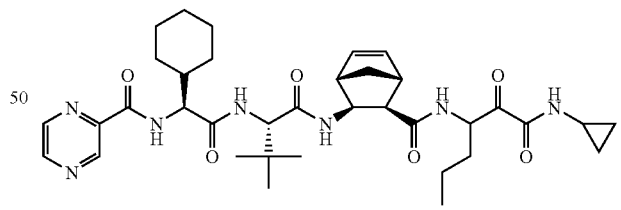

Part A. Preparation of 3-exo-aminobicyclo[2.2.1]hept-5-ene-2-exo-carboxylic acid methyl ester To the aminoacid 3-exo-aminobicyclo[2.2.1]hept-5-ene-2-exo-carboxylic acid (232.4 mg, 1.5 mmol) in methanol (15 mL) was added 4N HCl in dioxane (1 ml). The solution was refluxed overnight. The solution was concentrated in vacuo and the resulting clear oil dissolved in minimal DCM. Ether was added and the product crystallized. The crystals were collected and dried to give a white solid (266 mg, 86% yield).

Part B. Preparation of 3-(2-{2-Cyclohexyl-2-[(pyrazine-2-carbonyl)-amino]-acetylamino}-3,3-dimethyl-butyrylamino)-bicyclo[2.2.1]hept-5-ene-2-carboxylic acid methyl ester.

To a solution of the product from Example 1, Part G (150 mg, 0.4 mmol) in DCM (4 ml) was added HOBT (64.6 mg, 0.48 mmol) followed by EDAC (91.7 mg, 0.48 mmol). The mixture was stirred for 30 min then the ester product from Part A added followed by TEA (117 ul, 0.84 mmol). The mixture was stirred overnight, the milky suspension diluted with DCM and the resulting organic suspension washed with water, 1N HCl and brine. The organic layer was dried and concentrated in vacuo to give a pale yellow solid (208.2 mg, 99% yield). MS (APCI) m/z 526 [M+H]+.

Part C. Preparation of 3-(2-{2-Cyclohexyl-2-[(pyrazine-2-carbonyl)-amino]-acetylamino}-3,3-dimethyl-butyrylamino)-bicyclo[2.2.1]hept-5-ene-2-carboxylic acid.

To a solution of the product from Part B (208 mg, 0.4 mmol) in methanol was added 1N NaOH (1.6 mmol, 1.6 mL). The mixture was stirred over a weekend. The methanol was removed in vacuo and the aqueous solution acidified with 1N HCl then extracted with ethyl acetate. The organic layer was washed with brine, dried and concentrated in vacuo to give a white solid as a mixture of diastereomers (174 mg, 85% yield). The isomers were separable by RP-HPLC (0.1% TFA in water/CH3CN gradient) giving 55.5 mg of the more polar compound. MS (APCI) m/z 512 [M+H]+.

Part D. Preparation of Pyrazine-2-carboxylic acid [cyclohexyl-(1-{3-[1-(cyclopropyl carbamoyl-hydroxy-methyl)-butylcarbamoyl]-bicyclo[2.2.1]hept-5-en-2-ylcarbamoyl}-2,2-dimethyl-propylcarbamoyl)-methyl]-amide To a solution of the product from Part C (55.5 mg, 0.11 mmol) and TEA (45 ul, 0.33 mmol) in DCM (1.1 ml) was added HOBT (17.6 mg, 0.13 mmol) followed by EDAC (235 mg, 0.13 mmol). The mixture was stirred for 30 min then 3-amino-N-cyclopropyl-2-hydroxyhexanamide (WO2002018369-A2; Example 119, cpd xiii') (40.4 mg, 0.22 mmol) added as a solid. The mixture was stirred overnight then loaded on to a 10 g silica plug with DCM. The plug was eluted with 2-5% methanol in dichloromethane. Fractions were combined to give the product (36.7 mg, 50% yield) as a mixture of isomers. MS (APCI) m/z 680 [M+H]+.

Part E. Preparation of Title Product

To a solution of the product from Part D (36.7 mg, 0.05 mmol) in DCM (1.5 ml) was added Dess-Martin reagent (34.3 mg, 0.08 mmol) and the mixture stirred overnight. The cloudy suspension was quenched with 10% aqueous Na2S2O3 and stirred for 30 min. The now clear layers were separated and the organic layer dried and concentrated in vacuo to give the crude diketoamide. The crude material was loaded onto silica with DCM then the column eluted with hexane, 1:1 hexane/ethyl acetate, 1:2 hexane/ethyl acetate then ethyl acetate. Fractions were combined and concentrated to give the ketoamide (30.5 mg, 83% yield). MS (ESI) m/z 700 [M+Na]+, m/z 678 [M+H]+, m/z 676 [M−H]−.

Example 23

Preparation of 3-(2-{2-cyclohexyl-2-[(pyrazine-2-carbonyl)-amino]-acetylamino}-3,3-dimethyl-butyrylamino)-4-{1-[({[(dimethylcarbamoyl-phenyl-methyl)-carbamoyl]-methyl}-carbamoyl)-hydroxy-methyl]-butylcarbamoyl}-pyrrolidine-1-carboxylic acid benzyl ester

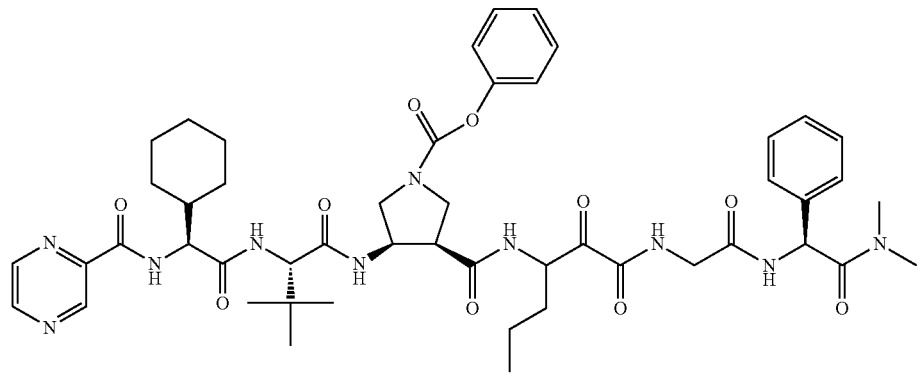 [SMILES: CCCC(NC(=O)[C@@H]1CN(C(=O)Oc2ccccc2)C[C@@H]1NC(=O)[C@@H](NC(=O)[C@@H](NC(=O)c1cnccn1)C1CCCCC1)C(C)(C)C)C(=O)C(=O)NCC(=O)N[C@H](C(=O)N(C)C)c1ccccc1]

Part A. Preparation of 4-(2-{2-cyclohexyl-2-[(pyrazine-2-carbonyl)-amino]-acetylamino}-3,3-dimethyl-butyrylamino)-pyrrolidine-1,3-dicarboxylic acid di-tert-butyl ester To a solution of the product from Example 1, Part G (310 mg, 0.82 mmol) in DCM (8.2 ml) was added HOBT (133.5 mg, 0.99 mmol) followed by EDAC (189.4 mg, 0.99 mmol). The mixture was stirred for 30 min then and (3R,4R)-di-tert-butyl 4-aminopyrrolidine-1,3-dicarboxylate (*Org. Biomol Chem.* 2004, 2, 2763-2776) (235.8 mg, 0.82 mmol) added. The mixture was stirred overnight then the reaction mixture diluted with DCM and the organic layer washed with water, 1N HCl, sat'd NaHCO3 and brine. The organic layer was dried and concentrated in vacuo to give a white solid which was purified on silica eluting with 0-100% ethyl acetate in hexanes to give the title compound as a white solid (502 mg, 95% yield). MS (ESI) m/z 667 [M+Na]+, m/z 645 [M+H]+, m/z 643 [M−H]−.

Part B. Preparation of 4-(2-{2-cyclohexyl-2-[(pyrazine-2-carbonyl)-amino]-acetylamino}-3,3-dimethyl-butyrylamino)-pyrrolidine-3-carboxylic acid tert-butyl ester The product from Part A (470 mg, 0.73 mmol) was dissolved in ethyl acetate (2.7 ml) and 4N HCl in dioxane (0.9 ml) added. The solution was allowed to stand and a ppt formed after about 1 hour. After 4 hours, the supernate was removed with a pipette and the solid washed with ethyl acetate then dried to give the hydrochloride salt (211.9 mg, 50% yield) as a white solid. MS (APCI) m/z 545 [M+H]+.

Part C. Preparation of 4-(2-{2-cyclohexyl-2-[(pyrazine-2-carbonyl)-amino]-acetylamino}-3,3-dimethyl-butyrylamino)-pyrrolidine-1,3-dicarboxylic acid 1-benzyl ester 3-tert-butyl ester The product from Part B (100 mg, 0.17 mmol) was dissolved in DCM (860 ul) then TEA (34.8 ul, 0.34 mmol) added followed by CBZ-Cl (49 ul, 0.34 mmol). The reaction was stirred overnight. The reaction mixture was loaded onto a silica plug then eluted with ethyl acetate to give the title compound (107.2 mg, 92% yield). MS (APCI) m/z 679 [M+H]+.

Part D. Preparation of 4-(2-{2-cyclohexyl-2-[(pyrazine-2-carbonyl)-amino]-acetylamino}-3,3-dimethyl-butyrylamino)-pyrrolidine-1,3-dicarboxylic acid 1-benzyl ester To the product from Part C (103 mg, 0.15 mmol) was added 4N HCl/dioxane (5 ml) and the reaction stirred overnight at RT. The solvent was removed in vacuo and the residue triturated with ether to give the acid as a white solid (94.3 mg, 100% yield). MS (APCI) m/z 623 [M+H]+.

Part E. Preparation of 3-(2-{2-cyclohexyl-2-[(pyrazine-2-carbonyl)-amino]-acetylamino}-3,3-dimethyl-butyrylamino)-4-{1-[({[(dimethylcarbamoyl-phenyl-methyl)-carbamoyl]-methyl}-carbamoyl)-hydroxy-methyl]-butylcarbamoyl}-pyrrolidine-1-carboxylic acid benzyl ester To a solution of the product from Part D (94.3 mg, 0.15 mmol), hydroxyamide (WO2003062265-A2; Example 6, cpd 2.3) (53.5 mg, 0.15 mmol) and DIPEA (153.3 ul, 0.88 mmol) in THF (1.5 ml) was added DEPBT (50.4 mg, 0.22 mmol). The mixture was stirred overnight. The reaction mixture was partitioned between ethyl acetate and sat'd Na$_2$CO$_3$. The organic layer was dried and concentrated then loaded on to a 10 g silica plug with DCM. The plug was eluted with 0-6% methanol in ethyl acetate to give the title compound (73 mg, 51% yield) as a mixture of isomers. MS (APCI) m/z 969 [M+H]+.

Part F. Preparation of Title Product

To a solution of the product from Part E (24 mg, 0.02 mmol) in DCM (0.7 ml) was added Dess-Martin reagent (15.8 mg, 0.04 mmol) and the mixture stirred overnight. The cloudy suspension was quenched with 10% aqueous Na$_2$S$_2$O$_3$ and stirred for 30 min. The now clear layers were separated and the organic layer dried and concentrated in vacuo to give the crude diketoamide. The crude material was loaded onto silica with DCM then the column eluted with 0-6% methanol in ethyl acetate to give the title compound (15.8 mg, 62.5% yield). MS (ESI) m/z 967 [M+H]+, m/z 965 [M–H]–.

Example 24

Preparation of pyrazine-2-carboxylic acid (cyclohexyl-{1-[4-(1-cyclopropyl aminooxalyl-butylcarbamoyl)-1-(toluene-4-sulfonyl)-pyrrolidin-3-ylcarbamoyl]-2,2-dimethylpropyl carbamoyl}-methyl)-amide

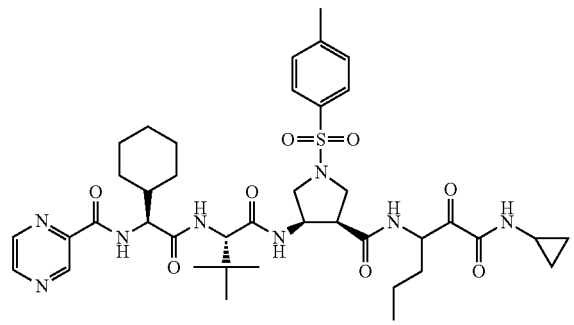 [SMILES: CCCC(NC(=O)[C@@H]1CN(S(=O)(=O)c2ccc(C)cc2)C[C@@H]1NC(=O)[C@@H](NC(=O)[C@@H](NC(=O)c1cnccn1)C1CCCCC1)C(C)(C)C)C(=O)C(=O)NC1CC1]

Part A. Preparation of 4-(2-{2-cyclohexyl-2-[(pyrazine-2-carbonyl)-amino]-acetylamino}-3,3-dimethyl-butyrylamino)-1-(toluene-4-sulfonyl)-pyrrolidine-3-carboxylic acid tert-butyl ester The product from Example 23, Part B (100 mg, 0.17 mmol) was dissolved in dichloromethane (1.7 ml). TEA (84 ul, 0.6 mmol) was added followed by the sulfonyl chloride (65.6 mg, 0.34 mmol). The reaction was stirred overnight then loaded onto a silica plug and eluted with ethyl acetate to give the title compound as a white solid (112 mg, 93% yield). MS (APCI) m/z 699 [M+H]+.

Part B. Preparation of 4-(2-{2-cyclohexyl-2-[(pyrazine-2-carbonyl)-amino]-acetylamino}-3,3-dimethyl-butyrylamino)-1-(toluene-4-sulfonyl)-pyrrolidine-3-carboxylic acid To the product from Part A (110 mg, 0.16 mmol) was added 4N HCl/dioxane (5 ml) and the mixture stirred overnight. The reaction mixture was concentrated in vacuo and the residue triturated with ether to give (100.3 mg, 100% yield) of a white solid. MS (APCI) m/z 643 [M+H]+.

Part C. Preparation of pyrazine-2-carboxylic acid (cyclohexyl-{1-[4-[1-(cyclopropyl carbamoyl-hydroxy-methyl)-butylcarbamoyl]-1-(toluene-4-sulfonyl)-pyrrolidin-3-ylcarbamoyl]-2,2-dimethyl-propyl-carbamoyl}-methyl)-amide To a solution of the product from Part B (50 mg, 0.08 mmol), 3-amino-N-cyclopropyl-2-hydroxyhexanamide (WO2002018369-A2; Example 119, cpd xiii') (14.5 mg, 0.08 mmol) and DIPEA (81.3 ul, 0147 mmol) in THF (0.78 ml) was added DEPBT (26.7 mg, 0.12 mmol). The mixture was stirred overnight then the reaction mixture partitioned between ethyl acetate and sat'd Na$_2$CO$_3$. The organic layer was dried and concentrated to give 50 mg crude product which was then loaded on to a 10 g silica plug with DCM. The plug was eluted with 0-6% methanol in ethyl acetate to give the desired compound (42 mg, 67% yield). MS (APCI) m/z 811 [M+H]+.

Part D. Preparation of Title Product

To a solution of the product from Part C (42 mg, 0.05 mmol) in DCM (1.5 ml) was added Dess-Martin reagent (32.9 mg, 0.08 mmol) and the mixture stirred overnight. The cloudy suspension was quenched with 10% aqueous $Na_2S_2O_3$ and stirred for 30 min. The now clear layers were separated and the organic layer dried and concentrated in vacuo to give the crude diketoamide. The crude material was loaded onto silica with DCM then the column eluted with 1:1 then 1:2 hexane/ethyl acetate followed by ethyl acetate to give the product (31 mg, 74% yield) as a white solid. MS (APCI) m/z 809 [M+H]+.

Example 25

Preparation of (3R,4R)-tert-butyl 3-((S)-2-((S)-2-cyclohexyl-2-(pyrazine-2-carboxamido)acetamido)-3,3-dimethylbutanamido)-4-((S)-1-(2-((S)-2-(dimethylamino)-2-oxo-1-phenylethylamino)-2-oxoethylamino)-1,2-dioxohexan-3-ylcarbamoyl)pyrrolidine-1-carboxylate

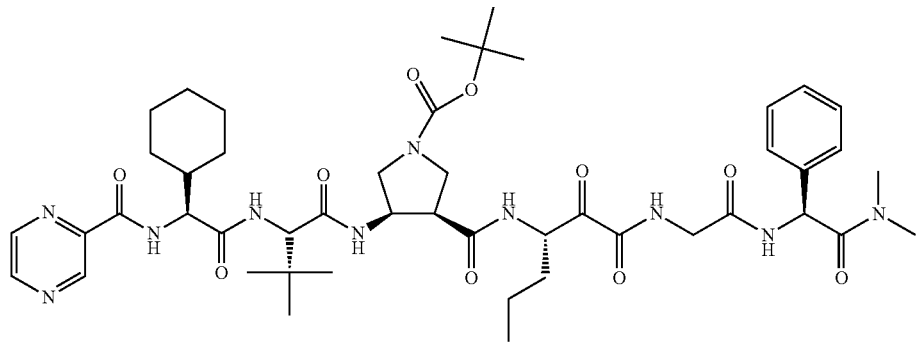

Part A. Preparation of (3R,4R)-di-tert-butyl 4-(benzyloxycarbonylamino)pyrrolidine-1,3-dicarboxylate To a solution of (3R,4R)-di-tert-butyl 4-aminopyrrolidine-1,3-dicarboxylate (*Org. Biomol. Chem.* 2004, 2, 2763-2776) (765 mg, 2.67 mmol) and Hunig's base (465 uL, 2.67 mmol) in N,N-dimethylformamide (5 mL) was added Cbz succinimide (665 mg, 2.67 mmol). The mixture was stirred for 3 hours and partitioned between EtOAc and water. The organic layer was washed repeatedly with brine, dried ($Na_2SO_4$) and concentrated to a clear oil (1.18 g, quantitative yield). MS ($DCI/NH_4$) m/z=438 $(M+NH_4)^+$.

Part B. Preparation of (3R,4R)-4-(benzyloxycarbonylamino)pyrrolidine-3-carboxylic acid compound with 2,2,2-trifluoroacetic acid (1:1).

To a solution of the product from Part A (1.18 g, 2.67 mmol) in dichloromethane (5 mL) was added trifluoroacetic acid (25 mL) at a fast drip. The light yellow solution was stirred at ambient temp for 3 hours, concentrated and the residue was azeotroped several times with mixtures of methanol and toluene to finally achieve a sticky solid. MS (DCI/$NH_4$) m/z=265 $(M+H)^+$.

Part C. Preparation of (3R,4R)-4-(benzyloxycarbonylamino)-1-(tert-butoxycarbonyl)pyrrolidine-3-carboxylic acid A solution of the product from Part B (900 mg, 2.49 mmol) in tetrahydrofuran/water (20 mL/5 mL) and 1 M NaOH (10 mL, 10 mmol) was treated with di-tert-butyl dicarbonate (1.44 g, 6.2 mmol), stirred for 16 hours and concentrated to remove the tetrahydrofuran. The aqueous solution was washed 2×50 mL with diethyl ether, acidified to pH 1 with 1M $H_3PO_4$ and extracted 3×40 mL with EtOAc. The extracts were combined, washed with 2 mL saturated brine, dried ($Na_2SO_4$) and concentrated to give a white foam (860 mg, 95%). MS ($DCI/NH_4$) m/z=382 $(M+NH_4)^+$.

Part D. Preparation of (3R,4R)-tert-butyl 3-(benzyloxycarbonylamino)-4-((3S)-1-(2-((S)-2-(dimethylamino)-2-oxo-1-phenylethylamino)-2-oxoethylamino)-2-hydroxy-1-oxohexan-3-ylcarbamoyl)pyrrolidine-1-carboxylate A mixture of the product from Part C (72.8 mg, 0.2 mmol), N-(3-dimethylaminopropyl)-N'-ethylcarbodiimide hydrochloride (58 mg, 0.3 mmol), 1-hydroxybenzotriazole (41 mg, 0.3 mmol), Hunig's base (105 uL, 0.6 mmol) and ((3S)-3-amino-N-(2-((S)-2-(dimethylamino)-2-oxo-1-phenylethylamino)-2-oxoethyl)-2-hydroxyhexanamide (WO2003062265-A2; Example 6, cpd 2.3) (72.8 mg, 0.2 mmol)) in dichloromethane (8 mL) was stirred for 16 hours and diluted with 100 mL EtOAc, washed with 10 mL 1 M $H_3PO_4$, 10 mL 10% $NaHCO_3$, 3×20 mL with brine, dried ($Na_2SO_4$), and concentrated to a white powder (120 mg, 84%). MS (ESI+) m/z=711 $(M+H)^+$.

Part E. Preparation of (3R,4R)-tert-butyl 3-amino-4-((3S)-1-(2-((S)-2-(dimethylamino)-2-oxo-1-phenylethylamino)-2-oxoethylamino)-2-hydroxy-1-oxohexan-3-ylcarbamoyl)pyrrolidine-1-carboxylate The product from Part D (73 mg, 0.1 mmol) and 10% Pd/C (50 mg) were combined in MeOH (10 mL) and degassed under vacuum. The mixture was placed under a balloon of $H_2$, stirred for 16 hours, filtered through Celite to remove catalyst and the filtrate was concentrated to a white powder (57 mg, 99%). MS (ESI+) m/z=577 $(M+H)^+$.

Part F. Preparation of (3R,4R)-tert-butyl 3-((S)-2-((S)-2-cyclohexyl-2-(pyrazine-2-carboxamido)acetamido)-3,3-dimethylbutanamido)-4-((3S)-1-(2-((S)-2-(dimethylamino)-2-oxo-1-phenylethylamino)-2-oxoethylamino)-2-hydroxy-1-oxohexan-3-ylcarbamoyl)pyrrolidine-1-carboxylate A mixture of the product from Part E (57 mg, 0.1 mmol), N-(3-dimethylaminopropyl)-N'-ethylcarbodiimide hydrochloride (29 mg, 0.15 mmol), 1-hydroxybenzotriazole (21 mg, 0.15 mmol), Hunig's base (52 uL, 0.3 mmol) and the product from Example 1, Part G (38 mg, 0.1 mmol)) in dichloromethane (4 mL) was stirred for 6 hours, diluted with 100 mL EtOAc, washed with 10 mL 1 M $H_3PO_4$, 10 mL 10% $NaHCO_3$, 3×20 mL with brine, dried ($Na_2SO_4$), and concentrated to a white powder (60 mg, 64%). MS (ESI+) m/z=936 (M+H)+.

Part G. Preparation of Title Product

The product from Part F (60 mg, 0.064 mmol) in dichloromethane (4 mL) was treated with Dess-Martin periodinane (33 mg, 0.077 mmol), stirred for 2 hours, treated with 10% aqueous sodium sulfite (2 mL), stirred for 10 minutes and diluted with 50 mL EtOAc. The EtOAc layer was then washed with 10% aqueous sodium bicarbonate, brine, dried ($Na_2SO_4$) and concentrated. The crude product was flash chromatographed on an Alltech 2 g silica cartridge eluting with dichloromethane→3% MeOH in dichloromethane to give a white powder (20 mg, 33%). MS (ESI−) m/z=932 (M−H)+.

Example 26

Preparation of N—((S)-1-cyclohexyl-2-((S)-1-((3R,4R)-4-((S)-1-(2-((S)-2-(dimethylamino)-2-oxo-1-phenylethylamino)-2-oxoethylamino)-1,2-dioxohexan-3-ylcarbamoyl)pyrrolidin-3-ylamino)-3,3-dimethyl-1-oxobutan-2-ylamino)-2-oxoethyl) pyrazine-2-carboxamide 2,2,2-trifluoroacetate.

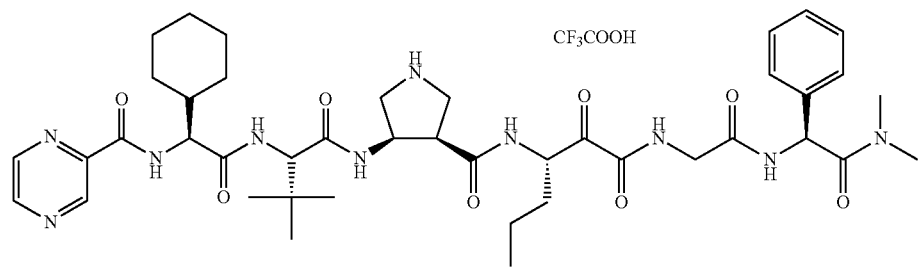

The product from Example 25, Part G (15 mg, 0.016 mmol) in dichloromethane (1 mL) was treated with trifluoroacetic acid (1 mL), stirred for 1 hour and concentrated to give the title compound as a white powder (13 mg, 95%). MS (ESI−) m/z=832 (M−H)+.

Example 27

Preparation of (3R,4R)-tert-butyl 3-(2-((S)-2-cyclohexyl-2-(pyrazine-2-carboxamido)acetamido)acetamido)-4-((S)-1-(2-((S)-2-(dimethylamino)-2-oxo-1-phenylethylamino)-2-oxoethyl amino)-1,2-dioxohexan-3-ylcarbamoyl)pyrrolidine-1-carboxylate

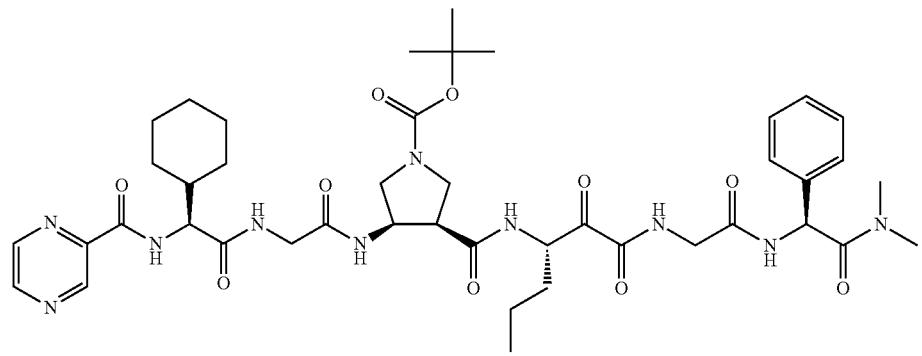 [SMILES: CCC[C@H](NC(=O)[C@@H]1CN(C(=O)OC(C)(C)C)C[C@@H]1NC(=O)CNC(=O)[C@@H](NC(=O)c1cnccn1)C1CCCCC1)C(=O)C(=O)NCC(=O)N[C@H](C(=O)N(C)C)c1ccccc1]

Part A. Preparation of (S)-tert-butyl 2-(2-cyclohexyl-2-(pyrazine-2-carboxamido) acetamido)acetate A mixture of the product from Example 1, Part G (132 mg, 0.5 mmol), N-(3-dimethylaminopropyl)-N'-ethylcarbodiimide hydrochloride (144 mg, 0.75 mmol), 1-hydroxybenzotriazole (102 mg, 0.75 mmol), Hunig's base (260 uL, 1.5 mmol) and tert-butyl 2-aminoacetate (69 mg, 0.52 mmol)) in dichloromethane (15 mL) was stirred for 2 hours, diluted with 100 mL EtOAc, washed with 10 mL 1 M H$_3$PO$_4$, 10 mL 10% NaHCO$_3$, 3×20 mL with brine, dried (Na$_2$SO$_4$), and concentrated. The crude material was chromatographed on an Alltech 2 g silica cartridge eluting with 2:1 hexane/EtOAc to give a white foam (76 mg, 40%). MS (ESI−) m/z=375 (M−H)⁺.

Example 28

Preparation of (3R,4R)-tert-butyl 3-((S)-2-((S)-2-cyclohexyl-2-(pyrazine-2-carboxamido)acetamido)-3-methylbutanamido)-4-((S)-1-(2-((S)-2-(dimethylamino)-2-oxo-1-phenyl ethylamino)-2-oxoethylamino)-1,2-dioxohexan-3-ylcarbamoyl)pyrrolidine-1-carboxylate

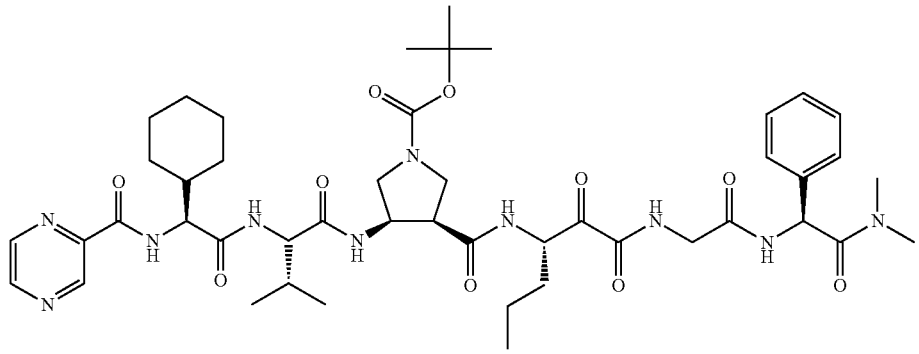

Part B. Preparation of (S)-2-(2-cyclohexyl-2-(pyrazine-2-carboxamido)acetamido)acetic acid The product from Part A (70 mg, 0.186 mmol) in dichloromethane (0.5 mL) was treated with trifluoroacetic acid (2 mL), stirred for 3 hour and concentrated to give a sticky solid (70 mg, 87%).

Part C. Preparation of (3R,4R)-tert-butyl 3-(2-((S)-2-cyclohexyl-2-(pyrazine-2-carboxamido)acetamido) acetamido)-4-((3S)-1-(2-((S)-2-(dimethylamino)-2-oxo-1-phenylethylamino)-2-oxoethylamino)-2-hydroxy-1-oxohexan-3-ylcarbamoyl)pyrrolidine-1-carboxylate A mixture of the product from Part B (40 mg, 0.12 mmol), N-(3-dimethylaminopropyl)-N'-ethylcarbodiimide hydrochloride (29 mg, 0.15 mmol), 1-hydroxybenzotriazole (21 mg, 0.15 mmol), Hunig's base (70 uL, 0.4 mmol) and the product from Example 25, Part E (57 mg, 0.1 mmol)) in dichloromethane (4 mL) was stirred for 3 hours, diluted with 100 mL EtOAc, washed with 10 mL 1 M H$_3$PO$_4$, 10 mL 10% NaHCO$_3$, 3×20 mL with brine, dried (Na$_2$SO$_4$), and concentrated to a yellow glass (70 mg, 80%). MS (ESI−) m/z=878 (M−H)⁺.

Part D. Preparation of Title Product

The product from Part C (70 mg, 0.08 mmol) in dichloromethane (4 mL) was treated with Dess-Martin periodinane (41 mg, 0.096 mmol), stirred for 2 hours, treated with 10% aqueous sodium sulfite (2 mL), stirred for 10 minutes and diluted with 50 mL EtOAc. The EtOAc layer was then washed with 10% aqueous sodium bicarbonate, brine, dried (Na$_2$SO$_4$) and concentrated. The crude product was flash chromatographed on an Alltech 2 g silica cartridge eluting with dichloromethane→5% MeOH in dichloromethane to give a white powder (28 mg, 32%). MS (ESI−) m/z=876 (M−H)⁺.

Part A. Preparation of (S)-tert-butyl 2-((S)-2-cyclohexyl-2-(pyrazine-2-carboxamido) acetamido)-3-methylbutanoate A mixture of the product from Example 1, Part G (132 mg, 0.5 mmol), N-(3-dimethyl aminopropyl)-N'-ethylcarbodiimide hydrochloride (144 mg, 0.75 mmol), 1-hydroxybenzotriazole (102 mg, 0.75 mmol), Hunig's base (350 uL, 2.0 mmol) and (S)-tert-butyl 2-amino-3-methylbutanoate hydrochloride (109 mg, 0.52 mmol)) in dichloromethane (15 mL) was stirred for 2 hours, diluted with 100 mL EtOAc, washed with 10 mL 1 M H$_3$PO$_4$, 10 mL 10% NaHCO$_3$, 3×20 mL with brine, dried (Na$_2$SO$_4$), and concentrated to give a yellow foam (195 mg, 93%). MS (ESI−) m/z=417 (M−H)⁺.

Part B. Preparation of (S)-2-((S)-2-cyclohexyl-2-(pyrazine-2-carboxamido)acetamido)-3-methylbutanoic acid The product from Part A (50 mg, 0.12 mmol) in dichloromethane (0.5 mL) was treated with trifluoroacetic acid (2 mL), stirred for 3 hour and concentrated to give a sticky solid. MS (ESI+) m/z=363 (M+H)⁺.

Part C. Preparation of (3R,4R)-tert-butyl 3-((S)-2-((S)-2-cyclohexyl-2-(pyrazine-2-carboxamido)acetamido)-3-methylbutanamido)-4-((3S)-1-(2-((S)-2-(dimethylamino)-2-oxo-1-phenyl ethylamino)-2-oxoethylamino)-2-hydroxy-1-oxohexan-3-ylcarbamoyl)pyrrolidine-1-carboxylate A mixture of the product from Part B (40 mg, 0.12 mmol), N-(3-dimethylaminopropyl)-N'-ethylcarbodiimide hydrochloride (29 mg, 0.15 mmol), 1-hydroxybenzotriazole (21 mg, 0.15 mmol), Hunig's base (70 uL, 0.4 mmol) and the product from Example 25, Part E (57 mg, 0.1 mmol)) in dichloromethane (4 mL) was stirred for 3 hours, diluted with 100 mL EtOAc, washed with 10 mL 1 M H$_3$PO$_4$, 10 mL 10% NaHCO$_3$, 3×20 mL with brine, dried (Na$_2$SO$_4$), and concentrated (51 mg, 55%). MS (ESI−) m/z=920 (M−H)⁺.

Part D. Preparation of Title Product

The product from Part C (50 mg, 0.054 mmol) in dichloromethane (4 mL) was treated with Dess-Martin periodinane (28 mg, 0.065 mmol), stirred for 2 hours, treated with 10% aqueous sodium sulfite (2 mL), stirred for 10 minutes and diluted with 50 mL EtOAc. The EtOAc layer was then washed with 10% aqueous sodium bicarbonate, brine, dried ($Na_2SO_4$) and concentrated. The crude product was flash chromatographed on an Alltech 2 g silica cartridge eluting with dichloromethane→4% MeOH in dichloromethane to give a white powder (20 mg, 40%). MS (ESI–) m/z=918 (M–H)$^+$.

Example 29

Preparation of N—((S)-1-cyclohexyl-2-((S)-1-((3R,4R)-4-((S)-1-(2-((S)-2-(dimethylamino)-2-oxo-1-phenylethylamino)-2-oxoethylamino)-1,2-dioxohexan-3-ylcarbamoyl)pyrrolidin-3-ylamino)-3-methyl-1-oxobutan-2-ylamino)-2-oxoethyl)pyrazine-2-carboxamide 2,2,2-trifluoroacetate.

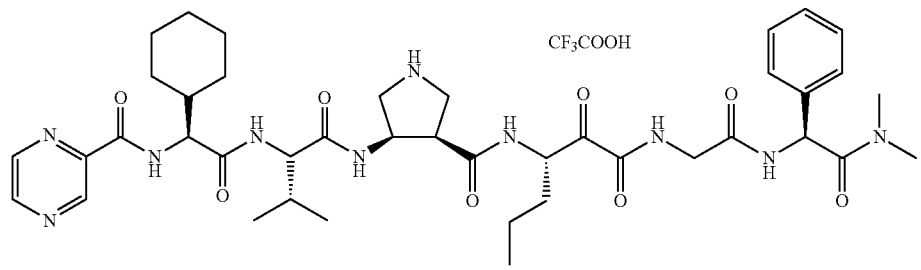

The product from Example 28, Part D (15 mg, 0.016 mmol) in dichloromethane (1 mL) was treated with trifluoroacetic acid (1 mL), stirred for 1 hour and concentrated to give the title compound as a tan powder (12 mg, 80%). MS (ESI) m/x=818 (M–H)$^+$.

Example 30

Preparation of (3R,4R)-tert-butyl 3-((S)-2-((S)-2-cyclohexyl-2-(pyrazine-2-carboxamido)acetamido)-3-phenylpropanamido)-4-((S)-1-(2-((S)-2-(dimethylamino)-2-oxo-1-phenyl ethylamino)-2-oxoethylamino)-1,2-dioxohexan-3-ylcarbamoyl)pyrrolidine-1-carboxylate

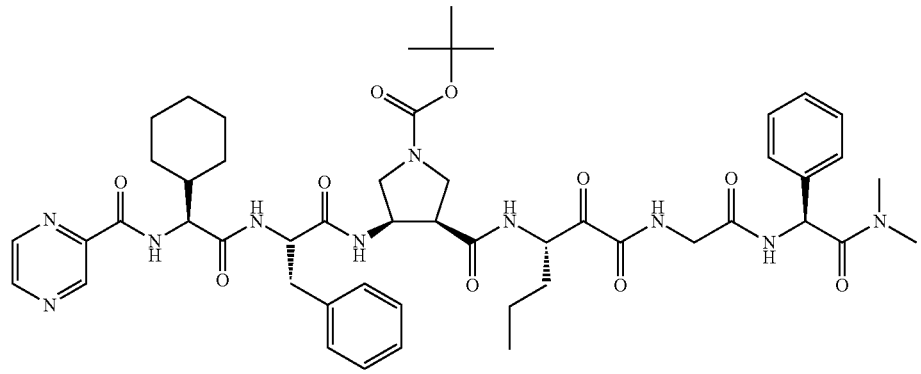

Part A. Preparation of (S)-tert-butyl 2-((S)-2-cyclohexyl-2-(pyrazine-2-carboxamido) acetamido)-3-phenylpropanoate A mixture of the product from Example 1, Part G (132 mg, 0.5 mmol), N-(3-dimethyl aminopropyl)-N'-ethylcarbodiimide hydrochloride (144 mg, 0.75 mmol), 1-hydroxybenzotriazole (102 mg, 0.75 mmol), Hunig's base (350 uL, 2.0 mmol) and (S)-tert-butyl 2-amino-3-phenylpropanoate hydrochloride (134 mg, 0.52 mmol)) in dichloromethane (15 mL) was stirred for 2 hours, diluted with 100 mL EtOAc, washed with 10 mL 1 M $H_3PO_4$, 10 mL 10% $NaHCO_3$, 3×20 mL with brine, dried ($Na_2SO_4$), and concentrated to give a yellow wax (190 mg, 82%). MS (ESI−) m/z=465 (M−H)$^+$.

Part B. Preparation of (S)-2-((S)-2-cyclohexyl-2-(pyrazine-2-carboxamido)acetamido)-3-phenylpropanoic acid The product from Part A (56 mg, 0.12 mmol) in dichloromethane (0.5 mL) was treated with trifluoroacetic acid (2 mL), stirred for 3 hour and concentrated to give a sticky solid. MS (ESI+) m/z=411 (M+H)$^+$.

Part C. Preparation of (3R,4R)-tert-butyl 3-((S)-2-((S)-2-cyclohexyl-2-(pyrazine-2-carboxamido)acetamido)-3-phenylpropanamido)-4-((3S)-1-(2-((S)-2-(dimethylamino)-2-oxo-1-phenyl ethylamino)-2-oxoethylamino)-2-hydroxy-1-oxohexan-3-ylcarbamoyl)pyrrolidine-1-carboxylate A mixture of the product from Part B (40 mg, 0.12 mmol), N-(3-dimethylaminopropyl)-N'-ethylcarbodiimide hydrochloride (29 mg, 0.15 mmol), 1-hydroxybenzotriazole (21 mg, 0.15 mmol), Hunig's base (70 uL, 0.4 mmol) and the product from Example 25, Part E (57 mg, 0.1 mmol)) in dichloromethane (4 mL) was stirred for 3 hours, diluted with 100 mL EtOAc, washed with 10 mL 1 M $H_3PO_4$, 10 mL 10% $NaHCO_3$, 3×20 mL with brine, dried ($Na_2SO_4$), and concentrated (85 mg, 88%). MS (ESI−) m/z=968 (M−H)$^+$.

Part D. Preparation of Title Product

The product from Part C (85 mg, 0.088 mmol) in dichloromethane (4 mL) was treated with Dess-Martin periodinane (50 mg, 1.14 mmol), stirred for 2 hours, treated with 10% aqueous sodium sulfite (2 mL), stirred for 10 minutes and diluted with 50 mL EtOAc. The EtOAc layer was then washed with 10% aqueous sodium bicarbonate, brine, dried ($Na_2SO_4$) and concentrated. The crude product was flash chromatographed on an Alltech 5 g silica cartridge eluting with dichloromethane→4% MeOH in dichloromethane to give a white powder (28 mg, 33%). MS (ESI−) m/z=966 (M−H).

Example 31

Preparation of N—((S)-1-cyclohexyl-2-((S)-1-((3R,4R)-4-((S)-1-(2-((S)-2-(dimethylamino)-2-oxo-1-phenylethylamino)-2-oxoethylamino)-1,2-dioxohexan-3-ylcarbamoyl)pyrrolidin-3-ylamino)-1-oxo-3-phenylpropan-2-ylamino)-2-oxoethyl)pyrazine-2-carboxamide 2,2,2-trifluoroacetate.

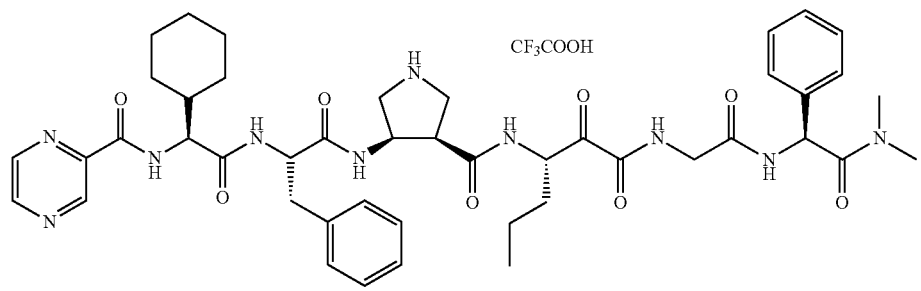

The product from Example 30, Part D (28 mg, 0.029 mmol) in dichloromethane (1 mL) was treated with trifluoroacetic acid (1 mL), stirred for 1 hour and concentrated to give the title compound as a tan powder (27.5 mg, 97%). MS (ESI−) m/z=866 (M−H)$^+$.

Example 32

Preparation of (3R,4R)-tert-butyl 3-((S)-3-cyclohexyl-2-((S)-2-cyclohexyl-2-(pyrazine-2-carboxamido)acetamido)propanamido)-4-((S)-1-(2-((S)-2-(dimethylamino)-2-oxo-1-phenyl ethylamino)-2-oxoethylamino)-1,2-dioxohexan-3-ylcarbamoyl)pyrrolidine-1-carboxylate

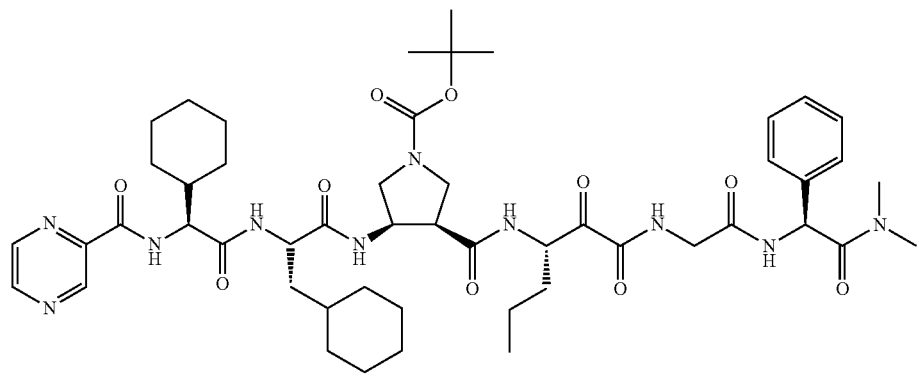

Part A. Preparation of (S)-methyl 3-cyclohexyl-2-((S)-2-cyclohexyl-2-(pyrazine-2-carboxamido)acetamido)propanoate A mixture of the product from Example 1, Part G (132 mg, 0.5 mmol), N-(3-dimethylamino propyl)-N'-ethylcarbodiimide hydrochloride (144 mg, 0.75 mmol), 1-hydroxybenzotriazole (102 mg, 0.75 mmol), Hunig's base (350 uL, 2.0 mmol) and (S)-methyl 2-amino-3-cyclohexylpropanoate hydrochloride (115 mg, 0.52 mmol)) in dichloromethane (15 mL) was stirred for 2 h, diluted with 100 mL EtOAc, washed with 10 mL 1 M $H_3PO_4$, 10 mL 10% $NaHCO_3$, 3×20 mL with brine, dried ($Na_2SO_4$), and concentrated (190 mg, 83%). The crude product was flash chromatographed on Alltech 5 g silica cartridge eluting with 2:1 hexane/EtOAc to give white powder (130 mg, 60%). MS (ESI−) m/z=429 (M−H)+.

Part B. Preparation of (S)-3-cyclohexyl-2-((S)-2-cyclohexyl-2-(pyrazine-2-carboxamido) acetamido) propanoic acid The product from Part A (130 mg, 0.3 mmol) in a solvent mixture of THF/water/methanol (1.5:1.5:0.5 ml) was treated with LiOH (63 mg, 1.5 mmol) and stirred for 3 hours. The mixture was diluted with 50 mL EtOAc and acidified with 10% $H_3PO_4$. The EtOAc layer was washed with brine, dried ($Na_2SO_4$), and concentrated to a white powder (119 mg, 95%). MS (ESI+) m/z=417 (M+H)+.

Part C. Preparation of (3R,4R)-tert-butyl 3-((S)-3-cyclohexyl-2-((S)-2-cyclohexyl-2-(pyrazine-2-carboxamido)acetamido)propanamido)-4-((3S)-1-(2-((S)-2-(dimethylamino)-2-oxo-1-phenyl ethylamino)-2-oxoethylamino)-2-hydroxy-1-oxo-hexan-3-ylcarbamoyl)pyrrolidine-1-carboxylate A mixture of the product from Part B (50 mg, 0.12 mmol), N-(3-dimethylaminopropyl)-N'-ethylcarbodiimide hydrochloride (29 mg, 0.15 mmol), 1-hydroxybenzotriazole (21 mg, 0.15 mmol), Hunig's base (70 uL, 0.4 mmol) and the product from Example 25, Part E (57 mg, 0.1 mmol)) in dichloromethane (4 mL) was stirred for 3 hours, diluted with 100 mL EtOAc, washed with 10 mL 1 M $H_3PO_4$, 10 mL 10% $NaHCO_3$, 3×20 mL with brine, dried ($Na_2SO_4$), and concentrated. The crude product was flash chromatographed on an Alltech 1 g silica cartridge eluting with DCM →10% MeOH in DCM to give a white powder (42 mg, 43%). MS (ESI−) m/z=974 (M−H)+.

Part D. Preparation of Title Product

The product from Part C (40 mg, 0.040 mmol) in dichloromethane (4 mL) was treated with Dess-Martin periodinane (21 mg, 0.049 mmol), stirred for 2 hours, treated with 10% aqueous sodium sulfite (2 mL), stirred for 10 minutes and diluted with 50 mL EtOAc. The EtOAc layer was then washed with 10% aqueous sodium bicarbonate, brine, dried ($Na_2SO_4$) and concentrated. The crude product was flash chromatographed on an Alltech 2 g silica cartridge eluting with dichloromethane→3% MeOH in dichloromethane to give a white powder (20 mg, 50%). MS (ESI−) m/z=972 (M−H)+.

Example 33

Preparation of N—((S)-1-cyclohexyl-2-((S)-3-cyclohexyl-1-((3R,4R)-4-((S)-1-(2-((S)-2-(dimethylamino)-2-oxo-1-phenylethylamino)-2-oxoethylamino)-1,2-dioxohexan-3-ylcarbamoyl)pyrrolidin-3-ylamino)-1-oxopropan-2-ylamino)-2-oxoethyl) pyrazine-2-carboxamide

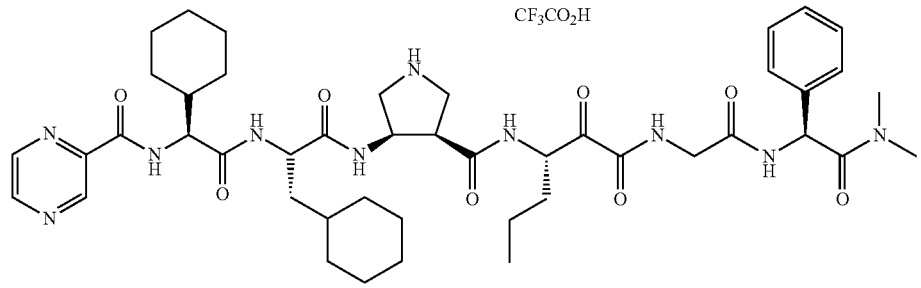

The product from Example 32, Part D (15 mg, 0.0154 mmol) in dichloromethane (0.3 mL) was treated with trifluoroacetic acid (2 mL), stirred for 1 hour and concentrated to give the title compound as a tan powder (16 mg, 99%). MS (ESI−) m/z=872 (M−H)+.

Example 34

Preparation of (3R,4R)-tert-butyl 3-((S)-1-((S)-2-cyclohexyl-2-(pyrazine-2-carboxamido)acetyl)pyrrolidine-2-carboxamido)-4-((S)-1-(2-((S)-2-(dimethylamino)-2-oxo-1-phenyl ethylamino)-2-oxoethylamino)-1,2-dioxohexan-3-ylcarbamoyl) pyrrolidine-1-carboxylate

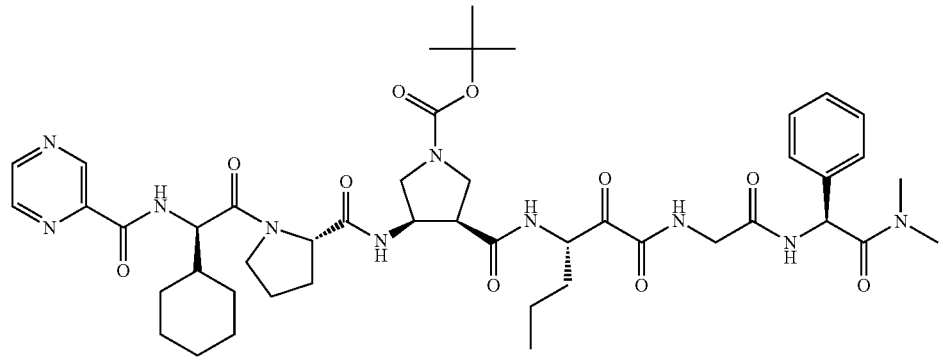 [SMILES: CCC[C@H](NC(=O)[C@@H]1CN(C(=O)OC(C)(C)C)C[C@@H]1NC(=O)[C@@H]1CCCN1C(=O)[C@H](NC(=O)c1cnccn1)C1CCCCC1)C(=O)C(=O)NCC(=O)N[C@H](C(=O)N(C)C)c1ccccc1]

Part A. Preparation of (S)-methyl 1-((S)-2-cyclohexyl-2-(pyrazine-2-carboxamido)acetyl)pyrrolidine-2-carboxylate A mixture of the product from Example 1, Part G (132 mg, 0.5 mmol), N-(3-dimethylamino propyl)-N'-ethylcarbodiimide hydrochloride (144 mg, 0.75 mmol), 1-hydroxybenzotriazole (102 mg, 0.75 mmol), Hunig's base (350 uL, 2.0 mmol) and (S)-methylpyrrolidine-2-carboxylate hydrochloride (86 mg, 0.52 mmol)) in dichloromethane (15 mL) was stirred for 2 hours, diluted with 100 mL EtOAc, washed with 10 mL 1 M $H_3PO_4$, 10 mL 10% $NaHCO_3$, 3×20 mL with brine, dried ($Na_2SO_4$), and concentrated to give a yellow oil (190 mg, 99%). MS (ESI+) m/z=375 (M+H)+.

Part B. Preparation of (S)-1-((S)-2-cyclohexyl-2-(pyrazine-2-carboxamido)acetyl)pyrrolidine-2-carboxylic acid The product from Part A (190 mg, 0.51 mmol) in a solvent mixture of THF/water/methanol (3:3:1 ml) was treated with LiOH (105 mg, 2.5 mmol) and stirred for 3 hours. The mixture was diluted with 50 mL EtOAc and acidified with 10% $H_3PO_4$. The EtOAc layer was washed with brine, dried ($Na_2SO_4$), and concentrated to an off-white powder (175 mg, 95%). MS (ESI+) m/z=361 (M+H)+.

Part C. Preparation of (3R,4R)-tert-butyl 3-((S)-1-((S)-2-cyclohexyl-2-(pyrazine-2-carboxamido) acetyl)pyrrolidine-2-carboxamido)-4-((3S)-1-(2-((S)-2-(dimethylamino)-2-oxo-1-phenyl ethylamino)-2-oxoethylamino)-2-hydroxy-1-oxohexan-3-ylcarbamoyl)pyrrolidine-1-carboxylate A mixture of the product from Part B (43 mg, 0.12 mmol), N-(3-dimethylaminopropyl)-N'-ethylcarbodiimide hydrochloride (29 mg, 0.15 mmol), 1-hydroxybenzotriazole (21 mg, 0.15 mmol), Hunig's base (70 uL, 0.4 mmol) and the product from Example 25, Part E (57 mg, 0.1 mmol)) in dichloromethane (4 mL) was stirred for 3 hours, diluted with 100 mL EtOAc, washed with 10 mL 1 M $H_3PO_4$, 10 mL 10% $NaHCO_3$, 3×20 mL with brine, dried ($Na_2SO_4$), and concentrated. The crude product was flash chromatographed on an Alltech 1 g silica cartridge eluting with DCM →6% MeOH in DCM to give a white powder (50 mg, 54%). MS (ESI−) m/z=918 (M−H)+.

Part D. Preparation of Title Product

The product from Part C (50 mg, 0.054 mmol) in dichloromethane (4 mL) was treated with Dess-Martin periodinane (69 mg, 0.162 mmol), stirred for 2 hours, treated with 10% aqueous sodium sulfite (2 mL), stirred for 10 minutes and diluted with 50 mL EtOAc. The EtOAc layer was then washed with 10% aqueous sodium bicarbonate, brine, dried ($Na_2SO_4$) and concentrated. The crude product was flash chromatographed on an Alltech 2 g silica cartridge eluting with dichloromethane →3% MeOH in dichloromethane to give a white powder (21 mg, 42%). MS (ESI−) m/z=916 (M−H)+.

Example 35

Preparation of (3R,4R)-tert-butyl 3-((S)-5-amino-2-((S)-2-cyclohexyl-2-(pyrazine-2-carboxamido)acetamido)-5-oxopentanamido)-4-((S)-1-(2-((S)-2-(dimethylamino)-2-oxo-1-phenylethylamino)-2-oxoethylamino)-1,2-dioxohexan-3-ylcarbamoyl)pyrrolidine-1-carboxylate

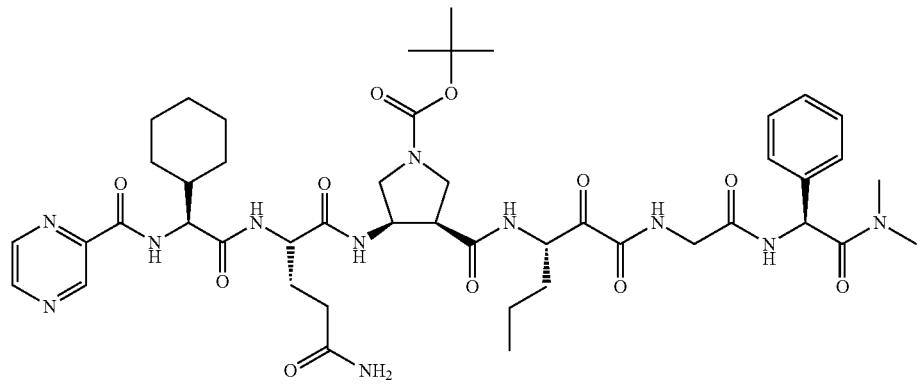

Part A. Preparation of (S)-tert-butyl 5-amino-2-((S)-2-cyclohexyl-2-(pyrazine-2-carboxamido)acetamido)-5-oxopentanoate A mixture of the product from Example 1, Part G (79 mg, 0.3 mmol), N-(3-dimethylamino propyl)-N'-ethylcarbodiimide hydrochloride (86 mg, 0.45 mmol), 1-hydroxybenzotriazole (61 mg, 0.45 mmol), Hunig's base (210 uL, 1.2 mmol) and (S)-tert-butyl 2,5-diamino-5-oxopentanoate hydrochloride (72 mg, 0.3 mmol)) in dichloromethane (8 mL) was stirred for 2 hours, diluted with 100 mL EtOAc, washed with 10 mL 1 M $H_3PO_4$, 10 mL 10% $NaHCO_3$, 3×20 mL with brine, dried ($Na_2SO_4$), and concentrated to give a yellow foam (117 mg, 87%). MS (ESI+) m/z=448 (M+H)+.

Part B. Preparation of (S)-5-amino-2-((S)-2-cyclohexyl-2-(pyrazine-2-carboxamido) acetamido)-5-oxopentanoic acid The product from Part A (117 mg, 0.26 mmol) in dichloromethane (3 mL) was treated with trifluoroacetic acid (3 mL), stirred for 2 hours and concentrated to give an orange foam (130 mg, 99%). MS (ESI+) m/z=392 (M+H)+.

Part C. Preparation of

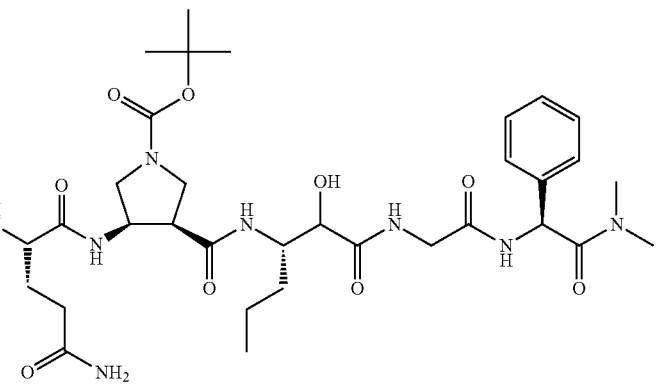

A mixture of the product from Part B (61 mg, 0.12 mmol), N-(3-dimethylaminopropyl)-N'-ethylcarbodiimide hydrochloride (29 mg, 0.15 mmol), 1-hydroxybenzotriazole (21 mg, 0.15 mmol), Hunig's base (70 uL, 0.4 mmol) and the product from Example 25, Part E (57 mg, 0.1 mmol)) in dichloromethane (4 mL) was stirred for 3 hours, diluted with 100 mL EtOAc, washed with 10 mL 1 M $H_3PO_4$, 10 mL 10% $NaHCO_3$, 3×20 mL with brine, dried ($Na_2SO_4$), and concentrated. The crude product was flash chromatographed on an Alltech 1 g silica cartridge eluting with DCM →6% MeOH in DCM to give a white powder (35 mg, 37%). MS (ESI−) m/z=949 (M−H)$^+$.

Part D. Preparation of Title Product

The product from Part C (35 mg, 0.037 mmol) in dichloromethane (4 mL) was treated with Dess-Martin periodinane (47 mg, 0.11 mmol), stirred for 2 hours, treated with 10% aqueous sodium sulfite (2 mL), stirred for 10 minutes and diluted with 50 mL EtOAc. The EtOAc layer was then washed with 10% aqueous sodium bicarbonate, brine, dried ($Na_2SO_4$) and concentrated. The crude product was flash chromatographed on an Alltech 1 g silica cartridge eluting with dichloromethane →6% MeOH in dichloromethane to give a white powder (28 mg, 80%). MS (ESI−) m/z=947 (M−H)$^+$.

Example 36

Preparation of (3R,4R)-tert-butyl 3-((R)-2-((S)-2-cyclohexyl-2-(pyrazine-2-carboxamido)acetamido)-3,3-dimethylbutanamido)-4-((S)-1-(2-((S)-2-(dimethylamino)-2-oxo-1-phenylethylamino)-2-oxoethylamino)-1,2-dioxohexan-3-ylcarbamoyl)pyrrolidine-1-carboxylate Alltech 1 g silica cartridge eluting with dichloromethane →2% MeOH in dichloromethane to give a white foam (58 mg, 50%). MS (ESI+) m/z=391 (M+H)$^+$ Part B. Preparation of (R)-2-((S)-2-cyclohexyl-2-(pyrazine-2-carboxamido)acetamido)-3,3-dimethylbutanoic acid The product from Part A (58 mg, 0.15 mmol) in a solvent mixture of THF/water/methanol (2:2:0.7 ml) was treated with LiOH (32 mg, 0.75 mmol) and stirred for 3 hours. The mixture was diluted with 50 mL EtOAc and acidified with 10% $H_3PO_4$. The EtOAc layer was washed with brine, dried ($Na_2SO_4$), and concentrated to a clear glass (60 mg, 99%). MS (ESI+) m/z=377 (M+H)$^+$.

Part C. Preparation of (3R,4R)-tert-butyl 3-((R)-2-((S)-2-cyclohexyl-2-(pyrazine-2-carboxamido)acetamido)-3,3-dimethylbutanamido)-4-((3S)-1-(2-((S)-2-(dimethylamino)-2-oxo-1-phenyl ethylamino)-2-oxoethylamino)-2-hydroxy-1-oxohexan-3-ylcarbamoyl)pyrrolidine-1-carboxylate A mixture of the product from Part B (45 mg, 0.12 mmol), N-(3-dimethylaminopropyl)-N'-ethylcarbodiimide hydrochloride (29 mg, 0.15 mmol), 1-hydroxybenzotriazole (21 mg, 0.15 mmol), Hunig's base (70 uL, 0.4 mmol) and the product from Example 25, Part E (57 mg, 0.1 mmol)) in dichloromethane (4 mL) was stirred for 3 hours, diluted with 100 mL EtOAc, washed with 10 mL 1 M $H_3PO_4$, 10 mL 10% $NaHCO_3$, 3×20 mL with brine, dried ($Na_2SO_4$), and concentrated. The crude product was flash chromatographed on an Alltech 1 g silica cartridge eluting with DCM →4% MeOH in DCM to give a white powder (18 mg, 19%). MS (ESI−) m/z=934 (M−H)$^+$.

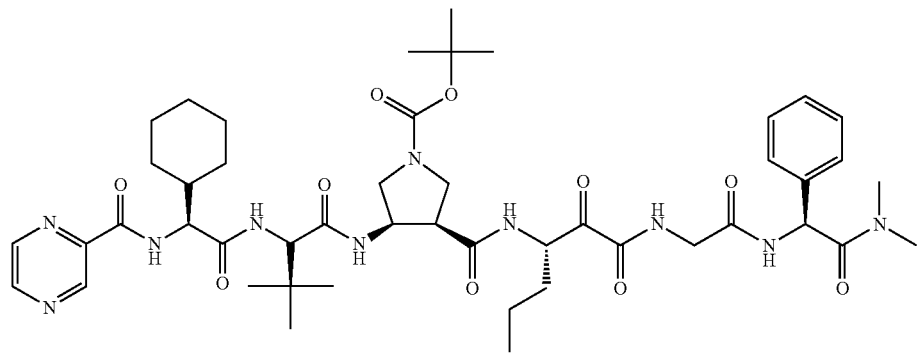

Part A. Preparation of (R)-methyl 2-((S)-2-cyclohexyl-2-(pyrazine-2-carboxamido) acetamido)-3,3-dimethylbutanoate A mixture of the product from Example 1, Part G (79 mg, 0.3 mmol), N-(3-dimethylamino propyl)-N'-ethylcarbodiimide hydrochloride (86 mg, 0.45 mmol), 1-hydroxybenzotriazole (61 mg, 0.45 mmol), Hunig's base (210 uL, 1.2 mmol) and (R)-methyl 2-amino-3-methylbutanoate 2,2,2-trifluoroacetate (78 mg, 0.3 mmol)) in dichloromethane (8 mL) was stirred for 2 hours, diluted with 100 mL EtOAc, washed with 10 mL 1 M $H_3PO_4$, 10 mL 10% $NaHCO_3$, 3×20 mL with brine, dried ($Na_2SO_4$), and The crude product was concentrated and the residue was flash chromatographed on an Part D. Preparation of Title Product The product from Part C (18 mg, 0.019 mmol) in dichloromethane (2 mL) was treated with Dess-Martin periodinane (24 mg, 0.056 mmol), stirred for 2 hours, treated with 10% aqueous sodium sulfite (2 mL), stirred for 10 minutes and diluted with 50 mL EtOAc. The EtOAc layer was then washed with 10% aqueous sodium bicarbonate, brine, dried ($Na_2SO_4$) and concentrated. The crude product was flash chromatographed on an Alltech 1 g silica cartridge eluting with dichloromethane →4% MeOH in dichloromethane to give a white powder (14 mg, 79%). MS (ESI−) m/z=932 (M−H)$^+$.

Example 37

Preparation of (3R,4R)-tert-butyl 3-((S)-2-cyclohexyl-2-((S)-2-cyclohexyl-2-(pyrazine-2-carboxamido)acetamido)acetamido)-4-((S)-1-(2-((S)-2-(dimethylamino)-2-oxo-1-phenyl ethylamino)-2-oxoethylamino)-1,2-dioxohexan-3-ylcarbamoyl)pyrrolidine-1-carboxylate

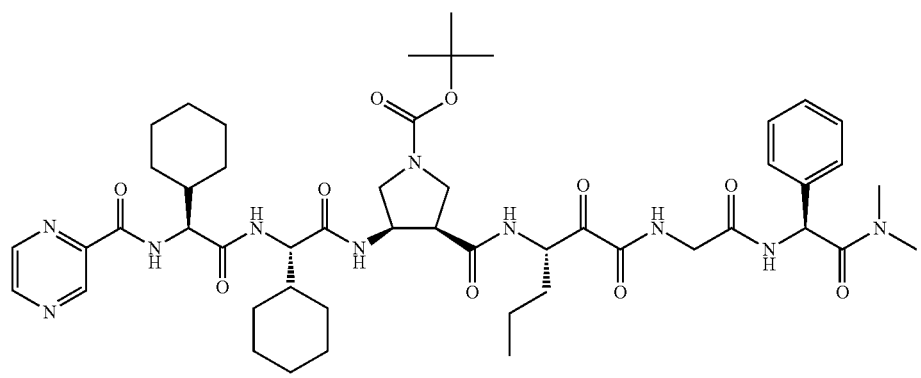 [SMILES: CCC[C@H](NC(=O)[C@@H]1CN(C(=O)OC(C)(C)C)C[C@@H]1NC(=O)[C@@H](NC(=O)[C@@H](NC(=O)c1cnccn1)C1CCCCC1)C1CCCCC1)C(=O)C(=O)NCC(=O)N[C@H](C(=O)N(C)C)c1ccccc1]

Part A. Preparation of (S)-tert-butyl 2-cyclohexyl-2-((S)-2-cyclohexyl-2-(pyrazine-2-carboxamido)acetamido)acetate A mixture of the product from Example 1, Part E (132 mg, 0.5 mmol), N-(3-dimethylamino propyl)-N'-ethylcarbodiimide hydrochloride (144 mg, 0.75 mmol), 1-hydroxybenzotriazole (102 mg, 0.75 mmol), Hunig's base (350 uL, 2.0 mmol) and (S)-tert-butyl 2-amino-2-cyclohexylacetate hydrochloride (130 mg, 0.52 mmol)) in dichloromethane (15 mL) was stirred for 2 hours, diluted with 100 mL EtOAc, washed with 10 mL 1 M $H_3PO_4$, 10 mL 10% $NaHCO_3$, 3×20 mL with brine, dried ($Na_2SO_4$), and concentrated to give a white foam (190 mg, 83%). MS (ESI−) m/z=457 (M−H)$^+$.

Part B. Preparation of (S)-2-cyclohexyl-2-((S)-2-cyclohexyl-2-(pyrazine-2-carboxamido) acetamido) acetic acid The product from Part A (55 mg, 0.12 mmol) in dichloromethane (0.5 mL) was treated with trifluoroacetic acid (2 mL), stirred for 3 hour and concentrated to give a sticky yellow foam. MS (ESI+) m/z=403 (M+H)$^+$.

Part C. Preparation of (3R,4R)-tert-butyl 3-((S)-2-cyclohexyl-2-((S)-2-cyclohexyl-2-(pyrazine-2-carboxamido)acetamido)acetamido)-4-((3S)-1-(2-((S)-2-(dimethylamino)-2-oxo-1-phenyl ethylamino)-2-oxoethylamino)-2-hydroxy-1-oxohexan-3-ylcarbamoyl)pyrrolidine-1-carboxylate A mixture of the product from Part B (48 mg, 0.12 mmol), N-(3-dimethylaminopropyl)-N'-ethylcarbodiimide hydrochloride (29 mg, 0.15 mmol), 1-hydroxybenzotriazole (21 mg, 0.15 mmol), Hunig's base (70 uL, 0.4 mmol) and the product from Example 25, Part E (58 mg, 0.1 mmol)) in dichloromethane (3 mL) was stirred for 1 hour, diluted with 100 mL EtOAc, washed with 10 mL 1 M $H_3PO_4$, 10 mL 10% $NaHCO_3$, 20 mL with brine, dried ($MgSO_4$), and concentrated to give the title compound (70 mg, 72%). MS (ESI+) m/z=961.6 (M+H)$^+$.

Part D. Preparation of Title Product

The product from Part C (67 mg, 0.07 mmol) in dichloromethane (2 mL) was treated with Dess-Martin periodinane (59 mg, 0.14 mmol), stirred for 2 hours, treated with 10% aqueous sodium sulfite (2 mL), stirred for 10 minutes and diluted with 50 mL EtOAc. The EtOAc layer was then washed with 10% aqueous sodium bicarbonate, brine, dried ($MgSO_4$) and concentrated. The crude product was flash chromatographed on an Alltech 5 g silica cartridge eluting with ethyl acetate/methanol (98/2) to give the title compound (24 mg, 36%). MS (ESI+) m/z=959.6 (M+H)$^+$.

Example 38

Preparation of N—((S)-1-cyclohexyl-2-((S)-1-cyclohexyl-2-((3R,4R)-4-((S)-1-(2-((S)-2-(dimethylamino)-2-oxo-1-phenylethylamino)-2-oxoethylamino)-1,2-dioxohexan-3-yl carbamoyl)pyrrolidin-3-ylamino)-2-oxoethylamino)-2-oxoethyl)pyrazine-2-carboxamide 2,2,2-trifluoroacetate

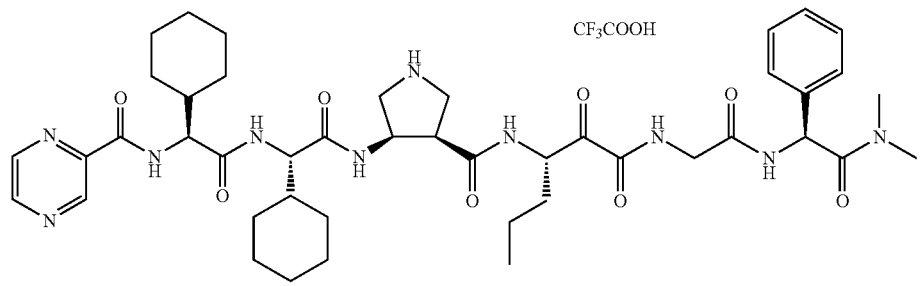 [SMILES: CCC[C@H](NC(=O)[C@@H]1CNC[C@@H]1NC(=O)[C@@H](NC(=O)[C@@H](NC(=O)c1cnccn1)C1CCCCC1)C1CCCCC1)C(=O)C(=O)NCC(=O)N[C@H](C(=O)N(C)C)c1ccccc1 ; "CF3COOH"]

The product from Example 37, Part D (17 mg, 0.018 mmol) in dichloromethane (0.5 mL) was treated with trifluoroacetic acid (1 mL), stirred for 1 hour and concentrated to give the title compound in quantitative yield. MS (ESI–) m/z=857.6 (M–H)+.

Example 39

Preparation of (3R,4R)-tert-butyl 3-((S)-2-((S)-2-cyclohexyl-2-(pyrazine-2-carboxamido)acetamido)pentanamido)-4-((S)-1-(2-((S)-2-(dimethylamino)-2-oxo-1-phenylethylamino)-2-oxoethylamino)-1,2-dioxohexan-3-ylcarbamoyl)pyrrolidine-1-carboxylate Part A. Preparation of (S)-tert-butyl 2-((S)-2-cyclohexyl-2-(pyrazine-2-carboxamido) acetamido)pentanoate A mixture of the product from Example 1, Part E (132 mg, 0.5 mmol), N-(3-dimethylamino propyl)-N'-ethylcarbodiimide hydrochloride (144 mg, 0.75 mmol), 1-hydroxybenzotriazole (102 mg, 0.75 mmol), Hunig's base (350 uL, 2.0 mmol) and (S)-tert-butyl 2-aminopentanoate hydrochloride (109 mg, 0.52 mmol)) in dichloromethane (15 mL) was stirred for 2 hours, diluted with 100 mL EtOAc, washed with 10 mL 1 M $H_3PO_4$, 10 mL 10% $NaHCO_3$, 3×20 mL with brine, dried ($Na_2SO_4$), and concentrated to give a white waxy solid (176 mg, 84%). MS (ESI–) m/z=417 (M–H)+.

Part B. Preparation of (S)-2-((S)-2-cyclohexyl-2-(pyrazine-2-carboxamido)acetamido) pentanoic acid The product from Part A (50 mg, 0.12 mmol) in dichloromethane (0.5 mL) was treated with trifluoroacetic acid (2.5 mL), stirred for 1 hour and concentrated to give a sticky solid.

Part C. Preparation of (3R,4R)-tert-butyl 3-((S)-2-((S)-2-cyclohexyl-2-(pyrazine-2-carboxamido)acetamido)pentanamido)-4-((3S)-1-(2-((S)-2-(dimethylamino)-2-oxo-1-phenylethylamino)-2-oxoethylamino)-2-hydroxy-1-oxohexan-3-ylcarbamoyl)pyrrolidine-1-carboxylate A mixture of the product from Part B (43 mg, 0.12 mmol), N-(3-dimethylaminopropyl)-N'-ethylcarbodiimide hydrochloride (29 mg, 0.15 mmol), 1-hydroxybenzotriazole (21 mg, 0.15 mmol), Hunig's base (70 uL, 0.4 mmol) and the product from Example 25, Part E (58 mg, 0.1 mmol)) in dichloromethane (3 mL) was stirred for 1 hour, diluted with

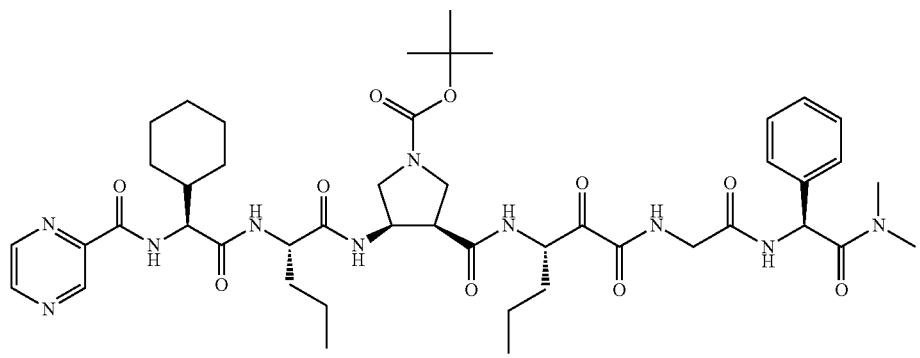 [SMILES: CCC[C@H](NC(=O)[C@@H](NC(=O)c1cnccn1)C1CCCCC1)C(=O)N[C@H]1CN(C(=O)OC(C)(C)C)C[C@H]1C(=O)N[C@@H](CCC)C(=O)C(=O)NCC(=O)N[C@H](C(=O)N(C)C)c1ccccc1]

100 mL EtOAc, washed with 10 mL 1 M $H_3PO_4$, 10 mL 10% $NaHCO_3$, 20 mL with brine, dried ($MgSO_4$), and concentrated to give the title compound (75 mg, 81%). MS (ESI+) m/z=921.6 (M+H)+.

Part D. Preparation of Title Product

The product from Part C (74 mg, 0.08 mmol) in dichloromethane (2 mL) was treated with Dess-Martin periodinane (68 mg, 0.16 mmol), stirred for 1 hour, treated with 10% aqueous sodium sulfite (2 mL), stirred for 10 minutes and diluted with 50 mL EtOAc. The EtOAc layer was then washed with 10% aqueous sodium bicarbonate, brine, dried (MgSO₄) and concentrated. The crude product was flash chromatographed on an Alltech 5 g silica cartridge eluting with ethyl acetate/methanol (98/2) to give the title compound (20 mg, 27%). MS (ESI+) m/z=919.6 (M+H)⁺.

Example 40

Preparation of N-((1S)-1-cyclohexyl-2-((2S)-1-((3R, 4R)-4-((3S)-1-(2-((S)-2-(dimethylamino)-2-oxo-1-phenylethylamino)-2-oxoethylamino)-2-hydroxy-1-oxohexan-3-yl carbamoyl)pyrrolidin-3-ylamino)-1-oxopentan-2-ylamino)-2-oxoethyl)pyrazine-2-carboxamide 2,2,2-trifluoroacetate.

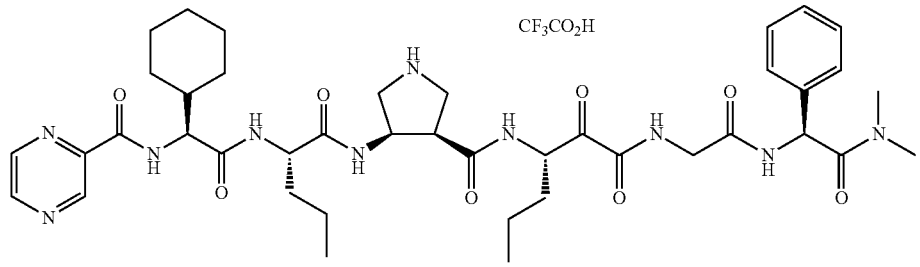 [SMILES: CCC[C@H](NC(=O)[C@@H](NC(=O)c1cnccn1)C1CCCCC1)C(=O)N[C@H]1CNC[C@H]1C(=O)N[C@@H](CCC)C(=O)C(=O)NCC(=O)N[C@H](C(=O)N(C)C)c1ccccc1 ; "CF3CO2H"]

The product from Example 39, Part D (13 mg, 0.014 mmol) in dichloromethane (0.5 mL) was treated with trifluoroacetic acid (1 mL), stirred for 1 hour and concentrated to give the title compound in quantitative yield. MS (ESI+) m/z=819.6 (M+H)⁺.

Example 41

Preparation of (3R,4R)-tert-butyl 3-((S)-2-((S)-2-cyclohexyl-2-(pyrazine-2-carboxamido)acetamido)-4-methylpentanamido)-4-((S)-1-(2-((S)-2-(dimethylamino)-2-oxo-1-phenylethylamino)-2-oxoethylamino)-1,2-dioxohexan-3-ylcarbamoyl)pyrrolidine-1-carboxylate

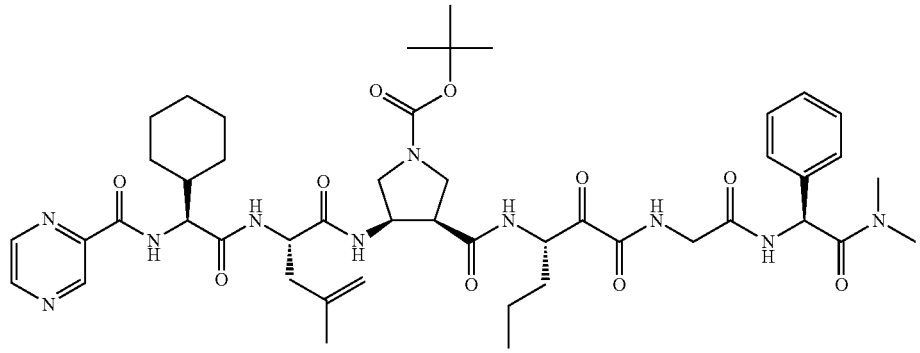 [SMILES: C=C(C)C[C@H](NC(=O)[C@@H](NC(=O)c1cnccn1)C1CCCCC1)C(=O)N[C@H]1CN(C(=O)OC(C)(C)C)C[C@H]1C(=O)N[C@@H](CCC)C(=O)C(=O)NCC(=O)N[C@H](C(=O)N(C)C)c1ccccc1]

Part A. Preparation of (S)-tert-butyl 2-((S)-2-cyclohexyl-2-(pyrazine-2-carboxamido) acetamido)-4-methylpentanoate A mixture of product from Example 1, Part E (132 mg, 0.5 mmol), N-(3-dimethylamino propyl)-N'-ethylcarbodiimide hydrochloride (144 mg, 0.75 mmol), 1-hydroxybenzotriazole (102 mg, 0.75 mmol), Hunig's base (350 uL, 2.0 mmol) and (S)-tert-butyl 2-amino-4-methylpentanoate HCl (116 mg, 0.52 mmol)) in dichloromethane (15 mL) was stirred for 2 h, diluted with 100 mL EtOAc, washed with 10 mL 1M H₃PO₄, 10 mL 10% NaHCO₃, 3×20 mL brine, dried (Na₂SO₄), and concentrated to give white waxy solid (182 mg, 84%). MS (ESI−) m/z=431 (M−H).

Part B. Preparation of (S)-2-((S)-2-cyclohexyl-2-(pyrazine-2-carboxamido)acetamido)-4-methylpentanoic acid The product from Part A (52 mg, 0.12 mmol) in dichloromethane (0.5 mL) was treated with trifluoroacetic acid (2 mL), stirred for 3 h and concentrated to give a sticky solid.

Part C. Preparation of (3R,4R)-tert-butyl 3-((S)-2-((S)-2-cyclohexyl-2-(pyrazine-2-carboxamido)acetamido)-4-methylpentanamido)-4-((3S)-1-(2-((S)-2-(dimethylamino)-2-oxo-1-phenylethyl amino)-2-oxoethylamino)-2-hydroxy-1-oxohexan-3-ylcarbamoyl)pyrrolidine-1-carboxylate A mixture of the product from Part B (45 mg, 0.12 mmol), N-(3-dimethylaminopropyl)-N'-ethylcarbodiimide hydrochloride (29 mg, 0.15 mmol), 1-hydroxybenzotriazole (21 mg, 0.15 mmol), Hunig's base (70 uL, 0.4 mmol) and the product from Example 25, Part E (58 mg, 0.1 mmol)) in dichloromethane (3 mL) was stirred for 1 hour, diluted with 100 mL EtOAc, washed with 10 mL 1 M H₃PO₄, 10 mL 10% NaHCO₃, 20 mL with brine, dried (MgSO₄), and concentrated to give the title compound (70 mg, 74%). MS (ESI+) m/z=935.6 (M+H)⁺.

Part D. Preparation of Title Product

The product from Part C (66 mg, 0.07 mmol) in dichloromethane (2 mL) was treated with Dess-Martin periodinane (59 mg, 0.14 mmol), stirred for 2 hours, treated with 10% aqueous sodium sulfite (2 mL), stirred for 10 minutes and diluted with 50 mL EtOAc. The EtOAc layer was then washed with 10% aqueous sodium bicarbonate, brine, dried (MgSO$_4$) and concentrated. The crude product was flash chromatographed on an Alltech 5 g silica cartridge eluting with ethyl acetate/methanol (98/2) to give the title compound (19 mg, 29%). MS (ESI−) m/z=931.7 (M−H)$^+$.

Example 42

Preparation of N—((S)-1-cyclohexyl-2-((S)-1-((3R,4R)-4-((S)-1-(2-((S)-2-(dimethylamino)-2-oxo-1-phenylethylamino)-2-oxoethylamino)-1,2-dioxohexan-3-ylcarbamoyl)pyrrolidin-3-ylamino)-4-methyl-1-oxopentan-2-ylamino)-2-oxoethyl) pyrazine-2-carboxamide 2,2,2-trifluoroacetate

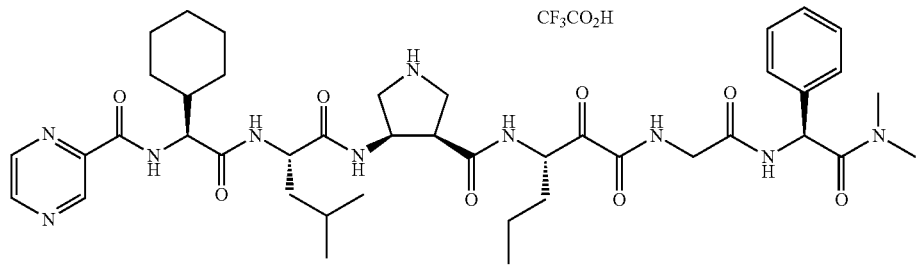 [SMILES: CCC[C@H](NC(=O)[C@@H]1CNC[C@@H]1NC(=O)[C@H](CC(C)C)NC(=O)[C@@H](NC(=O)c1cnccn1)C1CCCCC1)C(=O)C(=O)NCC(=O)N[C@H](C(=O)N(C)C)c1ccccc1 ; "CF3CO2H"]

The product from Example 41, Part D (12 mg, 0.013 mmol) in dichloromethane (0.5 mL) was treated with trifluoroacetic acid (1 mL), stirred for 1 hour and concentrated to give the title compound in quantitative yield. MS (ESI−) m/z=831.7 (M−H)$^+$ Example 43

Preparation of (3R,4R)-tert-butyl 3-((S)-2-((S)-2-cyclohexyl-2-(pyrazine-2-carboxamido)acetamido) butanamido)-4-((S)-1-(2-((S)-2-(dimethylamino)-2-oxo-1-phenylethylamino)-2-oxoethylamino)-1,2-dioxohexan-3-ylcarbamoyl)pyrrolidine-1-carboxylate.

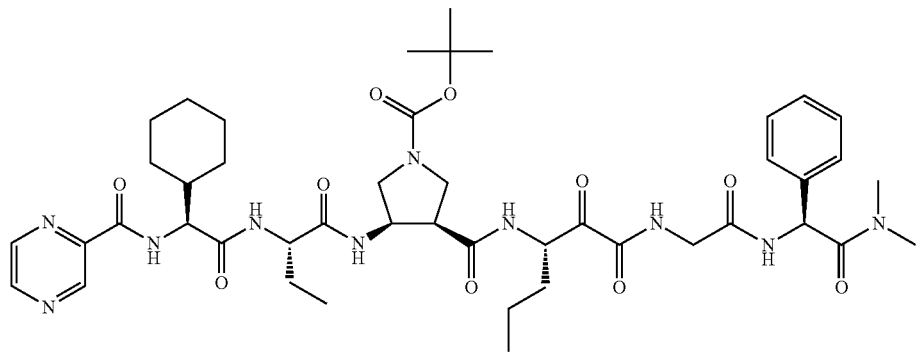 [SMILES: CCC[C@H](NC(=O)[C@@H]1CN(C(=O)OC(C)(C)C)C[C@@H]1NC(=O)[C@H](CC)NC(=O)[C@@H](NC(=O)c1cnccn1)C1CCCCC1)C(=O)C(=O)NCC(=O)N[C@H](C(=O)N(C)C)c1ccccc1]

Part A. Preparation of (S)-tert-butyl 2-((S)-2-cyclohexyl-2-(pyrazine-2-carboxamido) acetamido)butanoate A mixture of the product from Example 1, Part E (132 mg, 0.5 mmol), N-(3-dimethylamino propyl)-N'-ethylcarbodiimide hydrochloride (144 mg, 0.75 mmol), 1-hydroxybenzotriazole (102 mg, 0.75 mmol), Hunig's base (350 uL, 2.0 mmol) and (S)-tert-butyl 2-aminobutanoate hydrochloride (102 mg, 0.52 mmol)) in dichloromethane (15 mL) was stirred for 2 hours, diluted with 100 mL EtOAc, washed with 10 mL 1 M $H_3PO_4$, 10 mL 10% $NaHCO_3$, 3×20 mL with brine, dried ($Na_2SO_4$), and concentrated to give a white foam (182 mg, 90%). MS (ESI−) m/z=403 (M−H)$^-$.

Part B. Preparation of (S)-2-((S)-2-cyclohexyl-2-(pyrazine-2-carboxamido)acetamido) butanoic acid The product from Part A (49 mg, 0.12 mmol) in dichloromethane (0.5 mL) was treated with trifluoroacetic acid (2.5 mL), stirred for 1 hour and concentrated to give a sticky solid.

Part C. Preparation of (3R,4R)-tert-butyl 3-((S)-2-((S)-2-cyclohexyl-2-(pyrazine-2-carboxamido)acetamido)butanamido)-4-((3S)-1-(2-((S)-2-(dimethylamino)-2-oxo-1-phenylethylamino)-2-hydroxy-1-oxohexan-3-ylcarbamoyl)pyrrolidine-1-carboxylate A mixture of product from Part B (42 mg, 0.12 mmol), N-(3-dimethylaminopropyl)-N'-ethylcarbodiimide hydrochloride (29 mg, 0.15 mmol), 1-hydroxybenzotriazole (21 mg, 0.15 mmol), Hunig's base (70 uL, 0.4 mmol) and the product from Example 25, Part E (58 mg, 0.1 mmol)) in dichloromethane (3 mL) was stirred for 1 h, diluted with 100 mL EtOAc, washed with 10 mL 1 M $H_3PO_4$, 10 mL 10% $NaHCO_3$, 20 mL brine, dried ($MgSO_4$), and concentrated to title compound (54 mg, 59%). MS (ESI+) m/z=907.6 (M+H)$^+$.

Part D. Preparation of Title Product

The product from Part C (50 mg, 0.055 mmol) in dichloromethane (2 mL) was treated with Dess-Martin periodinane (47 mg, 0.11 mmol), stirred for 2 h, treated with 10% aqueous sodium sulfite (2 mL), stirred for 10 min and diluted with 50 mL EtOAc. EtOAc layer was washed with 10% aqueous sodium bicarbonate, brine, dried ($MgSO_4$) and concentrated. Crude product was flash chromatographed on an Alltech 5 g silica cartridge eluting with ethyl acetate/methanol (98/2) to give title compound (16 mg, 32%). MS (ESI+) m/z=905.6 (M+H)$^+$.

Example 44

Preparation of N—((S)-1-cyclohexyl-2-((S)-1-((3R,4R)-4-((S)-1-(2-((S)-2-(dimethylamino)-2-oxo-1-phenylethylamino)-2-oxoethylamino)-1,2-dioxohexan-3-ylcarbamoyl)pyrrolidin-3-ylamino)-1-oxobutan-2-ylamino)-2-oxoethyl)pyrazine-2-carboxamide 2,2,2-trifluoroacetate

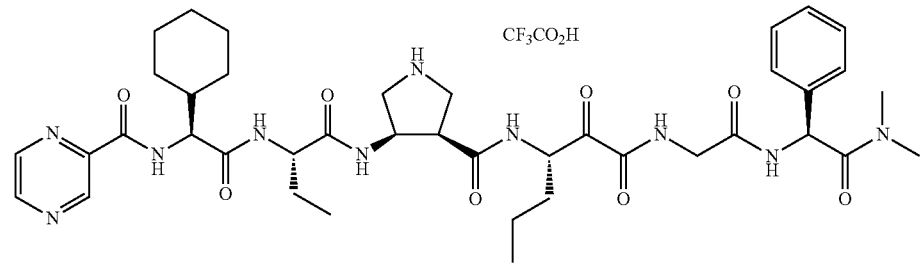 [SMILES: CCC[C@H](NC(=O)[C@@H]1CNC[C@@H]1NC(=O)[C@H](CC)NC(=O)[C@@H](NC(=O)c1cnccn1)C1CCCCC1)C(=O)C(=O)NCC(=O)N[C@H](C(=O)N(C)C)c1ccccc1 ; "CF3CO2H"]

The product from Example 43, Part D (9 mg, 0.01 mmol) in dichloromethane (0.5 mL) was treated with trifluoroacetic acid (1 mL), stirred for 1 hour and concentrated to give the title compound in quantitative yield. MS (ESI−) m/z=803.6 (M−H)$^+$.

Example 45

Preparation of (3R,4R)-tert-butyl 3-((S)-2-((S)-2-cyclohexyl-2-(pyrazine-2-carboxamido)acetamido)-N,3,3-trimethylbutanamido)-4-((S)-1-(2-((S)-2-(dimethylamino)-2-oxo-1-phenylethylamino)-2-oxoethylamino)-1,2-dioxohexan-3-ylcarbamoyl)pyrrolidine-1-carboxylate

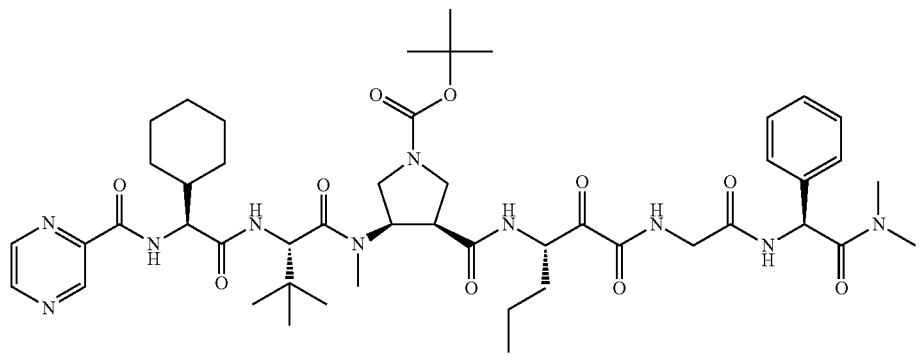 [SMILES: CCC[C@H](NC(=O)[C@@H]1CN(C(=O)OC(C)(C)C)C[C@@H]1N(C)C(=O)[C@@H](NC(=O)[C@@H](NC(=O)c1cnccn1)C1CCCCC1)C(C)(C)C)C(=O)C(=O)NCC(=O)N[C@H](C(=O)N(C)C)c1ccccc1]

Part A. Preparation of (3R,4R)-di-tert-butyl 4-(benzyl(methyl)amino)pyrrolidine-1,3-dicarboxylate To a solution of (3R,4R)-di-tert-butyl 4-aminopyrrolidine-1,3-dicarboxylate (*Org. Biomol. Chem.* 2004, 2, 2763-2776) (430 mg, 1.5 mmol) in dichloromethane/methanol (18 mL/2 mL) was added benzaldehyde (153 uL, 1.5 mmol) and sodium triacetoxyborohydride (1.89 g, 9.0 mmol). The mixture was stirred overnight and partitioned between ethyl acetate and water. The organic layer was washed with brine, dried with magnesium sulfate, filtered and evaporated. The residue was purified on silica gel eluting with ethyl acetate/hexane (1:3) to give the title compound (495 mg, 88%). MS (ESI+) m/z=377 (M+H)$^+$.

Part B. Preparation of (3R,4R)-di-tert-butyl 4-(benzyl(methyl)amino)pyrrolidine-1,3-dicarboxylate To a solution of the product from Part A (490 mg, 1.3 mmol) in dichloromethane/methanol (18 mL/2 mL) was added formaldehyde (104 uL, 37 wt. %, 1.4 mmol) and sodium triacetoxyborohydride (2.20 g, 10.4 mmol). The mixture was stirred overnight and partitioned between ethyl acetate and water. The organic layer was washed with brine, dried with magnesium sulfate, filtered and evaporated. The residue was purified on silica gel eluting with ethyl acetate/hexane (1:3) to give the title compound (369 mg, 73%). MS (ESI+) m/z=391 (M+H)$^+$.

Part C. Preparation of (3R,4R)-di-tert-butyl 4-(methylamino)pyrrolidine-1,3-dicarboxylate The product from Part B (360 mg, 0.92 mmol) was hydrogenated using 10% Pd/C (50 mg) in ethyl acetate (20 mL). The reaction mixture was stirred overnight under 1 atmosphere of H$_2$, filtered through celite and the filtrate was evaporated to give the title compound (275 mg, 99%). MS (ESI+) m/z=301 (M+H)$^+$.

Part D. Preparation of (3R,4R)-di-tert-butyl 4-((S)-2-(benzyloxycarbonylamino)-N,3,3-trimethylbutanamido)pyrrolidine-1,3-dicarboxylate A mixture of the product from Part C (270 mg, 0.9 mmol), O-(7-azabenzotriazol-1-yl)-1,1,3,3-tetramethyluronium hexafluorophosphate (380 mg, 1.0 mmol), Hunig's base (470 uL, 2.7 mmol) and (S)-2-(benzyloxycarbonylamino)-3,3-dimethylbutanoic acid (239 mg, 0.9 mmol)) in dichloromethane (5 mL) was stirred for 24 hours, diluted with 100 mL EtOAc, washed with 10 mL 1 M H$_3$PO$_4$, 10 mL 10% NaHCO$_3$, 20 mL with brine, dried (MgSO$_4$), and evaporated. The residue was purified on silica gel eluting with ethyl acetate/hexane (1:3) to give the title compound (402 mg, 82%). MS (ESI+) m/z=548 (M+H)$^+$.

Part E. Preparation of (3R,4R)-di-tert-butyl 4-((S)-2-amino-N,3,3-trimethylbutanamido) pyrrolidine-1,3-dicarboxylate The product from Part D (400 mg, 0.73 mmol) was hydrogenated using 10% Pd/C (50 mg) in methanol (20 mL). The reaction mixture was stirred overnight under 1 atmosphere of H$_2$, filtered through celite and evaporated to give the title compound (293 mg, 97%). MS (ESI+) m/z=414 (M+H)+.

Part F. Preparation of (3R,4R)-di-tert-butyl 4-((S)-2-((S)-2-cyclohexyl-2-(pyrazine-2-carboxamido)acetamido)-N,3,3-trimethylbutanamido)pyrrolidine-1,3-dicarboxylate A mixture of the product from Part E (290 mg, 0.70 mmol), N-(3-dimethylaminopropyl)-N'-ethylcarbodiimide hydrochloride (148 mg, 0.77 mmol), 1-hydroxybenzotriazole (104 mg, 0.77 mmol), Hunig's base (366 uL, 2.1 mmol) and the product from Example 1, Part E (184 mg, 0.7 mmol)) in dichloromethane (10 mL) was stirred for 3 hour, diluted with 100 mL EtOAc, washed with 10 mL 1 M H$_3$PO$_4$, 10 mL 10% NaHCO$_3$, 20 mL with brine, dried (MgSO$_4$), and concentrated to give the title compound (410 mg, 89%). MS (ESI+) m/z=660 (M+H)$^+$.

Part G. Preparation of (3R,4R)-4-((S)-2-((S)-2-cyclohexyl-2-(pyrazine-2-carboxamido) acetamido)-N,3,3-trimethylbutanamido)pyrrolidine-3-carboxylic acid The product from Part F (409 mg, 0.62 mmol) in dichloromethane (2 mL) was treated with trifluoroacetic acid (5 mL), stirred for 4 hour and concentrated to give the title compound in quantitative yield. MS (ESI+) m/z=503 (M+H)+.

Part H. Preparation of (3R,4R)-1-(tert-butoxycarbonyl)-4-((S)-2-((S)-2-cyclohexyl-2-(pyrazine-2-carboxamido)acetamido)-N,3,3-trimethylbutanamido)pyrrolidine-3-carboxylic acid The product from Part G (191 mg, 0.31 mmol) in THF/1M NaOH (5 mL/1.5 mL) was treated with di-tert-butyl dicarbonate (100 mg, 0.46 mmol) and stirred for 2 hours. The mixture was concentrated to remove THF, then added water and ethyl acetate, adjusted pH to 3 by adding 1M HCl. The aqueous layer was extracted by ethyl acetate again. The combined organic layers were dried with magnesium sulfate, filtered and evaporated to give the title compound (182 mg, 97%). MS (ESI−) m/z=601.5 (M−H)+.

Part I. Preparation of (3R,4R)-tert-butyl 3-((S)-2-((S)-2-cyclohexyl-2-(pyrazine-2-carboxamido)acetamido)-N,3,3-trimethylbutanamido)-4-((3S)-1-(2-((S)-2-(dimethylamino)-2-oxo-1-phenylethylamino)-2-oxoethylamino)-2-hydroxy-1-oxohexan-3-ylcarbamoyl)pyrrolidine-1-carboxylate A mixture from Part H (48 mg, 0.08 mmol), N-(3-dimethylaminopropyl)-N'-ethylcarbodiimide hydrochloride (17 mg, 0.09 mmol), 1-hydroxybenzotriazole (12 mg, 0.09 mmol), Hunig's base (42 uL, 0.24 mmol) and ((3S)-3-amino-N-(2-((S)-2-(dimethylamino)-2-oxo-1-phenylethylamino)-2-oxoethyl)-2-hydroxyhexanamide (WO2003062265-A2; Example 6, cpd 2.3) (29 mg, 0.08 mmol)) in dichloromethane (5 mL) was stirred for 3 hours and diluted with 100 mL EtOAc, washed with 10 mL 1 M H₃PO₄, 10 mL 10% NaHCO₃, 20 mL with brine, dried (MgSO₄), and concentrated to give the title compound (56 mg, 74%). MS (ESI−) m/z=947.7 (M−H)+.

Part J. Preparation of Title Product

The product from Part I (47 mg, 0.05 mmol) in dichloromethane (2 mL) was treated with Dess-Martin periodinane (42 mg, 0.10 mmol), stirred for 4 hours, treated with 10% aqueous sodium sulfite (2 mL), stirred for 10 minutes and diluted with 50 mL EtOAc. The EtOAc layer was then washed with 10% aqueous sodium bicarbonate, brine, dried (MgSO₄) and concentrated. The crude product was flash chromatographed on an Alltech 5 g silica cartridge eluting with ethyl acetate/methanol (98/2) to give the title compound (11 mg, 23%). MS (ESI−) m/z=945.7 (M−H)+.

Example 46

Preparation of N—((S)-1-cyclohexyl-2-((S)-1-(((3R,4R)-4-((S)-1-(2-((S)-2-(dimethylamino)-2-oxo-1-phenylethylamino)-2-oxoethylamino)-1,2-dioxohexan-3-ylcarbamoyl)pyrrolidin-3-yl)(methyl)amino)-3,3-dimethyl-1-oxobutan-2-ylamino)-2-oxoethyl)pyrazine-2-carboxamide 2,2,2-trifluoroacetate.

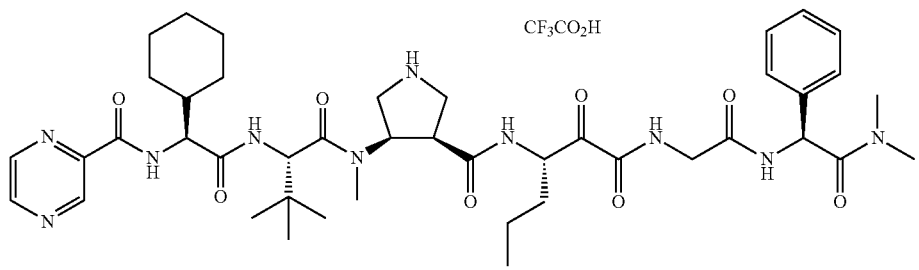 [SMILES: CCC[C@H](NC(=O)[C@@H]1CNC[C@@H]1N(C)C(=O)[C@@H](NC(=O)[C@@H](NC(=O)c1cnccn1)C1CCCCC1)C(C)(C)C)C(=O)C(=O)NCC(=O)N[C@H](C(=O)N(C)C)c1ccccc1 ; "CF3CO2H"]

The product from Example 45, Part J (6 mg, 0.006 mmol) in dichloromethane (0.5 mL) was treated with trifluoroacetic acid (1 mL), stirred for 1 hour and concentrated to give the title compound in quantitative yield. MS (ESI+) m/z=847.6 (M+H)+.

Example 47

Preparation of (3R,4R)-tert-butyl 3-((S)-2-((S)-2-cyclohexyl-2-(pyrazine-2-carboxamido)acetamido)-N,3,3-trimethylbutanamido)-4-((S)-1-(cyclopropylamino)-1,2-dioxohexan-3-ylcarbamoyl)pyrrolidine-1-carboxylate

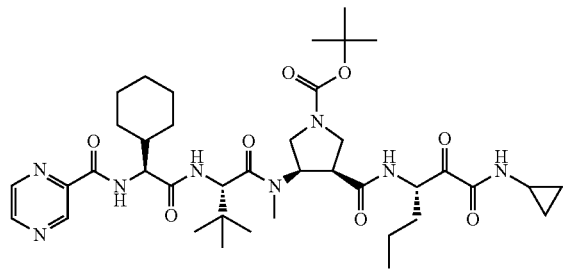 [SMILES: CCC[C@H](NC(=O)[C@@H]1CN(C(=O)OC(C)(C)C)C[C@@H]1N(C)C(=O)[C@@H](NC(=O)[C@@H](NC(=O)c1cnccn1)C1CCCCC1)C(C)(C)C)C(=O)C(=O)NC1CC1]

Part A. Preparation of (3R,4R)-tert-butyl 3-((S)-2-((S)-2-cyclohexyl-2-(pyrazine-2-carboxamido)acetamido)-N,3,3-trimethylbutanamido)-4-((3S)-1-(cyclopropylamino)-2-hydroxy-1-oxohexan-3-ylcarbamoyl)pyrrolidine-1-carboxylate A mixture the product from Example 45, Part H (48 mg, 0.08 mmol), N-(3-dimethylaminopropyl)-N'-ethylcarbodiimide hydrochloride (17 mg, 0.09 mmol), 1-hydroxybenzotriazole (12 mg, 0.09 mmol), Hunig's base (42 uL, 0.24 mmol) and 3-amino-N-cyclopropyl-2-hydroxyhexanamide (WO2002018369-A2; Example 119, cpd xiii') (15 mg, 0.08 mmol)) in dichloromethane (5 mL) was stirred for 3 hours and diluted with 100 mL EtOAc, washed with 10 mL 1 M H₃PO₄, 10 mL 10% NaHCO₃, 20 mL with brine, dried (MgSO₄), and concentrated to give the title compound (54 mg, 88%). MS (ESI+) m/z=771.6 (M+H)⁺.

Part B. Preparation of Title Product

The product from Part A (52 mg, 0.067 mmol) in dichloromethane (2 mL) was treated with Dess-Martin periodinane (59 mg, 0.14 mmol), stirred for 4 hours, treated with 10% aqueous sodium sulfite (2 mL), stirred for 10 minutes and diluted with 50 mL EtOAc. The EtOAc layer was then washed with 10% aqueous sodium bicarbonate, brine, dried (MgSO₄) and concentrated. The crude product was flash chromatographed on an Alltech 5 g silica cartridge eluting with ethyl acetate to give the title compound (27 mg, 52%). MS (ESI−) m/z=767.7 (M−H)⁺.

Example 48

Preparation of (3R,4R)-4-((S)-2-((S)-2-cyclohexyl-2-(pyrazine-2-carboxamido) acetamido)-N,3,3-trimethylbutanamido)-N3-((S)-1-(2-((S)-2-(dimethylamino)-2-oxo-1-phenylethyl amino)-2-oxoethylamino)-1,2-dioxohexan-3-yl)-N-phenylpyrrolidine-1,3-dicarboxamide

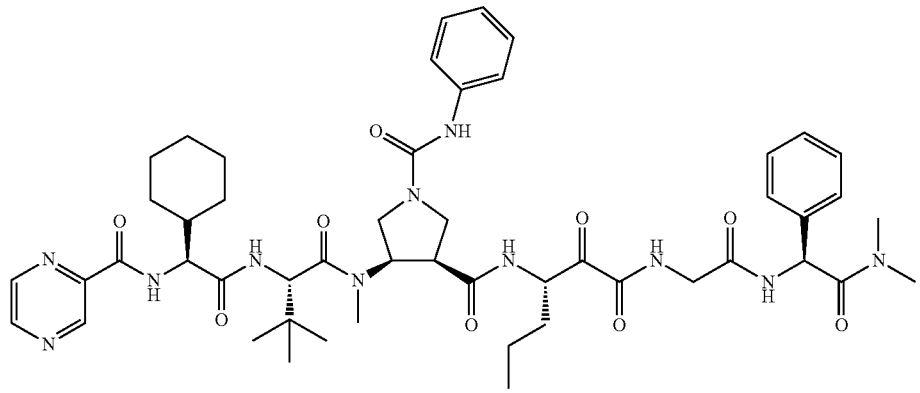 [SMILES: CCC[C@H](NC(=O)[C@@H]1CN(C(=O)Nc2ccccc2)C[C@@H]1N(C)C(=O)[C@@H](NC(=O)[C@@H](NC(=O)c1cnccn1)C1CCCCC1)C(C)(C)C)C(=O)C(=O)NCC(=O)N[C@H](C(=O)N(C)C)c1ccccc1]

Part A. Preparation of (3R,4R)-4-((S)-2-((S)-2-cyclohexyl-2-(pyrazine-2-carboxamido) acetamido)-N,3,3-trimethylbutanamido)-1-(phenylcarbamoyl)pyrrolidine-3-carboxylic acid The product from Example 45, Part G (191 mg, 0.31 mmol), phenyl isocyanate (37 uL, 0.34 mmol) and Hunig's base (162 uL, 0.93 mmol) in tetrahydrofuran (5 mL) was stirred for 2 hours. The mixture was diluted with water and ethyl acetate and the pH was adjusted to 3 by adding 1M HCl. The aqueous layer was extracted with ethyl acetate again. The combined organic layers were dried with magnesium sulfate, filtered and evaporated to give the title compound in quantitative yield. MS (ESI+) m/z=622.5 (M+H)⁺.

Part B. Preparation of (3R,4R)-4-((S)-2-((S)-2-cyclohexyl-2-(pyrazine-2-carboxamido) acetamido)-N,3,3-trimethylbutanamido)-N3-((3S)-1-(2-((S)-2-(dimethylamino)-2-oxo-1-phenylethyl amino)-2-oxoethylamino)-2-hydroxy-1-oxohexan-3-yl)-N1-phenylpyrrolidine-1,3-dicarboxamide A mixture the product from Part A (50 mg, 0.08 mmol), N-(3-dimethylaminopropyl)-N'-ethylcarbodiimide hydrochloride (17 mg, 0.09 mmol), 1-hydroxybenzotriazole (12 mg, 0.09 mmol), Hunig's base (42 uL, 0.24 mmol) and ((3S)-3-amino-N-(2-((S)-2-(dimethylamino)-2-oxo-1-phenylethylamino)-2-oxoethyl)-2-hydroxyhexanamide (WO2003062265-A2; Example 6, cpd 2.3) (29 mg, 0.08 mmol)) in dichloromethane (5 mL) was stirred for 3 hours and diluted with 100 mL EtOAc, washed with 10 mL 1 M H₃PO₄, 10 mL 10% NaHCO₃, 20 mL with brine, dried (MgSO₄), and concentrated to give the title compound (34 mg, 44%). MS (ESI+) m/z=968.6 (M+H)⁺.

Part C. Preparation of Title Product

The product from Part B (29 mg, 0.03 mmol) in dichloromethane (2 mL) was treated with Dess-Martin periodinane (26 mg, 0.06 mmol), stirred for 4 hours, treated with 10% aqueous sodium sulfite (2 mL), stirred for 10 minutes and diluted with 50 mL EtOAc. The EtOAc layer was then washed with 10% aqueous sodium bicarbonate, brine, dried (MgSO₄) and concentrated. The crude product was flash chromatographed on an Alltech 5 g silica cartridge eluting with ethyl acetate to give the title compound (15 mg, 52%). MS (ESI+) m/z=966.6 (M+H)⁺.

Example 49

Preparation of (3R,4R)-4-((S)-2-((S)-2-cyclohexyl-2-(pyrazine-2-carboxamido) acetamido)-N,3,3-trimethylbutanamido)-N3-((S)-1-(cyclopropylamino)-1,2-dioxohexan-3-yl)-N1-phenyl pyrrolidine-1,3-dicarboxamide

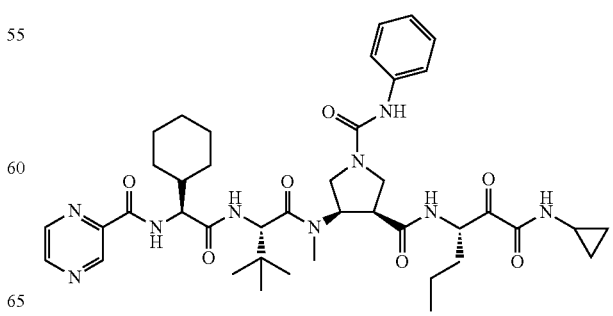

Part A. Preparation of (3R,4R)-4-((S)-2-((S)-2-cyclohexyl-2-(pyrazine-2-carboxamido) acetamido)-N,3,3-trimethylbutanamido)-N3-((3S)-1-(cyclopropylamino)-2-hydroxy-1-oxohexan-3-yl)-N1-phenylpyrrolidine-1,3-dicarboxamide A mixture of the product from Example 48, Part A (50 mg, 0.08 mmol), N-(3-dimethyl aminopropyl)-N'-ethylcarbodiimide hydrochloride (17 mg, 0.09 mmol), 1-hydroxybenzotriazole (12 mg, 0.09 mmol), Hunig's base (42 uL, 0.24 mmol) and 3-amino-N-cyclopropyl-2-hydroxyhexanamide (WO2002018369-A2; Example 119, cpd xiii') (15 mg, 0.08 mmol)) in dichloromethane (5 mL) was stirred for 3 hours and diluted with 100 mL EtOAc, washed with 10 mL 1 M $H_3PO_4$, 10 mL 10% $NaHCO_3$, 20 mL with brine, dried ($MgSO_4$), and concentrated to give the title compound (31 mg, 49%). MS (ESI+) m/z=790.7 $(M+H)^+$.

Part B. Preparation of Title Product

The product from Part A (24 mg, 0.03 mmol) in dichloromethane (2 mL) was treated with Dess-Martin periodinane (26 mg, 0.06 mmol), stirred for 4 hours, treated with 10% aqueous sodium sulfite (2 mL), stirred for 10 minutes and diluted with 50 mL EtOAc. The EtOAc layer was then washed with 10% aqueous sodium bicarbonate, brine, dried ($MgSO_4$) and concentrated. The crude product was flash chromatographed on an Alltech 5 g silica cartridge eluting with ethyl acetate to give the title compound (13 mg, 54%). MS (ESI+) m/z=788.7 $(M+H)^+$.

Example 50

Preparation of (3R,4R)-4-((S)-2-((S)-2-cyclohexyl-2-(pyrazine-2-carboxamido) acetamido)-3,3-dimethylbutanamido)-$N^3$—((S)-1-(2-((R)-2-(dimethylamino)-2-oxo-1-(thiophen-2-yl)ethyl amino)-2-oxoethylamino)-1,2-dioxohexan-3-yl)-$N^1$-phenylpyrrolidine-1,3-dicarboxamide

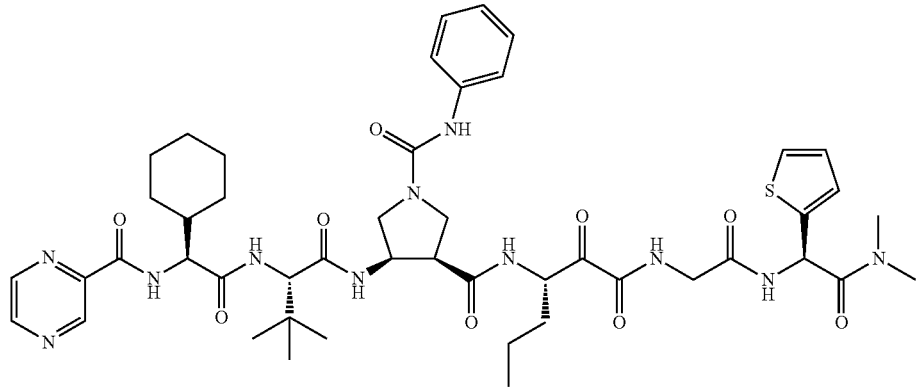 [SMILES: CCC[C@H](NC(=O)[C@@H]1CN(C(=O)Nc2ccccc2)C[C@@H]1NC(=O)[C@@H](NC(=O)[C@@H](NC(=O)c1cnccn1)C1CCCCC1)C(C)(C)C)C(=O)C(=O)NCC(=O)N[C@H](C(=O)N(C)C)c1cccs1]

Part A. Preparation of (R)-tert-butyl 2-(dimethylamino)-2-oxo-1-(thiophen-2-yl)ethyl carbamate To a solution of (R)-2-(tert-butoxycarbonylamino)-2-(thiophen-2-yl)acetic acid (250 mg, 0.9716 mmol) in DMF (5 mL) and methylene chloride (5 mL) was added dimethylamine hydrochloride (87 mg, 1.069 mmol), HOBt (158 mg, 1.166 mmol), and Hunig's Base (0.508 mL, 2.915 mmol) and the resulting solution stirred at 0° C. for 10 minutes. EDCI (248 mg, 1.166 mmol) was added and the reaction stirred at 25° C. for 18 hours. The mixture was concentrated in vacuo, the resulting residue was diluted with ethyl acetate (45 mL), brine (10 mL), and 5% $H_3PO_4$ aqueous solution (10 mL), and the layers were separated. The organic layer was washed with 5% $H_3PO_4$ aqueous solution (10 mL), twice with saturated aqueous sodium bicarbonate solution (15 mL), water (15 mL), and brine (15 mL). The organic layer was dried over sodium sulfate, filtered, and concentrated in vacuo to afford the title compound as a light colored solid. The crude material was taken on directly to the next step.

Part B. Preparation of (R)-2-amino-N,N-dimethyl-2-(thiophen-2-yl)acetamide hydrochloride To a solution of the product from Part A (276 mg, 0.9716 mmol) in methylene chloride (2 mL) was added 4N HCl in dioxane (2 mL) and the resulting solution stirred at 25° C. for 18 hours. The solution was concentrated in vacuo, triturated in diethyl ether, filtered, and dried under vacuum to afford the title compound as a light colored solid (152 mg, 71% yield for two steps). MS (DCI/$NH_4^+$) m/z=185 $(M+H)^+$.

Part C. Preparation of tert-butyl (3S)-1-(2-((R)-2-(dimethylamino)-2-oxo-1-(thiophen-2-yl)ethylamino)-2-oxoethylamino)-2-hydroxy-1-oxohexan-3-ylcarbamate To a solution of 2-((3S)-3-(tert-butoxycarbonylamino)-2-hydroxyhexanamido)acetic acid (WO2003062265-A2; Preparative Example 1, compound 1.1) (200 mg, 0.6572 mmol) in DMF (5 mL) and methylene chloride (5 mL) was added the product from Part B (152 mg, 0.6900 mmol), HOBt (107 mg, 0.7886 mmol), and Hunig's Base (0.343 mL, 1.971 mmol) and the resulting solution stirred at 0° C. for 10 minutes. EDCI (168 mg, 0.7886 mmol) was added and the reaction stirred at 25° C. for 18 hours. The mixture was concentrated in vacuo, the resulting residue was diluted with ethyl acetate (45 mL), brine (10 mL), and 5% $H_3PO_4$ aqueous solution (10 mL), and the layers were separated. The organic layer was washed with 5% $H_3PO_4$ aqueous solution (10 mL), twice with saturated aqueous sodium bicarbonate solution (15 mL), water (15 mL), and brine (15 mL). The organic layer was dried over sodium sulfate, filtered, and concentrated in vacuo to afford the title compound as a light colored solid. (172 mg, 56% yield) MS (ESI$^+$) m/z=471 $(M+H)^+$.

125

Part D. Preparation of (3S)-3-amino-N-(2-((R)-2-(dimethylamino)-2-oxo-1-(thiophen-2-yl)ethylamino)-2-oxoethyl)-2-hydroxyhexanamide hydrochloride To a solution of the product from Part C (172 mg, 0.3655 mmol) in methylene chloride (2 mL) was added 4N HCl in dioxane (2 mL) and the resulting solution stirred at 25° C. for 18 hours. The solution was concentrated in vacuo, triturated in diethyl ether, filtered, and dried under vacuum to afford the title compound as a light colored solid (147 mg, 99% yield). MS (ESI$^+$) m/z=371 (M+H)$^+$.

Part E. Preparation of (3R,4R)-4-((S)-2-((S)-2-cyclohexyl-2-(pyrazine-2-carboxamido) acetamido)-3,3-dimethylbutanamido)-N$^3$-((3S)-1-(2-((R)-2-(dimethylamino)-2-oxo-1-(thiophen-2-yl)ethylamino)-2-oxoethylamino)-2-hydroxy-1-oxohexan-3-yl)-N$^1$-phenylpyrrolidine-1,3-dicarboxamide To a solution of the product from Example 3, Part B (100 mg, 0.1646 mmol) in DMF (2 mL) was added the product from Part D (74 mg, 0.1810 mmol), HOBt (27 mg, 0.1975 mmol), and Hunig's Base (0.086 mL, 0.4937 mmol) and the resulting solution stirred at 0° C. for 10 minutes. EDCI (42 mg, 0.1975 mmol) was added and the reaction stirred at 25° C. for 18 hours. The mixture was concentrated in vacuo, the resulting residue was diluted with ethyl acetate (45 mL), brine (10 mL), and 5% H$_3$PO$_4$ aqueous solution (10 mL), and the layers were separated. The organic layer was washed with 5% H$_3$PO$_4$ aqueous solution (10 mL), twice with saturated aqueous sodium bicarbonate solution (15 mL), water (15 mL), and brine (15 mL). The organic layer was dried over sodium sulfate, filtered, and concentrated in vacuo to afford the title compound as a light colored solid. (103 mg, 65% yield) MS (ESI$^+$) m/z=961 (M+H)$^+$.

Part F. Preparation of Title Product

To a solution of the product from Part E (103 mg, 0.1073 mmol) in methylene chloride (1.5 mL) was added Dess-Martin Periodinane (68 mg, 0.1609 mmol) and the reaction mixture stirred at 25° C. for 18 hours. The solution was filtered and the filtrate was concentrated in vacuo and the residue was purified by reverse phase HPLC to afford the title compound as a white solid. (56 mg, 54% yield). MS (ESI$^+$) m/z=959 (M+H)$^+$.

126

Example 51

Preparation of (3R,4R)-4-((S)-2-((S)-2-cyclohexyl-2-(pyrazine-2-carboxamido) acetamido)-3,3-dimethylbutanamido)-N$^3$—((S)-1-(2-((S)-1-(dimethylamino)-3-methoxy-1-oxopropan-2-ylamino)-2-oxoethylamino)-1,2-dioxohexan-3-yl)-N$^1$-phenylpyrrolidine-1,3-dicarboxamide

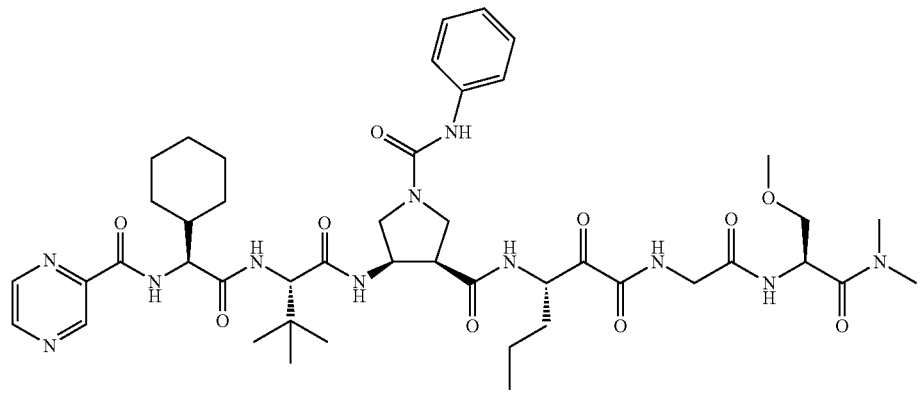 [SMILES: CCC[C@H](NC(=O)[C@@H]1CN(C(=O)Nc2ccccc2)C[C@@H]1NC(=O)[C@@H](NC(=O)[C@@H](NC(=O)c1cnccn1)C1CCCCC1)C(C)(C)C)C(=O)C(=O)NCC(=O)N[C@@H](COC)C(=O)N(C)C]

Part A. Preparation of (S)-tert-butyl 1-(dimethylamino)-3-methoxy-1-oxopropan-2-yl carbamate Same procedure described for Example 50, Part A was used, starting with (S)-2-(tert-butoxycarbonylamino)-3-methoxypropanoic acid. The crude product was taken onto the next step.

Part B. Preparation of (S)-2-amino-3-methoxy-N,N-dimethylpropanamide hydrochloride Same procedure described for Example 50, Part B was used, starting with the product from Part A (126 mg, 38% yield) MS (DCI/NH$_4^+$) m/z=147 (M+H)$^+$.

Part C. Preparation of tert-butyl (3S)-1-(2-((S)-1-(dimethylamino)-3-methoxy-1-oxopropan-2-ylamino)-2-oxoethylamino)-2-hydroxy-1-oxohexan-3-ylcarbamate Same procedure described for Example 50, Part C was used, starting with the product from Part B. (80 mg, 28% yield) MS (ESI$^+$) m/z=433 (M+H)$^+$

Part D. Preparation of (3S)-3-amino-N-(2-((S)-1-(dimethylamino)-3-methoxy-1-oxopropan-2-ylamino)-2-oxoethyl)-2-hydroxyhexanamide hydrochloride Same procedure described for Example 50, Part D was used, starting with the product from Part C. (53 mg, 78% yield) MS (ESI$^+$) m/z=333 (M+H)$^+$.

Part E. Preparation of (3R,4R)-4-((S)-2-((S)-2-cyclohexyl-2-(pyrazine-2-carboxamido) acetamido)-3,3-dimethylbutanamido)-N³-((3S)-1-(2-((S)-1-(dimethylamino)-3-methoxy-1-oxopropan-2-ylamino)-2-oxoethylamino)-2-hydroxy-1-oxohexan-3-yl)-N¹-phenylpyrrolidine-1,3-dicarboxamide Same procedure described for Example 50, Part E was used, starting with the product from Part D. (65 mg, 49% yield) MS (ESI⁺) m/z=923 (M+H)⁺.

Part F. Preparation of Title Product

Same procedure described for Example 50, Part F was used, starting with the product from Part E. (32 mg, 49% yield) MS (ESI⁺) m/z=921 (M+H)⁺.

Example 52

Preparation of (3R,4R)-4-((S)-2-((S)-2-cyclohexyl-2-(pyrazine-2-carboxamido) acetamido)-3,3-dimethylbutanamido)-N³—((S)-1,2-dioxo-1-(2-oxo-2-((R)-1-phenylethylamino) ethylamino)hexan-3-yl)-N¹-phenylpyrrolidine-1,3-dicarboxamide

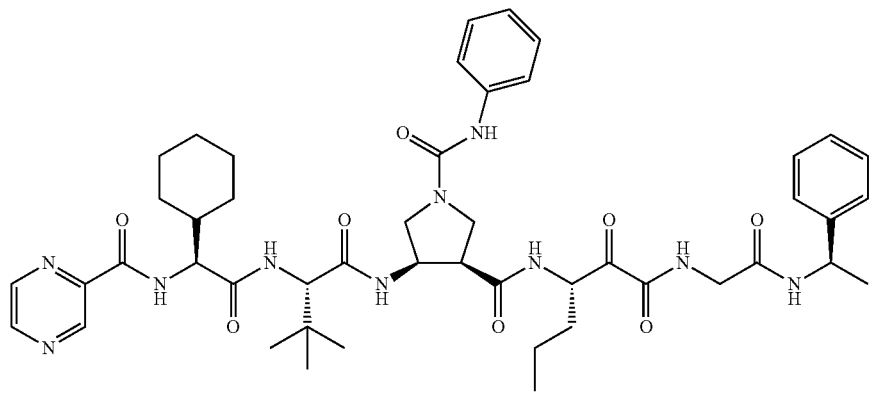 [SMILES: CCC[C@H](NC(=O)[C@@H]1CN(C(=O)Nc2ccccc2)C[C@@H]1NC(=O)[C@@H](NC(=O)[C@@H](NC(=O)c1cnccn1)C1CCCCC1)C(C)(C)C)C(=O)C(=O)NCC(=O)N[C@H](C)c1ccccc1]

Part A. Preparation of tert-butyl (3S)-2-hydroxy-1-oxo-1-(2-oxo-2-((R)-1-phenylethyl amino)ethylamino)hexan-3-ylcarbamate Same procedure described for Example 50, Part C was used, starting with (R)-1-phenyl ethanamine. (238 mg, 89% yield) MS (ESI⁺) m/z=408 (M+H)⁺.

Part B. Preparation of (3S)-3-amino-2-hydroxy-N-(2-oxo-2-((R)-1-phenylethylamino)ethyl) hexanamide hydrochloride Same procedure described for Example 50, Part D was used, starting with the product from Part A. (185 mg, 92% yield) MS (ESI⁺) m/z=308 (M+H)⁺.

Part C. Preparation of (3R,4R)-4-((S)-2-((S)-2-cyclo-
hexyl-2-(pyrazine-2-carboxamido) acetamido)-3,3-
dimethylbutanamido)-N³-((3S)-2-hydroxy-1-oxo-1-
(2-oxo-2-((R)-1-phenylethylamino) ethylamino)
hexan-3-yl)-N¹-phenylpyrrolidine-1,3-
dicarboxamide Same procedure described for Example 50, Part E was used, starting with the product from Part B. (106 mg, 72% yield) MS (ESI⁺) m/z=898 (M+H)⁺.

Part D. Preparation of Title Product

Same procedure described for Example 50, Part F was used, starting with the product from Part C. (65 mg, 61% yield) MS (ESI⁺) m/z=896 (M+H)⁺.

Example 53

Preparation of (3R,4R)-4-((S)-2-((S)-2-cyclohexyl-2-
(pyrazine-2-carboxamido) acetamido)-3,3-dimeth-
ylbutanamido)-N³—((S)-1-(2-((S)-1-(dimethy-
lamino)-3-methyl-1-oxobutan-2-yl amino)-2-
oxoethylamino)-1,2-dioxohexan-3-yl)-N¹-
phenylpyrrolidine-1,3-dicarboxamide Part C. Preparation of tert-butyl (3S)-1-(2-((S)-1-
(dimethylamino)-3-methyl-1-oxobutan-2-ylamino)-
2-oxoethylamino)-2-hydroxy-1-oxohexan-3-ylcar-
bamate Same procedure described for Example 50, Part C was used, starting with the product from Part B. (557 mg, 86% yield) MS (ESI⁺) m/z=431 (M+H)⁺.

Part D. Preparation of (3S)-3-amino-N-(2-((S)-1-
(dimethylamino)-3-methyl-1-oxobutan-2-ylamino)-
2-oxoethyl)-2-hydroxyhexanamide hydrochloride Same procedure described for Example 50, Part D was used, starting with the product from Part C. (473 mg, 99% yield) MS (ESI⁺) m/z=331 (M+H)⁺.

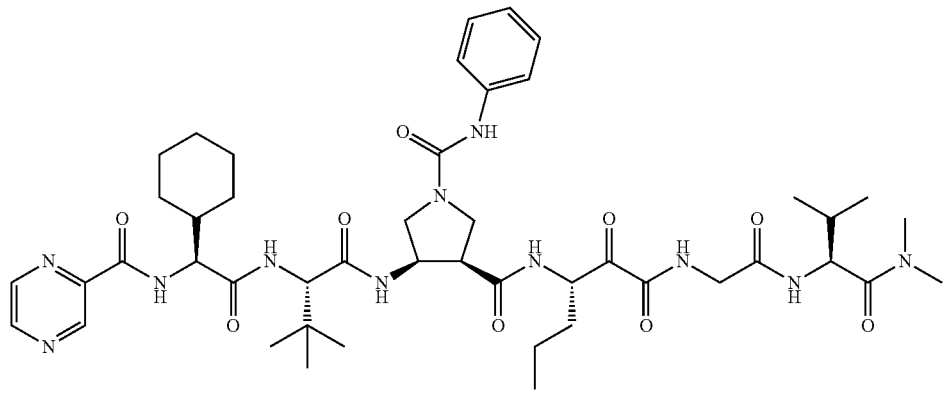 [SMILES: CCC[C@H](NC(=O)[C@@H]1CN(C(=O)Nc2ccccc2)C[C@@H]1NC(=O)[C@@H](NC(=O)[C@@H](NC(=O)c1cnccn1)C1CCCCC1)C(C)(C)C)C(=O)C(=O)NCC(=O)N[C@H](C(=O)N(C)C)C(C)C]

Part A. Preparation of (S)-tert-butyl 1-(dimethy-
lamino)-3-methyl-1-oxobutan-2-ylcarbamate Same procedure described for Example 50, Part A was used, starting with (S)-2-(tert-butoxycarbonylamino)-3-methylbutanoic acid. The crude material was taken on directly to the next step. MS (ESI⁺) m/z=245 (M+H)⁺.

Part B. Preparation of
(S)-2-amino-N,N,3-trimethylbutanamide
hydrochloride

Same procedure described for Example 50, Part B was used, starting with the product from Part A. (286 mg, 86% yield) MS (DCI/NH₄⁺) m/z=145 (M+H)⁺ (S)-2-amino-N,N,3-trimethylbutanamide hydrochloride.

Part E. Preparation of (3R,4R)-4-((S)-2-((S)-2-cyclo-
hexyl-2-(pyrazine-2-carboxamido) acetamido)-3,3-
dimethylbutanamido)-N³-((3S)-1-(2-((S)-1-(dim-
ethylamino)-3-methyl-1-oxobutan-2-ylamino)-2-
oxoethylamino)-2-hydroxy-1-oxohexan-3-yl)-N¹-
phenylpyrrolidine-1,3-dicarboxamide Same procedure described for Example 50, Part E was used, starting with the product from Part D. (98 mg, 65% yield) MS (ESI⁺) m/z=921 (M+H)⁺.

Part F. Preparation of Title Product

Same procedure described for Example 50, Part F was used, starting with the product from Part E. (55 mg, 56% yield) MS (ESI⁺) m/z=919 (M+H)⁺.

Example 54

Preparation of (3R,4R)-4-((S)-2-((S)-2-cyclohexyl-2-(pyrazine-2-carboxamido) acetamido)-3,3-dimethylbutanamido)-N³-((3S)-1-(2-((S)-1-(dimethylamino)-3,3-dimethyl-1-oxobutan-2-ylamino)-2-oxoethylamino)-2-hydroxy-1-oxohexan-3-yl)-N¹-phenylpyrrolidine-1,3-dicarboxamide

Part D. Preparation of (3S)-3-amino-N-(2-((S)-1-(dimethylamino)-3,3-dimethyl-1-oxobutan-2-ylamino)-2-oxoethyl)-2-hydroxyhexanamide hydrochloride Same procedure described for Example 50, Part D was used, starting with the product from Part C. The crude material was taken on directly to the next step. MS (ESI⁺) m/z=345 (M+H)⁺.

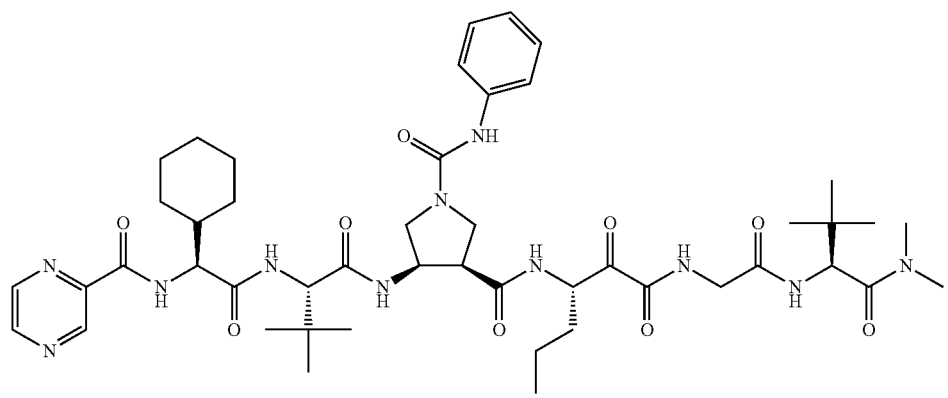 [SMILES: CCC[C@H](NC(=O)[C@@H]1CN(C(=O)Nc2ccccc2)C[C@@H]1NC(=O)[C@@H](NC(=O)[C@@H](NC(=O)c1cnccn1)C1CCCCC1)C(C)(C)C)C(=O)C(=O)NCC(=O)N[C@H](C(=O)N(C)C)C(C)(C)C]

Part A. Preparation of (S)-tert-butyl 1-(dimethylamino)-3,3-dimethyl-1-oxobutan-2-yl carbamate Same procedure described for Example 50, Part A was used, starting with (S)-2-(tert-butoxy carbonylamino)-3,3-dimethylbutanoic acid. The crude material was taken on directly to the next step. MS (ESI⁺) m/z=259 (M+H)⁺.

Part B. Preparation of (S)-2-amino-N,N,3,3-tetramethylbutanamide hydrochloride Same procedure described for Example 50, Part B was used, starting with the product from Part A. (287 mg, 80% yield) MS (DCI/NH₄⁺) m/z=159 (M+H)⁺.

Part C. Preparation of tert-butyl (3S)-1-(2-((S)-1-(dimethylamino)-3,3-dimethyl-1-oxobutan-2-ylamino)-2-oxoethylamino)-2-hydroxy-1-oxohexan-3-ylcarbamate Same procedure described for Example 50, Part C was used, starting with the product from Part B. (570 mg, 91% yield) MS (ESI⁺) m/z=445 (M+H)⁺.

Part E. Preparation of (3R,4R)-4-((S)-2-((S)-2-cyclohexyl-2-(pyrazine-2-carboxamido) acetamido)-3,3-dimethylbutanamido)-N³-((3S)-1-(2-((S)-1-(dimethylamino)-3,3-dimethyl-1-oxobutan-2-ylamino)-2-oxoethylamino)-2-hydroxy-1-oxohexan-3-yl)-N¹-phenylpyrrolidine-1,3-dicarboxamide Same procedure described for Example 50, Part E was used, starting with the product from Part D. (88 mg, 57% yield) MS (ESI⁺) m/z=935 (M+H)⁺.

Part F. Preparation of Title Product

Same procedure described for Example 50, Part F was used, starting with the product from Part E. (15 mg, 17% yield) MS (ESI⁺) m/z=933 (M+H)⁺.

Example 55

Preparation of (3R,4R)-4-((S)-2-((S)-2-cyclohexyl-2-(pyrazine-2-carboxamido) acetamido)-3,3-dimethylbutanamido)-N³—((S)-1-(2-((S)-1-(dimethylamino)-4-methyl-1-oxopentan-2-yl amino)-2-oxoethylamino)-1,2-dioxohexan-3-yl)-N¹-phenylpyrrolidine-1,3-dicarboxamide

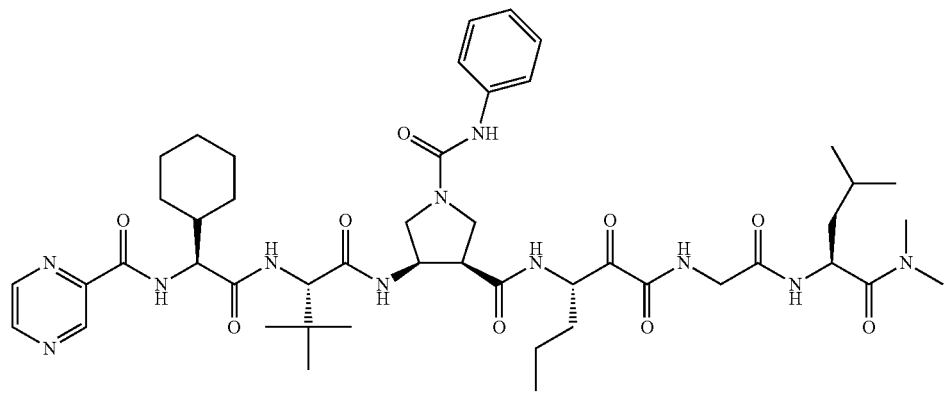 [SMILES: CCC[C@H](NC(=O)[C@@H]1CN(C(=O)Nc2ccccc2)C[C@@H]1NC(=O)[C@@H](NC(=O)[C@@H](NC(=O)c1cnccn1)C1CCCCC1)C(C)(C)C)C(=O)C(=O)NCC(=O)N[C@@H](CC(C)C)C(=O)N(C)C]

Part A. Preparation of (S)-tert-butyl 1-(dimethylamino)-4-methyl-1-oxopentan-2-yl carbamate Same procedure described for Example 50, Part A was used, starting with (S)-2-(tert-butoxycarbonylamino)-4-methylpentanoic acid. The crude material was taken on directly to the next step. (444 mg, 93% yield) MS (ESI⁺) m/z=259 (M+H)⁺.

Part B. Preparation of (S)-2-amino-N,N,4-trimethylpentanamide hydrochloride

Same procedure described for Example 50, Part B was used, starting with the product from Part A. (283 mg, 84% yield) MS (DCI/NH₄⁺) m/z=159 (M+H)⁺.

Part C. Preparation of tert-butyl (3S)-1-(2-((S)-1-(dimethylamino)-4-methyl-1-oxopentan-2-ylamino)-2-oxoethylamino)-2-hydroxy-1-oxohexan-3-ylcarbamate Same procedure described for Example 50, Part C was used, starting with the product from Part B. (547 mg, 89% yield) MS (ESI⁺) m/z=445 (M+H)⁺.

Part D. Preparation of (3S)-3-amino-N-(2-((S)-1-(dimethylamino)-4-methyl-1-oxopentan-2-ylamino)-2-oxoethyl)-2-hydroxyhexanamide hydrochloride Same procedure described for Example 50, Part D was used, starting with the product from Part C. (426 mg, 91% yield) MS (ESI⁺) m/z=345 (M+H)⁺.

Part E. Preparation of (3R,4R)-4-((S)-2-((S)-2-cyclohexyl-2-(pyrazine-2-carboxamido) acetamido)-3,3-dimethylbutanamido)-N³-((3S)-1-(2-((S)-1-(dimethylamino)-4-methyl-1-oxopentan-2-ylamino)-2-oxoethylamino)-2-hydroxy-1-oxohexan-3-yl)-N¹-phenylpyrrolidine-1,3-dicarboxamide Same procedure described for Example 50, Part E was used, starting with the product form Part D. (105 mg, 68% yield) MS (ESI⁺) m/z=935 (M+H)⁺.

Part F. Preparation of Title Product

Same procedure described for Example 50, Part F was used, starting with the product form Part E. (63 mg, 60% yield) MS (ESI⁺) m/z=933 (M+H)⁺.

Example 56

Preparation of (3R,4R)-4-((S)-2-((S)-2-cyclohexyl-2-(pyrazine-2-carboxamido) acetamido)-3,3-dimethylbutanamido)-N³—((S)-1-(2-((S)-1-cyclopentyl-2-(dimethylamino)-2-oxoethyl amino)-2-oxoethylamino)-1,2-dioxohexan-3-yl)-N¹-phenylpyrrolidine-1,3-dicarboxamide

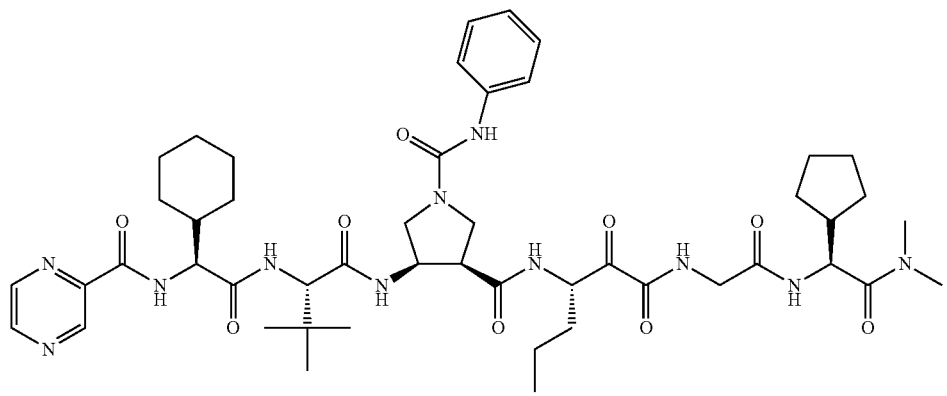 [SMILES: CCC[C@H](NC(=O)[C@@H]1CN(C(=O)Nc2ccccc2)C[C@@H]1NC(=O)[C@@H](NC(=O)[C@@H](NC(=O)c1cnccn1)C1CCCCC1)C(C)(C)C)C(=O)C(=O)NCC(=O)N[C@H](C(=O)N(C)C)C1CCCC1]

Part A. Preparation of (S)-tert-butyl 1-cyclopentyl-2-(dimethylamino)-2-oxoethylcarbamate Same procedure described for Example 50, Part A was used, starting with (S)-2-(tert-butoxy carbonylamino)-2-cyclopentylacetic acid. The crude material was taken on directly to the next step. (146 mg, 29% yield) MS (ESI⁺) m/z=271 (M+H)⁺.

Part B. Preparation of (S)-2-amino-2-cyclopentyl-N,N-dimethylacetamide hydrochloride Same procedure described for Example 50, Part B was used, starting with the product from Part A. (95 mg, 82% yield) MS (DCI/NH₄⁺) m/z=171 (M+H)⁺.

Part C. Preparation of tert-butyl (3S)-1-(2-((S)-1-cyclopentyl-2-(dimethylamino)-2-oxoethyl amino)-2-oxoethylamino)-2-hydroxy-1-oxohexan-3-ylcarbamate Same procedure described for Example 50, Part C was used, starting with the product from Part B. (185 mg, 93% yield) MS (ESI⁺) m/z=457 (M+H)⁺.

Part D. Preparation of (3S)-3-amino-N-(2-((S)-1-cyclopentyl-2-(dimethylamino)-2-oxoethyl amino)-2-oxoethyl)-2-hydroxyhexanamide hydrochloride Same procedure described for Example 50, Part D was used, starting with the product from Part C. (150 mg, 94% yield) MS (ESI⁺) m/z=357 (M+H)⁺.

Part E. Preparation of (3R,4R)-4-((S)-2-((S)-2-cyclohexyl-2-(pyrazine-2-carboxamido) acetamido)-3,3-dimethylbutanamido)-N³-((3S)-1-(2-((S)-1-cyclopentyl-2-(dimethylamino)-2-oxoethyl amino)-2-oxoethylamino)-2-hydroxy-1-oxohexan-3-yl)-N¹-phenylpyrrolidine-1,3-dicarboxamide Same procedure described for Example 50, Part E was used, starting with the product from Part D. (104 mg, 67% yield) MS (ESI⁺) m/z=947 (M+H)⁺.

Part F. Preparation of Title Product

Same procedure described for Example 50, Part F was used, starting with the product from Part E. (59 mg, 57% yield) MS (ESI+) m/z=945 (M+H)+.

Example 57

Preparation of (3R,4R)—N³—((S)-1-(2-((S)-1-cyclohexyl-2-(dimethylamino)-2-oxoethylamino)-2-oxoethylamino)-1,2-dioxohexan-3-yl)-4-((S)-2-((S)-2-cyclohexyl-2-(pyrazine-2-carboxamido) acetamido)-3,3-dimethylbutanamido)-N¹-phenylpyrrolidine-1,3-dicarboxamide Part C. Preparation of tert-butyl (3S)-1-(2-((S)-1-cyclohexyl-2-(dimethylamino)-2-oxoethyl amino)-2-oxoethylamino)-2-hydroxy-1-oxohexan-3-ylcarbamate Same procedure described for Example 50, Part C was used, starting with the product from Part B. (618 mg, 85% yield) MS (ESI+) m/z=471 (M+H)+.

Part D. Preparation of (3S)-3-amino-N-(2-((S)-1-cyclohexyl-2-(dimethylamino)-2-oxoethyl amino)-2-oxoethyl)-2-hydroxyhexanamide hydrochloride Same procedure described for Example 50, Part D was used, starting with the product from Part C. (525 mg, 98% yield) MS (ESI+) m/z=371 (M+H)+.

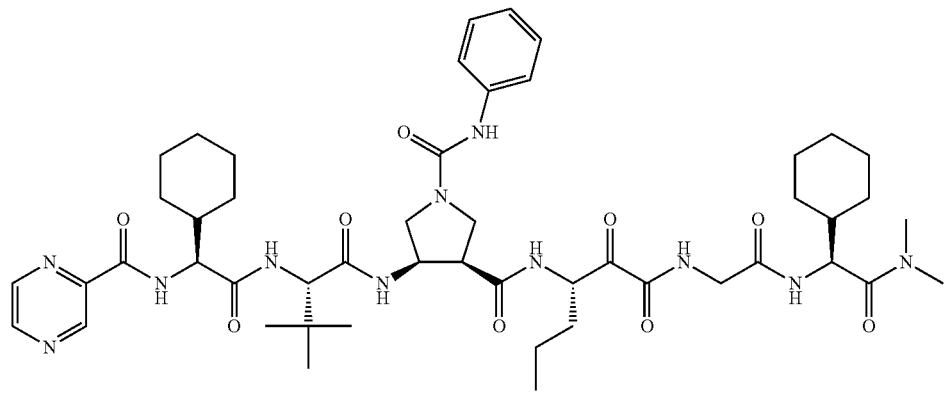 [SMILES: CCC[C@H](NC(=O)[C@@H]1CN(C(=O)Nc2ccccc2)C[C@@H]1NC(=O)[C@@H](NC(=O)[C@@H](NC(=O)c1cnccn1)C1CCCCC1)C(C)(C)C)C(=O)C(=O)NCC(=O)N[C@H](C(=O)N(C)C)C1CCCCC1]

Part A. Preparation of (S)-tert-butyl 1-cyclohexyl-2-(dimethylamino)-2-oxoethylcarbamate Same procedure described for Example 50, Part A was used, starting with (S)-2-(tert-butoxycarbonylamino)-2-cyclohexylacetic acid. The crude material was taken on directly to the next step. (500 mg, 95% yield) MS (ESI+) m/z=285 (M+H)+.

Part B. Preparation of (S)-2-amino-2-cyclohexyl-N,N-dimethylacetamide hydrochloride Same procedure described for Example 50, Part B was used, starting with the product form Part A. (358 mg, 92% yield) MS (DCI/NH₄+) m/z=185 (M+H)+.

Part E. Preparation of (3R,4R)—N³-((3S)-1-(2-((S)-1-cyclohexyl-2-(dimethylamino)-2-oxoethylamino)-2-oxoethylamino)-2-hydroxy-1-oxohexan-3-yl)-4-((S)-2-((S)-2-cyclohexyl-2-(pyrazine-2-carboxamido)acetamido)-3,3-dimethylbutanamido)-N¹-phenylpyrrolidine-1,3-dicarboxamide Same procedure described for Example 50, Part E was used, starting with the product from Part D. (94 mg, 59% yield) MS (ESI+) m/z=961 (M+H)+.

Part F. Preparation of Title Product

Same procedure described for Example 50, Part F was used, starting with the product from Part E. (49 mg, 52% yield) MS (ESI+) m/z=959 (M+H)+.

Example 58

Preparation of (3R,4R)-4-((S)-2-((S)-2-cyclohexyl-2-(pyrazine-2-carboxamido) acetamido)-3,3-dimethylbutanamido)-N³-((3S)-1-(2-(2-(dimethylamino)-1-(4-fluorophenyl)-2-oxoethyl amino)-2-oxoethylamino)-1,2-dioxohexan-3-yl)-N¹-phenylpyrrolidine-1,3-dicarboxamide

Part C. Preparation of tert-butyl (3S)-1-(2-(2-(dimethylamino)-1-(4-fluorophenyl)-2-oxoethylamino)-2-oxoethylamino)-2-hydroxy-1-oxohexan-3-ylcarbamate Same procedure described for Example 50, Part C was used, starting with the product from Part B. (340 mg, 66% yield). MS (ESI⁺) m/z=483 (M+H)⁺.

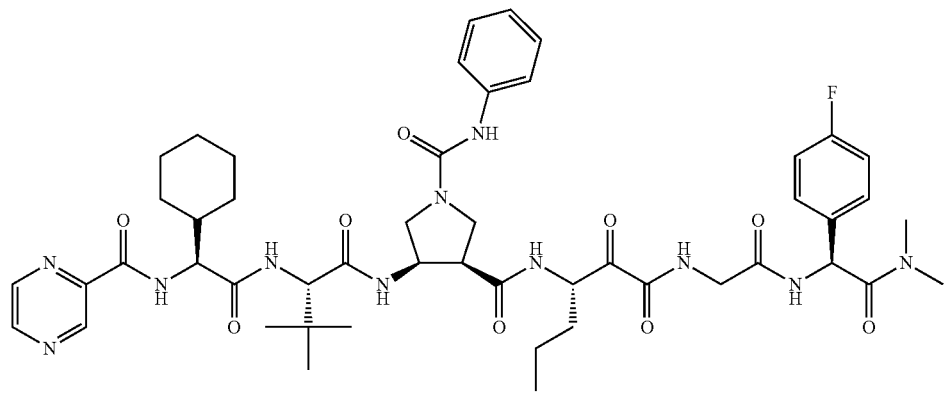 [SMILES: CCC[C@H](NC(=O)[C@@H]1CN(C(=O)Nc2ccccc2)C[C@@H]1NC(=O)[C@@H](NC(=O)[C@@H](NC(=O)c1cnccn1)C1CCCCC1)C(C)(C)C)C(=O)C(=O)NCC(=O)N[C@H](C(=O)N(C)C)c1ccc(F)cc1]

Part A. Preparation of tert-butyl 2-(dimethylamino)-1-(4-fluorophenyl)-2-oxoethyl carbamate Same procedure described for Example 50, Part A was used, starting with 2-(tert-butoxycarbonylamino)-2-(4-fluorophenyl)acetic acid. The crude material was taken on directly to the next step. MS (ESI⁺) m/z=297 (M+H)⁺.

Part B. Preparation of 2-amino-2-(4-fluorophenyl)-N,N-dimethylacetamide hydrochloride Same procedure described for Example 50, Part B was used, starting with the product from Part A. (391 mg, 91% yield) MS (DCI/NH₄⁺) m/z=197 (M+H)⁺.

Part D. Preparation of (3S)-3-amino-N-(2-(2-(dimethylamino)-1-(4-fluorophenyl)-2-oxo ethylamino)-2-oxoethyl)-2-hydroxyhexanamide hydrochloride Same procedure described for Example 50, Part D was used, starting with the product from Part C. (276 mg, 94% yield) The crude material was taken on directly to the next step.

Part E. Preparation of (3R,4R)-4-((S)-2-((S)-2-cyclohexyl-2-(pyrazine-2-carboxamido) acetamido)-3,3-dimethylbutanamido)-N³-((3S)-1-(2-(2-(dimethylamino)-1-(4-fluorophenyl)-2-oxoethyl amino)-2-oxoethylamino)-2-hydroxy-1-oxohexan-3-yl)-N¹-phenylpyrrolidine-1,3-dicarboxamide Same procedure described for Example 50, Pat E was used, starting with the product from Part D. (98 mg, 61% yield) MS (ESI⁺) m/z=973 (M+H)⁺.

Part F. Preparation of Title Product

Same procedure described for Example 50, Part F was used, starting with the product from Part E. (55 mg, 56% yield) MS (ESI⁺) m/z=971 (M+H)⁺.

Example 59

Preparation of (S)-2-(tert-butoxycarbonylamino)-2-(4-hydroxyphenyl)acetic acid

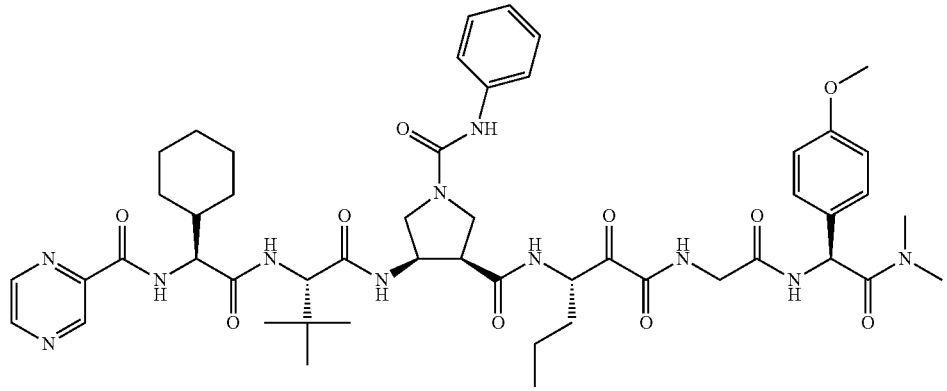 [SMILES: CCC[C@H](NC(=O)[C@@H]1CN(C(=O)Nc2ccccc2)C[C@@H]1NC(=O)[C@@H](NC(=O)[C@@H](NC(=O)c1cnccn1)C1CCCCC1)C(C)(C)C)C(=O)C(=O)NCC(=O)N[C@H](C(=O)N(C)C)c1ccc(OC)cc1]

Part A. Preparation of (S)-2-(tert-butoxycarbonylamino)-2-(4-hydroxyphenyl)acetic acid To a solution of (S)-2-amino-2-(4-hydroxyphenyl)acetic acid (2.00 g, 11.96 mmol) and Et$_3$N (1.67 mL, 11.96 mmol) in THF (30 mL) and H$_2$O (30 mL) at 0° C. was added di-tert-butyl dicarbonate (2.61 g. 11.96 mmol). The solution was stirred at 0° C. for 18 hours and then concentrated in vacuo. The residue was diluted with ethyl acetate and washed with 5% H$_3$PO$_4$ aqueous solution. The organic layer was dried over sodium sulfate, filtered, and concentrated in vacuo to afford the title compound as a light colored solid. The crude material was taken on directly to the next step. (2.85 g, 86% yield) MS (ESI$^+$) m/z=290 (M+Na)$^+$.

Part B. Preparation of (S)-methyl 2-(tert-butoxycarbonylamino)-2-(4-methoxyphenyl)acetate To a solution of the product from Part A (1.00 g, 3.62 mmol) in DMF (15 mL) was added potassium carbonate (1.226 g, 8.87 mmol) and methyl iodide (0.552 mL, 8.87 mmol). The solution was stirred at 25° C. for 18 hours and then diluted with ethyl acetate and washed with 5% H$_3$PO$_4$ aqueous solution and saturated aqueous sodium bicarbonate solution. The organic layer was dried over sodium sulfate, filtered, and concentrated in vacuo to afford the title compound as a light colored solid. The crude material was taken on directly to the next step. (1.06 g, 99% yield) MS (ESI$^+$) m/z=318 (M+Na)$^+$.

Part C. Preparation of (S)-2-(tert-butoxycarbonylamino)-2-(4-methoxyphenyl)acetic acid To a solution of the product from Part B (1.06 g, 3.59 mmol) in H$_2$O (2 mL) and THF (2 mL) was added lithium hydroxide (226 mg, 5.38 mmol) and the solution stirred for 18 hours and then concentrated in vacuo. The residue was diluted with ethyl acetate and washed with 5% H$_3$PO$_4$ aqueous solution. The organic layer was dried over sodium sulfate, filtered, and concentrated in vacuo to afford the title compound as a light colored solid. The crude material was taken on directly to the next step. (1.00 g, 99% yield) MS (ESI$^+$) m/z=304 (M+Na)$^+$.

Part D. Preparation of (S)-tert-butyl 2-(dimethylamino)-1-(4-methoxyphenyl)-2-oxoethyl carbamate Same procedure described for Example 50, Part A was used, starting with the product from Part C. The resulting solid was purified by flash chromatography on SiO$_2$ using ethyl acetate in hexanes as the mobile phase. (909 mg, 89% yield). MS (ESI$^+$) m/z=309 (M+H)$^+$.

Part E. Preparation of (S)-2-amino-2-(4-methoxyphenyl)-N,N-dimethylacetamide hydrochloride Same procedure described for Example 50, Part B was used, starting with the product from Part D. (718 mg, 99% yield) MS (ESI$^+$) m/z=209 (M+H)$^+$.

Part F. Preparation of tert-butyl (3S)-1-(2-((S)-2-(dimethylamino)-1-(4-methoxyphenyl)-2-oxoethylamino)-2-oxoethylamino)-2-hydroxy-1-oxohexan-3-ylcarbamate Same procedure described for Example 50, Part C was used, starting with Part E. (1.30 g, 99% yield). MS (ESI$^+$) m/z=495 (M+H)$^+$

Part G. Preparation of (3S)-3-amino-N-(2-((S)-2-(dimethylamino)-1-(4-methoxyphenyl)-2-oxoethylamino)-2-oxoethyl)-2-hydroxyhexanamide hydrochloride Same procedure described for Example 50, Part D was used, starting with the product from Part F. The crude material was taken on directly to the next step. (1.02 g, 90% yield) MS (ESI$^+$) m/z=395 (M+H)$^+$.

Part H. Preparation of (3R,4R)-4-((S)-2-((S)-2-cyclohexyl-2-(pyrazine-2-carboxamido) acetamido)-3,3-dimethylbutanamido)-N$^3$-((3S)-1-(2-((S)-2-(dimethylamino)-1-(4-methoxyphenyl)-2-oxo ethylamino)-2-oxoethylamino)-2-hydroxy-1-oxohexan-3-yl)-N$^1$-phenylpyrrolidine-1,3-dicarboxamide Same procedure described for Example 50, Part E was used, starting with the product from Part G. (140 mg, 86% yield) MS (ESI$^+$) m/z=985 (M+H)$^+$.

Part I. Preparation of Title Product

Same procedure described for Example 50, Part F was used, starting with the product from Part H. (33 mg, 24% yield) MS (ESI+) m/z=983 (M+H)+.

Example 60

Preparation of (3R,4R)-4-((S)-2-((S)-2-cyclohexyl-2-(pyrazine-2-carboxamido) acetamido)-3,3-dimethylbutanamido)-N³—((S)-1-(2-((S)-2-(methylamino)-2-oxo-1-phenylethylamino)-2-oxoethylamino)-1,2-dioxohexan-3-yl)-N¹-phenylpyrrolidine-1,3-dicarboxamide Part B. Preparation of (S)-2-amino-N-methyl-2-phenylacetamide hydrochloride Same procedure described for Example 50, Part B was used, starting with the product from Part A. (781 mg, 99% yield) MS (DCI/NH₄+) m/z=165 (M+H)+.

Part C. Preparation of tert-butyl (3S)-2-hydroxy-1-(2-((S)-2-(methylamino)-2-oxo-1-phenylethylamino)-2-oxoethylamino)-1-oxohexan-3-ylcarbamate Same procedure described for Example 50, Part C was used, starting with the product from Part B. (370 mg, 99% yield). MS (ESI+) m/z=451 (M+H)+.

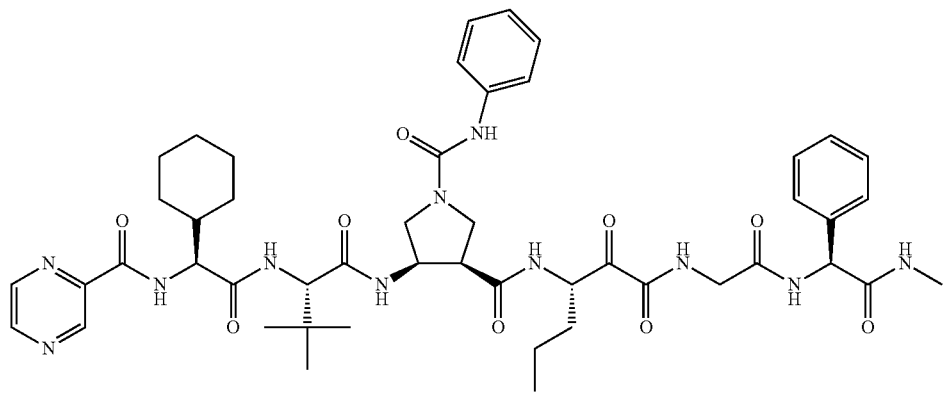 [SMILES: CCC[C@H](NC(=O)[C@@H]1CN(C(=O)Nc2ccccc2)C[C@@H]1NC(=O)[C@@H](NC(=O)[C@@H](NC(=O)c1cnccn1)C1CCCCC1)C(C)(C)C)C(=O)C(=O)NCC(=O)N[C@H](C(=O)NC)c1ccccc1]

Part A. Preparation of (S)-tert-butyl 2-(methylamino)-2-oxo-1-phenylethylcarbamate To a solution of (S)-2-(tert-butoxycarbonylamino)-2-phenylacetic acid (1.00 g, 3.98 mmol) in DMF (5 mL) and methylene chloride (5 mL) was added methylamine hydrochloride (403 mg, 5.97 mmol), HOBt (645 mg, 4.78 mmol), and Hunig's Base (1.73 mL, 9.95 mmol) and the resulting solution stirred at 0° C. for 10 minutes. EDCI (916 mg, 4.78 mmol) was added and the reaction stirred at 25° C. for 18 hours. The mixture was concentrated in vacuo, the resulting residue was diluted with ethyl acetate (45 mL), brine (10 mL), and 5% H₃PO₄ aqueous solution (10 mL), and the layers were separated. The organic layer was washed with 5% H₃PO₄ aqueous solution (10 mL), twice with saturated aqueous sodium bicarbonate solution (15 mL), water (15 mL), and brine (15 mL). The organic layer was dried over sodium sulfate, filtered, and concentrated in vacuo to afford the title compound as a light colored solid. The crude material was taken on directly to the next step. (1.04 g, 99% yield) MS (ESI+) m/z=265 (M+H)+.

Part D. Preparation of (3S)-3-amino-2-hydroxy-N-(2-((S)-2-(methylamino)-2-oxo-1-phenylethylamino)-2-oxoethyl)hexanamide hydrochloride Same procedure described for Example 50, Part D was used, starting with the product from Part C. The crude material was taken on directly to the next step. MS (ESI+) m/z=351 (M+H)+

Part E. Preparation of (3R,4R)-4-((S)-2-((S)-2-cyclohexyl-2-(pyrazine-2-carboxamido)acetamido)-3,3-dimethylbutanamido)-N³-((3S)-2-hydroxy-1-(2-((S)-2-(methylamino)-2-oxo-1-phenylethylamino)-2-oxoethylamino)-1-oxohexan-3-yl)-N¹-phenylpyrrolidine-1,3-dicarboxamide Same procedure described for Example 50, Part E was used, starting with the product from Part D. (107 mg, 69% yield) MS (ESI+) m/z=941 (M+H)+.

Part F. Preparation of Title Product

Same procedure described for Example 50, Part F was used, starting with the product from Part E. (49 mg, 46% yield) MS (ESI+) m/z=939 (M+H)+.

Example 61

Preparation of (3R,4R)—N³—((S)-1-(2-((S-2-amino-2-oxo-1-phenylethylamino)-2-oxoethylamino)-1,2-dioxohexan-3-yl)-4-((S)-2-((S)-2-cyclohexyl-2-(pyrazine-2-carboxamido) acetamido)-3,3-dimethylbutanamido)-N¹-phenylpyrrolidine-1,3-dicarboxamide

Part C. Preparation of tert-butyl (3S)-1-(2-((S)-2-amino-2-oxo-1-phenylethylamino)-2-oxoethylamino)-2-hydroxy-1-oxohexan-3-ylcarbamate Same procedure described for Example 50, Part C was used, starting with the product from Part B. (359 mg, 99% yield). MS (ESI⁺) m/z=437 (M+H)⁺.

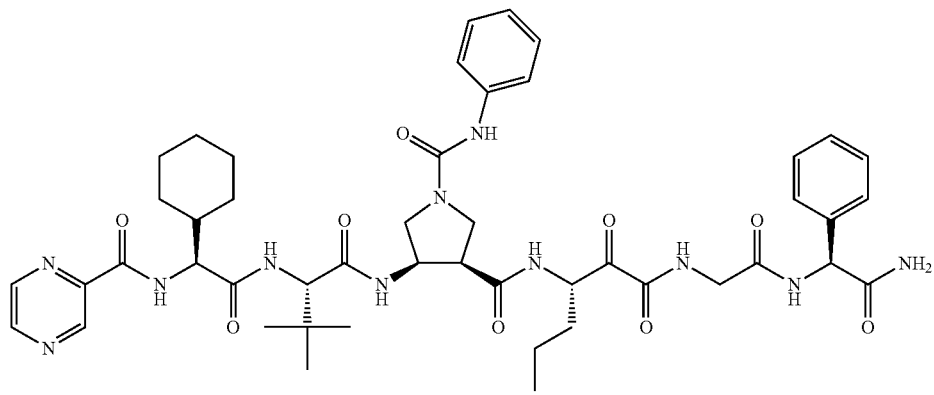 [SMILES: CCC[C@H](NC(=O)[C@@H]1CN(C(=O)Nc2ccccc2)C[C@@H]1NC(=O)[C@@H](NC(=O)[C@@H](NC(=O)c1cnccn1)C1CCCCC1)C(C)(C)C)C(=O)C(=O)NCC(=O)N[C@H](C(N)=O)c1ccccc1]

Part A. Preparation of (S)-tert-butyl 2-amino-2-oxo-1-phenylethylcarbamate

To a solution of (S)-2-(tert-butoxycarbonylamino)-2-phenylacetic acid (1.00 g, 3.98 mmol) in DMF (5 mL) and was added ammonium hydroxide (2.0 mL, excess), and HOBt (645 mg, 4.78 mmol) and the resulting solution stirred at 0° C. for 10 minutes. EDCI (916 mg, 4.78 mmol) was added and the reaction stirred at 25° C. for 18 hours. The mixture was concentrated in vacuo, the resulting residue was diluted with ethyl acetate (45 mL), brine (10 mL), and 5% H₃PO₄ aqueous solution (10 mL), and the layers were separated. The organic layer was washed with 5% H₃PO₄ aqueous solution (10 mL), twice with saturated aqueous sodium bicarbonate solution (15 mL), water (15 mL), and brine (15 mL). The organic layer was dried over sodium sulfate, filtered, and concentrated in vacuo to afford the title compound as a light colored solid. The crude material was taken on directly to the next step. (0.990 g, 99% yield) MS (ESI⁺) m/z=251 (M+H)⁺.

Part B. Preparation of (S)-2-amino-2-phenylacetamide hydrochloride

Same procedure described for Example 50, Part B was used, starting with the product from Part A. (680 mg, 92% yield) MS (DCI/NH₄⁺) m/z=151 (M+H)⁺.

Part D. Preparation of (3S)-3-amino-N-(2-((S)-2-amino-2-oxo-1-phenylethylamino)-2-oxoethyl)-2-hydroxyhexanamide hydrochloride Same procedure described for Example 50, Part D was used, starting with the product from Part C. The crude material was taken on directly to the next step. MS (ESI⁺) m/z=337 (M+H)⁺.

Part E. Preparation of (3R,4R)—N³-((3S)-1-(2-((S)-2-amino-2-oxo-1-phenylethylamino)-2-oxoethylamino)-2-hydroxy-1-oxohexan-3-yl)-4-((S)-2-((S)-2-cyclohexyl-2-(pyrazine-2-carboxamido) acetamido)-3,3-dimethylbutanamido)-N¹-phenylpyrrolidine-1,3-dicarboxamide Same procedure described for Example 50, Part E was used, starting with the product from Part D. (117 mg, 77% yield) MS (ESI⁺) m/z=927 (M+H)⁺.

Part F. Preparation of Title Product

Same procedure described for Example 50, Part F was used, starting with the product from Part E. (70 mg, 60% yield) MS (ESI⁺) m/z=925 (M+H)⁺.

Example 62

Preparation of (3R,4R)-4-((S)-2-((S)-2-cyclohexyl-2-(pyrazine-2-carboxamido)acetamido)-3,3-dimethylbutanamido)-N³—((S)-1-((S)-1-((S)-2-(dimethylamino)-2-oxo-1-phenylethylamino)-3-methyl-1-oxobutan-2-ylamino)-1,2-dioxohexan-3-yl)-N¹-phenylpyrrolidine-1,3-dicarboxamide.

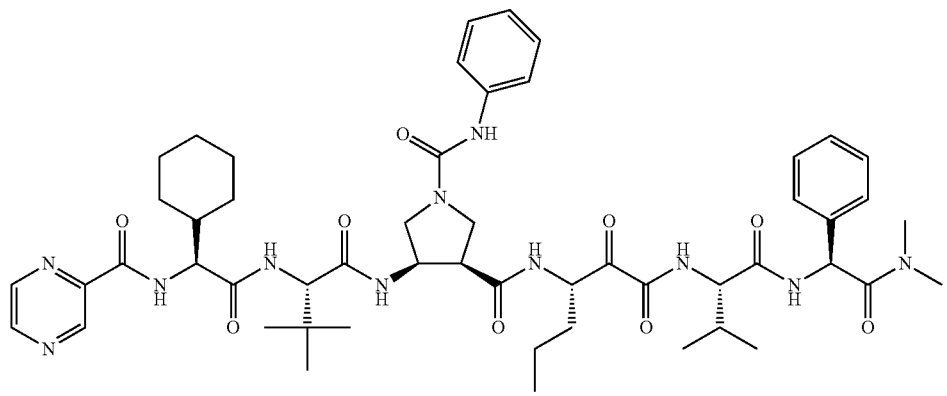 [SMILES: CCC[C@H](NC(=O)[C@@H]1CN(C(=O)Nc2ccccc2)C[C@@H]1NC(=O)[C@@H](NC(=O)[C@@H](NC(=O)c1cnccn1)C1CCCCC1)C(C)(C)C)C(=O)C(=O)N[C@H](C(=O)N[C@H](C(=O)N(C)C)c1ccccc1)C(C)C]

Part A. Preparation of (2)-benzyl 2-((3S)-3-(tert-butoxycarbonylamino)-2-hydroxyhexan amido)-3-methylbutanoate To a solution of (3S)-3-(tert-butoxycarbonylamino)-2-hydroxyhexanoic acid (WO2003062265-A2; Preparative Example 1, compound 1.08) (250 mg, 1.01 mmol) in DMF (5 mL) and methylene chloride (5 mL) was added (S)-benzyl 2-amino-3-methylbutanoate hydrochloride (271 mg, 1.11 mmol), HOBt (164 mg, 1.21 mmol), and Hunig's Base (0.440 mL, 2.53 mmol) and the resulting solution stirred at 0° C. for 10 minutes. EDCI (233 mg, 1.21 mmol) was added and the reaction stirred at 25° C. for 18 hours. The mixture was concentrated in vacuo, the resulting residue was diluted with ethyl acetate (45 mL), brine (10 mL), and 5% H$_3$PO$_4$ aqueous solution (10 mL), and the layers were separated. The organic layer was washed with 5% H$_3$PO$_4$ aqueous solution (10 mL), twice with saturated aqueous sodium bicarbonate solution (15 mL), water (15 mL), and brine (15 mL). The organic layer was dried over sodium sulfate, filtered, and concentrated in vacuo to afford the title compound as a light colored solid. The resulting solid was purified by flash chromatography on SiO$_2$ using ethyl acetate in hexanes as the mobile phase. (263 mg, 60% yield). MS (ESI$^+$) m/z=437 (M+H)$^+$.

Part B. Preparation of (2S)-2-((3S)-3-(tert-butoxycarbonylamino)-2-hydroxyhexanamido)-3-methylbutanoic acid To a solution of the product from Part A in ethanol (10 mL) was added palladium on carbon and the resulting suspension was stirred under hydrogen for 18 hours. The reaction vessel was purged with nitrogen gas and the suspension filtered through celite. The filtrate was concentrated and dried under vacuum to give the title compound as a colorless oil. (201 mg, 96% yield).

Part C. Preparation of tert-butyl (3S)-1-((S)-1-((S)-2-(dimethylamino)-2-oxo-1-phenylethyl amino)-3-methyl-1-oxobutan-2-ylamino)-2-hydroxy-1-oxohexan-3-ylcarbamate To a solution of the product from Part B (201 mg, 0.580 mmol) in DMF (2 mL) and methylene chloride (2 mL) was added (S)-2-amino-N,N-dimethyl-2-phenylacetamide hydrochloride (WO2003062265-A2; Preparative Example 5, step B, compound 2.1) (137 mg, 0.640 mmol), HOBt (94 mg, 0.700 mmol), and Hunig's Base (0.253 mL, 1.45 mmol) and the resulting solution stirred at 0° C. for 10 minutes. EDCI (133 mg, 0.700 mmol) was added and the reaction stirred at 25° C. for 18 hours. The mixture was concentrated in vacuo, the resulting residue was diluted with ethyl acetate (45 mL), brine (10 mL), and 5% H$_3$PO$_4$ aqueous solution (10 mL), and the layers were separated. The organic layer was washed with 5% H$_3$PO$_4$ aqueous solution (10 mL), twice with saturated aqueous sodium bicarbonate solution (15 mL), water (15 mL), and brine (15 mL). The organic layer was dried over sodium sulfate, filtered, and concentrated in vacuo to afford the title compound as a light colored solid. (133 mg, 45% yield). MS (ESI$^+$) m/z=507 (M+H)$^+$.

Part D. Preparation of (3S)-3-amino-N—((S)-1-((S)-2-(dimethylamino)-2-oxo-1-phenylethyl amino)-3-methyl-1-oxobutan-2-yl)-2-hydroxyhexanamide hydrochloride Same procedure described for Example 50, Part D was used, starting with the product from Part C. The crude material was taken on directly to the next step. MS (ESI$^+$) m/z=407 (M+H)$^+$.

Part E. Preparation of (3R,4R)-4-((S)-2-((S)-2-cyclohexyl-2-(pyrazine-2-carboxamido) acetamido)-3,3-dimethylbutanamido)-N³-((3S)-1-((S)-1-((S)-2-(dimethylamino)-2-oxo-1-phenylethyl amino)-3-methyl-1-oxobutan-2-ylamino)-2-hydroxy-1-oxohexan-3-yl)-N¹-phenylpyrrolidine-1,3-dicarboxamide.

Same procedure described for Example 50, Part E was used, starting with the product from Part D. (126 mg, 77% yield) MS (ESI$^+$) m/z=997 (M+H)$^+$.

Part F. Preparation of Title Product

Same procedure described for Example 50, Part F was used, starting with the product from Part E. (21 mg, 17% yield) MS (ESI$^+$) m/z=995 (M+H)$^+$.

Example 63

Preparation of (3R,4R)-4-((S)-2-((S)-2-cyclohexyl-2-(pyrazine-2-carboxamido) acetamido)-3,3-dimethylbutanamido)-$N^3$—((S)-1-((S)-1-((S)-2-(dimethylamino)-2-oxo-1-phenylethyl amino)-1-oxopropan-2-ylamino)-1,2-dioxohexan-3-yl)-$N^1$-phenylpyrrolidine-1,3-dicarboxamide

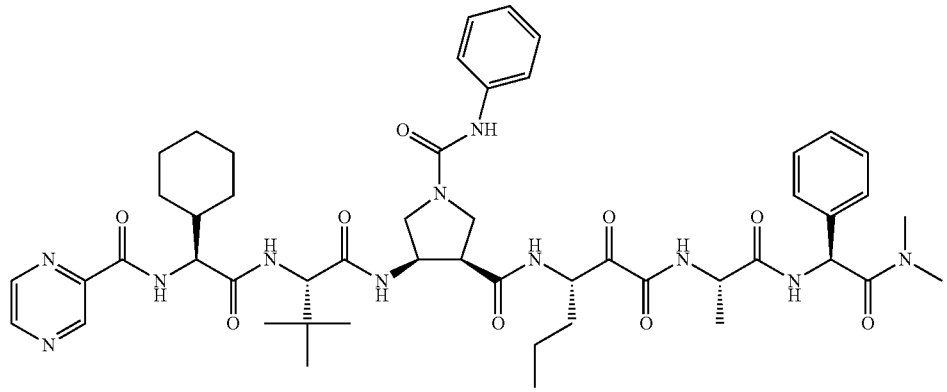 [SMILES: CCC[C@H](NC(=O)[C@@H]1CN(C(=O)Nc2ccccc2)C[C@@H]1NC(=O)[C@@H](NC(=O)[C@@H](NC(=O)c1cnccn1)C1CCCCC1)C(C)(C)C)C(=O)C(=O)N[C@@H](C)C(=O)N[C@H](C(=O)N(C)C)c1ccccc1]

Part A. Preparation of (2)-benzyl 2-((3S)-3-(tert-butoxycarbonylamino)-2-hydroxyhexan amido)propanoate Same procedure described for Example 62, Part A was used, starting with (S)-benzyl 2-aminopropanoate hydrochloride. The crude material was taken on directly to the next step. (200 mg, 48% yield) MS (ESI$^+$) m/z=409 (M+H)$^+$.

Part B. Preparation of (2S)-2-((3S)-3-(tert-butoxycarbonylamino)-2-hydroxyhexanamido) propanoic acid Same procedure described for Example 62, Part B was used, starting with the product from Part A. The crude material was taken on directly to the next step. (156 mg, 99% yield).

Part C. Preparation of tert-butyl (3S)-1-((S)-1-((S)-2-(dimethylamino)-2-oxo-1-phenylethyl amino)-1-oxopropan-2-ylamino)-2-hydroxy-1-oxohexan-3-ylcarbamate Same procedure described for Example 62, Part C was used, starting with the product from Part B. (221 mg, 94% yield) MS (ESI$^+$) m/z=479 (M+H)$^+$.

Part D. Preparation of (3S)-3-amino-N—((S)-1-((S)-2-(dimethylamino)-2-oxo-1-phenylethyl amino)-1-oxopropan-2-yl)-2-hydroxyhexanamide hydrochloride Same procedure described for Example 50, Part D was used, starting with the product from Part C. The crude material was taken on directly to the next step. (170 mg, 90% yield) MS (ESI$^+$) m/z=379 (M+H)$^+$

Part E. Preparation of (3R,4R)-4-((S)-2-((S)-2-cyclohexyl-2-(pyrazine-2-carboxamido) acetamido)-3,3-dimethylbutanamido)-$N^3$-((3S)-1-((S)-1-((S)-2-(dimethylamino)-2-oxo-1-phenylethyl amino)-1-oxopropan-2-ylamino)-2-hydroxy-1-oxohexan-3-yl)-$N^1$-phenylpyrrolidine-1,3-dicarboxamide Same procedure described for Example 50, Part E was used, starting with the product Part D. (114 mg, 72% yield) MS (ESI$^+$) m/z=969 (M+H)$^+$.

Part F. Preparation of Title Product

Same procedure described for Example 50, Part F was used, starting with the product from Part E. (38 mg, 33% yield) MS (ESI$^+$) m/z=967 (M+H)$^+$.

Example 64

Preparation of (3R,4R)—N3-((S)-4-amino-1-cyclobutyl-3,4-dioxobutan-2-yl)-4-((S)-2-((S)-2-cyclohexyl-2-(pyrazine-2-carboxamido)acetamido)-N,3,3-trimethylbutanamido)-N1-(naphthalen-2-yl)pyrrolidine-1,3-dicarboxamide

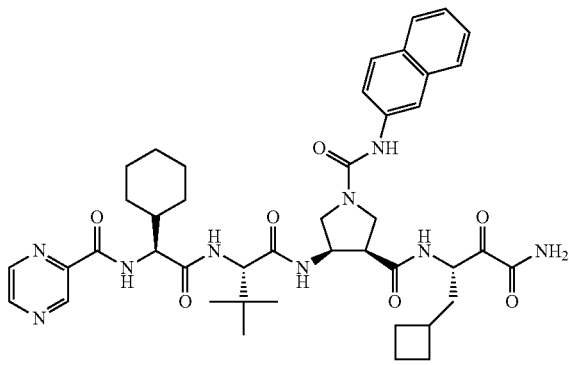 [SMILES: CC(C)(C)[C@H](NC(=O)[C@@H](NC(=O)c1cnccn1)C1CCCCC1)C(=O)N[C@H]1CN(C(=O)Nc2ccc3ccccc3c2)C[C@H]1C(=O)N[C@@H](CC1CCC1)C(=O)C(N)=O]

Part A. Preparation of (3R,4R)-4-((S)-2-((S)-2-cyclohexyl-2-(pyrazine-2-carboxamido) acetamido)-N,3,3-trimethylbutanamido)-1-(naphthalen-2-ylcarbamoyl)pyrrolidine-3-carboxylic acid A solution of the product from Example 45, Part G (400 mg, 0.65 mmol) and Hunig's base (350 uL, 2.0 mmol) in tetrahydrofuran (15 mL) was treated with 2-naphthyl isocyanate (115 mg, 0.68 mmol), stirred for 2 hours and concentrated under vacuum. The residue was partitioned between EtOAc and water and acidified to pH 1 with 1 M HCl. The EtOAc layer was then washed with brine, dried (Na$_2$SO$_4$) and concentrated to a yellow foam. MS (ESI$^+$) m/z=672 (M+H)$^+$.

Part B. Preparation of (3R,4R)—N3-((2S)-4-amino-1-cyclobutyl-3-hydroxy-4-oxobutan-2-yl)-4-((S)-2-((S)-2-cyclohexyl-2-(pyrazine-2-carboxamido)acetamido)-N,3,3-trimethylbutanamido)-N1-(naphthalen-2-yl)pyrrolidine-1,3-dicarboxamide A mixture of the product from Part A (250 mg, 0.37 mmol), N-(3-dimethylaminopropyl)-N'-ethylcarbodiimide hydrochloride (106 mg, 0.55 mmol), 1-hydroxybenzotriazole (75 mg, 0.55 mmol), Hunig's base (260 uL, 1.5 mmol) and (3S)-3-amino-4-cyclobutyl-2-hydroxybutanamide hydrochloride (104 mg, 0.5 mmol)) in dichloromethane (10 mL) was stirred for 16 hours, diluted with 100 mL EtOAc, washed with 10 mL 1 M H$_3$PO$_4$, 10 mL 10% NaHCO$_3$, 3×20 mL with brine, dried (Na$_2$SO$_4$), and concentrated. The residue was chromatographed on an ISCO 12 g silica cartridge eluting with 8% MeOH in DCM to give the title compound as a white powder (180 mg, 59% yield). MS (ESI+) m/z=826.4 (M+H)$^+$.

Part C. Preparation of Title Product

The product from Part B (83 mg, 0.1 mmol) in dichloromethane (2 mL) was treated with Dess-Martin periodinane (85 mg, 0.2 mmol), stirred for 4 hours, treated with 10% aqueous sodium sulfite (2 mL), stirred for 10 minutes and diluted with 20 mL EtOAc. The EtOAc layer was then washed with saturated aqueous sodium bicarbonate, brine, dried (MgSO$_4$) and concentrated. The crude product was flash chromatographed on an 5 g silica cartridge eluting with ethyl acetate →methanol/ethyl acetate (2/98) to give the title compound (7 mg, 8%). MS: (ESI+) m/z=824.6 (M+H)+.

Example 65

The following compounds were prepared utilizing the general method-of-preparation discussion and specific synthesis examples provided above:

A

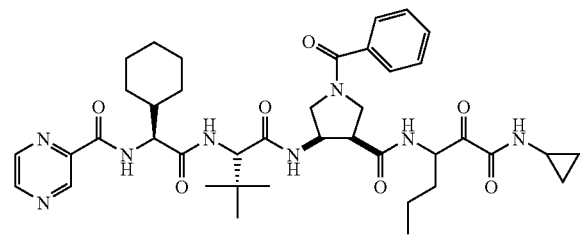

B

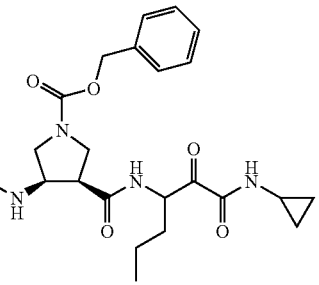

C

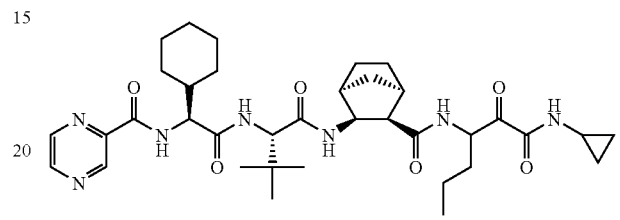

D

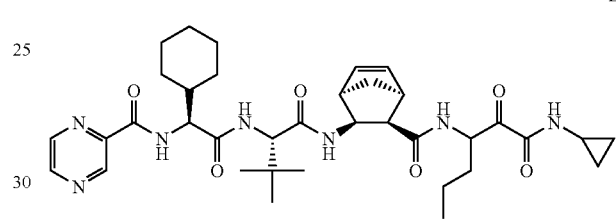

E

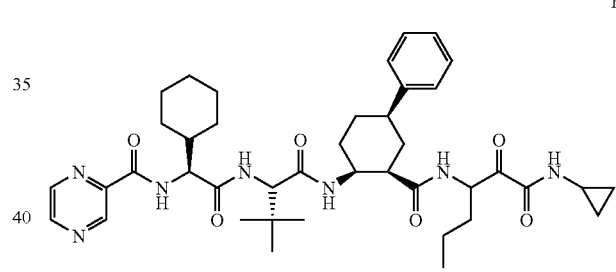

F

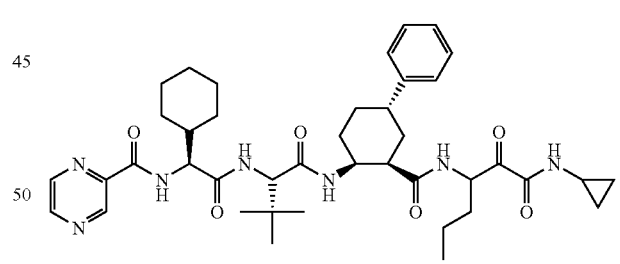

Example 66

Biochemical HCV Protease Assay

Furthermore compounds were assayed for biochemical activity by performing HCV protease assays. The assay provides an indication of how effective compounds of the present invention are in inhibiting HCV proteolytic activity. The inhibitor potency (IC$_{50}$) were detected for each compound to determine the most preferred compounds. The following assay procedure was followed:

The assay was performed in a 96-well white polystyrene half area-plate (Costar 3693; Corning Inc, Corning, N.Y.) or white microfluor U-bottom plates from Dynex. The release of the fluorescence product was measured in a Fluoroskan plate fluorimeter or a SpectraMAX Gemini XPS operated at wavelengths excitation 355 nm and emission 485 nm EDANS DABCYL substrate. The same conditions were used in the HPLC assay. In a typical experiment the assay volume was 200 μL or 100 μL depending on the assay plate used but the final concentrations of all reagents were the same. For the scNS3NS4A the protease (typically 30 nM) was diluted in assay buffer (50 mM Tris-HCl pH 7.5, 150 mM NaCl, 10% Glycerol and 5 mM DTT) and the mixture was incubated for 30-60 minutes at RT. Reaction was initiated with the addition of 20 μL (or 10 μL for the half area plate) substrate diluted in the same buffer. The final concentration of DMSO in the assay mix was 10%. Assay progress was monitored by acquiring data points every 30 sec for 30 minutes. Initial reaction rates, expressed as fluorescence units per minute, were calculated by least-squares analysis of data points using the Software GraphPad Prism 4. Inhibitor potency ($IC_{50}$) were determined by fitting the initial rates to the appropriate equations using least squares regression analysis performed by GraphPad Prism 4.

The $IC_{50}$ values for compounds were determined. Typically, the $IC_{50}$ value in the range of 0.0001 μm to 50 μm relative to the uninhibited control demonstrates desired inhibition activity.

\* \* \*

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, can be made without departing from the spirit and scope thereof.

All references (patent and non-patent) cited above are incorporated by reference into this patent application. The discussion of those references is intended merely to summarize the assertions made by their authors. No admission is made that any reference (or a portion of ay reference) is relevant prior art (or prior art at all). Applicants reserve the right to challenge the accuracy and pertinence of the cited references.

We claim:

1. A compound or salt thereof, wherein:
the compound corresponds in structure to any one of formulae (I-5) and (I-6):

(I-5)

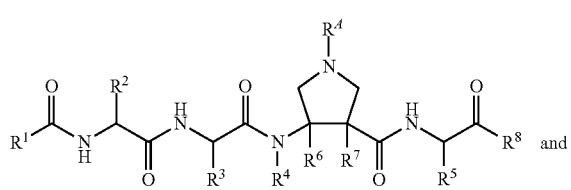

and (I-6)

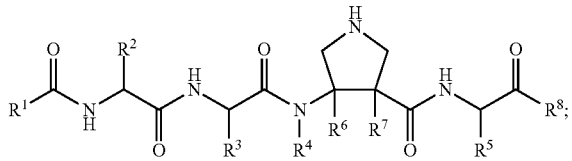

$R^A$ is selected from the group consisting of alkylcarbonyl, alkyloxycarbonyl, carbocyclylcarbonyl, carbocyclyloxycarbonyl, aminoalkylcarbonyl, carbocyclylaminocarbonyl, carbocyclylalkyloxycarbonyl, and alkylcarbocyclylsulfonyl, wherein:
the amino portion of the aminoalkylcarbonyl optionally is substituted with carbocyclylalkyloxycarbonyl;
$R^1$ is pyrizinyl;
$R^2$ is an optionally substituted carbocyclyl;
$R^3$ is selected from the group consisting of hydrogen, alkyl, carbocyclylalkylaminocarbonylalkyl, and carbocyclyl;
$R^4$ is selected from the group consisting hydrogen and alkyl;
$R^5$ is selected from the group consisting of hydrogen, alkyl and carbocyclylalkyl;
$R^6$ is hydrogen;
$R^7$ is hydrogen;
$R^8$ is aminocarbonyl optionally substituted with $R^B$;
each $R^B$ is independently selected from the group consisting of aminocarbonylalkyl and carbocyclyl, wherein:
the amino portion of the aminocarbonylalkyl optionally is substituted with one or two substituents independently selected from the group consisting of alkyl, wherein:
the alkyl optionally is substituted one or more substituents independently selected from the group consisting of alkyloxy, carbocyclyl, heterocyclyl, and aminocarbonyl, wherein:
the carbocyclyl and heterocyclyl optionally are substituted with one or more substituents independently selected from the group consisting of halo, alkyl and alkyloxy, and
the aminocarbonyl optionally is substituted with one or two independently selected alkyl.

2. The compound or salt of claim 1, wherein $R^A$ is selected from the group consisting of alkylcarbonyl, alkyloxycarbonyl, carbocyclylcarbonyl, carbocyclyloxycarbonyl, aminoalkylcarbonyl, carbocyclylaminocarbonyl, carbocyclylalkyloxycarbonyl, and alkylcarbocyclylsulfonyl, wherein:
the amino portion of the aminoalkylcarbonyl optionally is substituted with one or two substituents independently selected from the group consisting of carbocyclylalkyloxycarbonyl.

3. The compound or salt of claim 1, wherein each $R^A$ is independently selected from the group consisting of alkylcarbonyl, alkyloxycarbonyl, carbocyclylcarbonyl, carbocyclyloxycarbonyl, aminoalkylcarbonyl, carbocyclylalkyloxycarbonyl, and alkylcarbocyclylsulfonyl, wherein:
the amino portion of the aminoalkylcarbonyl optionally is substituted with one or two independently selected carbocyclylalkyloxycarbonyl.

4. The compound or salt of claim 1, wherein:
$R^8$ is aminocarbonyl substituted with $R^B$; and
$R^B$ is selected from the group consisting of aminocarbonylalkyl and carbocyclyl, wherein:
the amino portion of the aminocarbonylalkyl optionally is substituted with a substituent selected from the group consisting of alkyl, wherein:
the alkyl optionally are substituted with one or two substituents independently selected from the group consisting of alkyloxy, carbocyclyl, heterocyclyl, and aminocarbonyl, wherein:
the carbocyclyl and heterocyclyl optionally are substituted with one or more substituents independently selected from the group consisting of halo and alkyloxy, and
the aminocarbonyl optionally is substituted with one or two independently selected alkyl.

5. The compound or salt of claim 1, wherein:
$R^8$ is aminocarbonyl substituted with $R^B$; and
$R^B$ is selected from the group consisting of aminocarbonylalkyl and carbocyclyl, wherein:
the amino portion of the aminocarbonylalkyl optionally is substituted with alkyl, wherein:
the alkyl optionally is substituted with two substituents independently selected from the group consisting of alkyloxy, carbocyclyl, heterocyclyl, and aminocarbonyl, wherein:
the carbocyclyl and heterocyclyl optionally are substituted with one or more substituents independently selected from the group consisting of halo, and alkyloxy, and
the aminocarbonyl optionally is substituted with two independently selected alkyl.

6. The compound or salt of claim 1, wherein $R^2$ is $C_5$-$C_6$-cycloalkyl.

7. The compound or salt of claim 1, wherein $R^3$ is alkyl.

8. The compound or salt of claim 1, wherein $R^4$ is hydrogen.

9. The compound or salt of claim 1, wherein $R^5$ is alkyl.

10. The compound or salt of claim 1, wherein:
$R^A$ is selected from the group consisting of alkylcarbonyl, alkyloxycarbonyl, carbocyclylcarbonyl, carbocyclyloxycarbonyl, aminoalkylcarbonyl, carbocyclylalkyloxycarbonyl, and alkylcarbocyclylsulfonyl, wherein:
the amino portion of the aminoalkylcarbonyl optionally is substituted with carbocyclylalkyloxycarbonyl;
$R^2$ is $C_6$-carbocyclyl;
$R^3$ is selected from the group consisting of hydrogen, alkyl, carbocyclylalkyl, carbocyclyl, and aminocarbonylalkyl; and
$R^B$ is independently selected from the group consisting of aminocarbonylalkyl and carbocyclyl, wherein:
the amino portion of the aminocarbonylalkyl is substituted with alkyl, wherein:
the alkyl optionally is substituted with one or more substituents independently selected from the group consisting of carbocyclyl and aminocarbonyl, wherein:
the carbocyclyl optionally is substituted with one or more substituents selected from the group consisting of halo and alkyloxy, and
the aminocarbonyl optionally is substituted with one or two independently selected alkyl.

11. The compound or salt of claim 1, wherein:
$R^A$ is selected from the group consisting of alkylcarbonyl, alkyloxycarbonyl, carbocyclylcarbonyl, carbocyclyloxycarbonyl, aminoalkylcarbonyl, carbocyclylalkyloxycarbonyl, and alkylcarbocyclylsulfonyl, wherein:
the amino portion of the aminoalkylcarbonyl optionally is substituted with carbocyclylalkyloxycarbonyl;
$R^2$ is $C_6$-cycloalkyl;
$R^3$ is selected from the group consisting of hydrogen, alkyl, aminocarbonylalkyl, cycloalkyl, arylalkyl, and cycloalkylalkyl;
$R^4$ is hydrogen;
$R^5$ is selected from the group consisting of alkyl and cycloalkylalkyl; and
$R^B$ is independently selected from the group consisting of aminocarbonylalkyl and cycloalkyl, wherein:
the amino portion of the aminocarbonylalkyl optionally is substituted with alkyl, wherein:
the alkyl optionally is substituted with aminocarbonyl, wherein:
the aminocarbonyl optionally is substituted with one or two independently selected alkyl.

12. A pharmaceutical composition comprising one or more compounds and/or salts recited in claim 1.

13. A method for treating hepatitis C in a mammal in need of such treatment, wherein the method comprises administering to the mammal one or more compounds and/or salts recited in claim 1.

14. A compound, or salt thereof, having one of the following chemical structures:

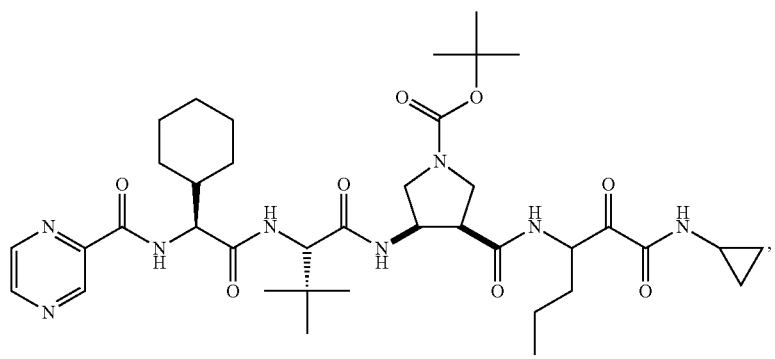

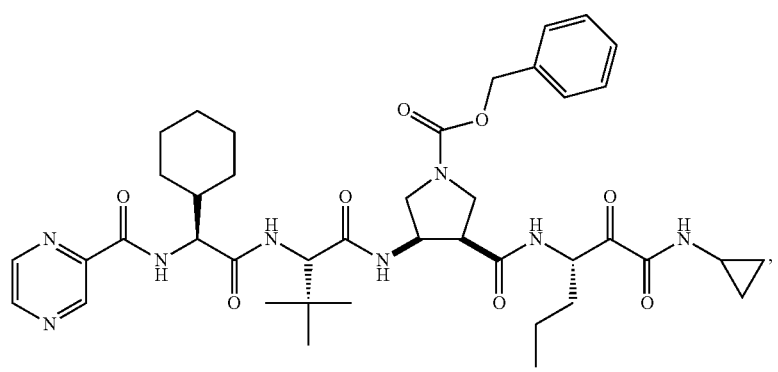
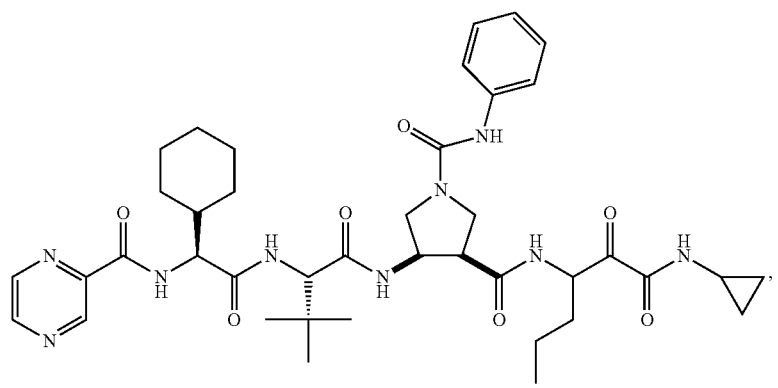
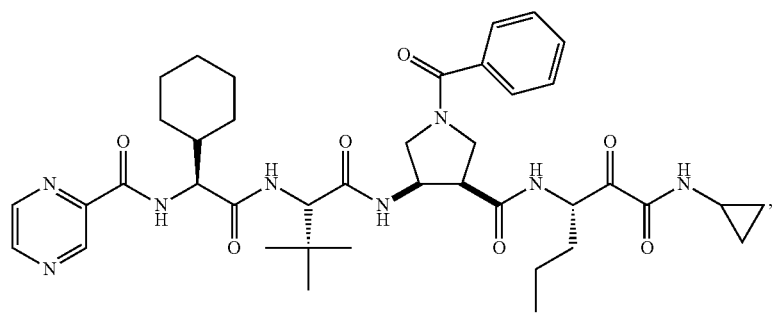
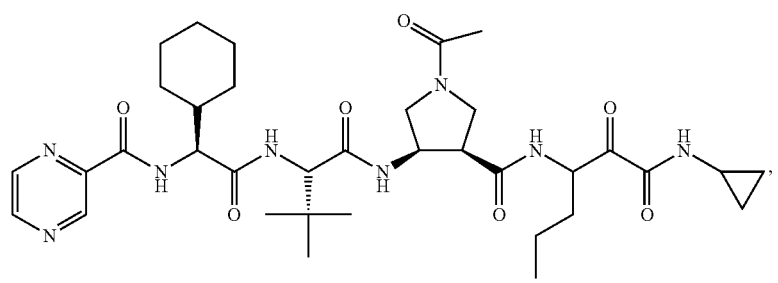

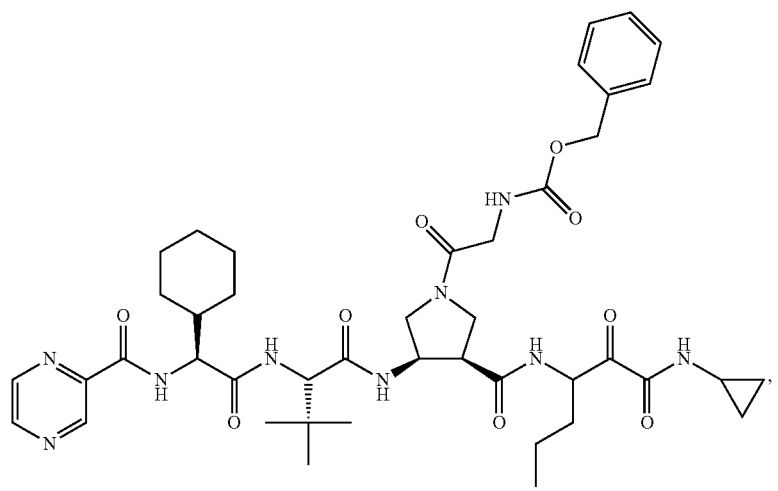
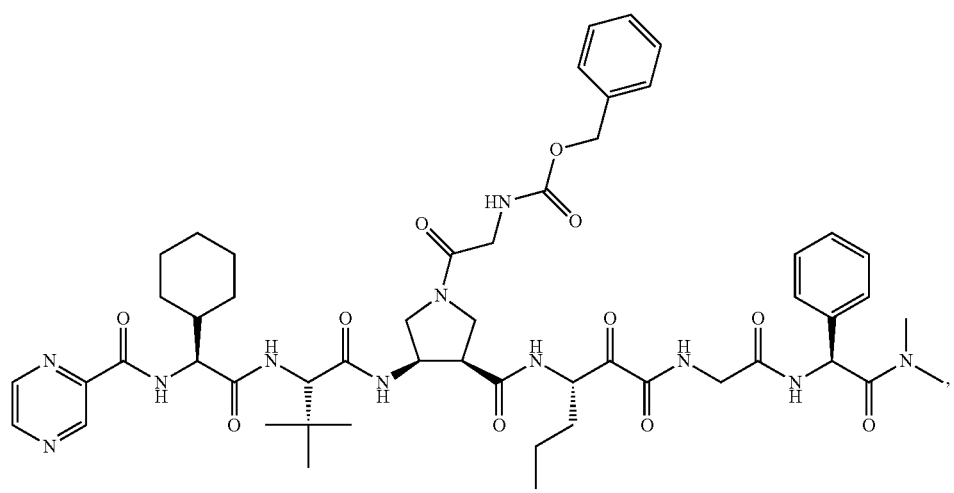
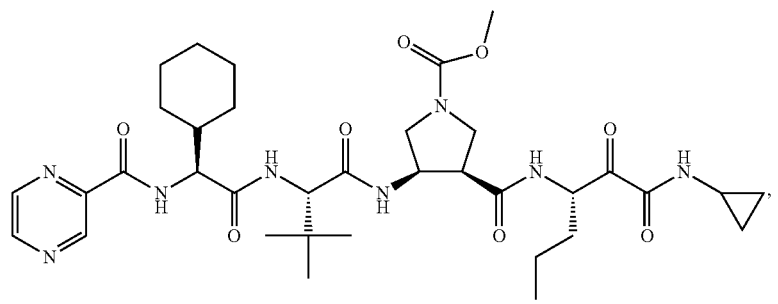
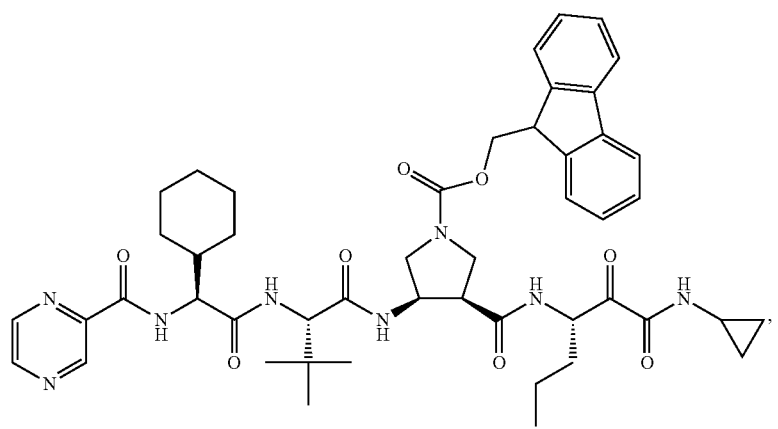

-continued
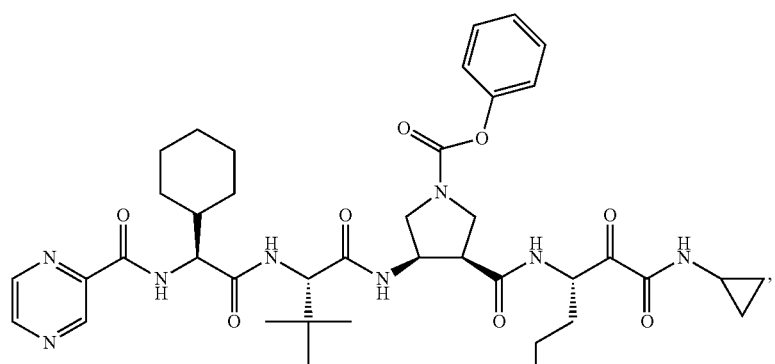
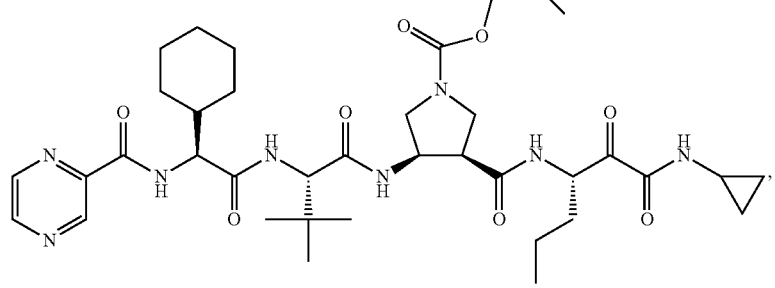
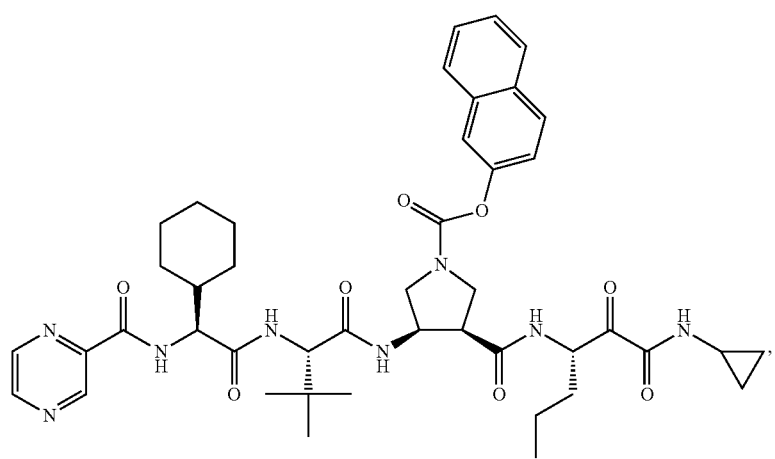
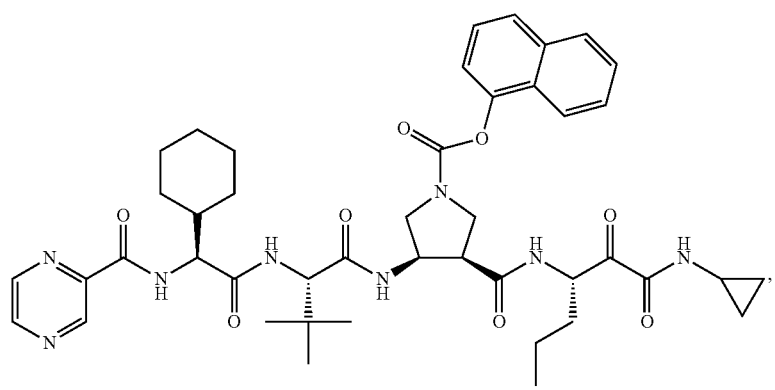

-continued
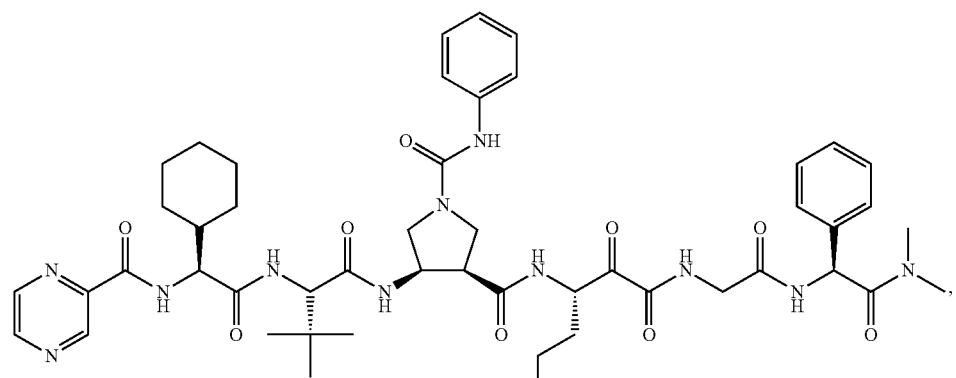
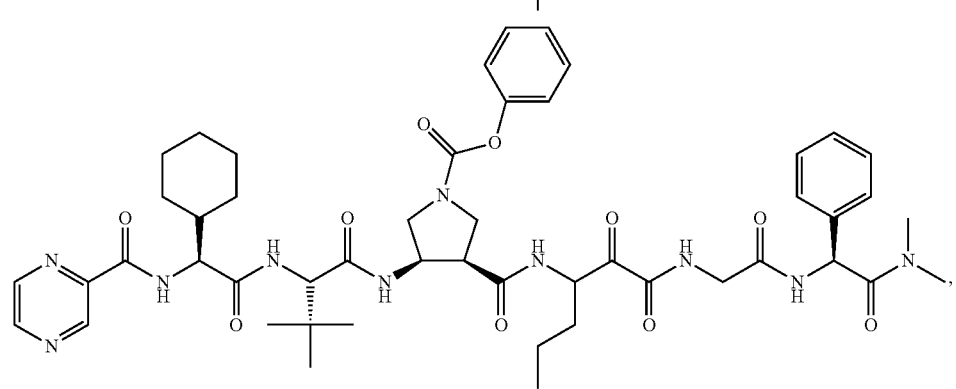
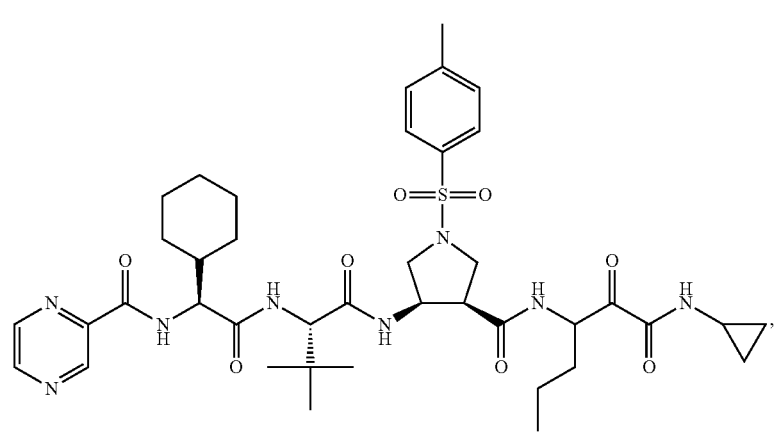
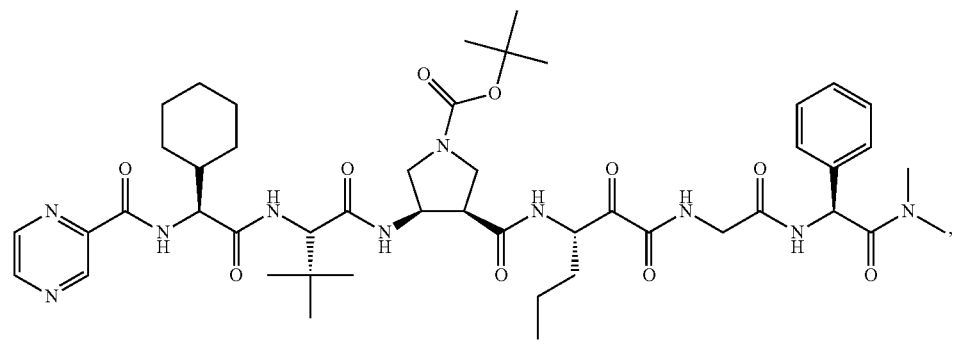

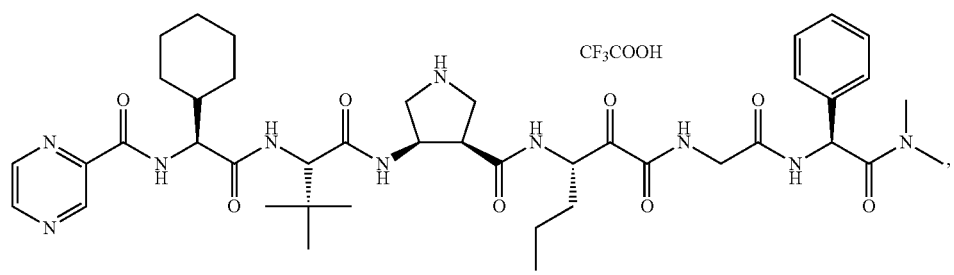
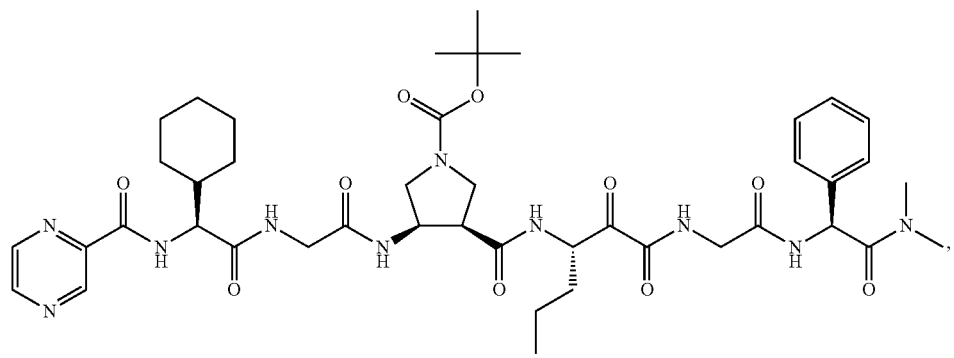
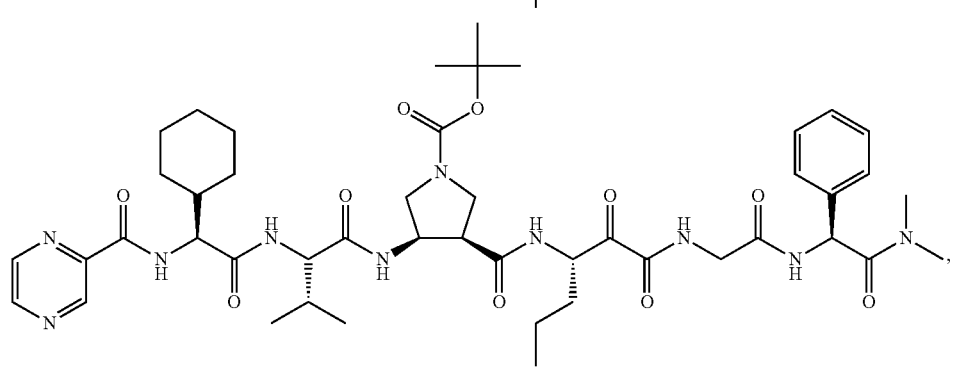
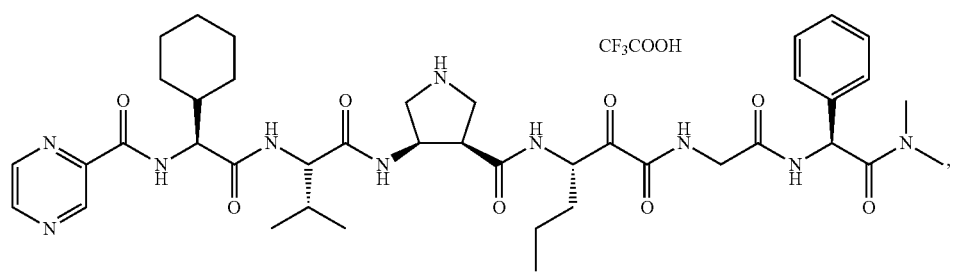
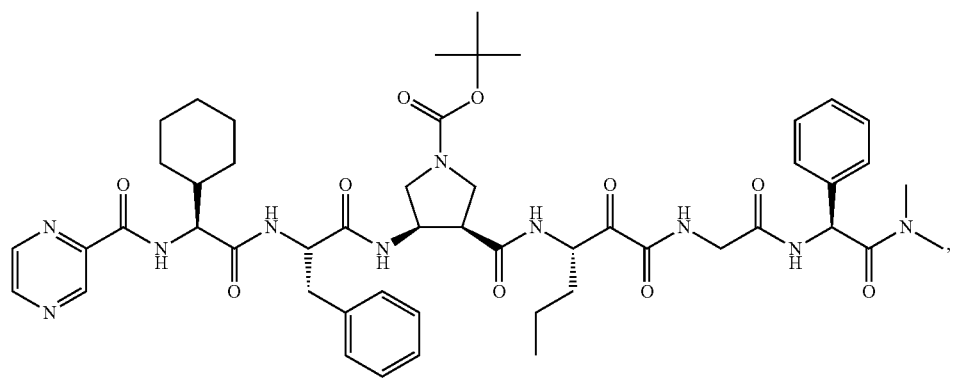

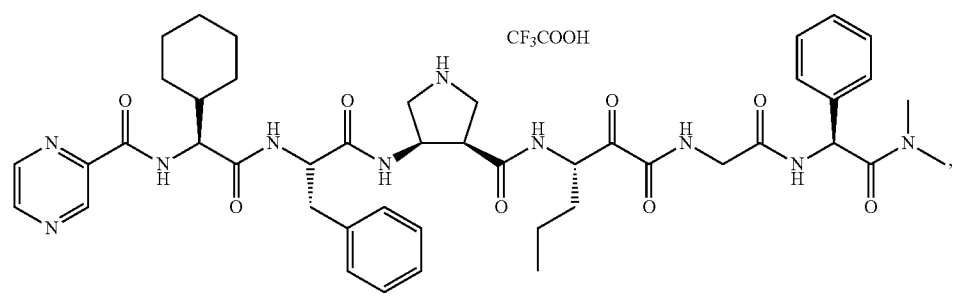
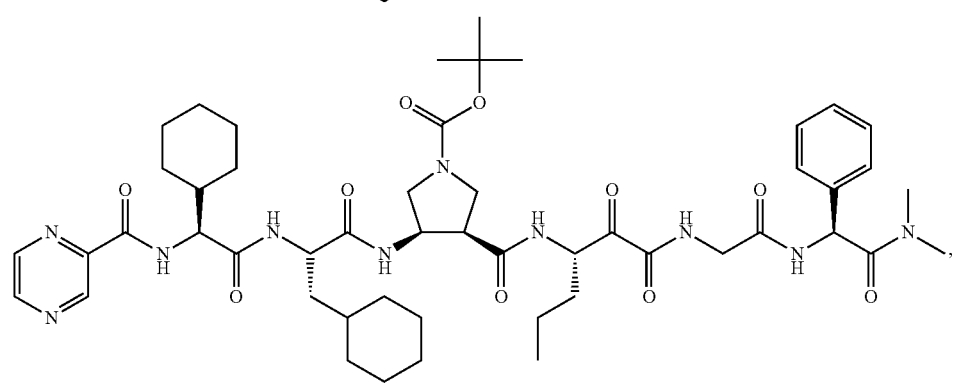
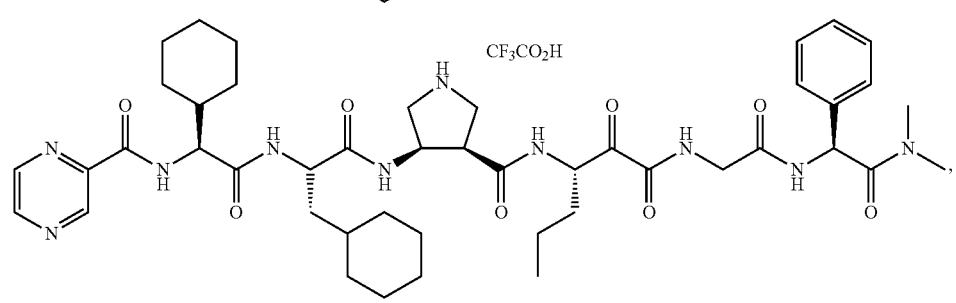
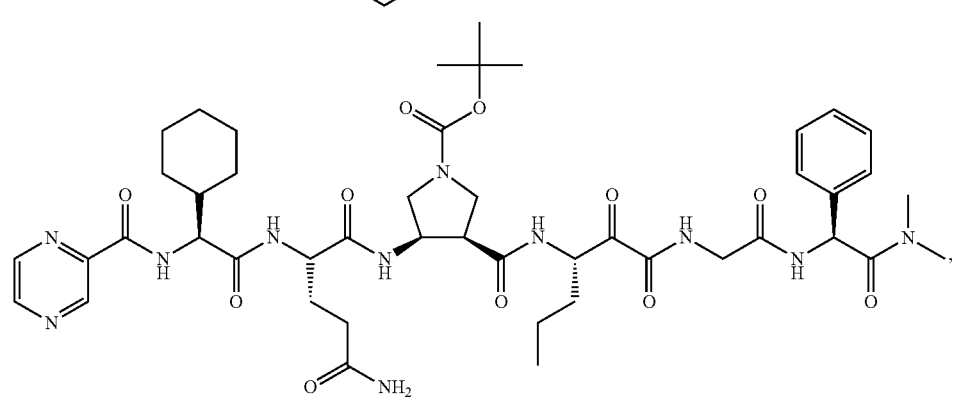
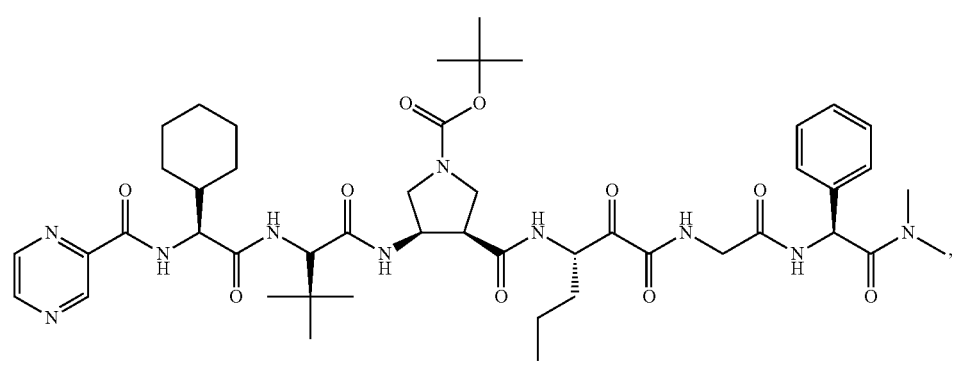

-continued
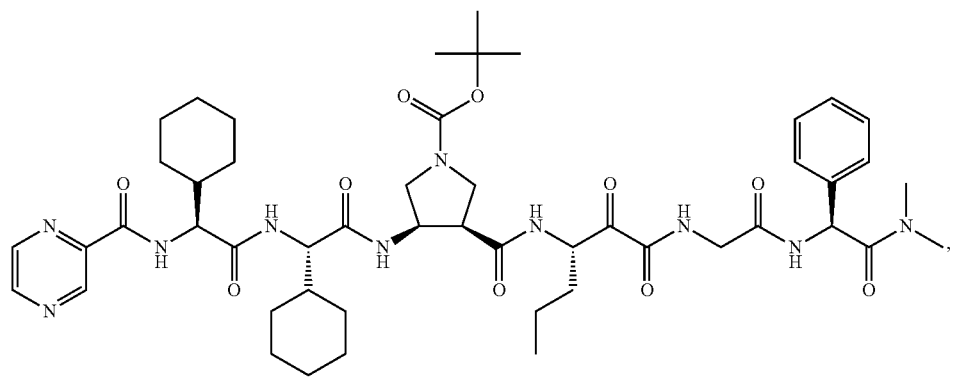
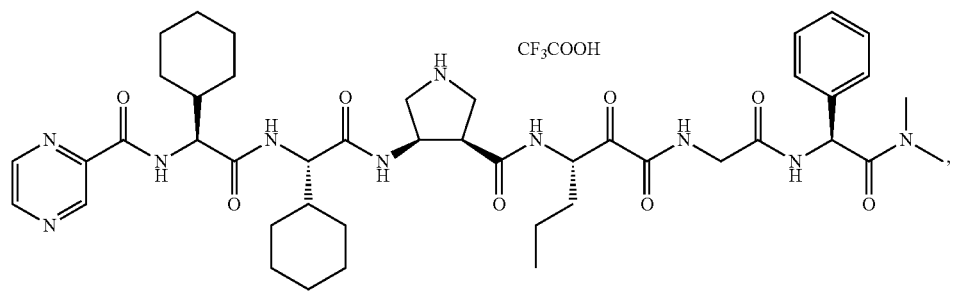
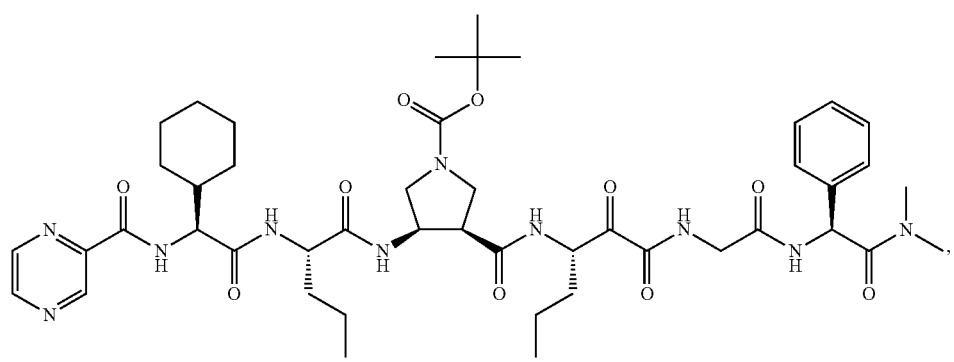
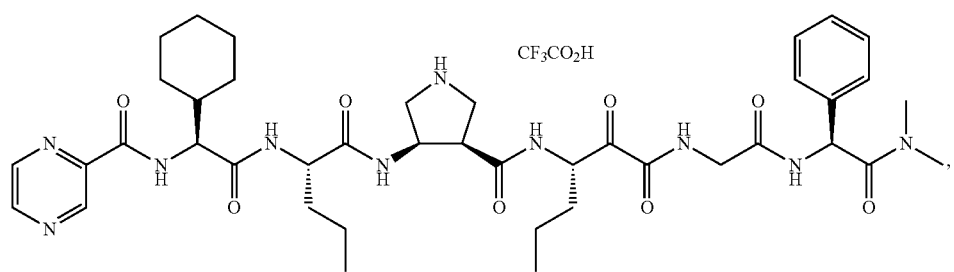
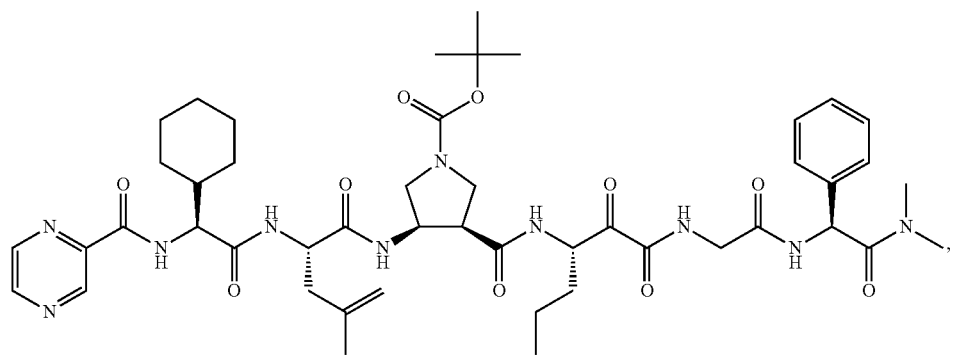

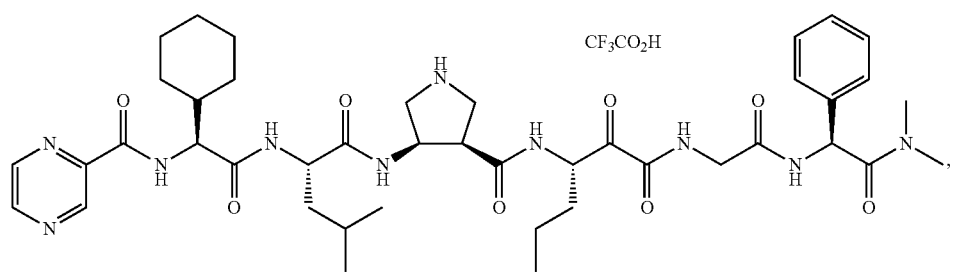
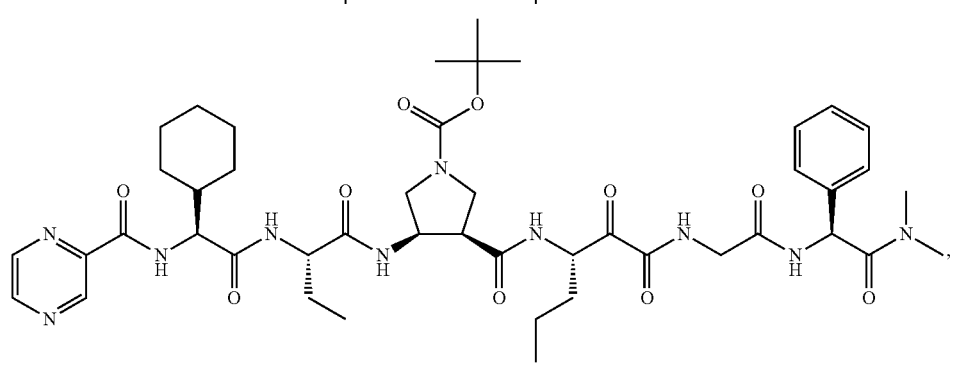
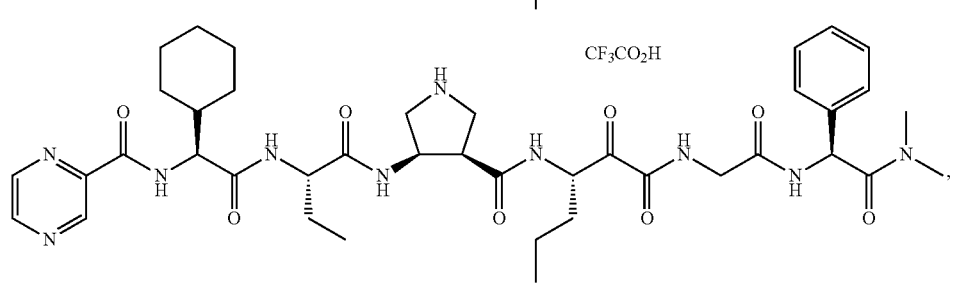
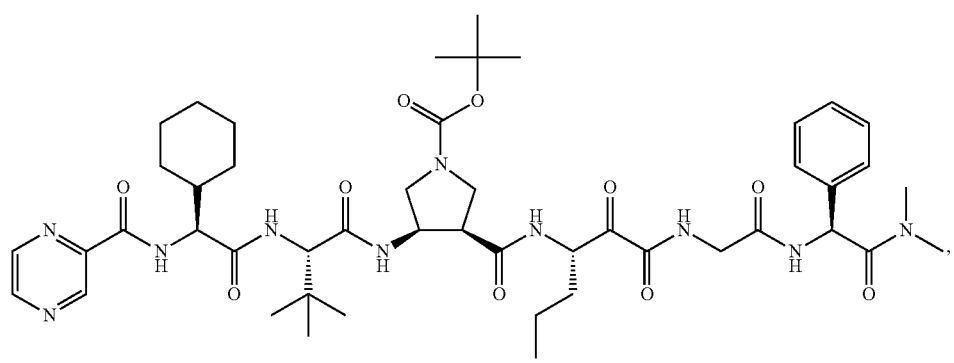
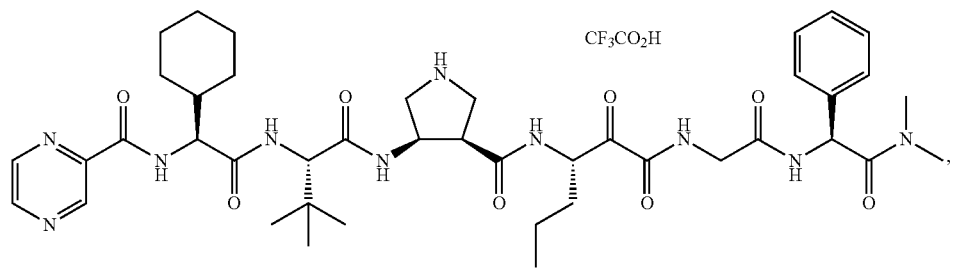

-continued
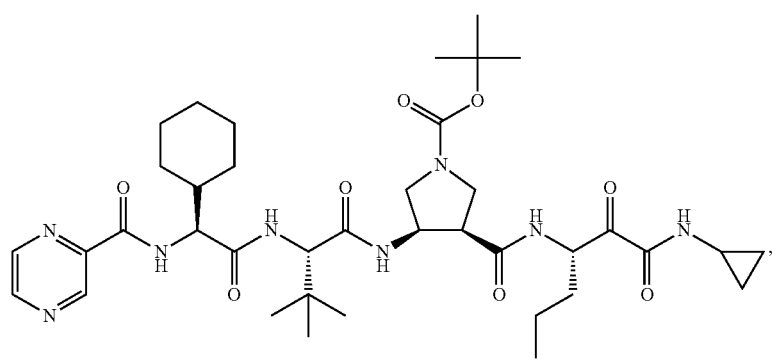
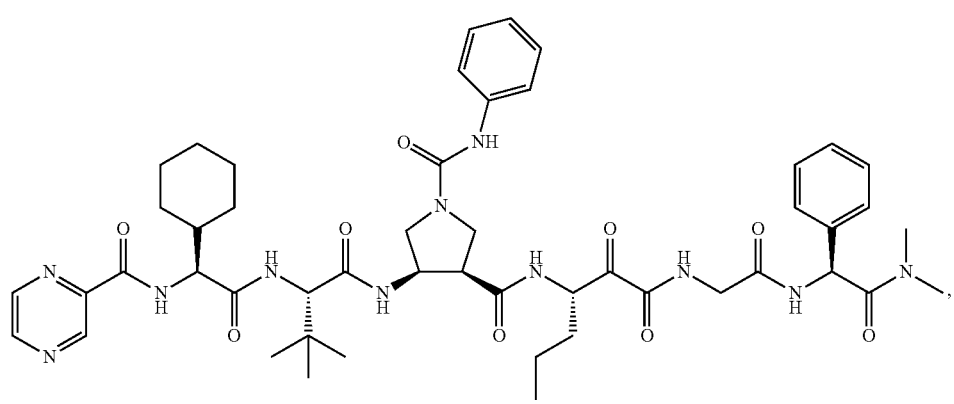
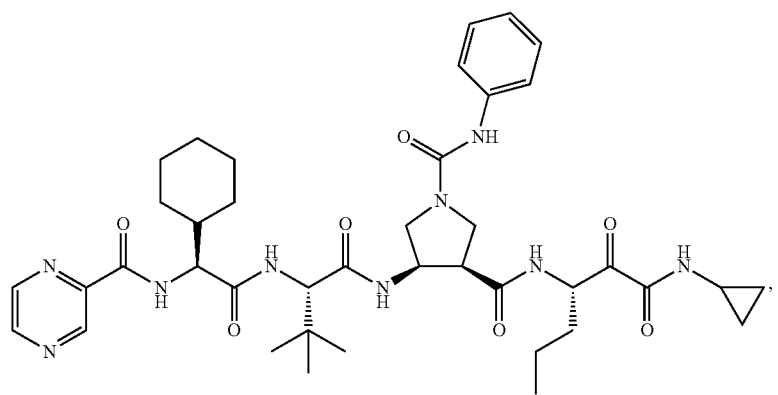
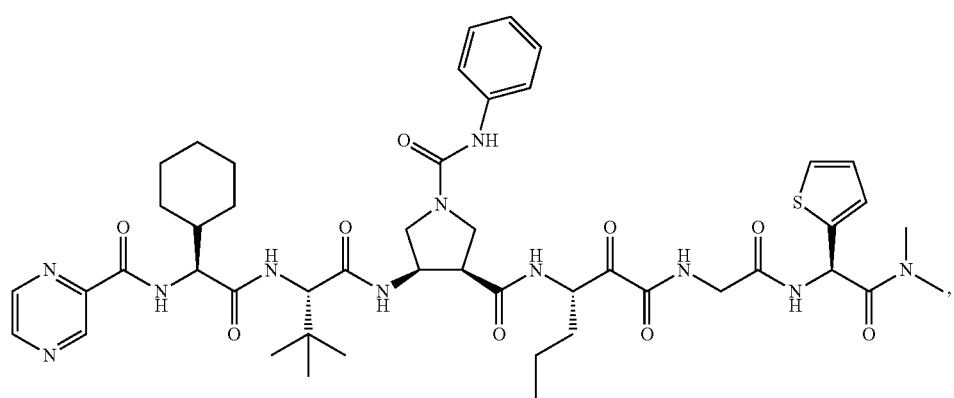

-continued
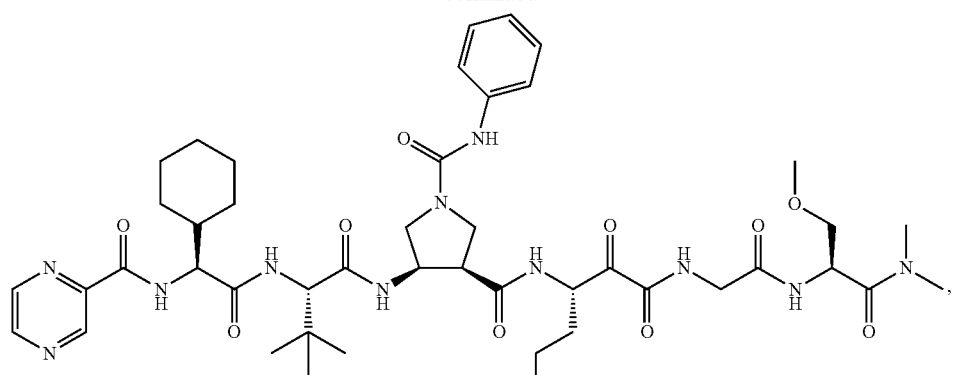
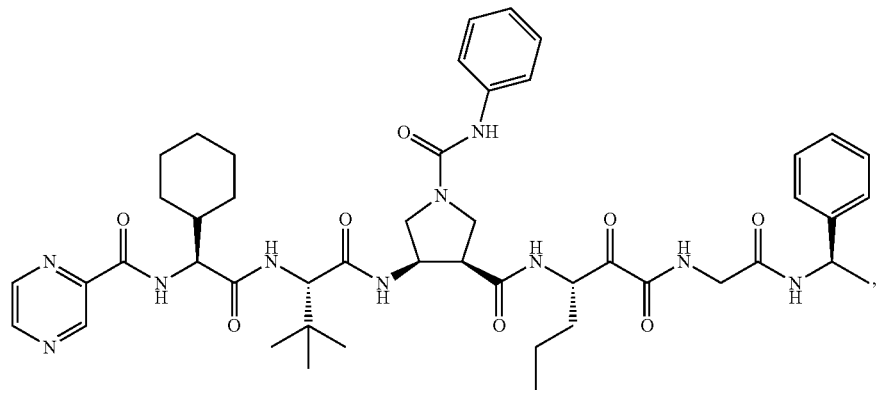
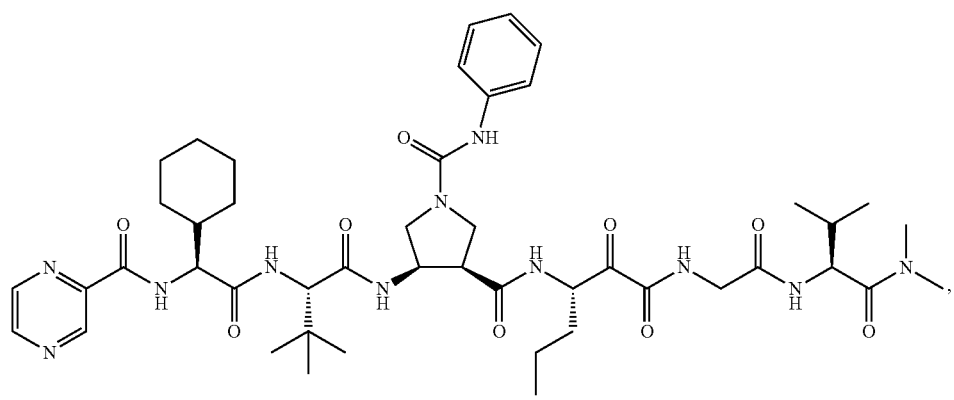
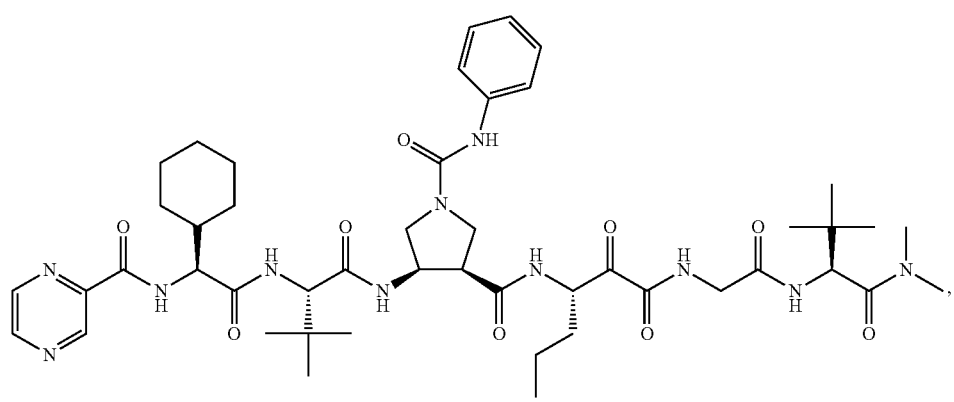

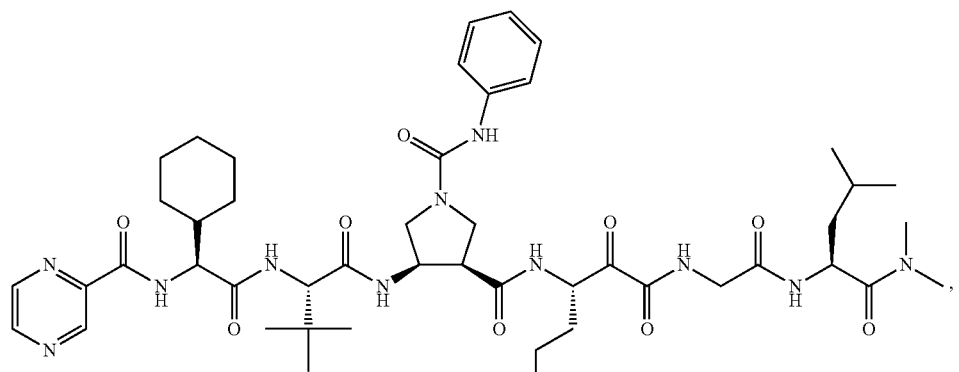
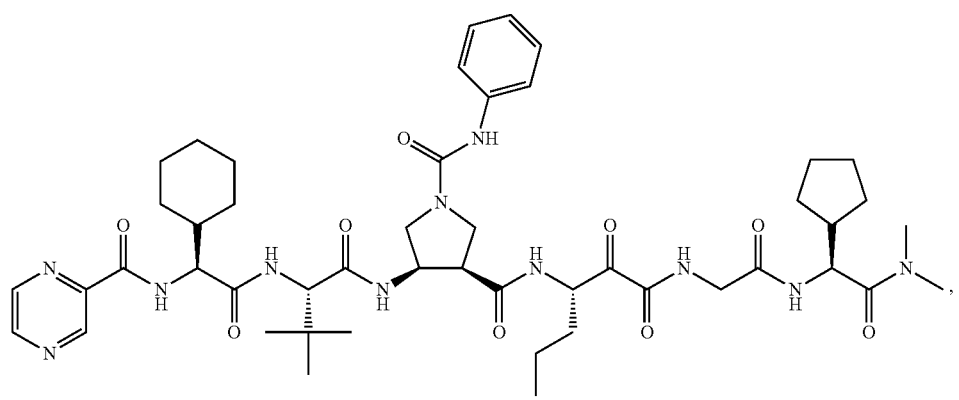
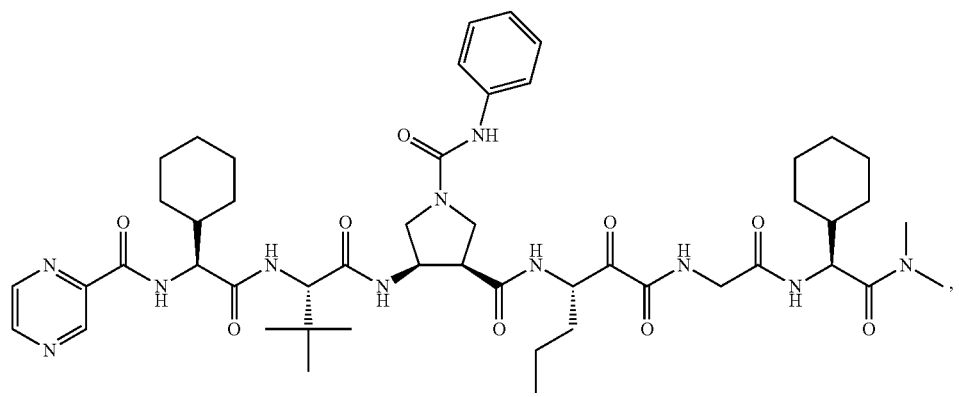
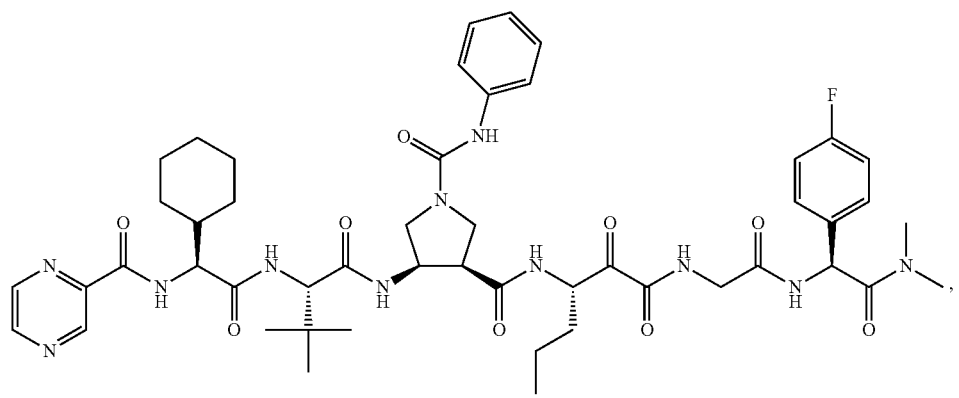

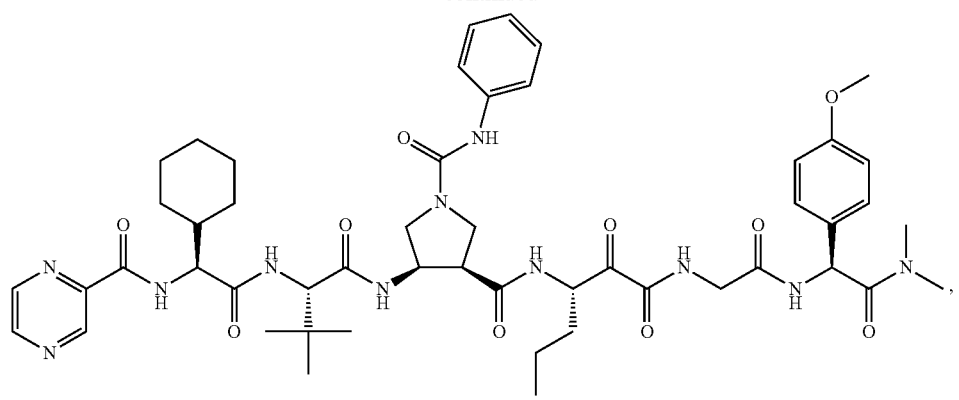
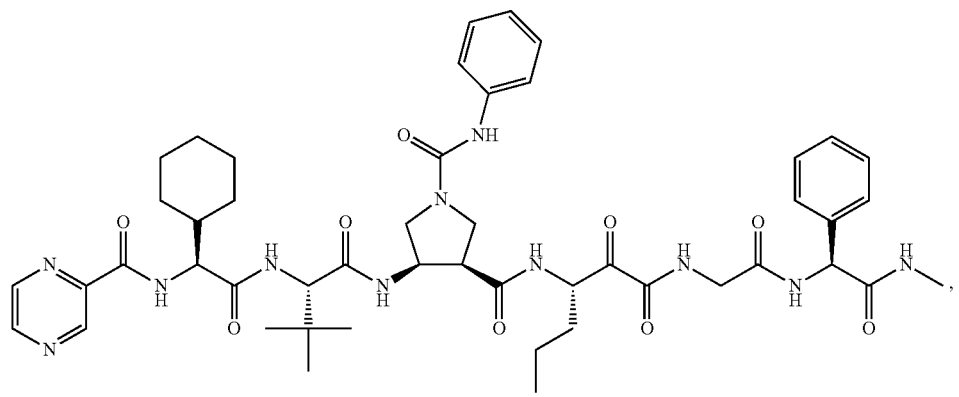
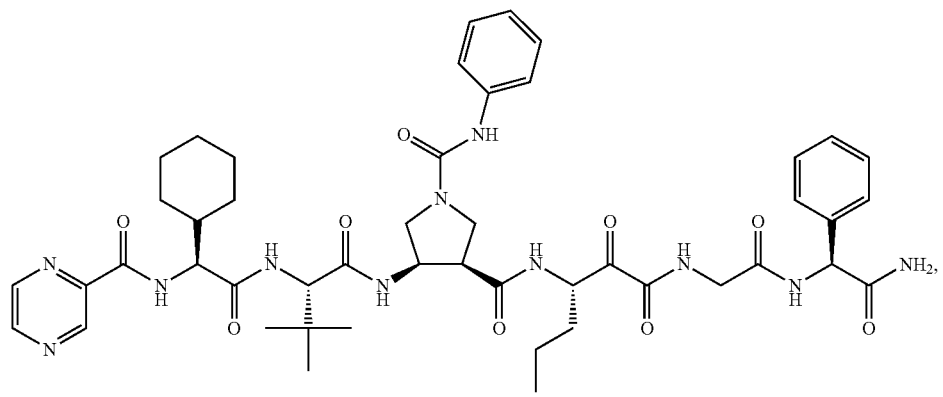
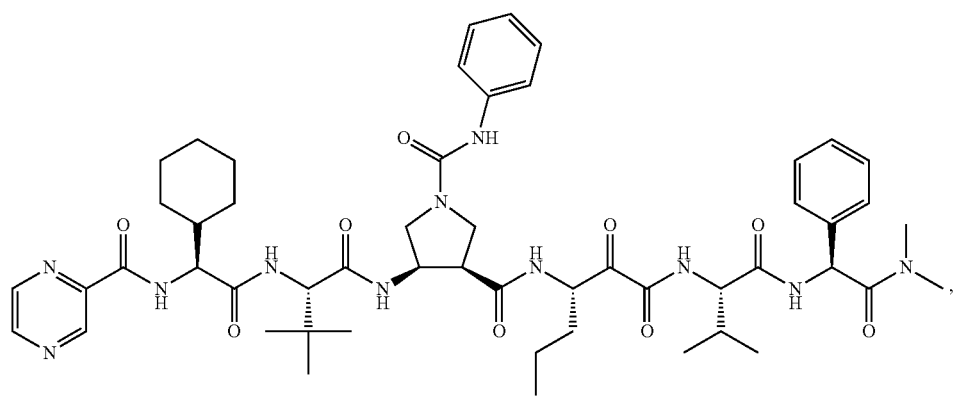

-continued
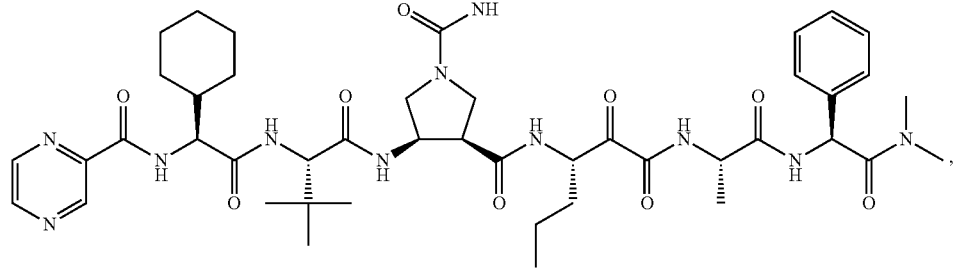
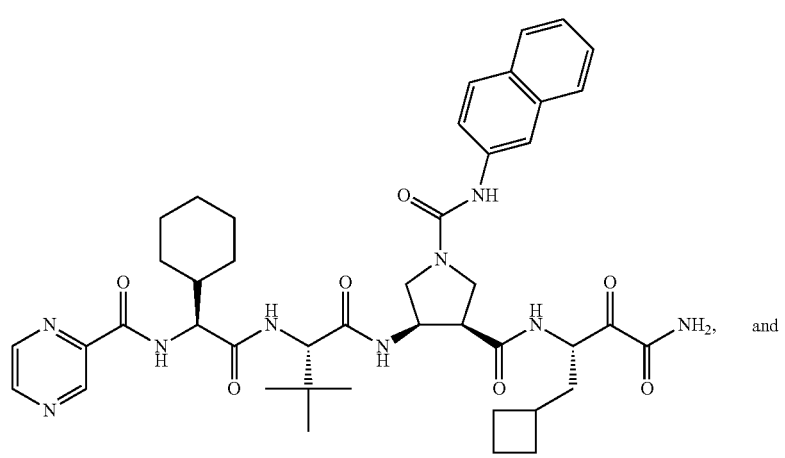
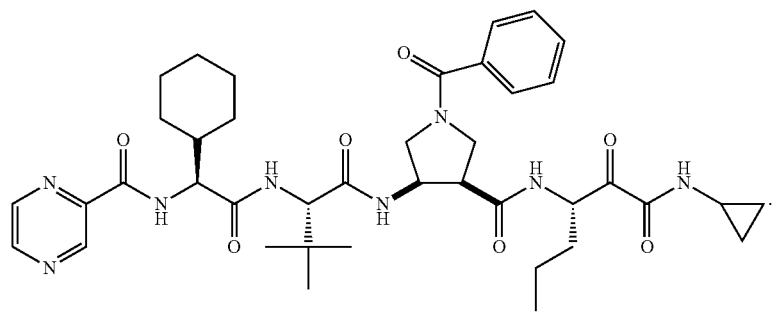
* * * * *